US009758777B2

(12) United States Patent
Vehmaanperä et al.

(10) Patent No.: US 9,758,777 B2
(45) Date of Patent: Sep. 12, 2017

(54) TREATMENT OF CELLULOSIC MATERIAL AND ENZYMES USEFUL THEREIN

(71) Applicants: Jari Vehmaanperä, Klaukkala (FI); Marika Alapuranen, Rajamäki (FI); Terhi Puranen, Nurmijärvi (FI); Matti Siika-Aho, Helsinki (FI); Jarno Kallio, Järvenpää (FI); Satu Hooman, Espoo (FI); Sanni Voutilainen, Lohja (FI); Teemu Halonen, Espoo (FI); Liisa Viikari, Helsinki (FI)

(72) Inventors: Jari Vehmaanperä, Klaukkala (FI); Marika Alapuranen, Rajamäki (FI); Terhi Puranen, Nurmijärvi (FI); Matti Siika-Aho, Helsinki (FI); Jarno Kallio, Järvenpää (FI); Satu Hooman, Espoo (FI); Sanni Voutilainen, Lohja (FI); Teemu Halonen, Espoo (FI); Liisa Viikari, Helsinki (FI)

(73) Assignee: Roal OY (FI)

(*) Notice: Subject to any disclaimer, the term of this patent is extended or adjusted under 35 U.S.C. 154(b) by 533 days.

(21) Appl. No.: 13/774,465

(22) Filed: Feb. 22, 2013

(65) Prior Publication Data

US 2013/0224801 A1 Aug. 29, 2013

Related U.S. Application Data

(60) Division of application No. 12/917,603, filed on Nov. 2, 2010, now Pat. No. 8,409,836, which is a division of application No. 12/141,976, filed on Jun. 19, 2008, now abandoned, which is a continuation of application No. PCT/FI2006/050558, filed on Dec. 15, 2006.

(60) Provisional application No. 60/753,258, filed on Dec. 22, 2005.

(30) Foreign Application Priority Data

Dec. 22, 2005 (FI) ..................................... 20051318

(51) Int. Cl.

| | |
|---|---|
| ***C12N 9/42*** | (2006.01) |
| ***C07H 21/04*** | (2006.01) |
| ***C12N 15/52*** | (2006.01) |
| ***C12N 9/34*** | (2006.01) |
| ***C12P 7/06*** | (2006.01) |
| ***C12N 9/96*** | (2006.01) |
| ***C12P 7/10*** | (2006.01) |
| ***C12P 19/02*** | (2006.01) |

(52) U.S. Cl.

CPC ............. *C12N 9/96* (2013.01); *C12N 9/2437* (2013.01); *C12N 9/2445* (2013.01); *C12P 7/10* (2013.01); *C12P 19/02* (2013.01); *C12Y 302/01004* (2013.01); *C12Y 302/01021* (2013.01); *C12Y 302/01091* (2013.01); *Y02E 50/16* (2013.01); *Y02E 50/17* (2013.01); *Y02P 20/52* (2015.11)

(58) Field of Classification Search

CPC .... C12Y 302/01004; C12Y 302/01021; C12Y 302/01008; C12Y 302/01003; C12Y 302/01006; C12N 9/2437; C12N 9/2445; C12N 19/14; C12P 19/02

USPC ....... 435/200, 210, 277, 69.7, 105, 106, 205

See application file for complete search history.

(56) References Cited

U.S. PATENT DOCUMENTS

| | | | | |
|---|---|---|---|---|
| 4,966,850 A | 10/1990 | Yu et al. | | |
| 5,763,254 A | 6/1998 | Woldike et al. | | |
| 5,912,157 A | 6/1999 | von der Osten et al. | | |
| 5,948,672 A | 9/1999 | Rasmussen et al. | | |
| 5,958,082 A | 9/1999 | Lund et al. | | |
| 6,001,639 A | 12/1999 | Schulein et al. | | |
| 6,022,725 A | 2/2000 | Fowler et al. | | |
| 6,071,735 A | 6/2000 | Schulein et al. | | |
| 6,103,464 A | 8/2000 | Fowler et al. | | |
| 6,197,564 B1 | 3/2001 | Kofod et al. | | |
| 7,785,853 B2 * | 8/2010 | Lange | C11D 3/38645 | 424/461 |
| 8,097,445 B2 * | 1/2012 | Bower | C12N 15/625 | 435/163 |
| 2002/0192774 A1 | 12/2002 | Ahring et al. | | |
| 2004/0005674 A1 | 1/2004 | Duck et al. | | |
| 2004/0053373 A1 | 3/2004 | Foody et al. | | |
| 2004/0197890 A1 * | 10/2004 | Lange | C11D 3/38645 | 435/209 |
| 2005/0164355 A1 | 7/2005 | Vlasenko et al. | | |
| 2005/0214920 A1 | 9/2005 | Harris et al. | | |
| 2006/0053514 A1 | 3/2006 | Wu et al. | | |

(Continued)

FOREIGN PATENT DOCUMENTS

| | | |
|---|---|---|
| EP | 0495258 A1 | 7/1992 |
| EP | 0562003 B1 | 9/2002 |

(Continued)

OTHER PUBLICATIONS

Linder et al. PNAS 1996, 93, pp. 12251-12255.*

Mar. 16, 2015 (EP) Office Action—Rule 94(3) Communication—App No. 12151852.6.

De Palma-Fernandez, E.R., "Purification and characterization of two β-glucosidases from the thermophilic fungus Thermoascus aurantiacus", Folia Microbiol., vol. 47, No. 6, 2002, pp. 685-690.

Tong, et al., "Purification and properties of the cellulases from the thermophilic fungus Thermoascus aurantiacus", Biochemical Journal, vol. 191, No. 1, Oct. 1, 1980, pp. 83-94.

(Continued)

*Primary Examiner* — Robert Mondesi
*Assistant Examiner* — Md. Younus Meah
(74) *Attorney, Agent, or Firm* — Banner & Witcoff, Ltd.

(57) ABSTRACT

The present invention relates to the production of sugar hydrolysates from cellulosic material. The method may be used e.g. for producing fermentable sugars for the production of bioethanol from lignocellulosic material. Cellulolytic enzymes and their production by recombinant technology is described, as well as uses of the enzymes and enzyme preparations.

15 Claims, 16 Drawing Sheets

(56) References Cited

U.S. PATENT DOCUMENTS

2006/0057672 A1* 3/2006 Bower ................ C12N 15/625 435/69.1
2007/0148732 A1 6/2007 Valtakari et al.

FOREIGN PATENT DOCUMENTS

| | | | |
|---|---|---|---|
| FR | 2786784 | A1 | 6/2000 |
| WO | 92/10581 | A1 | 6/1992 |
| WO | 97/13853 | | 4/1997 |
| WO | 98/06858 | | 2/1998 |
| WO | 01/42433 | A2 | 6/2001 |
| WO | 01/70998 | A1 | 9/2001 |
| WO | 02/24926 | A1 | 3/2002 |
| WO | 02/26979 | A1 | 4/2002 |
| WO | 02/095014 | A2 | 11/2002 |
| WO | 03/000941 | A2 | 1/2003 |
| WO | 03/062409 | A2 | 7/2003 |
| WO | 2004/053039 | A2 | 6/2004 |
| WO | 2005/074656 | A2 | 8/2005 |

OTHER PUBLICATIONS

Khandke, K.M., et al., "Purification of xylanase, β-glucosidase, endocellulase, and exocellulase from a thermophilic fungus, Thermoascus aurantiacus," Archives of Biochemistry and Biophysics, vol. 274, No. 2, Nov. 1, 1989, pp. 491-500.
Gomes, I, et al. "Simultaneous production of high activities of thermostable endoglucanase and β-glucosidase by the wild thermophilic fungus Thermoascus aurantiacus", Applied Mocrobiol Biotechnology, vol. 53, No. 4, Apr. 2000, pp. 461-468.
Parry, et al., "Biochemical characterization and mechanism of action of a thermostable β-glucosidase purified from Thermoascus aurantiacus", Biochemical Journal, vol. 353, No. 1, Jan. 1, 2001, pp. 117-127.
Mar. 16, 2015 (EP) Office Action—Rule 94(3) Communication—App No. 12151850.0.
Database EMBL [Online] Feb. 20, 2005, Magnaporth grisea beta-glucosidase-like protein mRNA, complete cds, retrieved from EBI accession No. EMHTG:AY849670, Database accession No. AY849670.
Database EMBL [Online] Mar. 12, 2004, p3fmgcf_004356 Normalized Magnaporthe grisea cDNA pRS423 library Magnaporthe grisea cDNA clone p3fmgcf_004356, mRNA sequence, retrieved from EBI accession No. EM_EST: CK917207, Database accession No. CK91 7207.
Database EMBL [Online] Oct. 28, 2005, "rbcmbO_00051 4 Chaetomium cupreum mycelium cDNA library Chaetomium cupreum cDNA, mRNA sequence", retrieved from EBI accession No. EM_EST:DV547597, Database accession No. DV547597.
Murray, P., et al, "Expression in Trichoderma reesei and characterisation of a thermostable family 3 beta-glucosidase from the moderately thermophilic fungus Talaromyces emersonii," Protein Expression and Purification, vol. 38, No. 2, Dec. 1, 2004, pp. 248-257.
Rahman, M.R., et al., "Isolation of thermophilic fungi and screening for their cellulase activity, saccharification, protein and biomass production," Bangladesh Journal of Microbiology, vol. 13, No. 1-2, Jun. 1996, pp. 57-62—Abstract and Database.
D. M. Coen, "The polymerase chain reaction," In: Current Protocols in Molecular Biology (2006) 15.0.1-15.0.3m John Wiley & Sons, Inc.
Gerd Gellissen, "Production of Recombinant Proteins," Novel, Microbial and Eukaryotic Expression Systems, Wiley-VCH Verlag Gmbh & Co. Weinheim, Germany.
T. K. Ghose, "Measurement of Cellulase Activities," IUPAC (International Union of Pure and Applied Chemistry) (1987) Pure & Appl. Chem., vol. 59, No. 2, pp. 257-268.
Nov. 4, 2014 (CA) Office Action—Application No. 2,833,029.
Dong, H. et al., "Beta-glucosidase-like protein", UniProtKB/Swiss-Prot Accession No. Q5EMW3, May 10, 2005 (Oct. 5, 2005).
Altschul S., (1990) "Basic local alignment search tool," J. Mol. Biol. 215: 403-410.
Badger, P.C.(2002) "Ethanol from cellulose: a general review," In: Trends in New Crops and New Uses, J. Janick and A. Whipkey (eds.). ASHS Press, Alexandria, VA, USA, pp. 17-21.
Bailey, M. J., (1981) "Induction, isolation and testing of stable Trichoderma reesei mutants with improved production of solubilizing cellulose," Enz. Microbiol. Technol., 3:153-157.
Bailey, M.J. (1989) "Production of xylanases by strains of Aspergillus," Appl. Microbiol. Biotechnol., 30:5-10.
Bailey, M.J. (1990) "Production of b-galactosidase by Aspergillus oryzae in submerged bioreactor cultivation," J. Biotechnol., 16:57-66.
Bailey, M.J. (1992) "Interlaboratory testing for assay of xylanase activity," J. Biotechnol., 23:257-270.
Bailey, M.J. (1993) "Hydrolytic properties of two cellulases of Trichoderma reesei expressed in yeast," Biotehnol. Appl. Biochem., 17:65-76.
Bendtsen, J. D., (2004) "Improved prediction of signal peptides: SignalP 3.0," J. Mol. Biol., 340:783-795.
Bernfeld, B. (1955) Amylases, ɑnd •,In: Methods in Enzymology, vol. 1, Eds. Colowick, S.P. and Kaplan, N.O. Academic Press, New York, pp. 149-158.
Biely, P., (1997) "Endo-beta-1,4-xylanase families: differences in catalytic properties," Journal of Biotechnology, 57:151-166.
Gasteiger, E., (2003) "ExPASy: the proteiomics server for in-depth protein knowledge and analysis," Nucleic Acids Res., 31:3784-3788.
Gill, S.C., (1989) "Calculation of protein extinction coefficients from amino acid sequence data," Anal. Biochem., 182:319-326.
Gupta, R., (2004) "Prediction of N-glycosyl-ation sites in human proteins," in preparation: www.cbs.dtu.dk/services/NetNGlyc/.
Haakana, H., (2004) "Cloning of cellulase genes from Melanocarpus albomyces and their efficient expression in Trichoderma reesei," Enz. Microbiol. Technol., 34:159-167.
Henrissat, B., (1991) "A classification of glycosyl hydrolases based on amino acid sequence similarities," Biochem. J., 280:309-316.
Henrissat, B., (1993) "New families in the classification of glycosyl hydrolases based on amino acid sequence similarities," Biochem. J., 293:781-788.
Henrissat, B., (1996) "Updating the sequence-based classification of glycosyl hydrolases," Biochem. J., 316:695-696.
Henrissat, B., (1998) "A scheme for designating enzymes that hydrolyse the polysaccharides in the cell wall of plants," FEBS Letters, 425:352-354.
Hong, J., (2003a) "Cloning of a gene encoding a thermo-stabile endo-•-1,4-glucanasdrom Thermoascus aurantiacus and its expression in yeast," Biotech. Letters, 25:657-661.
Hong, J., (2003b) "Cloning of a gene encoding thermostable cellobiohydrolase from Thermoascus aurantiacus and its expression in yeast," Appl. Microbiol. Biotechnol., 63:42-50.
IUPAC (International Union of Pure and Applied Chemistry) (1987) "Measurement of cellulase activities," Pure and Appl. Chem., 59:257-268.
Joutsjoki, V. V., (1993) "Transformation of Trichoderma reesei with the Hormoconis resinae glucoamylase P (gamP) gene: production of a heterologous glucoamylase by Trichoderma reesei," Curr. Genet., 24:223-228.
Karhunen, T., (1993) "High frequency one-step gene replacement in Trichoderma reesei. I. Endoglucanase I overproduction," Mol. Gen. Genet., 241:515-522.
Kurabi, A., (2005) "Enzymatic hydrolysis of steam-exploded and ethanol organosolv-pretreated Douglas-Fir by novel and commercial fungal cellulases," Appl. Biochem and Biotechn. vol. 121-124:219-229.
Leggio, L., (1999) "High resolution structure and sequence of the T. aurantiacus xylanase I: implications for evolution of thermostability in family 10 xylanases and enzymes with (beta) alpha-barrel architecture," Proteins 36(3):295-306.
Lever, M. (1972) "A new reaction for colorimetric determination of carbohydrates," Anal. Biochem., 47:276-279.
Lowry, O., (1951) "Protein measuremen with the Folin phenol reagent," J. Biol. Chem. 193:265-275.

(56) References Cited

OTHER PUBLICATIONS

Needleman, S., (1970) "A general method applicable to the search for similarities in the amino acid sequence of two proteins," Journal of Molecular Biology, 48:443-453.
Nielsen, H., (1997) "Identification of prokaryotic and eykaryotic signal peptides and prediction of their cleavage sites," Protein Engineering, 10:1-6.
Paloheimo, M., (2003) "High-yield production of a bacterial xylanase in the filamentous fungus Trichoderma reesei requires a carrier polypeptide with an intact domain structure," Appl. Env. Microbiol., 69:7073-7082.
Parry, N., (2002) "Biochemical characterization and mode of action of a thermostable endoglucanase purified from Thermoascus aurantiacus," Arch. of Biochem. and Biophys., 404:243-253.
Penttila, M., (1987) "A versatile transformation system for the cellulolytic filamentous fungus Trichoderma reesei," Gene, 61:155-164.
Raeder, U., (1985) "Rapid preparation of DNA from filamentous fungi," Lett. Appl. Microbiol., 1:17-20.
Rice, P., (2000). "EMBOSS: The European Molecular Biology Open Software Suite," Trends in Genetics, 16:276-277.
Srisodsuk, M., (1993) "Role of the interdomain linker peptide of Trichoderma reesei cellobiohydrolase I in its interaction with crystalline cellulose," J. Biol. Chem., Oct. 5, 268(28):20756-20761.
Sundberg, M., (1991) "Purification and properties of two acetylxylan esterases of Trichoderma reesei," Biotechnol. Appl. Biochem., 13:1-11.
Suurnakki, A., (2000) "Trichoderma reesei cellulases and their core domains in the hydrolysis and modification of chemical pulp," Cellulose 7:189-209.
Tenkanen, M., (1992) Two major xylanases of Trichoderma reesei. Enzyme Microbiol. Technol. 14: 566-574.
Tomme, P., (1988) "Chromatographic separation of cellulolytic enzymes," Methods in Enzymol., 160:187-192.
Tuohy, M., (2002) "Kinetic parameters and mode of action of cellobiohydrolases produced by Talaromyces emersonii," Biochem. Biophys. Acta, 1596:366-380 (abstract).
Van Petegem, et al., (2002) "Atomic resolution structure of major endoglucanase from Thermoascus aurantiacus," Biochem. and Biophys. Res. Comm., 296:161-166.
Van Tilbeurgh, H., (1988) "Fluorogenic and chromogenic glycosides as substrates and ligands of carbohydrases," Methods Enzymol., 160:45-59.
Wyman, C.E. (2001) "Twenty years of trials, tribulations, and research progress in bioethanol technology," Applied Biochemistry and Biotechnology, 91-93: 5-21.
Office Action issued for corresponding U.S. Appl. No. 14/045,236, dated Jun. 8, 2015.
GenBank Accession No. AAX07690.1, published Feb. 20, 2005.
Guo et al., "Protein tolerance to random amino acid change", Proceedings of the National Academy of Sciences USA, vol. 101, No. 25,pp. 9205-9210,2004.
Opposition issued for corresponding European Patent No. 2453014, dated Mar. 6, 2017.
Hong et al, Appl Microbial Biotechnol, 2007, 73, 1331-1339.
Hong et al, Appl Microbial Biotechnol, 2006, 73, 80-88.
Sun, et al., "Hydrolysis of lignocellulosic materials for ethanol production: a review" Bioresource Technology, 2002, 83, 1-11.
Speicher, et al., "Unit 11.10 N-Terminal Sequence Analysis of Proteins and Peptides" CwT Protoc Protein Sci May 2001; Chapter: Unit-11.10.
Declaration of Dr Paul Harris.
Bailey, M.J.; Buchert, J. and Viikari, L. Effect of pH on production of xylanase by Trichoderma reesei on xylan- and cellulose-based media. Appl. Microb. Biotechnol. 40: 224-229. 1993.
Xue, G.; Gobius, K.S.; Ropin, C.G. A novel polysaccharide hydrolase cDNA (celD) from Neocallimastix patriciarum encoding three multi-functional catalytic domains with high endoglucanase, cellobiohydrolase and xylanase activities. Journal of General Microbiol. vol. 138: 2397-2403. 1992.
International Search Report issued from corresponding PCT/FI2006/050558, dated Nov. 29, 2016.

* cited by examiner

SEQUENCE LISTING

```
<160> NUMBER OF SEQ ID NOS: 30

<210> SEQ ID NO 1
<211> LENGTH: 3192
<212> TYPE: DNA
<213> ORGANISM: Thermoascus aurantiacus
<220> FEATURE:
<221> NAME/KEY: CDS
<222> LOCATION: (1514)..(2122)
<220> FEATURE:
<221> NAME/KEY: Intron
<222> LOCATION: (2123)..(2187)
<220> FEATURE:
<221> NAME/KEY: CDS
<222> LOCATION: (2188)..(2949)

<400> SEQUENCE: 1

ctagaccttt atcctttcat ccgaccagac ttcccctttg accttggcgc cctgttgact      60

acctacctac ctaggtaggt aacgtcgtcg accctcttga atgatcctcg tcacactgca     120

aacatccgaa acatacggca aaagatgatt gggcatggat gcaggagaca tcgaatgagg     180

gcttagaagg aaatgaaaac ctgggaccag gacgctaggt acgatgaaat ccgccaatgg     240

tgaaacttta agtcgtgcct acagcacagg ctctgtgaag attgcgctgt tcagacttaa     300

tcttctcatc acagtccaag tctttatgaa aaggaaaaga gagagaagag cgctatttcg     360

agctgtcggc ctcataggga gacagtcgag cataccagcg gtatcgacgt tagactcaac     420

caagaataat gacgagaata aacacagaag tcaaccttga actgtatatc agggttccag     480

cagcagatag ttacttgcat aaagacaact ccccgagggc tctctgcata caccaggatg     540

ttccggaatt attcactgct cgtttccgac gtggcgtcag tgatccgtct ccacagaacc     600

tctacctggg gaataaccca ggggaggaat ctgcaagtaa gaacttaata ccaatccccg     660

gggctgccgg ggtgaatcaa atctcccgcg ggaaattaaa cccatacgat gtttttgcac     720

cacatgcatg cttggcacga tttctccgca agggagtcac agagaaagac atatttcgca     780

tactactgtg actctgcaga gttacatatc actcaggata cattgcagat cattgtccga     840

gcatcaaaca tggacctgca ggatcaacgg cccgacaaaa cacaagtggc taaagctggg     900

ggatgcccga acccgctgcg caatatcatt gatggatgtt cccccacatt tttaaaacat     960

cgacggatcg gcccgcatac taatcctttt atcaaccaaa agttccactc gactagagaa    1020

aaaaaggcca aggccactaa ttgcagtcgg atactggtct tttcgccgtc caacaccttc    1080

atccatgatc cccttagcca ccaatgcccc acataataca tgttgacata ggtacgtagc    1140

tctgttatcc aatcgcatcc gaacctcttt aacggacccc tcctacacac cttatcctaa    1200

cttcaggaga ctgttgccca ttggggattg aggaggtccg ggttgcagga tgcgttctag    1260

gctaaattct cggccggtag ccatctcgaa tctctcgtga agccttcatc tgaacggttg    1320

gcggcccgtc aagccgatga ccatgggttc ctgatagagc ttgtgcctga ccggccttgg    1380

cggcatagac gagctgaaca catcaggtat gaacagatca gatataaagt cggattgagt    1440

cctagtacga agcaatccgc caccaccaaa tcaagcaacg agcgacagca ataacaatat    1500

caatcgaatc gca atg tat cag cgc gct ctt ctc ttc tct ttc ttc ctc      1549
               Met Tyr Gln Arg Ala Leu Leu Phe Ser Phe Phe Leu
               1               5                   10

gcc gcc gcc cgc gcg cag cag gcc ggt acc gta acc gca gag aat cac      1597
Ala Ala Ala Arg Ala Gln Gln Ala Gly Thr Val Thr Ala Glu Asn His
        15                  20                  25

cct tcc ctg acc tgg cag caa tgc tcc agc ggc ggt agt tgt acc acg      1645
Pro Ser Leu Thr Trp Gln Gln Cys Ser Ser Gly Gly Ser Cys Thr Thr
```

```
    30                  35                  40

cag aat gga aaa gtc gtt atc gat gcg aac tgg cgt tgg gtc cat acc      1693
Gln Asn Gly Lys Val Val Ile Asp Ala Asn Trp Arg Trp Val His Thr
45                  50                  55                  60

acc tct gga tac acc aac tgc tac acg ggc aat acg tgg gac acc agt      1741
Thr Ser Gly Tyr Thr Asn Cys Tyr Thr Gly Asn Thr Trp Asp Thr Ser
                65                  70                  75

atc tgt ccc gac gac gtg acc tgc gct cag aat tgt gcc ttg gat gga      1789
Ile Cys Pro Asp Asp Val Thr Cys Ala Gln Asn Cys Ala Leu Asp Gly
            80                  85                  90

gcg gat tac agt ggc acc tat ggt gtt acg acc agt ggc aac gcc ctg      1837
Ala Asp Tyr Ser Gly Thr Tyr Gly Val Thr Thr Ser Gly Asn Ala Leu
        95                  100                 105

aga ctg aac ttt gtc acc caa agc tca ggg aag aac att ggc tcg cgc      1885
Arg Leu Asn Phe Val Thr Gln Ser Ser Gly Lys Asn Ile Gly Ser Arg
    110                 115                 120

ctg tac ctg ctg cag gac gac acc act tat cag atc ttc aag ctg ctg      1933
Leu Tyr Leu Leu Gln Asp Asp Thr Thr Tyr Gln Ile Phe Lys Leu Leu
125                 130                 135                 140

ggt cag gag ttt acc ttc gat gtc gac gtc tcc aat ctc cct tgc ggg      1981
Gly Gln Glu Phe Thr Phe Asp Val Asp Val Ser Asn Leu Pro Cys Gly
                145                 150                 155

ctg aac ggc gcc ctc tac ttt gtg gcc atg gac gcc gac ggc gga ttg      2029
Leu Asn Gly Ala Leu Tyr Phe Val Ala Met Asp Ala Asp Gly Gly Leu
            160                 165                 170

tcc aaa tac cct ggc aac aag gca ggc gct aag tat ggc act ggt tac      2077
Ser Lys Tyr Pro Gly Asn Lys Ala Gly Ala Lys Tyr Gly Thr Gly Tyr
        175                 180                 185

tgc gac tct cag tgc cct cgg gat ctc aag ttc atc aac ggt cag          2122
Cys Asp Ser Gln Cys Pro Arg Asp Leu Lys Phe Ile Asn Gly Gln
    190                 195                 200

gtacgtcaga agtgataact agccagcaga gcccatgaat cattaactaa cgctgtcaaa   2182

tacag gcc aat gtt gaa ggc tgg cag ccg tct gcc aac gac cca aat gcc   2232
      Ala Asn Val Glu Gly Trp Gln Pro Ser Ala Asn Asp Pro Asn Ala
          205                 210                 215

ggc gtt ggt aac cac ggt tcc tgc tgc gct gag atg gat gtc tgg gaa      2280
Gly Val Gly Asn His Gly Ser Cys Cys Ala Glu Met Asp Val Trp Glu
    220                 225                 230

gcc aac agc atc tct act gcg gtg acg cct cac cca tgc gac acc ccc      2328
Ala Asn Ser Ile Ser Thr Ala Val Thr Pro His Pro Cys Asp Thr Pro
235                 240                 245                 250

ggc cag acc atg tgc cag gga gac gac tgt ggt gga acc tac tcc tcc      2376
Gly Gln Thr Met Cys Gln Gly Asp Asp Cys Gly Gly Thr Tyr Ser Ser
                255                 260                 265

act cga tat gct ggt acc tgc gac cct gat ggc tgc gac ttc aat cct      2424
Thr Arg Tyr Ala Gly Thr Cys Asp Pro Asp Gly Cys Asp Phe Asn Pro
            270                 275                 280

tac cgc cag ggc aac cac tcg ttc tac ggc ccc ggg cag atc gtc gac      2472
Tyr Arg Gln Gly Asn His Ser Phe Tyr Gly Pro Gly Gln Ile Val Asp
        285                 290                 295

acc agc tcc aaa ttc acc gtc gtc acc cag ttc atc acc gac gac ggg      2520
Thr Ser Ser Lys Phe Thr Val Val Thr Gln Phe Ile Thr Asp Asp Gly
    300                 305                 310

acc ccc tcc ggc acc ctg acg gag atc aaa cgc ttc tac gtc cag aac      2568
Thr Pro Ser Gly Thr Leu Thr Glu Ile Lys Arg Phe Tyr Val Gln Asn
315                 320                 325                 330

ggc aag gta atc ccc cag tcg gag tcg acg atc agc ggc gtc acc ggc      2616
Gly Lys Val Ile Pro Gln Ser Glu Ser Thr Ile Ser Gly Val Thr Gly
                335                 340                 345
```

```
aac tca atc acc acc gag tat tgc acg gcc cag aag gcc gcc ttc ggc      2664
Asn Ser Ile Thr Thr Glu Tyr Cys Thr Ala Gln Lys Ala Ala Phe Gly
            350                 355                 360

gac aac acc ggc ttc ttc acg cac ggc ggg ctt cag aag atc agt cag      2712
Asp Asn Thr Gly Phe Phe Thr His Gly Gly Leu Gln Lys Ile Ser Gln
        365                 370                 375

gct ctg gct cag ggc atg gtc ctc gtc atg agc ctg tgg gac gat cac      2760
Ala Leu Ala Gln Gly Met Val Leu Val Met Ser Leu Trp Asp Asp His
    380                 385                 390

gcc gcc aac atg ctc tgg ctg gac agc acc tac ccg act gat gcg gac      2808
Ala Ala Asn Met Leu Trp Leu Asp Ser Thr Tyr Pro Thr Asp Ala Asp
395                 400                 405                 410

ccg gac acc cct ggc gtc gcg cgc ggt acc tgc ccc acg acc tcc ggc      2856
Pro Asp Thr Pro Gly Val Ala Arg Gly Thr Cys Pro Thr Thr Ser Gly
                415                 420                 425

gtc ccg gcc gac gtt gag tcg cag tac ccc aat tca tat gtt atc tac      2904
Val Pro Ala Asp Val Glu Ser Gln Tyr Pro Asn Ser Tyr Val Ile Tyr
            430                 435                 440

tcc aac atc aag gtc gga ccc atc aac tcg acc ttc acc gcc aac          2949
Ser Asn Ile Lys Val Gly Pro Ile Asn Ser Thr Phe Thr Ala Asn
        445                 450                 455

taagtaagta actggcactc taccaccgag agcttcgtga agatacaggg gtggttggga   3009

gattgtcgtg tacaggggac atgcgatgct caaaaatcta catcagtttg ccaattgaac   3069

catgaaaaaa agggggagat caaagaagtc tgtcaaaaga gggggctgt ggcagcttaa    3129

gccttgttgt agatcgagtc gacgccctat agtgagtcgt attagagctc gcggccgcga   3189

gct                                                                  3192
```

<210> SEQ ID NO 2
<211> LENGTH: 457
<212> TYPE: PRT
<213> ORGANISM: Thermoascus aurantiacus

<400> SEQUENCE: 2

```
Met Tyr Gln Arg Ala Leu Leu Phe Ser Phe Phe Leu Ala Ala Ala Arg
1               5                   10                  15

Ala Gln Gln Ala Gly Thr Val Thr Ala Glu Asn His Pro Ser Leu Thr
            20                  25                  30

Trp Gln Gln Cys Ser Ser Gly Gly Ser Cys Thr Thr Gln Asn Gly Lys
        35                  40                  45

Val Val Ile Asp Ala Asn Trp Arg Trp Val His Thr Thr Ser Gly Tyr
    50                  55                  60

Thr Asn Cys Tyr Thr Gly Asn Thr Trp Asp Thr Ser Ile Cys Pro Asp
65                  70                  75                  80

Asp Val Thr Cys Ala Gln Asn Cys Ala Leu Asp Gly Ala Asp Tyr Ser
                85                  90                  95

Gly Thr Tyr Gly Val Thr Thr Ser Gly Asn Ala Leu Arg Leu Asn Phe
            100                 105                 110

Val Thr Gln Ser Ser Gly Lys Asn Ile Gly Ser Arg Leu Tyr Leu Leu
        115                 120                 125

Gln Asp Asp Thr Thr Tyr Gln Ile Phe Lys Leu Leu Gly Gln Glu Phe
    130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Gly Leu Ser Lys Tyr Pro
                165                 170                 175
```

```
Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ala Asn Asp Pro Asn Ala Gly Val Gly Asn His Gly
    210                 215                 220

Ser Cys Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
            260                 265                 270

Cys Asp Pro Asp Gly Cys Asp Phe Asn Pro Tyr Arg Gln Gly Asn His
        275                 280                 285

Ser Phe Tyr Gly Pro Gly Gln Ile Val Asp Thr Ser Ser Lys Phe Thr
    290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Gly Asp Asn Thr Gly Phe Phe
        355                 360                 365

Thr His Gly Gly Leu Gln Lys Ile Ser Gln Ala Leu Ala Gln Gly Met
    370                 375                 380

Val Leu Val Met Ser Leu Trp Asp Asp His Ala Ala Asn Met Leu Trp
385                 390                 395                 400

Leu Asp Ser Thr Tyr Pro Thr Asp Ala Asp Pro Asp Thr Pro Gly Val
                405                 410                 415

Ala Arg Gly Thr Cys Pro Thr Thr Ser Gly Val Pro Ala Asp Val Glu
            420                 425                 430

Ser Gln Tyr Pro Asn Ser Tyr Val Ile Tyr Ser Asn Ile Lys Val Gly
        435                 440                 445

Pro Ile Asn Ser Thr Phe Thr Ala Asn
    450                 455
```

<210> SEQ ID NO 3
<211> LENGTH: 3055
<212> TYPE: DNA
<213> ORGANISM: Acremonium thermophilum
<220> FEATURE:
<221> NAME/KEY: CDS
<222> LOCATION: (972)..(1595)
<220> FEATURE:
<221> NAME/KEY: Intron
<222> LOCATION: (1596)..(1729)
<220> FEATURE:
<221> NAME/KEY: CDS
<222> LOCATION: (1730)..(2290)
<220> FEATURE:
<221> NAME/KEY: Intron
<222> LOCATION: (2291)..(2412)
<220> FEATURE:
<221> NAME/KEY: CDS
<222> LOCATION: (2413)..(2540)
<220> FEATURE:
<221> NAME/KEY: Intron
<222> LOCATION: (2541)..(2627)
<220> FEATURE:

```
<221> NAME/KEY: CDS
<222> LOCATION: (2628)..(2691)

<400> SEQUENCE: 3

gaattcggat cacaccgaga gcttcgcgat ggccagctgt ctcagcttgt acccgtctac      60

caacgttccg catcttcgtt accttgatag ctcgcgtttg ctggactgct ttgtgagggg     120

actgtgccac gcctgggaga cgggtgccgt accatcggtt actgcgcaga ctgagaaccg     180

tcgttgccga aacagccagg caggaagcct gtccaccttc atgtatcttc atatggaccc     240

cagcgcgccc ctctctttct cctcatttct tgcccaccac gatggacacc atgccaatct     300

atttcttgat cccttgactc ctcagccccc cagcagtccg acaatgtaca gtgatgggca     360

tctctttctg tacatacgtc ccctctcgcg gtgtccacgc gcggccgggg atgcctggga     420

cggagtgcca cccgcaggga acgagacttg gctgatgggg tgcggtgcat ggtggcacaa     480

gagatccagg ccccccgatc tcgttctcgc acgtatcctt cccccgccgg cgatgcccaa     540

gtgggaagtc ttcggagcgg cacccaggcc catcttgccg atgcccggca cggctctggc     600

ggttgccttc atctatcgtg gctgcacatc cgccgtgccc ccattgggaa agcaggcttt     660

gttcttcccg tctgtcgatc gtctcccacc taccctccct cctcgcaagg gcttaccctg     720

gcccctcact gctgcttcac ctcactgctg cttccccgca atgccccctc gcccccccc      780

cccccctctc ctttgcagta cagatctaca taatatcgag acgcccccca agctgtttct     840

ctggcacagc cctctcgcgc gtggtgcaag agcaagtcag agtatcaatt cccccatctc     900

tcatctcagc ccttctgccg tggtccaccc gacattctgg gcccgtagcc aagaccgatc     960

cgcctctcac c atg cac aag cgg gcg gcc acc ctc tcc gcc ctc gtc gtc     1010
             Met His Lys Arg Ala Ala Thr Leu Ser Ala Leu Val Val
             1               5                   10

gcc gcc gcc ggc ttc gcc cgc ggc cag ggc gtg ggc acg cag cag acg     1058
Ala Ala Ala Gly Phe Ala Arg Gly Gln Gly Val Gly Thr Gln Gln Thr
    15                  20                  25

gag acg cac ccc aag ctc acc ttc cag aag tgc tcc gcc gcc ggc agc     1106
Glu Thr His Pro Lys Leu Thr Phe Gln Lys Cys Ser Ala Ala Gly Ser
30                  35                  40                  45

tgc acg acc cag aac ggc gag gtg gtc atc gac gcc aac tgg cgc tgg     1154
Cys Thr Thr Gln Asn Gly Glu Val Val Ile Asp Ala Asn Trp Arg Trp
                50                  55                  60

gtg cac gac aag aac ggc tac acc aac tgc tac acg ggc aac gag tgg     1202
Val His Asp Lys Asn Gly Tyr Thr Asn Cys Tyr Thr Gly Asn Glu Trp
            65                  70                  75

aac acc acc atc tgc gcc gac gcc gcc tcg tgc gcc agc aac tgc gtc     1250
Asn Thr Thr Ile Cys Ala Asp Ala Ala Ser Cys Ala Ser Asn Cys Val
        80                  85                  90

gtc gac ggc gcc gac tac cag ggc acc tac ggc gcc tcc acc tcc ggc     1298
Val Asp Gly Ala Asp Tyr Gln Gly Thr Tyr Gly Ala Ser Thr Ser Gly
    95                  100                 105

aac gcc ctg acc ctc aag ttc gtc acc aag ggc agc tac gcc acc aac     1346
Asn Ala Leu Thr Leu Lys Phe Val Thr Lys Gly Ser Tyr Ala Thr Asn
110                 115                 120                 125

atc ggc tcg cgc atg tac ctg atg gcc agc ccc acc aag tac gcc atg     1394
Ile Gly Ser Arg Met Tyr Leu Met Ala Ser Pro Thr Lys Tyr Ala Met
                130                 135                 140

ttc acc ctg ctg ggc cac gag ttc gcc ttc gac gtc gac ctg agc aag     1442
Phe Thr Leu Leu Gly His Glu Phe Ala Phe Asp Val Asp Leu Ser Lys
            145                 150                 155

ctg ccc tgc ggc ctc aac ggc gcc gtc tac ttc gtc agc atg gac gag     1490
Leu Pro Cys Gly Leu Asn Gly Ala Val Tyr Phe Val Ser Met Asp Glu
```

```
        160                 165                 170

gac ggc ggc acc agc aag tac ccc tcc aac aag gcc ggc gcc aag tac     1538
Asp Gly Gly Thr Ser Lys Tyr Pro Ser Asn Lys Ala Gly Ala Lys Tyr
    175                 180                 185

ggc acg ggc tac tgc gac tcg cag tgt ccg cgc gac ctc aag ttt atc     1586
Gly Thr Gly Tyr Cys Asp Ser Gln Cys Pro Arg Asp Leu Lys Phe Ile
190                 195                 200                 205

gac ggc aag gtgagaaccc gcactagcgt cccgccttcc gtgtccctcc             1635
Asp Gly Lys

ttttgccttc ttcgaccgcc ctcttccctg cgggccaggg tcgctggggt gctgtcctcc   1695

tttctggtgg gcagcggtgc tgatcccgcg ccag gcc aac tcg gcc agc tgg cag   1750
                                      Ala Asn Ser Ala Ser Trp Gln
                                          210                 215

ccc tcg tcc aac gac cag aac gcc ggc gtg ggc ggc atg ggc tcg tgc     1798
Pro Ser Ser Asn Asp Gln Asn Ala Gly Val Gly Gly Met Gly Ser Cys
                220                 225                 230

tgc gcc gag atg gac atc tgg gag gcc aac tcc gtc tcc gcc gcc tac     1846
Cys Ala Glu Met Asp Ile Trp Glu Ala Asn Ser Val Ser Ala Ala Tyr
            235                 240                 245

acg ccg cac ccg tgc cag aac tac cag cag cac agc tgc agc ggc gac     1894
Thr Pro His Pro Cys Gln Asn Tyr Gln Gln His Ser Cys Ser Gly Asp
        250                 255                 260

gac tgc ggc ggc acc tac tcg gcc acc cgc ttc gcc ggc gac tgc gac     1942
Asp Cys Gly Gly Thr Tyr Ser Ala Thr Arg Phe Ala Gly Asp Cys Asp
    265                 270                 275

ccg gac ggc tgc gac tgg aac gcc tac cgc atg ggc gtg cac gac ttc     1990
Pro Asp Gly Cys Asp Trp Asn Ala Tyr Arg Met Gly Val His Asp Phe
280                 285                 290                 295

tac ggc aac ggc aag acc gtc gac acc ggc aag aag ttc tcc atc gtc     2038
Tyr Gly Asn Gly Lys Thr Val Asp Thr Gly Lys Lys Phe Ser Ile Val
                300                 305                 310

acc cag ttc aag ggc tcc ggc tcc acc ctg acc gag atc aag cag ttc     2086
Thr Gln Phe Lys Gly Ser Gly Ser Thr Leu Thr Glu Ile Lys Gln Phe
            315                 320                 325

tac gtc cag gac ggc agg aag atc gag aac ccc aac gcc acc tgg ccc     2134
Tyr Val Gln Asp Gly Arg Lys Ile Glu Asn Pro Asn Ala Thr Trp Pro
        330                 335                 340

ggc ctc gag ccc ttc aac tcc atc acc ccg gac ttc tgc aag gcc cag     2182
Gly Leu Glu Pro Phe Asn Ser Ile Thr Pro Asp Phe Cys Lys Ala Gln
    345                 350                 355

aag cag gtc ttc ggc gac ccc gac cgc ttc aac gac atg ggc ggc ttc     2230
Lys Gln Val Phe Gly Asp Pro Asp Arg Phe Asn Asp Met Gly Gly Phe
360                 365                 370                 375

acc aac atg gcc aag gcc ctg gcc aac ccc atg gtc ctg gtg ctg tcg     2278
Thr Asn Met Ala Lys Ala Leu Ala Asn Pro Met Val Leu Val Leu Ser
                380                 385                 390

ctg tgg gac gac gtgagccatt ttcgcattct ctcctgactc tcctccgctg         2330
Leu Trp Asp Asp
            395

ccatcaccac ctcttccacc accgccacga gggtgtagct tgatctccgc tgactgacgt   2390

gtgcccacac ccccgtttct ag cac tac tcc aac atg ctg tgg ctc gac tct    2442
                         His Tyr Ser Asn Met Leu Trp Leu Asp Ser
                                         400                 405

acc tac ccg acc gac gcc gat ccc agc gcg ccc ggc aag gga cgt ggc     2490
Thr Tyr Pro Thr Asp Ala Asp Pro Ser Ala Pro Gly Lys Gly Arg Gly
                410                 415                 420

acc tgc gac acc agc agc ggc gtg cca agc gac gtg gag tcg aag aat     2538
Thr Cys Asp Thr Ser Ser Gly Val Pro Ser Asp Val Glu Ser Lys Asn
```

```
            425                 430                 435

gg  gtgagtcgga tcttctgcat gcggcccgtt ttccgagcat tgcttggggt         2590
Gly

cctccctcag gctgacacac gcgcgccttc gatacag c gat gcg acc gtc atc      2643
                                           Asp Ala Thr Val Ile
                                               440

tac tcc aac atc aag ttt ggg ccg ctg gac tcc acc tac acg gct tcc     2691
Tyr Ser Asn Ile Lys Phe Gly Pro Leu Asp Ser Thr Tyr Thr Ala Ser
    445                 450                 455

tgagcagccg ctttgggttc ggtggggccg aagcacaaca agtgtgtgcg tagctgagat   2751

gatggccgat ctctgtcctt tgtctcctag tgtctctctt atcgaacaac cccccgacct   2811

gcagcgtcgg cgggcatcgt atagtctggt gtaactgtat atagctctgt gcgtgtgaat   2871

cgaacgagca ccgacgaaat gtggtgtttc atgctatcgt acatgctctt gcgagatctg   2931

aagtcgtcaa ttagacattg ccaccatcca acttggcgac tgtccacccg gtccatttgt   2991

atcactggct cttccgagac ccggtctctc tcacaccgta atcactgcaa gcagagttga   3051

attc                                                                3055


<210> SEQ ID NO 4
<211> LENGTH: 459
<212> TYPE: PRT
<213> ORGANISM: Acremonium thermophilum

<400> SEQUENCE: 4

Met His Lys Arg Ala Ala Thr Leu Ser Ala Leu Val Val Ala Ala Ala
1               5                   10                  15

Gly Phe Ala Arg Gly Gln Gly Val Gly Thr Gln Gln Thr Glu Thr His
            20                  25                  30

Pro Lys Leu Thr Phe Gln Lys Cys Ser Ala Ala Gly Ser Cys Thr Thr
        35                  40                  45

Gln Asn Gly Glu Val Val Ile Asp Ala Asn Trp Arg Trp Val His Asp
    50                  55                  60

Lys Asn Gly Tyr Thr Asn Cys Tyr Thr Gly Asn Glu Trp Asn Thr Thr
65                  70                  75                  80

Ile Cys Ala Asp Ala Ala Ser Cys Ala Ser Asn Cys Val Val Asp Gly
                85                  90                  95

Ala Asp Tyr Gln Gly Thr Tyr Gly Ala Ser Thr Ser Gly Asn Ala Leu
            100                 105                 110

Thr Leu Lys Phe Val Thr Lys Gly Ser Tyr Ala Thr Asn Ile Gly Ser
        115                 120                 125

Arg Met Tyr Leu Met Ala Ser Pro Thr Lys Tyr Ala Met Phe Thr Leu
    130                 135                 140

Leu Gly His Glu Phe Ala Phe Asp Val Asp Leu Ser Lys Leu Pro Cys
145                 150                 155                 160

Gly Leu Asn Gly Ala Val Tyr Phe Val Ser Met Asp Glu Asp Gly Gly
                165                 170                 175

Thr Ser Lys Tyr Pro Ser Asn Lys Ala Gly Ala Lys Tyr Gly Thr Gly
            180                 185                 190

Tyr Cys Asp Ser Gln Cys Pro Arg Asp Leu Lys Phe Ile Asp Gly Lys
        195                 200                 205

Ala Asn Ser Ala Ser Trp Gln Pro Ser Ser Asn Asp Gln Asn Ala Gly
    210                 215                 220

Val Gly Gly Met Gly Ser Cys Cys Ala Glu Met Asp Ile Trp Glu Ala
225                 230                 235                 240
```

```
Asn Ser Val Ser Ala Ala Tyr Thr Pro His Pro Cys Gln Asn Tyr Gln
                245                 250                 255

Gln His Ser Cys Ser Gly Asp Asp Cys Gly Gly Thr Tyr Ser Ala Thr
            260                 265                 270

Arg Phe Ala Gly Asp Cys Asp Pro Asp Gly Cys Asp Trp Asn Ala Tyr
        275                 280                 285

Arg Met Gly Val His Asp Phe Tyr Gly Asn Gly Lys Thr Val Asp Thr
    290                 295                 300

Gly Lys Lys Phe Ser Ile Val Thr Gln Phe Lys Gly Ser Gly Ser Thr
305                 310                 315                 320

Leu Thr Glu Ile Lys Gln Phe Tyr Val Gln Asp Gly Arg Lys Ile Glu
                325                 330                 335

Asn Pro Asn Ala Thr Trp Pro Gly Leu Glu Pro Phe Asn Ser Ile Thr
            340                 345                 350

Pro Asp Phe Cys Lys Ala Gln Lys Gln Val Phe Gly Asp Pro Asp Arg
        355                 360                 365

Phe Asn Asp Met Gly Gly Phe Thr Asn Met Ala Lys Ala Leu Ala Asn
    370                 375                 380

Pro Met Val Leu Val Leu Ser Leu Trp Asp Asp His Tyr Ser Asn Met
385                 390                 395                 400

Leu Trp Leu Asp Ser Thr Tyr Pro Thr Asp Ala Asp Pro Ser Ala Pro
                405                 410                 415

Gly Lys Gly Arg Gly Thr Cys Asp Thr Ser Ser Gly Val Pro Ser Asp
            420                 425                 430

Val Glu Ser Lys Asn Gly Asp Ala Thr Val Ile Tyr Ser Asn Ile Lys
        435                 440                 445

Phe Gly Pro Leu Asp Ser Thr Tyr Thr Ala Ser
    450                 455

<210> SEQ ID NO 5
<211> LENGTH: 3401
<212> TYPE: DNA
<213> ORGANISM: Acremonium thermophilum
<220> FEATURE:
<221> NAME/KEY: CDS
<222> LOCATION: (891)..(1299)
<220> FEATURE:
<221> NAME/KEY: Intron
<222> LOCATION: (1300)..(1387)
<220> FEATURE:
<221> NAME/KEY: CDS
<222> LOCATION: (1388)..(1442)
<220> FEATURE:
<221> NAME/KEY: Intron
<222> LOCATION: (1443)..(1495)
<220> FEATURE:
<221> NAME/KEY: CDS
<222> LOCATION: (1496)..(1643)
<220> FEATURE:
<221> NAME/KEY: Intron
<222> LOCATION: (1644)..(1697)
<220> FEATURE:
<221> NAME/KEY: CDS
<222> LOCATION: (1698)..(1928)
<220> FEATURE:
<221> NAME/KEY: Intron
<222> LOCATION: (1929)..(2014)
<220> FEATURE:
<221> NAME/KEY: CDS
<222> LOCATION: (2015)..(2740)

<400> SEQUENCE: 5

ctcgagtttc cctggtcggc cactctctgc tcatctcgct ctgcgcccct ggatgtgccg     60
```

```
tgtgtccagt cgtgtatctc ttgactgcac gacgtgttcc tcgcgactcg tctcgcgccg    120

gtggatgccc gtccactcat ttgtccgtct actgggtcag cctctcgtct cgaacgagct    180

tccacggccc actccccgga caacctcggc tctggatggc cctcctcccc ctccgtgtct    240

cccctcctgc ggggtccgtc gtgccctggc tgcatgctcc acatcgcttg atcacgctgc    300

gagccaccgc agagccccat ctccaaagcg accgtggcag cactacctct gtttctggga    360

tggggcccac gtcgatggcc tggcatccct tgccaccctc ctccatcccc ctgacctcac    420

tcccaaccga taggagaagt ggtcatgggc acgaccccgt gcacgtcttg gactcgacga    480

gcttgatcgg gccggaagcc gtcaacgacg ggggagccgt gtcttgccac gcgtggccgt    540

ccttcgacag tggacagcga gaaaactggt ggggaagagg gctgctacag tcttgtcttg    600

cgaggcccga cgctcctagt ccgagaacca cctacgtgtt tctcgcgaag acggggccag    660

cttagcggcc aaatttgccc cccgggccta gggtctagcg atggggatga tgaactggtg    720

tcgacgatgt ctatataacg acggcgatct cctgtctctg agatcccatc ctttcatctc    780

caacccactt catcccttcc tctctctctc cccctccctt ctctgacata ccgagtcctc    840

agaagcctcg tccgtcgtca cctattctca cttccccgcg aactccggcc atg tat       896
                                                       Met Tyr
                                                       1

acc aag ttc gcc gcc ctc gcc gcc ctc gtg gcc acc gtc cgc ggc cag      944
Thr Lys Phe Ala Ala Leu Ala Ala Leu Val Ala Thr Val Arg Gly Gln
        5                   10                  15

gcc gcc tgc tcg ctc acc gcc gag acc cac ccg tcg ctg cag tgg cag      992
Ala Ala Cys Ser Leu Thr Ala Glu Thr His Pro Ser Leu Gln Trp Gln
    20                  25                  30

aag tgc acc gcg ccc ggc agc tgc acc acc gtc agc ggc cag gtc acc     1040
Lys Cys Thr Ala Pro Gly Ser Cys Thr Thr Val Ser Gly Gln Val Thr
35                  40                  45                  50

atc gac gcc aac tgg cgc tgg ctg cac cag acc aac agc agc acc aac     1088
Ile Asp Ala Asn Trp Arg Trp Leu His Gln Thr Asn Ser Ser Thr Asn
                55                  60                  65

tgc tac acc ggc aac gag tgg gac acc agc atc tgc agc tcc gac acc     1136
Cys Tyr Thr Gly Asn Glu Trp Asp Thr Ser Ile Cys Ser Ser Asp Thr
            70                  75                  80

gac tgc gcc acc aag tgc tgc ctc gac ggc gcc gac tac acc ggc acc     1184
Asp Cys Ala Thr Lys Cys Cys Leu Asp Gly Ala Asp Tyr Thr Gly Thr
        85                  90                  95

tac ggc gtc acc gcc agc ggc aac tcg ctc aac ctc aag ttc gtc acc     1232
Tyr Gly Val Thr Ala Ser Gly Asn Ser Leu Asn Leu Lys Phe Val Thr
    100                 105                 110

cag ggg ccc tac tcc aag aac atc ggc tcg cgc atg tac ctc atg gag     1280
Gln Gly Pro Tyr Ser Lys Asn Ile Gly Ser Arg Met Tyr Leu Met Glu
115                 120                 125                 130

tcg gag tcc aag tac cag g gtgagcatat agatcacatc tttcgtcact          1329
Ser Glu Ser Lys Tyr Gln
                135

tgcgtccgtt tcgcacggca agcggtccag acgctaacgg gacggttctc ttctctag     1387

gc  ttc act ctc ctc ggt cag gag ttt acc ttt gac gtg gac gtc tcc     1434
Gly Phe Thr Leu Leu Gly Gln Glu Phe Thr Phe Asp Val Asp Val Ser
            140                 145                 150

aac ctc gg  gtaggtgatg acttctcccg catgagaaga gctctgctaa             1482
Asn Leu Gly
        155

ccgtgttgtc cag c tgc ggt ctg aac gga gcg ctc tac ttc gtg tcc atg    1532
                 Cys Gly Leu Asn Gly Ala Leu Tyr Phe Val Ser Met
```

-continued

```
                        160                 165

gac ctc gac ggc ggc gtg tcc aag tac acc acc aac aag gcc ggc gcc      1580
Asp Leu Asp Gly Gly Val Ser Lys Tyr Thr Thr Asn Lys Ala Gly Ala
        170                 175                 180

aag tac ggc acc ggc tac tgc gac tcc cag tgc ccg cgg gat ctc aag      1628
Lys Tyr Gly Thr Gly Tyr Cys Asp Ser Gln Cys Pro Arg Asp Leu Lys
    185                 190                 195

ttc atc aac ggc cag gtgggtcgag agaccctctt cccctctcag tgaacgatgt      1683
Phe Ile Asn Gly Gln
200

ctgaccctct ctag gcc aac atc gac ggc tgg caa ccg tcg tcc aac gac      1733
                Ala Asn Ile Asp Gly Trp Gln Pro Ser Ser Asn Asp
                205                 210                 215

gcc aac gcc ggc ctc ggg aac cac ggc agc tgc tgc tcc gag atg gac      1781
Ala Asn Ala Gly Leu Gly Asn His Gly Ser Cys Cys Ser Glu Met Asp
            220                 225                 230

atc tgg gag gcc aac aag gtc tcc gcc gcc tac acg ccg cac ccc tgc      1829
Ile Trp Glu Ala Asn Lys Val Ser Ala Ala Tyr Thr Pro His Pro Cys
        235                 240                 245

acc acc atc ggc cag acc atg tgc acc ggc gac gac tgc ggc ggc acc      1877
Thr Thr Ile Gly Gln Thr Met Cys Thr Gly Asp Asp Cys Gly Gly Thr
    250                 255                 260

tat tcg tcg gac cgc tat gcc ggc atc tgc gac ccc gac ggt tgc gat      1925
Tyr Ser Ser Asp Arg Tyr Ala Gly Ile Cys Asp Pro Asp Gly Cys Asp
265                 270                 275                 280

ttt gtaggttctt tctctcgccg ctccctgacg acctatatgt gtgaagggac           1978
Phe

gcacagaaaa gacaaggtca aagctgacca gagcag aac tcg tac cgc atg ggc      2032
                                        Asn Ser Tyr Arg Met Gly
                                                    285

gac acc agc ttc tac ggc ccc ggc aag acg gtc gac acc ggc tcc aag      2080
Asp Thr Ser Phe Tyr Gly Pro Gly Lys Thr Val Asp Thr Gly Ser Lys
        290                 295                 300

ttc acc gtc gtg acc cag ttc ctc acg ggc tcc gac ggc aac ctc agc      2128
Phe Thr Val Val Thr Gln Phe Leu Thr Gly Ser Asp Gly Asn Leu Ser
    305                 310                 315

gag atc aag cgc ttc tac gtg cag aac ggc aag gtc atc ccc aac tcc      2176
Glu Ile Lys Arg Phe Tyr Val Gln Asn Gly Lys Val Ile Pro Asn Ser
320                 325                 330                 335

gag tcc aag atc gcc ggc gtc tcc ggc aac tcc atc acc acc gac ttc      2224
Glu Ser Lys Ile Ala Gly Val Ser Gly Asn Ser Ile Thr Thr Asp Phe
                340                 345                 350

tgc acc gcc cag aag acc gcc ttc ggc gac acc aac gtc ttc gag gag      2272
Cys Thr Ala Gln Lys Thr Ala Phe Gly Asp Thr Asn Val Phe Glu Glu
            355                 360                 365

cgc ggc ggc ctc gcc cag atg ggc aag gcc ctg gcc gag ccc atg gtc      2320
Arg Gly Gly Leu Ala Gln Met Gly Lys Ala Leu Ala Glu Pro Met Val
        370                 375                 380

ctg gtc ctg tcc gtc tgg gac gac cac gcc gtc aac atg ctc tgg ctc      2368
Leu Val Leu Ser Val Trp Asp Asp His Ala Val Asn Met Leu Trp Leu
    385                 390                 395

gac tcc acc tac ccc acc gac agc acc aag ccc ggc gcc gcc cgc ggc      2416
Asp Ser Thr Tyr Pro Thr Asp Ser Thr Lys Pro Gly Ala Ala Arg Gly
400                 405                 410                 415

gac tgc ccc atc acc tcc ggc gtg ccc gcc gac gtc gag tcc cag gcg      2464
Asp Cys Pro Ile Thr Ser Gly Val Pro Ala Asp Val Glu Ser Gln Ala
                420                 425                 430

ccc aac tcc aac gtc atc tac tcc aac atc cgc ttc ggc ccc atc aac      2512
Pro Asn Ser Asn Val Ile Tyr Ser Asn Ile Arg Phe Gly Pro Ile Asn
```

```
            435                 440                 445

tcc acc tac acc ggc acc ccc agc ggc ggc aac ccc ccc ggc ggc ggg     2560
Ser Thr Tyr Thr Gly Thr Pro Ser Gly Gly Asn Pro Pro Gly Gly Gly
        450                 455                 460

acc acc acc acc acc acc acc acc acc tcc aag ccc tcc ggc ccc acc     2608
Thr Thr Thr Thr Thr Thr Thr Thr Thr Ser Lys Pro Ser Gly Pro Thr
    465                 470                 475

acc acc acc aac ccc tcg ggt ccg cag cag acg cac tgg ggt cag tgc     2656
Thr Thr Thr Asn Pro Ser Gly Pro Gln Gln Thr His Trp Gly Gln Cys
480                 485                 490                 495

ggc ggc cag gga tgg acc ggc ccc acg gtc tgc cag agc ccc tac acc     2704
Gly Gly Gln Gly Trp Thr Gly Pro Thr Val Cys Gln Ser Pro Tyr Thr
                500                 505                 510

tgc aag tac tcc aac gac tgg tac tcg cag tgc ctg taagccataa          2750
Cys Lys Tyr Ser Asn Asp Trp Tyr Ser Gln Cys Leu
            515                 520

gcccccctgta cgttcggaag acggtggcaa cagacaaacc cctcccccga gcacaccccc   2810

cagggatcta agggggttgt ggttaagaca taagaatgcg ccgtggcttg gcctacgcca   2870

cggtcatgaa agtgcagtga aaatgggggc aagagtcgga aaaagtgagt ttgcttgcaa   2930

gggagagagg atgtcgagag gtgatgactt cgtttgtaca tagttggctc ttcgtgattg   2990

ggaacgggag gagtgtcggg gggagccctc cagactcctt ggcctctccg ctcgttccat   3050

ctttctcagt acatatacat ctgcattttc atccacgtct ctggcgtctc tggatgtgaa   3110

cgaatccgac aactggtggg ctgagatgaa tcgcaaggag agtatcttgc gaggatatca   3170

cagtcagaaa gtagcatttg agccactact aaaaggtcaa ccagtatgcg aagcttagca   3230

attatataca gcagctcaac ttcagaacga agtattgcat gtggcagaga atcttgggaa   3290

atgagccatg aagacctcgt cgagagagta cctctcaccg ccaaataacc agctagcggg   3350

ttgggagagg agcaatagga cgagcgcgat ggacagatat acgaactcga g            3401


<210> SEQ ID NO 6
<211> LENGTH: 523
<212> TYPE: PRT
<213> ORGANISM: Acremonium thermophilum

<400> SEQUENCE: 6

Met Tyr Thr Lys Phe Ala Ala Leu Ala Ala Leu Val Ala Thr Val Arg
1               5                   10                  15

Gly Gln Ala Ala Cys Ser Leu Thr Ala Glu Thr His Pro Ser Leu Gln
            20                  25                  30

Trp Gln Lys Cys Thr Ala Pro Gly Ser Cys Thr Thr Val Ser Gly Gln
        35                  40                  45

Val Thr Ile Asp Ala Asn Trp Arg Trp Leu His Gln Thr Asn Ser Ser
    50                  55                  60

Thr Asn Cys Tyr Thr Gly Asn Glu Trp Asp Thr Ser Ile Cys Ser Ser
65                  70                  75                  80

Asp Thr Asp Cys Ala Thr Lys Cys Cys Leu Asp Gly Ala Asp Tyr Thr
                85                  90                  95

Gly Thr Tyr Gly Val Thr Ala Ser Gly Asn Ser Leu Asn Leu Lys Phe
            100                 105                 110

Val Thr Gln Gly Pro Tyr Ser Lys Asn Ile Gly Ser Arg Met Tyr Leu
        115                 120                 125

Met Glu Ser Glu Ser Lys Tyr Gln Gly Phe Thr Leu Leu Gly Gln Glu
    130                 135                 140
```

```
Phe Thr Phe Asp Val Asp Val Ser Asn Leu Gly Cys Gly Leu Asn Gly
145                 150                 155                 160

Ala Leu Tyr Phe Val Ser Met Asp Leu Asp Gly Gly Val Ser Lys Tyr
                165                 170                 175

Thr Thr Asn Lys Ala Gly Ala Lys Tyr Gly Thr Gly Tyr Cys Asp Ser
            180                 185                 190

Gln Cys Pro Arg Asp Leu Lys Phe Ile Asn Gly Gln Ala Asn Ile Asp
        195                 200                 205

Gly Trp Gln Pro Ser Ser Asn Asp Ala Asn Ala Gly Leu Gly Asn His
    210                 215                 220

Gly Ser Cys Cys Ser Glu Met Asp Ile Trp Glu Ala Asn Lys Val Ser
225                 230                 235                 240

Ala Ala Tyr Thr Pro His Pro Cys Thr Thr Ile Gly Gln Thr Met Cys
                245                 250                 255

Thr Gly Asp Asp Cys Gly Gly Thr Tyr Ser Ser Asp Arg Tyr Ala Gly
            260                 265                 270

Ile Cys Asp Pro Asp Gly Cys Asp Phe Asn Ser Tyr Arg Met Gly Asp
        275                 280                 285

Thr Ser Phe Tyr Gly Pro Gly Lys Thr Val Asp Thr Gly Ser Lys Phe
    290                 295                 300

Thr Val Val Thr Gln Phe Leu Thr Gly Ser Asp Gly Asn Leu Ser Glu
305                 310                 315                 320

Ile Lys Arg Phe Tyr Val Gln Asn Gly Lys Val Ile Pro Asn Ser Glu
                325                 330                 335

Ser Lys Ile Ala Gly Val Ser Gly Asn Ser Ile Thr Thr Asp Phe Cys
            340                 345                 350

Thr Ala Gln Lys Thr Ala Phe Gly Asp Thr Asn Val Phe Glu Glu Arg
        355                 360                 365

Gly Gly Leu Ala Gln Met Gly Lys Ala Leu Ala Glu Pro Met Val Leu
    370                 375                 380

Val Leu Ser Val Trp Asp Asp His Ala Val Asn Met Leu Trp Leu Asp
385                 390                 395                 400

Ser Thr Tyr Pro Thr Asp Ser Thr Lys Pro Gly Ala Ala Arg Gly Asp
                405                 410                 415

Cys Pro Ile Thr Ser Gly Val Pro Ala Asp Val Glu Ser Gln Ala Pro
            420                 425                 430

Asn Ser Asn Val Ile Tyr Ser Asn Ile Arg Phe Gly Pro Ile Asn Ser
        435                 440                 445

Thr Tyr Thr Gly Thr Pro Ser Gly Gly Asn Pro Pro Gly Gly Gly Thr
    450                 455                 460

Thr Thr Thr Thr Thr Thr Thr Thr Ser Lys Pro Ser Gly Pro Thr Thr
465                 470                 475                 480

Thr Thr Asn Pro Ser Gly Pro Gln Gln Thr His Trp Gly Gln Cys Gly
                485                 490                 495

Gly Gln Gly Trp Thr Gly Pro Thr Val Cys Gln Ser Pro Tyr Thr Cys
            500                 505                 510

Lys Tyr Ser Asn Asp Trp Tyr Ser Gln Cys Leu
        515                 520
```

<210> SEQ ID NO 7
<211> LENGTH: 3649
<212> TYPE: DNA
<213> ORGANISM: Chaetomium thermophilum
<220> FEATURE:
<221> NAME/KEY: CDS

```
<222> LOCATION: (1290)..(2879)
<220> FEATURE:
<221> NAME/KEY: Intron
<222> LOCATION: (2880)..(2943)
<220> FEATURE:
<221> NAME/KEY: CDS
<222> LOCATION: (2944)..(2949)

<400> SEQUENCE: 7

tctagagctg tcgacgcggc cgcgtaatac gactcactat agggcgaaga attcggatcg      60

gactagagct cgtcacgggc tcgcgccgac gaggcgatga ggacgaaggg ccgacataat     120

ccgtacttta cgctacatga cgactctcga aaattgtaaa gggccggcat ttcggagcga     180

gtgctgcgag ggcgcattcg cggcgtacct ggaattcctg gaatggtaag caatggccag     240

caatgggcca ggtatggacc agcttgaatc ctggttgcgg cgtcaccagg cccagcatgg     300

tgcccagaat ggcccaccgt ggcccatcgt cctaagaaac aagctgcgtc ccgcgatcca     360

aaaacgtcgt cttcggcgca cgtcctccgt ggtccccccg gctggacacc ctggctggcc     420

ctccaatgag cggcatttgc ccctgtcgag cgtgtcggca accttaatcg actccatctc     480

tcggctccac gccgtccatc ctgtcctcga cctcgtcatc tgtgctcccc ttgccctccc     540

ttgcccttcc ttgcctccgc cacgacgtgc cacaatgtga ccctgctgcc cggagcgccc     600

agcgccatgc accgtttggg cttgtcgccg tgtcgccagt ctccatcgag cgattcgacc     660

gtgtgcctct ctccaccagc gttccccgcg ctctccatag tccatgctac ttcgagccgt     720

tgcctcacaa gctgccagcg gcatggctct gtcggtctcg cctctccttt tcccgtgaag     780

cgctgccata caattctccg tctgccccag tccttgaggc gccgctattc ccaatcggcc     840

atggcactgg ccagcccgat ccatgttcga tcgagcttcg acgggccgtg agccgtctgc     900

acggaggagc ttgcgagcct gcgaacctgg cggacctgga gaagcctggc ccatctccct     960

ggatggagat actgggtgcg ctagcaccac ggcgtgccac ggccaagctc cggccgaccc    1020

ggaggcggga agagggttgc gttgctgtct tcggcggctg tcagggcaaa gggtaatcgt    1080

caatgtggga aaaggggctc atctccatga gattcatgac tcggacatcg tctatataag    1140

tcgagtcccc catcctccaa cagccgattc tgctcctcat cccatcacca ccctcgtcca    1200

caaccacgca gttgtgtaca tcaaaacaag ttcgctcctt ttacatcttc accacaacaa    1260

cagcacatcc tctcctttcg gctttcaag atg atg tat aag aag ttc gcc gct     1313
                                Met Met Tyr Lys Lys Phe Ala Ala
                                1               5

ctc gcc gcc ctc gtg gct ggc gcc tcc gcc cag cag gct tgc tcc ctc     1361
Leu Ala Ala Leu Val Ala Gly Ala Ser Ala Gln Gln Ala Cys Ser Leu
    10                  15                  20

acc gct gag aac cac cct agc ctc acc tgg aag cgc tgc acc tct ggc     1409
Thr Ala Glu Asn His Pro Ser Leu Thr Trp Lys Arg Cys Thr Ser Gly
25                  30                  35                  40

ggc agc tgc tcg acc gtg aac ggc gcc gtc acc atc gat gcc aac tgg     1457
Gly Ser Cys Ser Thr Val Asn Gly Ala Val Thr Ile Asp Ala Asn Trp
                45                  50                  55

cgc tgg act cac acc gtc tcc ggc tcg acc aac tgc tac acc ggc aac     1505
Arg Trp Thr His Thr Val Ser Gly Ser Thr Asn Cys Tyr Thr Gly Asn
            60                  65                  70

cag tgg gat acc tcc ctc tgc act gat ggc aag agc tgc gcc cag acc     1553
Gln Trp Asp Thr Ser Leu Cys Thr Asp Gly Lys Ser Cys Ala Gln Thr
        75                  80                  85

tgc tgc gtc gat ggc gct gac tac tct tcg acc tat ggt atc acc acc     1601
Cys Cys Val Asp Gly Ala Asp Tyr Ser Ser Thr Tyr Gly Ile Thr Thr
    90                  95                  100
```

```
agc ggt gac tcc ctg aac ctc aag ttc gtc acc aag cac cag tac ggc      1649
Ser Gly Asp Ser Leu Asn Leu Lys Phe Val Thr Lys His Gln Tyr Gly
105                 110                 115                 120

acc aac gtc ggc tcc cgt gtc tat ctg atg gag aac gac acc aag tac      1697
Thr Asn Val Gly Ser Arg Val Tyr Leu Met Glu Asn Asp Thr Lys Tyr
                125                 130                 135

cag atg ttc gag ctc ctc ggc aac gag ttc acc ttc gat gtc gat gtc      1745
Gln Met Phe Glu Leu Leu Gly Asn Glu Phe Thr Phe Asp Val Asp Val
            140                 145                 150

tcc aac ctg ggc tgc ggt ctc aac ggc gcc ctc tac ttc gtt tcc atg      1793
Ser Asn Leu Gly Cys Gly Leu Asn Gly Ala Leu Tyr Phe Val Ser Met
        155                 160                 165

gat gct gat ggt ggc atg agc aaa tac tct ggc aac aag gct ggc gcc      1841
Asp Ala Asp Gly Gly Met Ser Lys Tyr Ser Gly Asn Lys Ala Gly Ala
    170                 175                 180

aag tac ggt acc ggc tac tgc gat gct cag tgc ccg cgc gac ctc aag      1889
Lys Tyr Gly Thr Gly Tyr Cys Asp Ala Gln Cys Pro Arg Asp Leu Lys
185                 190                 195                 200

ttc atc aac ggc gag gcc aac gtt ggg aac tgg acc ccc tcg acc aac      1937
Phe Ile Asn Gly Glu Ala Asn Val Gly Asn Trp Thr Pro Ser Thr Asn
                205                 210                 215

gat gcc aac gcc ggc ttc ggc cgc tat ggc agc tgc tgc tct gag atg      1985
Asp Ala Asn Ala Gly Phe Gly Arg Tyr Gly Ser Cys Cys Ser Glu Met
            220                 225                 230

gat gtc tgg gag gcc aac aac atg gct act gcc ttc act cct cac cct      2033
Asp Val Trp Glu Ala Asn Asn Met Ala Thr Ala Phe Thr Pro His Pro
        235                 240                 245

tgc acc acc gtt ggc cag agc cgc tgc gag gcc gac acc tgc ggt ggc      2081
Cys Thr Thr Val Gly Gln Ser Arg Cys Glu Ala Asp Thr Cys Gly Gly
    250                 255                 260

acc tac agc tct gac cgc tat gct ggt gtt tgc gac cct gat ggc tgc      2129
Thr Tyr Ser Ser Asp Arg Tyr Ala Gly Val Cys Asp Pro Asp Gly Cys
265                 270                 275                 280

gac ttc aac gcc tac cgc caa ggc gac aag acc ttc tac ggc aag ggc      2177
Asp Phe Asn Ala Tyr Arg Gln Gly Asp Lys Thr Phe Tyr Gly Lys Gly
                285                 290                 295

atg act gtc gac acc aac aag aag atg acc gtc gtc acc cag ttc cac      2225
Met Thr Val Asp Thr Asn Lys Lys Met Thr Val Val Thr Gln Phe His
            300                 305                 310

aag aac tcg gct ggc gtc ctc agc gag atc aag cgc ttc tac gtc cag      2273
Lys Asn Ser Ala Gly Val Leu Ser Glu Ile Lys Arg Phe Tyr Val Gln
        315                 320                 325

gac ggc aag atc att gcc aac gct gag tcc aag atc ccc ggc aac ccc      2321
Asp Gly Lys Ile Ile Ala Asn Ala Glu Ser Lys Ile Pro Gly Asn Pro
    330                 335                 340

gga aac tcc att acc cag gag tat tgc gat gcc cag aag gtc gcc ttc      2369
Gly Asn Ser Ile Thr Gln Glu Tyr Cys Asp Ala Gln Lys Val Ala Phe
345                 350                 355                 360

agt aac acc gat gac ttc aac cgc aag ggc ggt atg gct cag atg agc      2417
Ser Asn Thr Asp Asp Phe Asn Arg Lys Gly Gly Met Ala Gln Met Ser
                365                 370                 375

aag gcc ctc gca ggc ccc atg gtc ctg gtc atg tcc gtc tgg gat gac      2465
Lys Ala Leu Ala Gly Pro Met Val Leu Val Met Ser Val Trp Asp Asp
            380                 385                 390

cac tac gcc aac atg ctc tgg ctc gac tcg acc tac ccc atc gac cag      2513
His Tyr Ala Asn Met Leu Trp Leu Asp Ser Thr Tyr Pro Ile Asp Gln
        395                 400                 405

gcc ggc gcc ccc ggc gcc gag cgc ggt gct tgc ccg acc acc tcc ggt      2561
Ala Gly Ala Pro Gly Ala Glu Arg Gly Ala Cys Pro Thr Thr Ser Gly
```

```
    410                 415                 420

gtc cct gcc gag atc gag gcc cag gtc ccc aac agc aac gtc atc ttc     2609
Val Pro Ala Glu Ile Glu Ala Gln Val Pro Asn Ser Asn Val Ile Phe
425                 430                 435                 440

tcc aac atc cgt ttc ggc ccc atc ggc tcg acc gtc cct ggc ctt gac     2657
Ser Asn Ile Arg Phe Gly Pro Ile Gly Ser Thr Val Pro Gly Leu Asp
                445                 450                 455

ggc agc aac ccc ggc aac ccg acc acc acc gtc gtt cct ccc gct tct     2705
Gly Ser Asn Pro Gly Asn Pro Thr Thr Thr Val Val Pro Pro Ala Ser
            460                 465                 470

acc tcc acc tcc cgt ccg acc agc agc act agc tct ccc gtt tcg acc     2753
Thr Ser Thr Ser Arg Pro Thr Ser Ser Thr Ser Ser Pro Val Ser Thr
        475                 480                 485

ccg act ggc cag ccc ggc ggc tgc acc acc cag aag tgg ggc cag tgc     2801
Pro Thr Gly Gln Pro Gly Gly Cys Thr Thr Gln Lys Trp Gly Gln Cys
    490                 495                 500

ggc ggt atc ggc tac acc ggc tgc act aac tgc gtt gct ggc acc acc     2849
Gly Gly Ile Gly Tyr Thr Gly Cys Thr Asn Cys Val Ala Gly Thr Thr
505                 510                 515                 520

tgc act cag ctc aac ccc tgg tac agc cag gtatgtttct cttccccctt       2899
Cys Thr Gln Leu Asn Pro Trp Tyr Ser Gln
                525                 530

ctagactcgc ttggatttga cagttgctaa catctgctca acag tgc ctg            2949
                                                 Cys Leu

taaacaactc gcttcgtccg cacgacggag gagggccatg agaaagaatg ggcaacatag   3009

attctttgcg cggttgtgga ctacttgggt attttctgga tgtacatagt tttatcacgt   3069

catgaggctg tcatgtgggg atgtgtatct ttttcgcttc ttcgtacata aatttacgca   3129

ttgagctttt cacccccccaa aaacagttcc ctgatttgct ggagtaactt gatggtaaag  3189

cttggtcata agctcttcaa tggaaaaaac gatacagtca tgccttgaca catcctccca   3249

aagtcttcgt ccatgacatc acggtcgatc cttaagcaca agttcaataa ccccatgtgg   3309

cgttgccttg tcctgaaaca cagatgagat cttcagccca gccgcatcgg ccacttcctt   3369

gaactgagcc aacgagcgtt ccttcccgcc gattgagagc atcgcatagt ccttgaaggc   3429

tgcatagaga ggaatagggg gcttgtttcc ggtagttggg ctgccggaac tcggatctgt   3489

tggcgcaagg gggtcagggt tgatctgctc ggcgatgagg acgcgtccat cggggtttgt   3549

tagtgcacga gcgacattgc gcaggatggt gactgccaca gggtcggagt aatcgcggag   3609

gatgtggcgg aggtagtaga ccagtgcacc tggaatcgat                         3649


<210> SEQ ID NO 8
<211> LENGTH: 532
<212> TYPE: PRT
<213> ORGANISM: Chaetomium thermophilum

<400> SEQUENCE: 8

Met Met Tyr Lys Lys Phe Ala Ala Leu Ala Ala Leu Val Ala Gly Ala
1               5                   10                  15

Ser Ala Gln Gln Ala Cys Ser Leu Thr Ala Glu Asn His Pro Ser Leu
            20                  25                  30

Thr Trp Lys Arg Cys Thr Ser Gly Gly Ser Cys Ser Thr Val Asn Gly
        35                  40                  45

Ala Val Thr Ile Asp Ala Asn Trp Arg Trp Thr His Thr Val Ser Gly
    50                  55                  60

Ser Thr Asn Cys Tyr Thr Gly Asn Gln Trp Asp Thr Ser Leu Cys Thr
65                  70                  75                  80
```

```
Asp Gly Lys Ser Cys Ala Gln Thr Cys Cys Val Asp Gly Ala Asp Tyr
                85                  90                  95

Ser Ser Thr Tyr Gly Ile Thr Thr Ser Gly Asp Ser Leu Asn Leu Lys
            100                 105                 110

Phe Val Thr Lys His Gln Tyr Gly Thr Asn Val Gly Ser Arg Val Tyr
        115                 120                 125

Leu Met Glu Asn Asp Thr Lys Tyr Gln Met Phe Glu Leu Leu Gly Asn
    130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
            180                 185                 190

Ala Gln Cys Pro Arg Asp Leu Lys Phe Ile Asn Gly Glu Ala Asn Val
        195                 200                 205

Gly Asn Trp Thr Pro Ser Thr Asn Asp Ala Asn Ala Gly Phe Gly Arg
    210                 215                 220

Tyr Gly Ser Cys Cys Ser Glu Met Asp Val Trp Glu Ala Asn Asn Met
225                 230                 235                 240

Ala Thr Ala Phe Thr Pro His Pro Cys Thr Thr Val Gly Gln Ser Arg
                245                 250                 255

Cys Glu Ala Asp Thr Cys Gly Gly Thr Tyr Ser Ser Asp Arg Tyr Ala
            260                 265                 270

Gly Val Cys Asp Pro Asp Gly Cys Asp Phe Asn Ala Tyr Arg Gln Gly
        275                 280                 285

Asp Lys Thr Phe Tyr Gly Lys Gly Met Thr Val Asp Thr Asn Lys Lys
    290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Ile Ile Ala Asn Ala
                325                 330                 335

Glu Ser Lys Ile Pro Gly Asn Pro Gly Asn Ser Ile Thr Gln Glu Tyr
            340                 345                 350

Cys Asp Ala Gln Lys Val Ala Phe Ser Asn Thr Asp Asp Phe Asn Arg
        355                 360                 365

Lys Gly Gly Met Ala Gln Met Ser Lys Ala Leu Ala Gly Pro Met Val
    370                 375                 380

Leu Val Met Ser Val Trp Asp Asp His Tyr Ala Asn Met Leu Trp Leu
385                 390                 395                 400

Asp Ser Thr Tyr Pro Ile Asp Gln Ala Gly Ala Pro Gly Ala Glu Arg
                405                 410                 415

Gly Ala Cys Pro Thr Thr Ser Gly Val Pro Ala Glu Ile Glu Ala Gln
            420                 425                 430

Val Pro Asn Ser Asn Val Ile Phe Ser Asn Ile Arg Phe Gly Pro Ile
        435                 440                 445

Gly Ser Thr Val Pro Gly Leu Asp Gly Ser Asn Pro Gly Asn Pro Thr
    450                 455                 460

Thr Thr Val Val Pro Pro Ala Ser Thr Ser Thr Ser Arg Pro Thr Ser
465                 470                 475                 480

Ser Thr Ser Ser Pro Val Ser Thr Pro Thr Gly Gln Pro Gly Gly Cys
                485                 490                 495
```

```
Thr Thr Gln Lys Trp Gly Gln Cys Gly Gly Ile Gly Tyr Thr Gly Cys
            500                 505                 510

Thr Asn Cys Val Ala Gly Thr Thr Cys Thr Gln Leu Asn Pro Trp Tyr
        515                 520                 525

Ser Gln Cys Leu
    530


<210> SEQ ID NO 9
<211> LENGTH: 1339
<212> TYPE: DNA
<213> ORGANISM: Thermoascus aurantiacus
<220> FEATURE:
<221> NAME/KEY: CDS
<222> LOCATION: (17)..(122)
<220> FEATURE:
<221> NAME/KEY: Intron
<222> LOCATION: (123)..(177)
<220> FEATURE:
<221> NAME/KEY: CDS
<222> LOCATION: (178)..(236)
<220> FEATURE:
<221> NAME/KEY: Intron
<222> LOCATION: (237)..(296)
<220> FEATURE:
<221> NAME/KEY: CDS
<222> LOCATION: (297)..(449)
<220> FEATURE:
<221> NAME/KEY: Intron
<222> LOCATION: (450)..(508)
<220> FEATURE:
<221> NAME/KEY: CDS
<222> LOCATION: (509)..(573)
<220> FEATURE:
<221> NAME/KEY: Intron
<222> LOCATION: (574)..(647)
<220> FEATURE:
<221> NAME/KEY: CDS
<222> LOCATION: (648)..(745)
<220> FEATURE:
<221> NAME/KEY: Intron
<222> LOCATION: (746)..(806)
<220> FEATURE:
<221> NAME/KEY: CDS
<222> LOCATION: (807)..(1330)

<400> SEQUENCE: 9

ccgcggactg cgcatc atg aag ctc ggc tct ctc gtg ctc gct ctc agc gca     52
                  Met Lys Leu Gly Ser Leu Val Leu Ala Leu Ser Ala
                  1               5                   10

gct agg ctt aca ctg tcg gcc cct ctc gca gac agg aag cag gag acc      100
Ala Arg Leu Thr Leu Ser Ala Pro Leu Ala Asp Arg Lys Gln Glu Thr
        15                  20                  25

aag cgt gcg aaa gta ttc caa t gttcgtaaca tccacgtctg gcttgctggc       152
Lys Arg Ala Lys Val Phe Gln
    30                  35

ttactggcaa ctgacaatgg cgaag gg  ttc ggt tca aac gag tcc ggt gct      203
                            Trp Phe Gly Ser Asn Glu Ser Gly Ala
                                            40

gaa ttc gga agc cag aac ctt cca gga gtc gag gtcagcatgc ctgtactctc    256
Glu Phe Gly Ser Gln Asn Leu Pro Gly Val Glu
45                  50                  55

tgcattatat taatatctca agaggcttac tctttcgcag gga aag gat tat ata      311
                                            Gly Lys Asp Tyr Ile
                                                            60

tgg cct gat ccc aac acc att gac aca ttg atc agc aag ggg atg aac      359
Trp Pro Asp Pro Asn Thr Ile Asp Thr Leu Ile Ser Lys Gly Met Asn
                65                  70                  75

atc ttt cgt gtc ccc ttt atg atg gag aga ttg gtt ccc aac tca atg      407
```

```
Ile Phe Arg Val Pro Phe Met Met Glu Arg Leu Val Pro Asn Ser Met
            80                  85                  90

acc ggc tct ccg gat ccg aac tac ctg gca gat ctc ata gcg              449
Thr Gly Ser Pro Asp Pro Asn Tyr Leu Ala Asp Leu Ile Ala
        95                  100                 105

gtacatttca attccaccat gtttggagct gtcttcgttg tgctgacatt taatggtag     508

act gta aat gca atc acc cag aaa ggt gcc tac gcc gtc gtc gat cct      556
Thr Val Asn Ala Ile Thr Gln Lys Gly Ala Tyr Ala Val Val Asp Pro
            110                 115                 120

cat aac tac ggc aga ta  gtgaggtccc cggttctggt attgctgctg             603
His Asn Tyr Gly Arg Tyr
        125

tatatctaag tagatatgtg tttctaacat ttccacgatt tcag c tac aat tct       657
                                                   Tyr Asn Ser
                                                       130

ata atc tcg agc cct tcc gat ttc cag acc ttc tgg aaa acg gtc gcc      705
Ile Ile Ser Ser Pro Ser Asp Phe Gln Thr Phe Trp Lys Thr Val Ala
            135                 140                 145

tca cag ttt gct tcg aat cca ctg gtc atc ttc gac act a gtaagctgaa     755
Ser Gln Phe Ala Ser Asn Pro Leu Val Ile Phe Asp Thr
        150                 155                 160

cacccgaaat taactgagtc tgagcatgtc tgacaagacg atccatgaaa g at  aac     811
                                                         Asn Asn

gaa tac cac gat atg gac cag acc tta gtc ctc aat ctc aac cag gcc      859
Glu Tyr His Asp Met Asp Gln Thr Leu Val Leu Asn Leu Asn Gln Ala
        165                 170                 175

gct atc gac ggc atc cgt tcc gcc gga gcc act tcc cag tac atc ttt      907
Ala Ile Asp Gly Ile Arg Ser Ala Gly Ala Thr Ser Gln Tyr Ile Phe
    180                 185                 190

gtc gag ggc aat tcg tgg acc ggg gca tgg acc tgg acg aac gtg aac      955
Val Glu Gly Asn Ser Trp Thr Gly Ala Trp Thr Trp Thr Asn Val Asn
195                 200                 205                 210

gat aac atg aaa agc ctg acc gac cca tct gac aag atc ata tac gag     1003
Asp Asn Met Lys Ser Leu Thr Asp Pro Ser Asp Lys Ile Ile Tyr Glu
                215                 220                 225

atg cac cag tac ctg gac tct gac gga tcc ggg aca tca gcg acc tgc     1051
Met His Gln Tyr Leu Asp Ser Asp Gly Ser Gly Thr Ser Ala Thr Cys
            230                 235                 240

gta tct tcg acc atc ggt caa gag cga atc acc agc gca acg caa tgg     1099
Val Ser Ser Thr Ile Gly Gln Glu Arg Ile Thr Ser Ala Thr Gln Trp
        245                 250                 255

ctc agg gcc aac ggg aag aag ggc atc atc ggc gag ttt gcg ggc gga     1147
Leu Arg Ala Asn Gly Lys Lys Gly Ile Ile Gly Glu Phe Ala Gly Gly
    260                 265                 270

gcc aac gac gtc tgc gag acg gcc atc acg ggc atg ctg gac tac atg     1195
Ala Asn Asp Val Cys Glu Thr Ala Ile Thr Gly Met Leu Asp Tyr Met
275                 280                 285                 290

gcc cag aac acg gac gtc tgg act ggc gcc atc tgg tgg gcg gcc ggg     1243
Ala Gln Asn Thr Asp Val Trp Thr Gly Ala Ile Trp Trp Ala Ala Gly
                295                 300                 305

ccg tgg tgg gga gac tac ata ttc tcc atg gag ccg gac aat ggc atc     1291
Pro Trp Trp Gly Asp Tyr Ile Phe Ser Met Glu Pro Asp Asn Gly Ile
            310                 315                 320

gcg tat cag cag ata ctt cct att ttg act ccg tat ctt tgactgcag       1339
Ala Tyr Gln Gln Ile Leu Pro Ile Leu Thr Pro Tyr Leu
        325                 330                 335

<210> SEQ ID NO 10
<211> LENGTH: 335
```

```
<212> TYPE: PRT
<213> ORGANISM: Thermoascus aurantiacus

<400> SEQUENCE: 10

Met Lys Leu Gly Ser Leu Val Leu Ala Leu Ser Ala Ala Arg Leu Thr
1               5                   10                  15

Leu Ser Ala Pro Leu Ala Asp Arg Lys Gln Glu Thr Lys Arg Ala Lys
            20                  25                  30

Val Phe Gln Trp Phe Gly Ser Asn Glu Ser Gly Ala Glu Phe Gly Ser
        35                  40                  45

Gln Asn Leu Pro Gly Val Glu Gly Lys Asp Tyr Ile Trp Pro Asp Pro
    50                  55                  60

Asn Thr Ile Asp Thr Leu Ile Ser Lys Gly Met Asn Ile Phe Arg Val
65                  70                  75                  80

Pro Phe Met Met Glu Arg Leu Val Pro Asn Ser Met Thr Gly Ser Pro
                85                  90                  95

Asp Pro Asn Tyr Leu Ala Asp Leu Ile Ala Thr Val Asn Ala Ile Thr
            100                 105                 110

Gln Lys Gly Ala Tyr Ala Val Val Asp Pro His Asn Tyr Gly Arg Tyr
        115                 120                 125

Tyr Asn Ser Ile Ile Ser Ser Pro Ser Asp Phe Gln Thr Phe Trp Lys
    130                 135                 140

Thr Val Ala Ser Gln Phe Ala Ser Asn Pro Leu Val Ile Phe Asp Thr
145                 150                 155                 160

Asn Asn Glu Tyr His Asp Met Asp Gln Thr Leu Val Leu Asn Leu Asn
                165                 170                 175

Gln Ala Ala Ile Asp Gly Ile Arg Ser Ala Gly Ala Thr Ser Gln Tyr
            180                 185                 190

Ile Phe Val Glu Gly Asn Ser Trp Thr Gly Ala Trp Thr Trp Thr Asn
        195                 200                 205

Val Asn Asp Asn Met Lys Ser Leu Thr Asp Pro Ser Asp Lys Ile Ile
    210                 215                 220

Tyr Glu Met His Gln Tyr Leu Asp Ser Asp Gly Ser Gly Thr Ser Ala
225                 230                 235                 240

Thr Cys Val Ser Ser Thr Ile Gly Gln Glu Arg Ile Thr Ser Ala Thr
                245                 250                 255

Gln Trp Leu Arg Ala Asn Gly Lys Lys Gly Ile Ile Gly Glu Phe Ala
            260                 265                 270

Gly Gly Ala Asn Asp Val Cys Glu Thr Ala Ile Thr Gly Met Leu Asp
        275                 280                 285

Tyr Met Ala Gln Asn Thr Asp Val Trp Thr Gly Ala Ile Trp Trp Ala
    290                 295                 300

Ala Gly Pro Trp Trp Gly Asp Tyr Ile Phe Ser Met Glu Pro Asp Asn
305                 310                 315                 320

Gly Ile Ala Tyr Gln Gln Ile Leu Pro Ile Leu Thr Pro Tyr Leu
                325                 330                 335


<210> SEQ ID NO 11
<211> LENGTH: 2334
<212> TYPE: DNA
<213> ORGANISM: Acremonium thermophilum
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: CDS
```

```
<222> LOCATION: (715)..(797)
<220> FEATURE:
<221> NAME/KEY: Intron
<222> LOCATION: (798)..(856)
<220> FEATURE:
<221> NAME/KEY: CDS
<222> LOCATION: (857)..(1105)
<220> FEATURE:
<221> NAME/KEY: Intron
<222> LOCATION: (1106)..(1228)
<220> FEATURE:
<221> NAME/KEY: CDS
<222> LOCATION: (1229)..(1787)

<400> SEQUENCE: 11

tctgtctctt gtntcagaac agatctcctg gcggcctgct ttgccggtcc gaattgcgat      60

cgatgcaacg tcgattgcat acgagctaag cccgtctcgt gataaccgca aggggtcttc     120

cgagtttctg tctgcgaccc aggcattttc cgatttgtgt gcggggaccc aactgtcttc     180

tggggagtac ctggtgacaa aagcacagat aaacagatgg atgacggtat tgctgtgata     240

tcgccgtggc gctgaatcct ttctcttcgc taccaagata tttattcccc gttgtgaaat     300

cttctattca gcccatccca tccggcaaca cgcatctgct tttcgttccg gcattccgat     360

acctggttcc tggagtgcct accgagcctc gcttcctggg atcgggcgtt gcaccccgcc     420

aaaccctatg ccccaaacgg tacggacaag gatgccggac cccggttttg tccagaaagg     480

ttgcattcct acccacctcg ctggagccac aacatgcaga tcaccgcccg agggaggaca     540

tgtgtggtgc agggacgttg gcaactctgc tgtgtctgaa gtatatgagg ccgatggttc     600

tccttgcaca aagcagagaa tggagtagcc agctcctcct caccagagtc gcctttgcag     660

cgtctcggca ttgcaggctc cccatcgtca gcatttcact tctcagcaac gaac atg       717
                                                            Met
                                                            1

cgc tcc tca ccc ttt ctc cgc gca gct ctg gct gcc gct ctg cct ctg       765
Arg Ser Ser Pro Phe Leu Arg Ala Ala Leu Ala Ala Ala Leu Pro Leu
            5                   10                  15

agc gcc cat gcc ctc gac gga aag tcg acg ag  gtatgccaat cctcgtacct     817
Ser Ala His Ala Leu Asp Gly Lys Ser Thr Arg
        20                  25

ctgccctctg tagaaacaag tgaccgactg caaagacag a tac tgg gac tgc tgc      872
                                             Tyr Trp Asp Cys Cys
                                                 30

aag ccg tcc tgc ggc tgg ccg gga aag gcc tcg gtg aac cag ccc gtc       920
Lys Pro Ser Cys Gly Trp Pro Gly Lys Ala Ser Val Asn Gln Pro Val
    35                  40                  45

ttc tcg tgc tcg gcc gac tgg cag cgc atc agc gac ttc aac gcg aag       968
Phe Ser Cys Ser Ala Asp Trp Gln Arg Ile Ser Asp Phe Asn Ala Lys
50                  55                  60                  65

tcg ggc tgc gac gga ggc tcc gcc tac tcg tgc gcc gac cag acg ccc      1016
Ser Gly Cys Asp Gly Gly Ser Ala Tyr Ser Cys Ala Asp Gln Thr Pro
                70                  75                  80

tgg gcg gtc aac gac aac ttc tcg tac ggc ttc gca gcc acg gcc atc      1064
Trp Ala Val Asn Asp Asn Phe Ser Tyr Gly Phe Ala Ala Thr Ala Ile
            85                  90                  95

gcc ggc ggc tcc gag tcc agc tgg tgc tgc gcc tgc tat gc               1105
Ala Gly Gly Ser Glu Ser Ser Trp Cys Cys Ala Cys Tyr Ala
        100                 105                 110

gtgagttctc tgcaagccgc ttcccacccc cgctttctgt gcaggccgct tccccccctac   1165

ccacccactt cccccccccc gcctctgtga tcgggcatcc gagctaagtt gcgtgtcgtc    1225

cag a ctc acc ttc aac tcg ggc ccc gtc gcg ggc aag acc atg gtg gtg    1274
```

```
      Leu Thr Phe Asn Ser Gly Pro Val Ala Gly Lys Thr Met Val Val
                  115                 120                 125

cag tcg acc agc acc ggc ggc gac ctg ggc agc aac cag ttc gac ctc     1322
Gln Ser Thr Ser Thr Gly Gly Asp Leu Gly Ser Asn Gln Phe Asp Leu
            130                 135                 140

gcc atc ccc ggc ggc ggc gtg ggc atc ttc aac ggc tgc gcc tcc cag     1370
Ala Ile Pro Gly Gly Gly Val Gly Ile Phe Asn Gly Cys Ala Ser Gln
        145                 150                 155

ttc ggc ggc ctc ccc ggc gcc cag tac ggc ggc atc agc gac cgc agc     1418
Phe Gly Gly Leu Pro Gly Ala Gln Tyr Gly Gly Ile Ser Asp Arg Ser
    160                 165                 170

cag tgc tcg tcc ttc ccc gcg ccg ctc cag ccg ggc tgc cag tgg cgc     1466
Gln Cys Ser Ser Phe Pro Ala Pro Leu Gln Pro Gly Cys Gln Trp Arg
175                 180                 185

ttc gac tgg ttc cag aac gcc gac aac ccc acc ttc acc ttc cag cgc     1514
Phe Asp Trp Phe Gln Asn Ala Asp Asn Pro Thr Phe Thr Phe Gln Arg
                195                 200                 205

gtg cag tgc ccg tcc gag ctc acg tcc cgc acg ggc tgt aag cgc gac     1562
Val Gln Cys Pro Ser Glu Leu Thr Ser Arg Thr Gly Cys Lys Arg Asp
            210                 215                 220

gac gac gcc agc tat ccc gtc ttc aac ccg cct agc ggt ggc tcc ccc     1610
Asp Asp Ala Ser Tyr Pro Val Phe Asn Pro Pro Ser Gly Gly Ser Pro
        225                 230                 235

agc acc acc agc acc acc acc agc tcc ccg tcc ggt ccc acg ggc aac     1658
Ser Thr Thr Ser Thr Thr Thr Ser Ser Pro Ser Gly Pro Thr Gly Asn
    240                 245                 250

cct cct gga ggc ggt ggc tgc act gcc cag aag tgg gcc cag tgc ggc     1706
Pro Pro Gly Gly Gly Gly Cys Thr Ala Gln Lys Trp Ala Gln Cys Gly
255                 260                 265                 270

ggc act ggc ttc acg ggc tgc acc acc tgc gtc tcg ggc acc acc tgc     1754
Gly Thr Gly Phe Thr Gly Cys Thr Thr Cys Val Ser Gly Thr Thr Cys
                275                 280                 285

cag gtg cag aac cag tgg tat tcc cag tgt ctg tgagcgggag ggttgttggg   1807
Gln Val Gln Asn Gln Trp Tyr Ser Gln Cys Leu
            290                 295

gtccgtttcc ctagggctga ggctgacgtg aactgggtcc tcttgtccgc cccatcacgg   1867

gttcgtattc gcgcgcttag ggagaggagg atgcagtttg agggggccac attttgaggg   1927

ggacgcagtc tggggtcgaa gcttgtcggt tagggctgcc gtgacgtggt agagcagatg   1987

ggaccaagtg cggagctagg caggtgggtg gttgtggtgg tggcttacct tctgtaacgc   2047

aatggcatct catctcactc gcctgctccc tgattggtgg ctctgttcgg cctggcgctt   2107

tttgggaccg ctggctggaa tggattgctc cggaacgcca ggttgagctg ggctggcgcg   2167

agtagattgg ccgctccgag ctgcaaccat aataaaattt tcggaccctg taagccgcac   2227

ccgaccaggt ctccattggc ggacatgcac gacgtccttc gcaggcacgg cctgcccgcc   2287

tctgatcacc cgcagttttc gtaccgtcag accagataca agccccg                 2334


<210> SEQ ID NO 12
<211> LENGTH: 297
<212> TYPE: PRT
<213> ORGANISM: Acremonium thermophilum

<400> SEQUENCE: 12

Met Arg Ser Ser Pro Phe Leu Arg Ala Ala Leu Ala Ala Ala Leu Pro
1               5                   10                  15

Leu Ser Ala His Ala Leu Asp Gly Lys Ser Thr Arg Tyr Trp Asp Cys
            20                  25                  30
```

```
Cys Lys Pro Ser Cys Gly Trp Pro Gly Lys Ala Ser Val Asn Gln Pro
        35                  40                  45

Val Phe Ser Cys Ser Ala Asp Trp Gln Arg Ile Ser Asp Phe Asn Ala
    50                  55                  60

Lys Ser Gly Cys Asp Gly Gly Ser Ala Tyr Ser Cys Ala Asp Gln Thr
65                  70                  75                  80

Pro Trp Ala Val Asn Asp Asn Phe Ser Tyr Gly Phe Ala Ala Thr Ala
                85                  90                  95

Ile Ala Gly Gly Ser Glu Ser Ser Trp Cys Cys Ala Cys Tyr Ala Leu
            100                 105                 110

Thr Phe Asn Ser Gly Pro Val Ala Gly Lys Thr Met Val Val Gln Ser
        115                 120                 125

Thr Ser Thr Gly Gly Asp Leu Gly Ser Asn Gln Phe Asp Leu Ala Ile
    130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
            180                 185                 190

Trp Phe Gln Asn Ala Asp Asn Pro Thr Phe Thr Phe Gln Arg Val Gln
        195                 200                 205

Cys Pro Ser Glu Leu Thr Ser Arg Thr Gly Cys Lys Arg Asp Asp Asp
    210                 215                 220

Ala Ser Tyr Pro Val Phe Asn Pro Pro Ser Gly Gly Ser Pro Ser Thr
225                 230                 235                 240

Thr Ser Thr Thr Thr Ser Ser Pro Ser Gly Pro Thr Gly Asn Pro Pro
                245                 250                 255

Gly Gly Gly Gly Cys Thr Ala Gln Lys Trp Ala Gln Cys Gly Gly Thr
            260                 265                 270

Gly Phe Thr Gly Cys Thr Thr Cys Val Ser Gly Thr Thr Cys Gln Val
        275                 280                 285

Gln Asn Gln Trp Tyr Ser Gln Cys Leu
    290                 295
```

<210> SEQ ID NO 13
<211> LENGTH: 2033
<212> TYPE: DNA
<213> ORGANISM: Acremonium thermophilum
<220> FEATURE:
<221> NAME/KEY: CDS
<222> LOCATION: (259)..(702)
<220> FEATURE:
<221> NAME/KEY: Intron
<222> LOCATION: (703)..(857)
<220> FEATURE:
<221> NAME/KEY: CDS
<222> LOCATION: (858)..(888)
<220> FEATURE:
<221> NAME/KEY: Intron
<222> LOCATION: (889)..(990)
<220> FEATURE:
<221> NAME/KEY: CDS
<222> LOCATION: (991)..(1268)

<400> SEQUENCE: 13

```
ctcgaggaga ggaaccgagt ttgaaagatg ctatatatcg atagactacc ggcgtcgcct     60

cgccctgtcc gctctcttgc attccccctg ttgatgagac gagacaaaat tcctggttag    120

aaaagatccg tcgccgagat ttcaccagtg gtaagtcccg agaattggtc attcgacgtt    180
```

```
caatatgagt gtcaaagcta tgggtcctaa caaagaagga agcaagagct ttaaagagac    240

agaataacag cagcaaag atg cgt ctc cca cta ccg act ctg ctc gcc ctc      291
                    Met Arg Leu Pro Leu Pro Thr Leu Leu Ala Leu
                    1               5                   10

ttg ccc tac tac ctc gaa gtg tcc gct cag ggg gca tcc gga acc ggc      339
Leu Pro Tyr Tyr Leu Glu Val Ser Ala Gln Gly Ala Ser Gly Thr Gly
            15                  20                  25

acg aca aca cgt tac tgg gat tgc tgc aag ccg agc tgc gcg tgg cct      387
Thr Thr Thr Arg Tyr Trp Asp Cys Cys Lys Pro Ser Cys Ala Trp Pro
        30                  35                  40

ctg aag ggc aat tcg ccc agc ccg gtg cag act tgc gac aag aat gac      435
Leu Lys Gly Asn Ser Pro Ser Pro Val Gln Thr Cys Asp Lys Asn Asp
    45                  50                  55

agg ccg ctg aac gat ggg gga aac acc aag tcc ggc tgc gac aac ggt      483
Arg Pro Leu Asn Asp Gly Gly Asn Thr Lys Ser Gly Cys Asp Asn Gly
60                  65                  70                  75

ggc ggg gcc ttc atg tgc tca tcc cag agt ccc tgg gcc gtc aat gag      531
Gly Gly Ala Phe Met Cys Ser Ser Gln Ser Pro Trp Ala Val Asn Glu
                80                  85                  90

acc acc agc tac ggc tgg gca gcc gtt cgt atc gcc ggc agt acc gag      579
Thr Thr Ser Tyr Gly Trp Ala Ala Val Arg Ile Ala Gly Ser Thr Glu
            95                  100                 105

tcg gcc tgg tgc tgt gcc tgc tac gag ctc acc ttc acc agt ggg ccc      627
Ser Ala Trp Cys Cys Ala Cys Tyr Glu Leu Thr Phe Thr Ser Gly Pro
        110                 115                 120

gtc agt gga aag aag ctc ata gtc cag gcc acg aac act ggt gga gac      675
Val Ser Gly Lys Lys Leu Ile Val Gln Ala Thr Asn Thr Gly Gly Asp
    125                 130                 135

ctt ggg agc aac cac ttt gac ctt gcg gtatgtgggg tttttctttc            722
Leu Gly Ser Asn His Phe Asp Leu Ala
140                 145

ttcatcatcg ctctcaccat ggattcctcg gcgcaaggac caagattgag aagcgtcaat    782

gccgggttgg acacgggagc cgggatagga acacagaggc cgtttaagac cgtcagctga    842

cagcagagca attag att ccc gga ggt ggt gtt ggt cag tcc aat g           888
                 Ile Pro Gly Gly Gly Val Gly Gln Ser Asn
                     150                 155

gtaggttcct tccctgaagt accggcaaca gcctgtgcgt tgctgtatac ccccttttaat    948

catagcatct tcctgctgga tacaagccaa cccattttct ag ct  tgc acg aac      1001
                                              Ala Cys Thr Asn
                                                  160

cag tat ggt gcg ccc ccg aac ggc tgg ggc gac agg tat ggt ggc gtg     1049
Gln Tyr Gly Ala Pro Pro Asn Gly Trp Gly Asp Arg Tyr Gly Gly Val
        165                 170                 175

cac tcg cgg agc gac tgc gac agc ttc ccc gcg gcg ctc aag gcc ggc     1097
His Ser Arg Ser Asp Cys Asp Ser Phe Pro Ala Ala Leu Lys Ala Gly
    180                 185                 190

tgc tac tgg cga ttc gac tgg ttc cag ggc gcc gac aac ccg tcc gtg     1145
Cys Tyr Trp Arg Phe Asp Trp Phe Gln Gly Ala Asp Asn Pro Ser Val
195                 200                 205                 210

agc ttc aaa cag gta gcc tgc ccg gca gcc atc aca gct aag agc ggc     1193
Ser Phe Lys Gln Val Ala Cys Pro Ala Ala Ile Thr Ala Lys Ser Gly
                215                 220                 225

tgt act cgc cag aac gat gcc atc aac gag act ccg act ggg ccc agc     1241
Cys Thr Arg Gln Asn Asp Ala Ile Asn Glu Thr Pro Thr Gly Pro Ser
            230                 235                 240

act gtg cct acc tac acc gcg tca ggc tgaaagtcgg ctggggcacc           1288
Thr Val Pro Thr Tyr Thr Ala Ser Gly
```

```
        245                 250

attgcccagg tgatggttgg gcatgtgtta gtctcactca ccagggacat ttgtcgcgac   1348

ctgatcatag gcgccagggg agttgaaagg ggttgccgta cgagaagaca ttttgtcgcc   1408

gtcttactcc cagccacttc tgtacatatt caatgacatt acatagcccg caaatatgtt   1468

catatatcgt ggccgcccaa accgccccgg tttgcttagg ctggagctga agtggctcgc   1528

cgatggctgt caaaggcagt cggaatattc ctcgttgctt cggcaacacg gtagctgctt   1588

gaaccgtacc cagcattaga acaccccccg ccgagggctt gctacgtcaa tggcggggtc   1648

tccaacccct gcgcggcaca aaaccaacca cgccctcgtc ttttatgatg tcctcgctca   1708

aacgtcccgt gacgacactc cgctcatggt ctggtcctct gatgtagaag ggtaggtca    1768

gccgatggtc gtcaccgtcg tcaatgcttc cctcaagctt cttgcggcct ttatcctcca   1828

actcttccca catgagaact ccatctttcc gccttttcac aaagccactg ccctccttgt   1888

caagggccaa aaaccaacgc cgctgatgaa tgcttccgat cgtgtttgac gcgcccgggg   1948

tatgcatttg gttcggcgca ctttttcgt cctccagctc ccttaactcc cgttccatct    2008

gagagggtga ctcgtctact cgact                                         2033


<210> SEQ ID NO 14
<211> LENGTH: 251
<212> TYPE: PRT
<213> ORGANISM: Acremonium thermophilum

<400> SEQUENCE: 14

Met Arg Leu Pro Leu Pro Thr Leu Leu Ala Leu Leu Pro Tyr Tyr Leu
1               5                   10                  15

Glu Val Ser Ala Gln Gly Ala Ser Gly Thr Gly Thr Thr Thr Arg Tyr
            20                  25                  30

Trp Asp Cys Cys Lys Pro Ser Cys Ala Trp Pro Leu Lys Gly Asn Ser
        35                  40                  45

Pro Ser Pro Val Gln Thr Cys Asp Lys Asn Asp Arg Pro Leu Asn Asp
    50                  55                  60

Gly Gly Asn Thr Lys Ser Gly Cys Asp Asn Gly Gly Gly Ala Phe Met
65                  70                  75                  80

Cys Ser Ser Gln Ser Pro Trp Ala Val Asn Glu Thr Thr Ser Tyr Gly
                85                  90                  95

Trp Ala Ala Val Arg Ile Ala Gly Ser Thr Glu Ser Ala Trp Cys Cys
            100                 105                 110

Ala Cys Tyr Glu Leu Thr Phe Thr Ser Gly Pro Val Ser Gly Lys Lys
        115                 120                 125

Leu Ile Val Gln Ala Thr Asn Thr Gly Gly Asp Leu Gly Ser Asn His
    130                 135                 140

Phe Asp Leu Ala Ile Pro Gly Gly Gly Val Gly Gln Ser Asn Ala Cys
145                 150                 155                 160

Thr Asn Gln Tyr Gly Ala Pro Pro Asn Gly Trp Gly Asp Arg Tyr Gly
                165                 170                 175

Gly Val His Ser Arg Ser Asp Cys Asp Ser Phe Pro Ala Ala Leu Lys
            180                 185                 190

Ala Gly Cys Tyr Trp Arg Phe Asp Trp Phe Gln Gly Ala Asp Asn Pro
        195                 200                 205

Ser Val Ser Phe Lys Gln Val Ala Cys Pro Ala Ala Ile Thr Ala Lys
    210                 215                 220

Ser Gly Cys Thr Arg Gln Asn Asp Ala Ile Asn Glu Thr Pro Thr Gly
```

```
225                 230                 235                 240

Pro Ser Thr Val Pro Thr Tyr Thr Ala Ser Gly
                245                 250


 <210> SEQ ID NO 15
<211> LENGTH: 2800
<212> TYPE: DNA
<213> ORGANISM: Chaetomium thermophilum
<220> FEATURE:
<221> NAME/KEY: CDS
<222> LOCATION: (768)..(2042)
<220> FEATURE:
<221> NAME/KEY: modified_base
<222> LOCATION: (2786)..(2786)
<223> OTHER INFORMATION: a, c, t, g, unknown or other

<400> SEQUENCE: 15

ggatccaaga ccgatcccga ggattctcgg attatgtttg catctcaccc tccgaaaccg      60

catgaaaaat tgaaatgggc aactgtcgct gtgtttaatg ctttgcacat catgggatca     120

tgttcacccg ctctaatctc tcatcctcca gatcctatct atcctccgca tctagccggc     180

ttcttgcttg tgatccaaag ccctgatccc acgcggcttc tagacgcttt agaaattaca     240

ccgaatctcc ccatgccctt cttgcaatat cttcccgacc aggaacttcg ggtgctcaac     300

atccgcgagc ttgacgacga cccttcttgg ccggcttggc atgcgactct gttcgggact     360

caatgcaact ctgggccctt caatgccgcg catgaccgtt actgaggctt agccgcccca     420

atcgcttggc acggtacctt gcagacggaa tcccgggccc gttgtccgat ctgctttggt     480

tccggtagag aagcctcgga ggaagagaca cacggacaca acgattgcgg gccccaatgc     540

gctgctccta attgaggctc cgaggtcgtg tgccgtgtgg agaggccgcg actgggtctg     600

gggtgcggag gattgcggag atgaagataa tctgggtgca accgtggata cataaaaggg     660

agtagttctc ccctctgtga aaccttcttc cccaggattc tcctcgcctc taagagtcca     720

aagtcattca agacatccta cagcggggtc agtgagattc cataatc atg act cgc      776
                                                    Met Thr Arg
                                                    1

aag ttc gca ctc gtt ccc ctc ctt ctg ggt ctt gcc tcg gcc cag aaa      824
Lys Phe Ala Leu Val Pro Leu Leu Leu Gly Leu Ala Ser Ala Gln Lys
    5                   10                  15

ccc ggc aac act cca gaa gtc cac ccc aag atc acc act tac cgc tgc      872
Pro Gly Asn Thr Pro Glu Val His Pro Lys Ile Thr Thr Tyr Arg Cys
20                  25                  30                  35

agc cac cgc cag gga tgc cgc ccg gag acg aac tac atc gtc ctc gac      920
Ser His Arg Gln Gly Cys Arg Pro Glu Thr Asn Tyr Ile Val Leu Asp
                40                  45                  50

tcc ctc acc cat ccc gtg cac cag ttg aac tcc aac gcg aac tgc ggc      968
Ser Leu Thr His Pro Val His Gln Leu Asn Ser Asn Ala Asn Cys Gly
            55                  60                  65

gac tgg ggt aac ccg ccc ccg cgc agc gtc tgc cct gat gtc gag acc     1016
Asp Trp Gly Asn Pro Pro Pro Arg Ser Val Cys Pro Asp Val Glu Thr
        70                  75                  80

tgc gcg cag aat tgc atc atg gag ggc atc caa gac tac tcc acc tac     1064
Cys Ala Gln Asn Cys Ile Met Glu Gly Ile Gln Asp Tyr Ser Thr Tyr
    85                  90                  95

ggc gtg acc acc tct ggc tct tcc ctt cgc ctg aag cag atc cac cag     1112
Gly Val Thr Thr Ser Gly Ser Ser Leu Arg Leu Lys Gln Ile His Gln
100                 105                 110                 115

ggc cgc gtc acc tct cct cgt gtc tac ctc ctc gac aag acg gag cag     1160
Gly Arg Val Thr Ser Pro Arg Val Tyr Leu Leu Asp Lys Thr Glu Gln
                120                 125                 130
```

```
cag tat gag atg atg cgt ctc acc ggc ttc gag ttc act ttc gac gtc      1208
Gln Tyr Glu Met Met Arg Leu Thr Gly Phe Glu Phe Thr Phe Asp Val
            135                 140                 145

gac acc acc aag ctc ccc tgc ggc atg aac gct gcg ctc tat ctc tcc      1256
Asp Thr Thr Lys Leu Pro Cys Gly Met Asn Ala Ala Leu Tyr Leu Ser
        150                 155                 160

gag atg gac gct acc ggc gct cgc tcc cgc ctc aac cct ggc ggt gcc      1304
Glu Met Asp Ala Thr Gly Ala Arg Ser Arg Leu Asn Pro Gly Gly Ala
    165                 170                 175

tac tac ggc acg ggt tac tgc gat gca cag tgc ttc gtc acc ccc ttc      1352
Tyr Tyr Gly Thr Gly Tyr Cys Asp Ala Gln Cys Phe Val Thr Pro Phe
180                 185                 190                 195

atc aat ggc atc ggc aac atc gag ggc aag ggc tcg tgc tgc aac gag      1400
Ile Asn Gly Ile Gly Asn Ile Glu Gly Lys Gly Ser Cys Cys Asn Glu
                200                 205                 210

atg gac att tgg gag gcc aac tcg cgt agt cag tcc att gct ccg cac      1448
Met Asp Ile Trp Glu Ala Asn Ser Arg Ser Gln Ser Ile Ala Pro His
            215                 220                 225

ccc tgc aac aag cag ggt ctg tac atg tgc tcc ggc cag gag tgc gag      1496
Pro Cys Asn Lys Gln Gly Leu Tyr Met Cys Ser Gly Gln Glu Cys Glu
        230                 235                 240

ttc gac ggc gtc tgc gac gag tgg gga tgc aca tgg aac ccg tac aag      1544
Phe Asp Gly Val Cys Asp Glu Trp Gly Cys Thr Trp Asn Pro Tyr Lys
    245                 250                 255

gtc aac gtt acc gac tac tat ggc cgc ggt ccg cag ttc aag gtc gac      1592
Val Asn Val Thr Asp Tyr Tyr Gly Arg Gly Pro Gln Phe Lys Val Asp
260                 265                 270                 275

acg acc cgt ccc ttc acc gtc atc aca cag ttt cca gcc gac cag aac      1640
Thr Thr Arg Pro Phe Thr Val Ile Thr Gln Phe Pro Ala Asp Gln Asn
                280                 285                 290

ggc aag ctg acg tcg atc cat cgc atg tat gtg caa gat ggc aag ttg      1688
Gly Lys Leu Thr Ser Ile His Arg Met Tyr Val Gln Asp Gly Lys Leu
            295                 300                 305

atc gag gcg cat acc gtc aac ctg ccg ggt tat cct caa gtg aac gcg      1736
Ile Glu Ala His Thr Val Asn Leu Pro Gly Tyr Pro Gln Val Asn Ala
        310                 315                 320

ctg aac gat gac ttc tgc cgt gcc acg gga gcc gcg acg aag tat ctt      1784
Leu Asn Asp Asp Phe Cys Arg Ala Thr Gly Ala Ala Thr Lys Tyr Leu
    325                 330                 335

gaa ctg ggt gcc act gcg ggt atg ggc gag gct ctg agg cgt ggt atg      1832
Glu Leu Gly Ala Thr Ala Gly Met Gly Glu Ala Leu Arg Arg Gly Met
340                 345                 350                 355

gtg ctg gct atg agc atc tgg tgg gat gag agc ggc ttc atg aac tgg      1880
Val Leu Ala Met Ser Ile Trp Trp Asp Glu Ser Gly Phe Met Asn Trp
                360                 365                 370

ctt gat agc ggc gag tct ggg ccg tgc aac ccg aac gag ggt aac cca      1928
Leu Asp Ser Gly Glu Ser Gly Pro Cys Asn Pro Asn Glu Gly Asn Pro
            375                 380                 385

cag aac att cgc cag att gag ccc gag ccg gag gtt acc tat agc aac      1976
Gln Asn Ile Arg Gln Ile Glu Pro Glu Pro Glu Val Thr Tyr Ser Asn
        390                 395                 400

ctg cgc tgg ggt gag att ggg tcg act tat aag cac aat ctg aag ggc      2024
Leu Arg Trp Gly Glu Ile Gly Ser Thr Tyr Lys His Asn Leu Lys Gly
    405                 410                 415

ggg tgg act ggc agg aac taagtgttgg ggattagagc ctgtgattgg              2072
Gly Trp Thr Gly Arg Asn
420                 425

atacctgtgg gttaaacggg gctcggtttg agagggttgt tgaaatttat ttctcgtaca    2132
```

```
tagttggcgt cttggcgaat atatgccccc aggactttga tccagtcttc gtccatttct   2192

ctgtgactta gttggtgcaa gtatcattgt tatgtcctgg gtgagacaaa gcaatctctt   2252

cagtggtcat gggtaaataa tctacaggct gtgaatggcg ttgcgtcagc ctcattaact   2312

taaacgattg gactcccctt ttcctaatca tcgccgttgc cgtgtaactc tcctagatct   2372

cttgttgtat atggcttcaa ctcgaagtga agaaaaatgg atacggcgac ctctttgtgc   2432

caattttctt gctgttcttc cggtattgac cctcggcaag acaactatgg ccaatattct   2492

gttatagtcg gcagttagtg ttgtgtcgta caagtcgtgc gggagcaata ctcaacagcc   2552

gcccttaata tggttattta cgccacgacg cacttcatta cacggctttg gggggtatat   2612

attccgttca actctatccc tcattcggtg tgattgaacg tctccaacag tgaaagtata   2672

agtctgacaa aaatgcccaa ccgccatgcc actgatgatc ctgttgagat gctcgtggtc   2732

tataacatcc tgtctaagtg ttacctccct aatgttagcc ccagttctgc tctncttgtc   2792

tcgacagc                                                            2800


<210> SEQ ID NO 16
<211> LENGTH: 425
<212> TYPE: PRT
<213> ORGANISM: Chaetomium thermophilum

<400> SEQUENCE: 16

Met Thr Arg Lys Phe Ala Leu Val Pro Leu Leu Leu Gly Leu Ala Ser
1               5                   10                  15

Ala Gln Lys Pro Gly Asn Thr Pro Glu Val His Pro Lys Ile Thr Thr
            20                  25                  30

Tyr Arg Cys Ser His Arg Gln Gly Cys Arg Pro Glu Thr Asn Tyr Ile
        35                  40                  45

Val Leu Asp Ser Leu Thr His Pro Val His Gln Leu Asn Ser Asn Ala
    50                  55                  60

Asn Cys Gly Asp Trp Gly Asn Pro Pro Pro Arg Ser Val Cys Pro Asp
65                  70                  75                  80

Val Glu Thr Cys Ala Gln Asn Cys Ile Met Glu Gly Ile Gln Asp Tyr
                85                  90                  95

Ser Thr Tyr Gly Val Thr Thr Ser Gly Ser Ser Leu Arg Leu Lys Gln
            100                 105                 110

Ile His Gln Gly Arg Val Thr Ser Pro Arg Val Tyr Leu Leu Asp Lys
        115                 120                 125

Thr Glu Gln Gln Tyr Glu Met Met Arg Leu Thr Gly Phe Glu Phe Thr
    130                 135                 140

Phe Asp Val Asp Thr Thr Lys Leu Pro Cys Gly Met Asn Ala Ala Leu
145                 150                 155                 160

Tyr Leu Ser Glu Met Asp Ala Thr Gly Ala Arg Ser Arg Leu Asn Pro
                165                 170                 175

Gly Gly Ala Tyr Tyr Gly Thr Gly Tyr Cys Asp Ala Gln Cys Phe Val
            180                 185                 190

Thr Pro Phe Ile Asn Gly Ile Gly Asn Ile Glu Gly Lys Gly Ser Cys
        195                 200                 205

Cys Asn Glu Met Asp Ile Trp Glu Ala Asn Ser Arg Ser Gln Ser Ile
    210                 215                 220

Ala Pro His Pro Cys Asn Lys Gln Gly Leu Tyr Met Cys Ser Gly Gln
225                 230                 235                 240

Glu Cys Glu Phe Asp Gly Val Cys Asp Glu Trp Gly Cys Thr Trp Asn
                245                 250                 255
```

```
Pro Tyr Lys Val Asn Val Thr Asp Tyr Tyr Gly Arg Gly Pro Gln Phe
            260                 265                 270

Lys Val Asp Thr Thr Arg Pro Phe Thr Val Ile Thr Gln Phe Pro Ala
        275                 280                 285

Asp Gln Asn Gly Lys Leu Thr Ser Ile His Arg Met Tyr Val Gln Asp
    290                 295                 300

Gly Lys Leu Ile Glu Ala His Thr Val Asn Leu Pro Gly Tyr Pro Gln
305                 310                 315                 320

Val Asn Ala Leu Asn Asp Asp Phe Cys Arg Ala Thr Gly Ala Ala Thr
                325                 330                 335

Lys Tyr Leu Glu Leu Gly Ala Thr Ala Gly Met Gly Glu Ala Leu Arg
            340                 345                 350

Arg Gly Met Val Leu Ala Met Ser Ile Trp Trp Asp Glu Ser Gly Phe
        355                 360                 365

Met Asn Trp Leu Asp Ser Gly Glu Ser Gly Pro Cys Asn Pro Asn Glu
    370                 375                 380

Gly Asn Pro Gln Asn Ile Arg Gln Ile Glu Pro Glu Pro Glu Val Thr
385                 390                 395                 400

Tyr Ser Asn Leu Arg Trp Gly Glu Ile Gly Ser Thr Tyr Lys His Asn
                405                 410                 415

Leu Lys Gly Gly Trp Thr Gly Arg Asn
            420                 425


<210> SEQ ID NO 17
<211> LENGTH: 1943
<212> TYPE: DNA
<213> ORGANISM: Thermoascus aurantiacus
<220> FEATURE:
<221> NAME/KEY: CDS
<222> LOCATION: (13)..(256)
<220> FEATURE:
<221> NAME/KEY: Intron
<222> LOCATION: (257)..(329)
<220> FEATURE:
<221> NAME/KEY: CDS
<222> LOCATION: (330)..(370)
<220> FEATURE:
<221> NAME/KEY: Intron
<222> LOCATION: (371)..(444)
<220> FEATURE:
<221> NAME/KEY: CDS
<222> LOCATION: (445)..(493)
<220> FEATURE:
<221> NAME/KEY: Intron
<222> LOCATION: (494)..(561)
<220> FEATURE:
<221> NAME/KEY: CDS
<222> LOCATION: (562)..(683)
<220> FEATURE:
<221> NAME/KEY: Intron
<222> LOCATION: (684)..(786)
<220> FEATURE:
<221> NAME/KEY: CDS
<222> LOCATION: (787)..(932)
<220> FEATURE:
<221> NAME/KEY: Intron
<222> LOCATION: (933)..(1001)
<220> FEATURE:
<221> NAME/KEY: CDS
<222> LOCATION: (1002)..(1090)
<220> FEATURE:
<221> NAME/KEY: Intron
<222> LOCATION: (1091)..(1155)
<220> FEATURE:
<221> NAME/KEY: CDS
<222> LOCATION: (1156)..(1174)
<220> FEATURE:
```

```
<221> NAME/KEY: Intron
<222> LOCATION: (1175)..(1267)
<220> FEATURE:
<221> NAME/KEY: CDS
<222> LOCATION: (1268)..(1295)
<220> FEATURE:
<221> NAME/KEY: Intron
<222> LOCATION: (1296)..(1361)
<220> FEATURE:
<221> NAME/KEY: CDS
<222> LOCATION: (1362)..(1451)
<220> FEATURE:
<221> NAME/KEY: Intron
<222> LOCATION: (1452)..(1551)
<220> FEATURE:
<221> NAME/KEY: CDS
<222> LOCATION: (1552)..(1617)
<220> FEATURE:
<221> NAME/KEY: Intron
<222> LOCATION: (1618)..(1829)
<220> FEATURE:
<221> NAME/KEY: CDS
<222> LOCATION: (1830)..(1922)

<400> SEQUENCE: 17

ccgcgggaag cc atg gtt cga cca acg atc cta ctt act tca ctc ctg cta      51
              Met Val Arg Pro Thr Ile Leu Leu Thr Ser Leu Leu Leu
              1               5                   10

gct ccc ttc gca gct gcg agc cct atc ctc gag gaa cgc caa gct gca        99
Ala Pro Phe Ala Ala Ala Ser Pro Ile Leu Glu Glu Arg Gln Ala Ala
    15                  20                  25

cag agt gtc gac caa ctg atc aag gct cgc ggc aag gtg tac ttt ggc       147
Gln Ser Val Asp Gln Leu Ile Lys Ala Arg Gly Lys Val Tyr Phe Gly
30                  35                  40                  45

gtc gcc acg gac caa aac cgg ctg acg acc ggc aag aat gcg gct atc       195
Val Ala Thr Asp Gln Asn Arg Leu Thr Thr Gly Lys Asn Ala Ala Ile
                50                  55                  60

atc cag gct gat ttc ggc cag gtc acg ccg gag aat agt atg aaa tgg       243
Ile Gln Ala Asp Phe Gly Gln Val Thr Pro Glu Asn Ser Met Lys Trp
            65                  70                  75

gac gct act gaa c gtgcgtgaga aagataattt gattttttc ttctatgacc          296
Asp Ala Thr Glu
        80

gctcggaccg ttctgactag gtttataata tag ct  tct caa gga aac ttc aac      349
                                      Pro Ser Gln Gly Asn Phe Asn
                                                  85

ttt gcc ggt gct gat tac ctt gtacgtacat acgaccactt gacgtttctt          400
Phe Ala Gly Ala Asp Tyr Leu
    90                  95

gcacgcaact gcgattgagg agaagatact aatcttcttg aaag gtc aat tgg gcc      456
                                                 Val Asn Trp Ala

cag caa aat gga aag ctg atc cgt ggc cat act ctt g gttagtagaa          503
Gln Gln Asn Gly Lys Leu Ile Arg Gly His Thr Leu
100                 105                 110

cgccaacctg cttccctaac ttactgaaga aggaaaaccg aattgaccgt cccccaag       561

ta  tgg cac tcg cag ctg ccc tcg tgg gtg agc tcc atc acc gac aag       608
Val Trp His Ser Gln Leu Pro Ser Trp Val Ser Ser Ile Thr Asp Lys
            115                 120                 125

aat acg ctg acc aac gtg atg aaa aat cac atc acc acc ttg atg acc       656
Asn Thr Leu Thr Asn Val Met Lys Asn His Ile Thr Thr Leu Met Thr
        130                 135                 140

cgg tac aag ggc aag atc cgt gca tgg gtcagtcatc ctaccctaag             703
Arg Tyr Lys Gly Lys Ile Arg Ala Trp
    145                 150
```

```
ctgcgtttca atgaagagac aaataagaac acacgtattt gcccgggcgt ttcagaatca    763

gaactgacag aatcactgaa tag gac gtg gtg aac gag gca ttc aac gag gat    816
                          Asp Val Val Asn Glu Ala Phe Asn Glu Asp
                                  155                 160

ggc tcc ctc cgc cag act gtc ttc ctc aac gtc atc ggg gag gat tac      864
Gly Ser Leu Arg Gln Thr Val Phe Leu Asn Val Ile Gly Glu Asp Tyr
        165                 170                 175

atc ccg att gct ttc cag acc gcc cgc gcc gct gac ccg aat gcc aag      912
Ile Pro Ile Ala Phe Gln Thr Ala Arg Ala Ala Asp Pro Asn Ala Lys
    180                 185                 190

ctg tac atc aac gat tac aa  gtaagattta aggctcagtg atattccatt         962
Leu Tyr Ile Asn Asp Tyr Asn
195                 200

tagtgtgaga agcattgctt atgagcatct gtattacag c ctc gac agt gcc tcg    1017
                                             Leu Asp Ser Ala Ser
                                                         205

tac ccc aag acg cag gcc att gtc aac cgc gtc aag caa tgg cgt gca     1065
Tyr Pro Lys Thr Gln Ala Ile Val Asn Arg Val Lys Gln Trp Arg Ala
            210                 215                 220

gct gga gtc ccg att gac ggc ata g gtatgtctct ctttctgttt             1110
Ala Gly Val Pro Ile Asp Gly Ile
        225                 230

gtgatgtgac cgatttgaaa ccagtctaac gttagctggg tctag ga  tcg caa acg   1166
                                                  Gly Ser Gln Thr

cac ctc ag  gtaaataatc gggaatgcct cggagaataa aagagaaaaa             1214
His Leu Ser
235

aaatgattgt cttatcagat cgtatcgact gactcatggc ttgtccaaaa tag c gct    1271
                                                             Ala

ggt cag gga gcc ggt gtt cta caa taagtgcccc cctcccctat tttttactat    1325
Gly Gln Gly Ala Gly Val Leu Gln
    240                 245

tattgcgaga gcggaatagg ctgacaaccc caaacg gct ctt ccg ctc ctt gct     1379
                                        Ala Leu Pro Leu Leu Ala
                                                    250

agt gcc gga act ccc gag gtc gct atc acg gaa ctg gac gtg gct ggt     1427
Ser Ala Gly Thr Pro Glu Val Ala Ile Thr Glu Leu Asp Val Ala Gly
        255                 260                 265

gct agc ccg acg gat tac gtc aat gtatgtacct cgttgtccct atccccccttg   1481
Ala Ser Pro Thr Asp Tyr Val Asn
    270                 275

gatactttgt ataattatta tcttcccgga gcctgttgat cagatctgac gatcatttct   1541

cgtttttttag gtc gtg aac gct tgc ctc aac gtg cag tcc tgc gtg ggc     1590
           Val Val Asn Ala Cys Leu Asn Val Gln Ser Cys Val Gly
                       280                 285

atc acc gtc tgg ggc gtg gca gat ccg gtaagcgcgg ttcttccgta           1637
Ile Thr Val Trp Gly Val Ala Asp Pro
290                 295

ctccgtaccc aactagagtt cggggctgtca cgtcatgtct tagtcgtctt cagtcaggcc  1697

aaggccaaga cacaggacct gaaacgggca ggcagcagct gctagcagcc caagaagcag   1757

ccacatgatg catgattatt attattatat ctccgagttc tgggctaacg attggtgata   1817

ataaataaat ag gac tca tgg cgt gct agc acg acg cct ctc ctc ttc gac   1868
              Asp Ser Trp Arg Ala Ser Thr Thr Pro Leu Leu Phe Asp
                  300                 305                 310

ggc aac ttc aac ccg aag ccg gcg tac aac gcc att gtg cag gac ctg     1916
Gly Asn Phe Asn Pro Lys Pro Ala Tyr Asn Ala Ile Val Gln Asp Leu
            315                 320                 325
```

```
cag cag tgagtataga ccggtggatc c                                      1943
Gln Gln


<210> SEQ ID NO 18
<211> LENGTH: 329
<212> TYPE: PRT
<213> ORGANISM: Thermoascus aurantiacus

<400> SEQUENCE: 18

Met Val Arg Pro Thr Ile Leu Leu Thr Ser Leu Leu Leu Ala Pro Phe
1               5                   10                  15

Ala Ala Ala Ser Pro Ile Leu Glu Glu Arg Gln Ala Ala Gln Ser Val
            20                  25                  30

Asp Gln Leu Ile Lys Ala Arg Gly Lys Val Tyr Phe Gly Val Ala Thr
        35                  40                  45

Asp Gln Asn Arg Leu Thr Thr Gly Lys Asn Ala Ala Ile Ile Gln Ala
    50                  55                  60

Asp Phe Gly Gln Val Thr Pro Glu Asn Ser Met Lys Trp Asp Ala Thr
65                  70                  75                  80

Glu Pro Ser Gln Gly Asn Phe Asn Phe Ala Gly Ala Asp Tyr Leu Val
                85                  90                  95

Asn Trp Ala Gln Gln Asn Gly Lys Leu Ile Arg Gly His Thr Leu Val
            100                 105                 110

Trp His Ser Gln Leu Pro Ser Trp Val Ser Ser Ile Thr Asp Lys Asn
        115                 120                 125

Thr Leu Thr Asn Val Met Lys Asn His Ile Thr Thr Leu Met Thr Arg
    130                 135                 140

Tyr Lys Gly Lys Ile Arg Ala Trp Asp Val Val Asn Glu Ala Phe Asn
145                 150                 155                 160

Glu Asp Gly Ser Leu Arg Gln Thr Val Phe Leu Asn Val Ile Gly Glu
                165                 170                 175

Asp Tyr Ile Pro Ile Ala Phe Gln Thr Ala Arg Ala Ala Asp Pro Asn
            180                 185                 190

Ala Lys Leu Tyr Ile Asn Asp Tyr Asn Leu Asp Ser Ala Ser Tyr Pro
        195                 200                 205

Lys Thr Gln Ala Ile Val Asn Arg Val Lys Gln Trp Arg Ala Ala Gly
    210                 215                 220

Val Pro Ile Asp Gly Ile Gly Ser Gln Thr His Leu Ser Ala Gly Gln
225                 230                 235                 240

Gly Ala Gly Val Leu Gln Ala Leu Pro Leu Leu Ala Ser Ala Gly Thr
                245                 250                 255

Pro Glu Val Ala Ile Thr Glu Leu Asp Val Ala Gly Ala Ser Pro Thr
            260                 265                 270

Asp Tyr Val Asn Val Val Asn Ala Cys Leu Asn Val Gln Ser Cys Val
        275                 280                 285

Gly Ile Thr Val Trp Gly Val Ala Asp Pro Asp Ser Trp Arg Ala Ser
    290                 295                 300

Thr Thr Pro Leu Leu Phe Asp Gly Asn Phe Asn Pro Lys Pro Ala Tyr
305                 310                 315                 320

Asn Ala Ile Val Gln Asp Leu Gln Gln
                325


<210> SEQ ID NO 19
<211> LENGTH: 2955
<212> TYPE: DNA
```

```
<213> ORGANISM: Acremonium thermophilum
<220> FEATURE:
<221> NAME/KEY: CDS
<222> LOCATION: (1335)..(1671)
<220> FEATURE:
<221> NAME/KEY: Intron
<222> LOCATION: (1672)..(1806)
<220> FEATURE:
<221> NAME/KEY: CDS
<222> LOCATION: (1807)..(2032)
<220> FEATURE:
<221> NAME/KEY: Intron
<222> LOCATION: (2033)..(2117)
<220> FEATURE:
<221> NAME/KEY: CDS
<222> LOCATION: (2118)..(2802)

<400> SEQUENCE: 19

tctagagctg tcgacgcggc cgcgtaatac gactcactat agggcgaaga attcggatca     60

cgtttgcttc agcaagtcgt tcgctacgac accacgtcca tgatggaggc cctgattcaa    120

tcataccaag gacggggcat gatggctgat ggctggactc gaagtgagtg gcccgtggct    180

gaattttcct tcccgttctc tacagtcctt ccctcagcga cacatccgca gttttgacag    240

cggaaatcgt caggatgctc cgccttctct cgcaacctga gtgcccaggc gtctcggcca    300

ccgtctctta tatatggccg ctgggtccgc ctttcgatcg gttttcgatt tggtctctcc    360

tagttccctc agctgacccg ggatatcgct tgtggctccg aaacctcacc atcccagacg    420

agcaagttct ccgcagtcca cctcagctca tccggccctt ggtagcatcg cagcgacccc    480

agacgaaggc accaaagaag catactatat attaggctaa atcgagcccc acgtggaata    540

tttgccatcg aggaggggtg gttgggcttc ttgtcctcgc aggtgctgcg cctgtaccta    600

cctggtgctc cagctggtgc tcccgctggt gctgttccag tcgccgtctg gccccaatgc    660

tctgtatctc ggttcgtccc gcactccttt cgccaagcgc taccaatgct ttgacgaacc    720

cggtaaattt gcagtggacc tgcagctggg caaacccgca gtgggaacca cagacctggt    780

tcgttcgaca cactccaatc gcaaccccgc ccgcgcaaac cttgcaccac atgtcgcccc    840

tttcccagtt gggtccctga agacacggag ccacttccgt gatcgtcggc tccccaagcc    900

gacagtcgga cgctgcaata ggatgccagc acccgtggat ccaagggcca gtgaccccaa    960

ctctttcgcg gtattctggc cctcccaaag gtatgccagg acttccctgt ctttgctacc   1020

accagctctc ctccacggcg gaacggatac gccgtctcgc cggctcttgc tcgacaacat   1080

gcgagggggc gcgaaggcta ggttgtgacg atgcgacggt gcgatgtcac catttggcag   1140

tgatgttttc cgttgtcccc ttctccaccc tgcgccgttt cctcaaagac gccccaacca   1200

taaatacgat gcgacgccaa ccttcatgtg ttcgtggcat cttgcctgac cagtctcagc   1260

aagaaacctg tggcggcgcg attgtcttga ccttctgatt gaaaacggat ctgcgtcctc   1320

ctcgatagcc gacc atg cgc gcc aag caa ctc ctg gcg gcc ggc ctg ctg     1370
                Met Arg Ala Lys Gln Leu Leu Ala Ala Gly Leu Leu
                1               5                   10

gcc ccc gcg tcc gtc tcg gcc cag ctc aac agc ctc gcc gtg gcg gct     1418
Ala Pro Ala Ser Val Ser Ala Gln Leu Asn Ser Leu Ala Val Ala Ala
        15                  20                  25

ggc ctc aag tac ttc ggc acg gcc gtg cgg gag gcc aac gtc aac ggc     1466
Gly Leu Lys Tyr Phe Gly Thr Ala Val Arg Glu Ala Asn Val Asn Gly
    30                  35                  40

gac gcc acc tac atg tcg tac gtc aac aac aag tcc gag ttc ggc cag     1514
Asp Ala Thr Tyr Met Ser Tyr Val Asn Asn Lys Ser Glu Phe Gly Gln
45                  50                  55                  60
```

```
gtg acg ccc gag aac ggc cag aag tgg gat tcc acc gag ccc agc cag      1562
Val Thr Pro Glu Asn Gly Gln Lys Trp Asp Ser Thr Glu Pro Ser Gln
                65                  70                  75

ggc cag ttc agc tac agc cag ggc gac atc gtc ccc ggc gtc gcg aag      1610
Gly Gln Phe Ser Tyr Ser Gln Gly Asp Ile Val Pro Gly Val Ala Lys
            80                  85                  90

aag aac ggc cag gtg ctg cgc tgc cac acc ctg gtg tgg tac agc cag      1658
Lys Asn Gly Gln Val Leu Arg Cys His Thr Leu Val Trp Tyr Ser Gln
        95                  100                 105

ctc ccc agc tgg g gtcagtgact ctctctttct ctctgtcttt ctctttgtct       1711
Leu Pro Ser Trp
    110

ttctctcttt ctctctctct ctctctctct ctctctctct ctctctccca tccagcatcg   1771

actgctgatc ttgctgacca gaagctcgtg tgcag tg  tca tcc gga agt tgg      1823
                                       Val Ser Ser Gly Ser Trp
                                                   115

acc cgc gcg acg ctt cag tcc gtc atc gag acg cac atc tcg aac gtg      1871
Thr Arg Ala Thr Leu Gln Ser Val Ile Glu Thr His Ile Ser Asn Val
    120                 125                 130

atg ggc cac tac aag ggc cag tgc tac gcc tgg gac gtg gtc aac gag      1919
Met Gly His Tyr Lys Gly Gln Cys Tyr Ala Trp Asp Val Val Asn Glu
135                 140                 145                 150

gcc atc aac gac gac ggc acg tgg cgg acc agc gtc ttc tac aac acc      1967
Ala Ile Asn Asp Asp Gly Thr Trp Arg Thr Ser Val Phe Tyr Asn Thr
                155                 160                 165

ttc aac acc gac tac ctg gcc att gcc ttc aac gcc gcg aag aag gcc      2015
Phe Asn Thr Asp Tyr Leu Ala Ile Ala Phe Asn Ala Ala Lys Lys Ala
            170                 175                 180

gat gcg ggc gcg aag ct  gtaggtgtcg gcctttacgt tgccgcagcg             2062
Asp Ala Gly Ala Lys Leu
        185

cacctccgcg acatgagccc cagagcgcgt ggctaatagt tcctcacgca cgcag g      2118

tac tac aac gac tac aat ctc gag tac aac ggc gcc aag acc aac acg      2166
Tyr Tyr Asn Asp Tyr Asn Leu Glu Tyr Asn Gly Ala Lys Thr Asn Thr
    190                 195                 200

gcc gtg cag ctg gtg cag atc gtg cag cag gcc ggc gcg ccc atc gac      2214
Ala Val Gln Leu Val Gln Ile Val Gln Gln Ala Gly Ala Pro Ile Asp
205                 210                 215                 220

ggg gtg ggc ttc cag ggc cac ctg atc gtg ggg tca acg ccg tcg cgc      2262
Gly Val Gly Phe Gln Gly His Leu Ile Val Gly Ser Thr Pro Ser Arg
                225                 230                 235

agc tcc ctg gcc acg gcg ctg aag cgc ttc acg gcg ctt ggc ctg gag       231
Ser Ser Leu Ala Thr Ala Leu Lys Arg Phe Thr Ala Leu Gly Leu Glu
            240                 245                 250

gtg gcg tac acg gag ctg gac atc cgg cac tcg agc ctg ccg ccg tcg      2358
Val Ala Tyr Thr Glu Leu Asp Ile Arg His Ser Ser Leu Pro Pro Ser
        255                 260                 265

tcg gcg gcg ctg gcg acg cag ggc aac gac ttc gcc agc gtg gtg ggc      2406
Ser Ala Ala Leu Ala Thr Gln Gly Asn Asp Phe Ala Ser Val Val Gly
    270                 275                 280

tcg tgc ctc gac gtg gcg ggc tgc gtg ggc atc acc atc tgg ggg ttc      2454
Ser Cys Leu Asp Val Ala Gly Cys Val Gly Ile Thr Ile Trp Gly Phe
285                 290                 295                 300

acg gac aag tac agc tgg gtg ccc gac acg ttc ccc ggc tcg ggc gcg      2502
Thr Asp Lys Tyr Ser Trp Val Pro Asp Thr Phe Pro Gly Ser Gly Ala
                305                 310                 315

gcg ctg ctg tac gac gcg aac tac agc aag aag ccg gcg tgg acg tcg      2550
Ala Leu Leu Tyr Asp Ala Asn Tyr Ser Lys Lys Pro Ala Trp Thr Ser
            320                 325                 330
```

```
gtc tcg tcg gtg ctg gcg gcc aag gcg acg aac ccg ccc ggc ggc ggg     2598
Val Ser Ser Val Leu Ala Ala Lys Ala Thr Asn Pro Pro Gly Gly Gly
        335                 340                 345

aac cca ccc ccc gtc acc acc acg acc acg acc acg acc acg tcg aag     2646
Asn Pro Pro Pro Val Thr Thr Thr Thr Thr Thr Thr Thr Thr Ser Lys
    350                 355                 360

ccg tcg cag ccc acc acc acg acc acg acc acc agc ccg cag ggt ccg     2694
Pro Ser Gln Pro Thr Thr Thr Thr Thr Thr Thr Ser Pro Gln Gly Pro
365                 370                 375                 380

cag cag acg cac tgg ggc cag tgc ggc ggg atc ggc tgg acg ggg ccg     2742
Gln Gln Thr His Trp Gly Gln Cys Gly Gly Ile Gly Trp Thr Gly Pro
                385                 390                 395

cag tcg tgc cag agc ccg tgg acg tgc cag aag cag aac gac tgg tac     2790
Gln Ser Cys Gln Ser Pro Trp Thr Cys Gln Lys Gln Asn Asp Trp Tyr
            400                 405                 410

tct cag tgc ctg tgaccaccac ggctgaccag ctgccattcc gaccacgggg         2842
Ser Gln Cys Leu
        415

cccggactac aaaaagaggg gacggtgtaa ataaagagcc gaacgggtct acgtacactg   2902

ttttgacctt ttctccgcag acgtatatta tcaattatag ttggatttct aga          2955


<210> SEQ ID NO 20
<211> LENGTH: 416
<212> TYPE: PRT
<213> ORGANISM: Acremonium thermophilum

<400> SEQUENCE: 20

Met Arg Ala Lys Gln Leu Leu Ala Ala Gly Leu Leu Ala Pro Ala Ser
1               5                   10                  15

Val Ser Ala Gln Leu Asn Ser Leu Ala Val Ala Ala Gly Leu Lys Tyr
            20                  25                  30

Phe Gly Thr Ala Val Arg Glu Ala Asn Val Asn Gly Asp Ala Thr Tyr
        35                  40                  45

Met Ser Tyr Val Asn Asn Lys Ser Glu Phe Gly Gln Val Thr Pro Glu
    50                  55                  60

Asn Gly Gln Lys Trp Asp Ser Thr Glu Pro Ser Gln Gly Gln Phe Ser
65                  70                  75                  80

Tyr Ser Gln Gly Asp Ile Val Pro Gly Val Ala Lys Lys Asn Gly Gln
                85                  90                  95

Val Leu Arg Cys His Thr Leu Val Trp Tyr Ser Gln Leu Pro Ser Trp
            100                 105                 110

Val Ser Ser Gly Ser Trp Thr Arg Ala Thr Leu Gln Ser Val Ile Glu
        115                 120                 125

Thr His Ile Ser Asn Val Met Gly His Tyr Lys Gly Gln Cys Tyr Ala
    130                 135                 140

Trp Asp Val Val Asn Glu Ala Ile Asn Asp Asp Gly Thr Trp Arg Thr
145                 150                 155                 160

Ser Val Phe Tyr Asn Thr Phe Asn Thr Asp Tyr Leu Ala Ile Ala Phe
                165                 170                 175

Asn Ala Ala Lys Lys Ala Asp Ala Gly Ala Lys Leu Tyr Tyr Asn Asp
            180                 185                 190

Tyr Asn Leu Glu Tyr Asn Gly Ala Lys Thr Asn Thr Ala Val Gln Leu
        195                 200                 205

Val Gln Ile Val Gln Gln Ala Gly Ala Pro Ile Asp Gly Val Gly Phe
    210                 215                 220
```

```
Gln Gly His Leu Ile Val Gly Ser Thr Pro Ser Arg Ser Ser Leu Ala
225                 230                 235                 240

Thr Ala Leu Lys Arg Phe Thr Ala Leu Gly Leu Glu Val Ala Tyr Thr
                245                 250                 255

Glu Leu Asp Ile Arg His Ser Ser Leu Pro Pro Ser Ser Ala Ala Leu
            260                 265                 270

Ala Thr Gln Gly Asn Asp Phe Ala Ser Val Val Gly Ser Cys Leu Asp
        275                 280                 285

Val Ala Gly Cys Val Gly Ile Thr Ile Trp Gly Phe Thr Asp Lys Tyr
    290                 295                 300

Ser Trp Val Pro Asp Thr Phe Pro Gly Ser Gly Ala Ala Leu Leu Tyr
305                 310                 315                 320

Asp Ala Asn Tyr Ser Lys Lys Pro Ala Trp Thr Ser Val Ser Ser Val
                325                 330                 335

Leu Ala Ala Lys Ala Thr Asn Pro Pro Gly Gly Gly Asn Pro Pro Pro
            340                 345                 350

Val Thr Thr Thr Thr Thr Thr Thr Thr Thr Ser Lys Pro Ser Gln Pro
        355                 360                 365

Thr Thr Thr Thr Thr Thr Thr Ser Pro Gln Gly Pro Gln Gln Thr His
    370                 375                 380

Trp Gly Gln Cys Gly Gly Ile Gly Trp Thr Gly Pro Gln Ser Cys Gln
385                 390                 395                 400

Ser Pro Trp Thr Cys Gln Lys Gln Asn Asp Trp Tyr Ser Gln Cys Leu
                405                 410                 415


<210> SEQ ID NO 21
<211> LENGTH: 5092
<212> TYPE: DNA
<213> ORGANISM: Thermoascus aurantiacus
<220> FEATURE:
<221> NAME/KEY: CDS
<222> LOCATION: (669)..(728)
<220> FEATURE:
<221> NAME/KEY: Intron
<222> LOCATION: (729)..(872)
<220> FEATURE:
<221> NAME/KEY: CDS
<222> LOCATION: (873)..(1015)
<220> FEATURE:
<221> NAME/KEY: Intron
<222> LOCATION: (1016)..(1082)
<220> FEATURE:
<221> NAME/KEY: CDS
<222> LOCATION: (1083)..(1127)
<220> FEATURE:
<221> NAME/KEY: Intron
<222> LOCATION: (1128)..(1183)
<220> FEATURE:
<221> NAME/KEY: CDS
<222> LOCATION: (1184)..(1236)
<220> FEATURE:
<221> NAME/KEY: Intron
<222> LOCATION: (1237)..(1300)
<220> FEATURE:
<221> NAME/KEY: CDS
<222> LOCATION: (1301)..(1717)
<220> FEATURE:
<221> NAME/KEY: Intron
<222> LOCATION: (1718)..(1776)
<220> FEATURE:
<221> NAME/KEY: CDS
<222> LOCATION: (1777)..(2489)
<220> FEATURE:
<221> NAME/KEY: Intron
<222> LOCATION: (2490)..(2599)
<220> FEATURE:
<221> NAME/KEY: CDS
```

```
<222> LOCATION: (2600)..(3469)
<220> FEATURE:
<221> NAME/KEY: Intron
<222> LOCATION: (3470)..(3531)
<220> FEATURE:
<221> NAME/KEY: CDS
<222> LOCATION: (3532)..(3759)

<400> SEQUENCE: 21

ggatccgtcc gcggacacag gcagagagac ggcacgggga ctcgacctga tcctcccagg     60

gcggggtgtt gtttgtggcg agggagcgat gctgatgttc ttccagctcc gttgctacct    120

tcccacggcc atttagccgg cggacggcat gtaacatgtc aaacatgtgg gctcggcagt    180

gggggcgtga gacgcagcac ctgacccggc ggcgcggcgc ttgcagggtc cagggacagc    240

cggccgtggt cgtttgcggg gaaggcgaca cagacgactt ggcgcggccc gccggaaggc    300

gaggaatcat gagtgcgacg gagacatggc aagaccacgg ccttcctggc gaagaagaag    360

atgaataatc gcaggggcag tgtggcatgg accgcacggc cgccagggac ctgccccgtg    420

aggtttctcg ggtgtttcca ctggttccat cgctgggggc gatcccgagc ccgtgtgccc    480

gtgtaactat tattgacgat caacatgcca tggccagcca gcttctataa taatcatata    540

taacaccccc cgttctcccg ctgccttgct ccgtggtctt cctggtcctg cttgaggttc    600

acgagtctcc ttgcatggtc aactcgtcct ctgcttcatc cgctgcttga ctccgtacct    660

cagcaacc atg agg ctt ggg tgg ctg gag ctg gcc gtc gcg gcg gcc gca     710
         Met Arg Leu Gly Trp Leu Glu Leu Ala Val Ala Ala Ala Ala
         1               5                   10

acc gtc gcc agc gcc aag gtgcgtcaga ccctcccccg gatcgacctt             758
Thr Val Ala Ser Ala Lys
15                  20

taggtgcttc ttcagcaagt gcgcgccggc cgcgacatcc gccgccgctg ccctcaccga    818

cgcagcaccc atatgcagca ggagagaagg catctctgac gaaagctccc ccag gat      875
                                                            Asp

gac ttg gcc tac tcg ccg cct ttc tac ccg tcg cca tgg atg aac gga      923
Asp Leu Ala Tyr Ser Pro Pro Phe Tyr Pro Ser Pro Trp Met Asn Gly
            25                  30                  35

aac gga gag tgg gcg gag gcc tac cgc agg gct gtc gac ttc gtc tcg      971
Asn Gly Glu Trp Ala Glu Ala Tyr Arg Arg Ala Val Asp Phe Val Ser
        40                  45                  50

cag ctg acc ctc gcg gag aag gtc aac ctg acg acc ggt gtc gg          1015
Gln Leu Thr Leu Ala Glu Lys Val Asn Leu Thr Thr Gly Val Gly
    55                  60                  65

gtgagtccat tgacctctac cgagcccccg ttccatgtcc attgagcaat tggctgacgt   1075

cttgaag c tgg atg cag gag aaa tgt gtc ggt gaa acg ggc agc att ccg   1125
          Trp Met Gln Glu Lys Cys Val Gly Glu Thr Gly Ser Ile Pro
              70                  75                  80

ag  gtaggctcac ttcccaatgc cgctgcaaag gaggtgtcta aactggaata aatcag   1183
Arg

a ctg ggg ttc cgt gga ctg tgc ctc caa gac tcg ccc ctt ggt gtc aga   1232
  Leu Gly Phe Arg Gly Leu Cys Leu Gln Asp Ser Pro Leu Gly Val Arg
      85                  90                  95

ttt g gtaggtcttt caacagagaa caagggtcgt cgcgggagag atgctgatcg        1286
Phe
100

atacctactt ttag ct  gac tac gtt tct gcc ttc ccc gcc ggt gtc aat     1335
                Ala Asp Tyr Val Ser Ala Phe Pro Ala Gly Val Asn
                                105                 110

gtc gct gca acg tgg gat aag aac ctc gcc tac ctt cgt ggg aag gcg     1383
```

-continued

```
Val Ala Ala Thr Trp Asp Lys Asn Leu Ala Tyr Leu Arg Gly Lys Ala
        115                 120                 125

atg ggt gag gaa cac cgt ggt aag ggc gtc gac gtc cag ctg gga cct      1431
Met Gly Glu Glu His Arg Gly Lys Gly Val Asp Val Gln Leu Gly Pro
    130                 135                 140

gtc gcc ggc cct ctt ggc aga cac ccc gac ggt ggc aga aac tgg gag      1479
Val Ala Gly Pro Leu Gly Arg His Pro Asp Gly Gly Arg Asn Trp Glu
145                 150                 155                 160

ggt ttc tct cct gac ccc gtc ctg acc ggt gtg ctt atg gcg gag acg      1527
Gly Phe Ser Pro Asp Pro Val Leu Thr Gly Val Leu Met Ala Glu Thr
                165                 170                 175

atc aag ggt atc cag gat gcc ggt gtg att gct tgc gcc aag cac ttc      1575
Ile Lys Gly Ile Gln Asp Ala Gly Val Ile Ala Cys Ala Lys His Phe
            180                 185                 190

att ggt aac gag atg gag cac ttc cgg caa gcc ggt gag gct gtt ggc      1623
Ile Gly Asn Glu Met Glu His Phe Arg Gln Ala Gly Glu Ala Val Gly
        195                 200                 205

tat ggt ttc gat att acc gag agt gtc agc tca aat atc gac gac aag      1671
Tyr Gly Phe Asp Ile Thr Glu Ser Val Ser Ser Asn Ile Asp Asp Lys
    210                 215                 220

acg ctt cac gag ctg tac ctt tgg ccc ttt gcg gat gct gtt cgc g        1717
Thr Leu His Glu Leu Tyr Leu Trp Pro Phe Ala Asp Ala Val Arg
225                 230                 235

gtaagcagtc ccccctcat aggtgattgt acatgtgtat ttctgactcg ctttcaaag      1776

ct  ggc gtt ggt tcg ttc atg tgc tcc tac aac cag gtt aac aac agc      1823
Ala Gly Val Gly Ser Phe Met Cys Ser Tyr Asn Gln Val Asn Asn Ser
240                 245                 250                 255

tac agc tgc tcg aac agc tac ctc cta aac aag ttg ctc aaa tcg gag      1871
Tyr Ser Cys Ser Asn Ser Tyr Leu Leu Asn Lys Leu Leu Lys Ser Glu
                260                 265                 270

ctt gat ttt cag ggc ttc gtg atg agt gac tgg gga gcg cac cac agc      1919
Leu Asp Phe Gln Gly Phe Val Met Ser Asp Trp Gly Ala His His Ser
            275                 280                 285

ggc gtt gga gct gcc ctg gct ggc ctt gac atg tcg atg cca gga gac      1967
Gly Val Gly Ala Ala Leu Ala Gly Leu Asp Met Ser Met Pro Gly Asp
        290                 295                 300

acc gcc ttt ggt acc ggc aaa tcc ttc tgg gga acc aac ctg acc atc      2015
Thr Ala Phe Gly Thr Gly Lys Ser Phe Trp Gly Thr Asn Leu Thr Ile
    305                 310                 315

gcc gtt ctc aac ggt act gtt ccg gaa tgg cgt gtg gat gac atg gct      2063
Ala Val Leu Asn Gly Thr Val Pro Glu Trp Arg Val Asp Asp Met Ala
320                 325                 330                 335

gtt cgc atc atg gcg gcc ttt tac aag gtt ggt cgc gac cgt tac cag      2111
Val Arg Ile Met Ala Ala Phe Tyr Lys Val Gly Arg Asp Arg Tyr Gln
                340                 345                 350

gtg ccg gtc aac ttc gac tcg tgg acg aag gat gaa tac ggt tac gag      2159
Val Pro Val Asn Phe Asp Ser Trp Thr Lys Asp Glu Tyr Gly Tyr Glu
            355                 360                 365

cac gca ctg gtt ggc cag aac tat gtc aag gtc aat gac aag gtg gat      2207
His Ala Leu Val Gly Gln Asn Tyr Val Lys Val Asn Asp Lys Val Asp
        370                 375                 380

gtt cgt gcc gac cat gcg gac atc atc cgt caa att ggg tct gct agt      2255
Val Arg Ala Asp His Ala Asp Ile Ile Arg Gln Ile Gly Ser Ala Ser
    385                 390                 395

gtt gtc ctt ctt aag aac gat gga gga ctc cca ttg acc ggc tat gaa      2303
Val Val Leu Leu Lys Asn Asp Gly Gly Leu Pro Leu Thr Gly Tyr Glu
400                 405                 410                 415

aag ttc acc gga gtt ttt gga gag gat gcc gga tcg aac cgt tgg ggc      2351
Lys Phe Thr Gly Val Phe Gly Glu Asp Ala Gly Ser Asn Arg Trp Gly
```

-continued

```
                420                 425                 430

gct gac ggc tgc tct gat cgt ggt tgc gac aac ggc acg ttg gca atg     2399
Ala Asp Gly Cys Ser Asp Arg Gly Cys Asp Asn Gly Thr Leu Ala Met
            435                 440                 445

ggt tgg ggc agt ggc act gct gac ttc ccc tac ctt gtc act ccc gag     2447
Gly Trp Gly Ser Gly Thr Ala Asp Phe Pro Tyr Leu Val Thr Pro Glu
        450                 455                 460

cag gca atc cag aat gaa atc ctt tcc aag ggg aag ggg tta             2489
Gln Ala Ile Gln Asn Glu Ile Leu Ser Lys Gly Lys Gly Leu
    465                 470                 475

gtgagtgctg tcaccgacaa tggtgccctt gaccagatgg aacaggttgc gtctcaggcc   2549

aggtattcct tcctccgtat ccctagcaat cgaatctcca ctgactttag gac agc      2605
                                                       Asp Ser

gtt tct atc gtt ttc gtc aac gcc gac tct ggt gaa ggc tac atc aac     2653
Val Ser Ile Val Phe Val Asn Ala Asp Ser Gly Glu Gly Tyr Ile Asn
480                 485                 490                 495

gtt gat ggc aac gaa ggt gat cgg aag aac ctc acc ctc tgg aaa gga     2701
Val Asp Gly Asn Glu Gly Asp Arg Lys Asn Leu Thr Leu Trp Lys Gly
                500                 505                 510

ggc gag gag gtg atc aag act gtt gca gcc aac tgc aac aac acc att     2749
Gly Glu Glu Val Ile Lys Thr Val Ala Ala Asn Cys Asn Asn Thr Ile
            515                 520                 525

gtt gtg atg cac act gtg gga cct gtc ttg atc gat gag tgg tat gac     2797
Val Val Met His Thr Val Gly Pro Val Leu Ile Asp Glu Trp Tyr Asp
        530                 535                 540

aac ccc aac gtc acc gcc atc gtc tgg gcc ggt ctt cca ggc cag gag     2845
Asn Pro Asn Val Thr Ala Ile Val Trp Ala Gly Leu Pro Gly Gln Glu
    545                 550                 555

agc ggc aac agt ctc gtc gat gtg ctc tac ggc cgt gtc agc ccc gga     2893
Ser Gly Asn Ser Leu Val Asp Val Leu Tyr Gly Arg Val Ser Pro Gly
560                 565                 570                 575

gga aag acg ccg ttt acg tgg gga aag act cgc gag tcg tac ggc gct     2941
Gly Lys Thr Pro Phe Thr Trp Gly Lys Thr Arg Glu Ser Tyr Gly Ala
                580                 585                 590

cct ctg ctc acc aaa ccc aac aac ggc aag ggt gct ccc cag gac gac     2989
Pro Leu Leu Thr Lys Pro Asn Asn Gly Lys Gly Ala Pro Gln Asp Asp
            595                 600                 605

ttc acc gag ggc gtc ttc atc gac tac aga agg ttc gac aag tac aac     3037
Phe Thr Glu Gly Val Phe Ile Asp Tyr Arg Arg Phe Asp Lys Tyr Asn
        610                 615                 620

gag acg ccc atc tat gag ttc ggg ttt ggt ctg agt tat act act ttt     3085
Glu Thr Pro Ile Tyr Glu Phe Gly Phe Gly Leu Ser Tyr Thr Thr Phe
    625                 630                 635

gaa tac tcg aac atc tac gtc cag ccc ctt aac gca cga cct tac acc     3133
Glu Tyr Ser Asn Ile Tyr Val Gln Pro Leu Asn Ala Arg Pro Tyr Thr
640                 645                 650                 655

cca gcc tcc ggc agc acc aag gcg gct cct acc ttt ggg aat atc agc     3181
Pro Ala Ser Gly Ser Thr Lys Ala Ala Pro Thr Phe Gly Asn Ile Ser
                660                 665                 670

acg gac tat gca gat tac ttg tac cct gag gat ata cac aag gtc cca     3229
Thr Asp Tyr Ala Asp Tyr Leu Tyr Pro Glu Asp Ile His Lys Val Pro
            675                 680                 685

tta tac atc tat cct tgg ctt aac acg acg gac ccc gaa gaa gtc ctc     3277
Leu Tyr Ile Tyr Pro Trp Leu Asn Thr Thr Asp Pro Glu Glu Val Leu
        690                 695                 700

cgg cga tcc cga ctt acg gaa atg aag gcc gag gac tac atc cca tct     3325
Arg Arg Ser Arg Leu Thr Glu Met Lys Ala Glu Asp Tyr Ile Pro Ser
    705                 710                 715
```

```
ggc gcg act gat gga tct cct cag ccc atc ctt ccg gca ggc ggt gct      3373
Gly Ala Thr Asp Gly Ser Pro Gln Pro Ile Leu Pro Ala Gly Gly Ala
720                 725                 730                 735

cct ggt ggc aac ccg ggt ctc tat gat gag atg tac agg gta tct gca      3421
Pro Gly Gly Asn Pro Gly Leu Tyr Asp Glu Met Tyr Arg Val Ser Ala
                740                 745                 750

atc atc acc aac acc ggt aac gtt gtt ggt gat gag gtt cct cag ctg      3469
Ile Ile Thr Asn Thr Gly Asn Val Val Gly Asp Glu Val Pro Gln Leu
            755                 760                 765

gtgagtttcg cagtctcatt gatatatgtc tttcgagttg gtcactgacc cgcgatctat   3529

ag tat gtc tct ctt ggt ggt cca gat gac ccc aag gtc gtg ctc cgc       3576
   Tyr Val Ser Leu Gly Gly Pro Asp Asp Pro Lys Val Val Leu Arg
           770                 775                 780

aac ttt gac cgc atc acg ctc cac ccc ggc caa cag aca atg tgg acc      3624
Asn Phe Asp Arg Ile Thr Leu His Pro Gly Gln Gln Thr Met Trp Thr
        785                 790                 795

acg aca ttg acg cga cgc gat atc tcg aac tgg gac cct gcc tcc cag      3672
Thr Thr Leu Thr Arg Arg Asp Ile Ser Asn Trp Asp Pro Ala Ser Gln
    800                 805                 810

aat tgg gtt gtg acc aaa tat ccc aag aca gtc tac atc ggc agc tct      3720
Asn Trp Val Val Thr Lys Tyr Pro Lys Thr Val Tyr Ile Gly Ser Ser
815                 820                 825                 830

tcg cgg aaa ctg cac ctg cag gca ccg ctt ccc cct tac tgaggtttta       3769
Ser Arg Lys Leu His Leu Gln Ala Pro Leu Pro Pro Tyr
                835                 840

tccggaagga ggaagtaaaa acacaatgtt ttagttgtac aggcgtcttt cgtttgtgat   3829

tatccatagg catatcaaga ccactttggg ttatatatat atatatatat ataagcggcc   3889

gaggaaaggc aatgggtagc atggttcaag gggaggaacc gtcttgaaac tactctcaat   3949

ttctttcagt agatagtgca ctccggttga gtcccaaata tagttttaat aatggtaaat   4009

ggttcagaaa aagaaaatgt agaggtttca aacacgctag ttgaccctga taggaattga   4069

gcatgaatgc ctacacattc caagtcgtgt tagcgagtcg atagccgatg aacctattcc   4129

gtaggttgag gttcacccta caaataagcc aggatttaag taaatacctg ctcgtgaaat   4189

ctacaacgca tcagatcaga ggaaaattca aatggcagaa gtgcgagcac ctcggtgaga   4249

agagatcgag ctgtcgaagt cggctggaac acaggtaaag agaagtaata caattcattg   4309

atttttacat cgtttaacat gtagaaggta tctaaaatag taagtccaga tatgggccat   4369

ggagatcgcc tcggcgatct tcgggagtat ctcgggagac gcacatgacc gcgcttaacc   4429

ctgtcggttg gacccgagtc cgaccgacgt catcagcgca gcgcaggtca ggctgcgcgc   4489

aacgtcaatg ccaggggggtg ctgggacagt tgcatatcaa tcgatcagtc aattaaagca   4549

tctgctttcc acgttctttt tttatcacct ttcacttccc ctgtcccact tgccttggga   4609

ttgttgagcc caaagaagaa ggagaagaaa atgggctcga caccccggaa cgggtggtcg   4669

acgagcacat catcagcagc gtcttattat caacattccc aaccaccggc cctcgttctc   4729

ctcgtctacc cgctcactct cctcctcggc tccctgtaca gagccatttc ccccaccgcg   4789

cgggtgaggc acgatgctgc agaccctgct ctggccccga ccatagcgtc cgacatcaac   4849

ctgtcccagt catcccggta ttcccattcc catagcaaca gcaacagccc ggtcaattac   4909

ttcgcccgca aggacaacat ctttaacgtc tacttcgtca agatcggctg gttctggacg   4969

accctcgcct tcctcacgtt actcctcacc cagcctgcct acacaaacgc cggtcccctg   5029

cgcgcccgac gcaccctcca agccctgtcc cgctacgcca tcgtcaccct actacctgga   5089

tcc                                                                  5092
```

<210> SEQ ID NO 22
<211> LENGTH: 843
<212> TYPE: PRT
<213> ORGANISM: Thermoascus aurantiacus

<400> SEQUENCE: 22

```
Met Arg Leu Gly Trp Leu Glu Leu Ala Val Ala Ala Ala Ala Thr Val
1               5                   10                  15

Ala Ser Ala Lys Asp Asp Leu Ala Tyr Ser Pro Pro Phe Tyr Pro Ser
            20                  25                  30

Pro Trp Met Asn Gly Asn Gly Glu Trp Ala Glu Ala Tyr Arg Arg Ala
        35                  40                  45

Val Asp Phe Val Ser Gln Leu Thr Leu Ala Glu Lys Val Asn Leu Thr
    50                  55                  60

Thr Gly Val Gly Trp Met Gln Glu Lys Cys Val Gly Glu Thr Gly Ser
65                  70                  75                  80

Ile Pro Arg Leu Gly Phe Arg Gly Leu Cys Leu Gln Asp Ser Pro Leu
                85                  90                  95

Gly Val Arg Phe Ala Asp Tyr Val Ser Ala Phe Pro Ala Gly Val Asn
            100                 105                 110

Val Ala Ala Thr Trp Asp Lys Asn Leu Ala Tyr Leu Arg Gly Lys Ala
        115                 120                 125

Met Gly Glu Glu His Arg Gly Lys Gly Val Asp Val Gln Leu Gly Pro
    130                 135                 140

Val Ala Gly Pro Leu Gly Arg His Pro Asp Gly Gly Arg Asn Trp Glu
145                 150                 155                 160

Gly Phe Ser Pro Asp Pro Val Leu Thr Gly Val Leu Met Ala Glu Thr
                165                 170                 175

Ile Lys Gly Ile Gln Asp Ala Gly Val Ile Ala Cys Ala Lys His Phe
            180                 185                 190

Ile Gly Asn Glu Met Glu His Phe Arg Gln Ala Gly Glu Ala Val Gly
        195                 200                 205

Tyr Gly Phe Asp Ile Thr Glu Ser Val Ser Ser Asn Ile Asp Asp Lys
    210                 215                 220

Thr Leu His Glu Leu Tyr Leu Trp Pro Phe Ala Asp Ala Val Arg Ala
225                 230                 235                 240

Gly Val Gly Ser Phe Met Cys Ser Tyr Asn Gln Val Asn Asn Ser Tyr
                245                 250                 255

Ser Cys Ser Asn Ser Tyr Leu Leu Asn Lys Leu Leu Lys Ser Glu Leu
            260                 265                 270

Asp Phe Gln Gly Phe Val Met Ser Asp Trp Gly Ala His His Ser Gly
        275                 280                 285

Val Gly Ala Ala Leu Ala Gly Leu Asp Met Ser Met Pro Gly Asp Thr
    290                 295                 300

Ala Phe Gly Thr Gly Lys Ser Phe Trp Gly Thr Asn Leu Thr Ile Ala
305                 310                 315                 320

Val Leu Asn Gly Thr Val Pro Glu Trp Arg Val Asp Asp Met Ala Val
                325                 330                 335

Arg Ile Met Ala Ala Phe Tyr Lys Val Gly Arg Asp Arg Tyr Gln Val
            340                 345                 350

Pro Val Asn Phe Asp Ser Trp Thr Lys Asp Glu Tyr Gly Tyr Glu His
        355                 360                 365

Ala Leu Val Gly Gln Asn Tyr Val Lys Val Asn Asp Lys Val Asp Val
```

```
    370                 375                 380

Arg Ala Asp His Ala Asp Ile Ile Arg Gln Ile Gly Ser Ala Ser Val
385                 390                 395                 400

Val Leu Leu Lys Asn Asp Gly Gly Leu Pro Leu Thr Gly Tyr Glu Lys
                405                 410                 415

Phe Thr Gly Val Phe Gly Glu Asp Ala Gly Ser Asn Arg Trp Gly Ala
            420                 425                 430

Asp Gly Cys Ser Asp Arg Gly Cys Asp Asn Gly Thr Leu Ala Met Gly
        435                 440                 445

Trp Gly Ser Gly Thr Ala Asp Phe Pro Tyr Leu Val Thr Pro Glu Gln
    450                 455                 460

Ala Ile Gln Asn Glu Ile Leu Ser Lys Gly Lys Gly Leu Asp Ser Val
465                 470                 475                 480

Ser Ile Val Phe Val Asn Ala Asp Ser Gly Glu Gly Tyr Ile Asn Val
                485                 490                 495

Asp Gly Asn Glu Gly Asp Arg Lys Asn Leu Thr Leu Trp Lys Gly Gly
            500                 505                 510

Glu Glu Val Ile Lys Thr Val Ala Ala Asn Cys Asn Asn Thr Ile Val
        515                 520                 525

Val Met His Thr Val Gly Pro Val Leu Ile Asp Glu Trp Tyr Asp Asn
    530                 535                 540

Pro Asn Val Thr Ala Ile Val Trp Ala Gly Leu Pro Gly Gln Glu Ser
545                 550                 555                 560

Gly Asn Ser Leu Val Asp Val Leu Tyr Gly Arg Val Ser Pro Gly Gly
                565                 570                 575

Lys Thr Pro Phe Thr Trp Gly Lys Thr Arg Glu Ser Tyr Gly Ala Pro
            580                 585                 590

Leu Leu Thr Lys Pro Asn Asn Gly Lys Gly Ala Pro Gln Asp Asp Phe
        595                 600                 605

Thr Glu Gly Val Phe Ile Asp Tyr Arg Arg Phe Asp Lys Tyr Asn Glu
    610                 615                 620

Thr Pro Ile Tyr Glu Phe Gly Phe Gly Leu Ser Tyr Thr Thr Phe Glu
625                 630                 635                 640

Tyr Ser Asn Ile Tyr Val Gln Pro Leu Asn Ala Arg Pro Tyr Thr Pro
                645                 650                 655

Ala Ser Gly Ser Thr Lys Ala Ala Pro Thr Phe Gly Asn Ile Ser Thr
            660                 665                 670

Asp Tyr Ala Asp Tyr Leu Tyr Pro Glu Asp Ile His Lys Val Pro Leu
        675                 680                 685

Tyr Ile Tyr Pro Trp Leu Asn Thr Thr Asp Pro Glu Glu Val Leu Arg
    690                 695                 700

Arg Ser Arg Leu Thr Glu Met Lys Ala Glu Asp Tyr Ile Pro Ser Gly
705                 710                 715                 720

Ala Thr Asp Gly Ser Pro Gln Pro Ile Leu Pro Ala Gly Gly Ala Pro
                725                 730                 735

Gly Gly Asn Pro Gly Leu Tyr Asp Glu Met Tyr Arg Val Ser Ala Ile
            740                 745                 750

Ile Thr Asn Thr Gly Asn Val Val Gly Asp Glu Val Pro Gln Leu Tyr
        755                 760                 765

Val Ser Leu Gly Gly Pro Asp Asp Pro Lys Val Val Leu Arg Asn Phe
    770                 775                 780

Asp Arg Ile Thr Leu His Pro Gly Gln Gln Thr Met Trp Thr Thr Thr
785                 790                 795                 800
```

```
Leu Thr Arg Arg Asp Ile Ser Asn Trp Asp Pro Ala Ser Gln Asn Trp
                805                 810                 815

Val Val Thr Lys Tyr Pro Lys Thr Val Tyr Ile Gly Ser Ser Ser Arg
            820                 825                 830

Lys Leu His Leu Gln Ala Pro Leu Pro Pro Tyr
        835                 840


<210> SEQ ID NO 23
<211> LENGTH: 3510
<212> TYPE: DNA
<213> ORGANISM: Acremonium thermophilum
<220> FEATURE:
<221> NAME/KEY: CDS
<222> LOCATION: (391)..(447)
<220> FEATURE:
<221> NAME/KEY: Intron
<222> LOCATION: (448)..(539)
<220> FEATURE:
<221> NAME/KEY: CDS
<222> LOCATION: (540)..(685)
<220> FEATURE:
<221> NAME/KEY: Intron
<222> LOCATION: (686)..(759)
<220> FEATURE:
<221> NAME/KEY: CDS
<222> LOCATION: (760)..(1148)
<220> FEATURE:
<221> NAME/KEY: Intron
<222> LOCATION: (1149)..(1217)
<220> FEATURE:
<221> NAME/KEY: CDS
<222> LOCATION: (1218)..(3208)

<400> SEQUENCE: 23

gcaggtagct acgacattcg acggtccacg cccagtggcg tctgctcggc cgtctgggaa      60

ccatgcacgc ccgcctctta ggtcgagcga ggtataacat actatctgca cggctaccta     120

tatattacgt cgatgtcacc cgcaggatgc gagcaccatt acttcgtgtc tcacccgccc     180

ttccgctccg catctcgtga acctaaaccc acgcgggcac actgcttctt gtgagagcct     240

ctacccgttc cacaagagcc atagctagag agagaagggc agccaaggga ccggtcaagc     300

ggcgctcttc atcgcaccaa tctcgacaac ccggcagacg tcaccaccgg ctcccgccgc     360

acgacgtcac acgggactga ctacgaagac atg agg cag gcc ctt gtt tcg ctg      414
                                 Met Arg Gln Ala Leu Val Ser Leu
                                 1               5

gcc ttg ctg gcc agc agc cct gtt tcg gcg gcg gtgaccgcca gggacgccca     467
Ala Leu Leu Ala Ser Ser Pro Val Ser Ala Ala
    10                  15

ggtatggtcc caactgctct tcctccctgt ttcctcctct accggtgctg acaacgacaa     527

tagctgcacc ag cga gaa ctc gcc act tcc gac cct ttc tat cct tcg cca     578
              Arg Glu Leu Ala Thr Ser Asp Pro Phe Tyr Pro Ser Pro
              20                  25                  30

tgg atg aac cct gaa gcc aat ggc tgg gag gac gcc tac gcc aag gcc       626
Trp Met Asn Pro Glu Ala Asn Gly Trp Glu Asp Ala Tyr Ala Lys Ala
        35                  40                  45

aag gcg ttc gtt tcc cag ctg acg ctc ttg gaa aag gtc aac ctg acg       674
Lys Ala Phe Val Ser Gln Leu Thr Leu Leu Glu Lys Val Asn Leu Thr
    50                  55                  60

act ggc atc gg  gtgagtcttg ttctctcctg tagaaccgcc taccagaaga           725
Thr Gly Ile Gly
65

cattcaggaa gtgctaatga tgggcggttg acag c tgg caa gga gga caa tgc       778
                                        Trp Gln Gly Gly Gln Cys
```

```
                                        70

gtg ggc aac gtc ggt tcc gtc ccg cgt ctc ggc ctt cgc agc ctg tgc      826
Val Gly Asn Val Gly Ser Val Pro Arg Leu Gly Leu Arg Ser Leu Cys
75                  80                  85                  90

atg cag gac tcc ccc gtg ggt atc cgc ttt ggg gac tac gtc tcc gtc      874
Met Gln Asp Ser Pro Val Gly Ile Arg Phe Gly Asp Tyr Val Ser Val
                95                  100                 105

ttc ccc tct ggt cag acc acg gct gcc acc ttc gac aag ggt ctg atg      922
Phe Pro Ser Gly Gln Thr Thr Ala Ala Thr Phe Asp Lys Gly Leu Met
            110                 115                 120

aac cgt cgc ggc aat gcc atg ggc cag gag cac aaa gga aag ggt gtc      970
Asn Arg Arg Gly Asn Ala Met Gly Gln Glu His Lys Gly Lys Gly Val
        125                 130                 135

aac gtc ctg ctc ggc ccg gtc gct ggc ccc att ggc cgt acg ccc gag     1018
Asn Val Leu Leu Gly Pro Val Ala Gly Pro Ile Gly Arg Thr Pro Glu
    140                 145                 150

ggg gga cga aac tgg gag ggc ttc tcc ccc gac ccc gtc cta acg ggt     1066
Gly Gly Arg Asn Trp Glu Gly Phe Ser Pro Asp Pro Val Leu Thr Gly
155                 160                 165                 170

att gcc ttg gcc gaa acg atc aag gga atc cag gat gct ggt gtc att     1114
Ile Ala Leu Ala Glu Thr Ile Lys Gly Ile Gln Asp Ala Gly Val Ile
                175                 180                 185

gct tgc gcc aag cat ttc atc gcg aac gaa cag g gtgcgtgatg            1158
Ala Cys Ala Lys His Phe Ile Ala Asn Glu Gln
            190                 195

gaacgcggga cgtgctctga tgcaaaccca cgagcactga ccacgctttc ctcgaacag    1217

aa  cac ttc cgc cag tcc ggc gag gcc cag ggc tac ggc ttt gac atc     1264
Glu His Phe Arg Gln Ser Gly Glu Ala Gln Gly Tyr Gly Phe Asp Ile
        200                 205                 210

tcc gag tcg ctg tcg tcc aac atc gac gac aag acc atg cac gag ctg     1312
Ser Glu Ser Leu Ser Ser Asn Ile Asp Asp Lys Thr Met His Glu Leu
    215                 220                 225

tat ctg tgg ccc ttc gcc gac ggc gtg cgt gcc ggc gtc ggc gcc atc     1360
Tyr Leu Trp Pro Phe Ala Asp Gly Val Arg Ala Gly Val Gly Ala Ile
230                 235                 240                 245

atg tgc tcg tac aac cag atc aac aac tcg tac ggg tgc cag aac tcc     1408
Met Cys Ser Tyr Asn Gln Ile Asn Asn Ser Tyr Gly Cys Gln Asn Ser
                250                 255                 260

aag acc ctg aac aac ctg ctc aag aac gag ctc ggc ttc cag ggc ttc     1456
Lys Thr Leu Asn Asn Leu Leu Lys Asn Glu Leu Gly Phe Gln Gly Phe
            265                 270                 275

gtc atg agc gac tgg cag gcc cag cac acc ggc gcg gcc agc gcc gtc     1504
Val Met Ser Asp Trp Gln Ala Gln His Thr Gly Ala Ala Ser Ala Val
        280                 285                 290

gcc ggc ctg gac atg acc atg ccc ggc gac acc agc ttc aac acc ggc     1552
Ala Gly Leu Asp Met Thr Met Pro Gly Asp Thr Ser Phe Asn Thr Gly
    295                 300                 305

ctc agc tac tgg ggc acg aac ctc acc ctc gcc gtc ctg aac ggc acc     1600
Leu Ser Tyr Trp Gly Thr Asn Leu Thr Leu Ala Val Leu Asn Gly Thr
310                 315                 320                 325

gtc ccc gag tac cgc atc gac gac atg gtc atg cgc atc atg gcc gcc     1648
Val Pro Glu Tyr Arg Ile Asp Asp Met Val Met Arg Ile Met Ala Ala
                330                 335                 340

ttc ttc aag acc ggc cag acc ctg gac ctg ccg ccc atc aac ttc gac     1696
Phe Phe Lys Thr Gly Gln Thr Leu Asp Leu Pro Pro Ile Asn Phe Asp
            345                 350                 355

tcg tgg acc acc gac acc ttc ggc ccg ctc cac ttc gcc gtc aac gag     1744
Ser Trp Thr Thr Asp Thr Phe Gly Pro Leu His Phe Ala Val Asn Glu
        360                 365                 370
```

```
gac cgc cag cag atc aac tgg cac gtc aac gtc cag gac aac cat ggc      1792
Asp Arg Gln Gln Ile Asn Trp His Val Asn Val Gln Asp Asn His Gly
    375                 380                 385

agc ctc atc cgc gag atc gcg gcc aag gga acc gtc ctg ctg aag aac      1840
Ser Leu Ile Arg Glu Ile Ala Ala Lys Gly Thr Val Leu Leu Lys Asn
390                 395                 400                 405

acc ggg tcc ctc ccg ctc aac aag ccc aag ttc ctc gtc gtg gtc ggc      1888
Thr Gly Ser Leu Pro Leu Asn Lys Pro Lys Phe Leu Val Val Val Gly
                410                 415                 420

gac gac gcg ggc ccc aac ccg gcg gga ccc aac gcc tgc ccc gac cgc      1936
Asp Asp Ala Gly Pro Asn Pro Ala Gly Pro Asn Ala Cys Pro Asp Arg
            425                 430                 435

gga tgc gac gtc ggc acc ctc ggc atg gcc tgg ggc tcc ggc tcg gcc      1984
Gly Cys Asp Val Gly Thr Leu Gly Met Ala Trp Gly Ser Gly Ser Ala
        440                 445                 450

aac ttc ccc tac ctg atc acc ccg gac gcc gcg ctg cag gcg cag gcg      2032
Asn Phe Pro Tyr Leu Ile Thr Pro Asp Ala Ala Leu Gln Ala Gln Ala
    455                 460                 465

atc aag gac ggc acc cgc tac gag agc gtg ctg tcc aac tac cag ctc      2080
Ile Lys Asp Gly Thr Arg Tyr Glu Ser Val Leu Ser Asn Tyr Gln Leu
470                 475                 480                 485

gac cag acc aag gcg ctg gtc acc cag gcc aac gcc acg gcc atc gtc      2128
Asp Gln Thr Lys Ala Leu Val Thr Gln Ala Asn Ala Thr Ala Ile Val
                490                 495                 500

ttc gtc aac gcc gac tcg ggc gag ggc tac atc aac gtc gac ggc aac      2176
Phe Val Asn Ala Asp Ser Gly Glu Gly Tyr Ile Asn Val Asp Gly Asn
            505                 510                 515

gag ggc gac cgc aag aac ctc acg ctc tgg cac gac ggc gac gcc ctg      2224
Glu Gly Asp Arg Lys Asn Leu Thr Leu Trp His Asp Gly Asp Ala Leu
        520                 525                 530

atc aag agc gtg gcc ggc tgg aac ccg aac acc atc gtc gtc atc cac      2272
Ile Lys Ser Val Ala Gly Trp Asn Pro Asn Thr Ile Val Val Ile His
    535                 540                 545

tcg acc ggc ccc gtc ctc gtg acc gac tgg tac gac cac ccc aac atc      2320
Ser Thr Gly Pro Val Leu Val Thr Asp Trp Tyr Asp His Pro Asn Ile
550                 555                 560                 565

acc gcc atc ctg tgg gcc ggc gtg ccc ggg cag gag tcc ggc aac gcc      2368
Thr Ala Ile Leu Trp Ala Gly Val Pro Gly Gln Glu Ser Gly Asn Ala
                570                 575                 580

atc acc gac gtc ctc tac gga aaa gtc aac ccg tcg ggc cgc agc ccc      2416
Ile Thr Asp Val Leu Tyr Gly Lys Val Asn Pro Ser Gly Arg Ser Pro
            585                 590                 595

ttc acc tgg ggt ccg acc cgc gag agc tac ggc acc gac gtc ctc tac      2464
Phe Thr Trp Gly Pro Thr Arg Glu Ser Tyr Gly Thr Asp Val Leu Tyr
        600                 605                 610

act ccc aac aac ggc aag ggc gcg ccg cag cag gcc ttc tcc gag ggc      2512
Thr Pro Asn Asn Gly Lys Gly Ala Pro Gln Gln Ala Phe Ser Glu Gly
    615                 620                 625

gtc ttc atc gac tac cgc cac ttc gac cgc acc aac gcg tcc gtc atc      2560
Val Phe Ile Asp Tyr Arg His Phe Asp Arg Thr Asn Ala Ser Val Ile
630                 635                 640                 645

tac gag ttc ggc cac ggc ctc agc tac acg acg ttc cag tac agc aac      2608
Tyr Glu Phe Gly His Gly Leu Ser Tyr Thr Thr Phe Gln Tyr Ser Asn
                650                 655                 660

atc cag gtg gtc aag tcc aac gcc ggc gcg tac aag ccc acg acg ggc      2656
Ile Gln Val Val Lys Ser Asn Ala Gly Ala Tyr Lys Pro Thr Thr Gly
            665                 670                 675

acg acc atc ccc gcg ccc acg ttt ggc agc ttc tcc aag gac ctc aag      2704
Thr Thr Ile Pro Ala Pro Thr Phe Gly Ser Phe Ser Lys Asp Leu Lys
```

```
        680                 685                 690

gac tac ctc ttc ccg tcg gac cag ttc cgc tac atc acc cag tac atc     2752
Asp Tyr Leu Phe Pro Ser Asp Gln Phe Arg Tyr Ile Thr Gln Tyr Ile
    695                 700                 705

tac ccg tac ctc aac tcc acc gac ccg gcc aag gcg tcg ctc gac ccg     2800
Tyr Pro Tyr Leu Asn Ser Thr Asp Pro Ala Lys Ala Ser Leu Asp Pro
710                 715                 720                 725

cac tac ggc aag acg gcg gcc gag ttt ctg ccg ccg cac gcg ctg gac     2848
His Tyr Gly Lys Thr Ala Ala Glu Phe Leu Pro Pro His Ala Leu Asp
                730                 735                 740

agc aac ccg cag ccg ctg ctg cgg tcg tcg ggc aag aac gag ccc ggc     2896
Ser Asn Pro Gln Pro Leu Leu Arg Ser Ser Gly Lys Asn Glu Pro Gly
            745                 750                 755

ggc aac cgc cag ctg tac gac atc ctg tac acg gtg acg gcg gac atc     2944
Gly Asn Arg Gln Leu Tyr Asp Ile Leu Tyr Thr Val Thr Ala Asp Ile
        760                 765                 770

acc aac acg ggc agc atc gtg ggt gcg gag gtg ccg cag ctg tac gtg     2992
Thr Asn Thr Gly Ser Ile Val Gly Ala Glu Val Pro Gln Leu Tyr Val
    775                 780                 785

tcg ctg ggc ggg ccc gac gac ccc aaa gtg gtc ctg cgc ggg ttc gac     3040
Ser Leu Gly Gly Pro Asp Asp Pro Lys Val Val Leu Arg Gly Phe Asp
790                 795                 800                 805

cgc atc cgc atc gac ccg ggc aag acg gcg cag ttc cgc gtc acc ctg     3088
Arg Ile Arg Ile Asp Pro Gly Lys Thr Ala Gln Phe Arg Val Thr Leu
                810                 815                 820

acc cgc cgg gat ctc agc aac tgg gac ccg gcg atc cag gac tgg gtc     3136
Thr Arg Arg Asp Leu Ser Asn Trp Asp Pro Ala Ile Gln Asp Trp Val
            825                 830                 835

atc agc aag tac ccc aag aag gtg tac atc ggc cgg agc agc agg aag     3184
Ile Ser Lys Tyr Pro Lys Lys Val Tyr Ile Gly Arg Ser Ser Arg Lys
        840                 845                 850

ctg gaa ctc tcc gcc gac ctc gcg tgatccggcg acggccaagt acgtatgtgg    3238
Leu Glu Leu Ser Ala Asp Leu Ala
    855                 860

actgccatcc gaacacctat actttttggc taggtagggg gagcagcaag gcctgagcat   3298

atactctctc cattgcacat ttctaatgta aatatatata tcattaattg ggagacccaa   3358

actcgaattt atgcatgcgt acaaagtgtg ttgaacaagt ttcggtccag cagatagtaa   3418

ccgtcttagt tcgtccatcc ctctctcgaa tgcgctgtat acacatgcgt atatagacgt   3478

tgtataggtg ccattgctag caatgcaagc tt                                 3510


<210> SEQ ID NO 24
<211> LENGTH: 861
<212> TYPE: PRT
<213> ORGANISM: Acremonium thermophilum

<400> SEQUENCE: 24

Met Arg Gln Ala Leu Val Ser Leu Ala Leu Leu Ala Ser Ser Pro Val
1               5                   10                  15

Ser Ala Ala Arg Glu Leu Ala Thr Ser Asp Pro Phe Tyr Pro Ser Pro
            20                  25                  30

Trp Met Asn Pro Glu Ala Asn Gly Trp Glu Asp Ala Tyr Ala Lys Ala
        35                  40                  45

Lys Ala Phe Val Ser Gln Leu Thr Leu Leu Glu Lys Val Asn Leu Thr
    50                  55                  60

Thr Gly Ile Gly Trp Gln Gly Gly Gln Cys Val Gly Asn Val Gly Ser
65                  70                  75                  80
```

```
Val Pro Arg Leu Gly Leu Arg Ser Leu Cys Met Gln Asp Ser Pro Val
                85                  90                  95

Gly Ile Arg Phe Gly Asp Tyr Val Ser Val Phe Pro Ser Gly Gln Thr
            100                 105                 110

Thr Ala Ala Thr Phe Asp Lys Gly Leu Met Asn Arg Arg Gly Asn Ala
        115                 120                 125

Met Gly Gln Glu His Lys Gly Lys Gly Val Asn Val Leu Leu Gly Pro
    130                 135                 140

Val Ala Gly Pro Ile Gly Arg Thr Pro Glu Gly Gly Arg Asn Trp Glu
145                 150                 155                 160

Gly Phe Ser Pro Asp Pro Val Leu Thr Gly Ile Ala Leu Ala Glu Thr
                165                 170                 175

Ile Lys Gly Ile Gln Asp Ala Gly Val Ile Ala Cys Ala Lys His Phe
            180                 185                 190

Ile Ala Asn Glu Gln Glu His Phe Arg Gln Ser Gly Glu Ala Gln Gly
        195                 200                 205

Tyr Gly Phe Asp Ile Ser Glu Ser Leu Ser Ser Asn Ile Asp Asp Lys
    210                 215                 220

Thr Met His Glu Leu Tyr Leu Trp Pro Phe Ala Asp Gly Val Arg Ala
225                 230                 235                 240

Gly Val Gly Ala Ile Met Cys Ser Tyr Asn Gln Ile Asn Asn Ser Tyr
                245                 250                 255

Gly Cys Gln Asn Ser Lys Thr Leu Asn Asn Leu Leu Lys Asn Glu Leu
            260                 265                 270

Gly Phe Gln Gly Phe Val Met Ser Asp Trp Gln Ala Gln His Thr Gly
        275                 280                 285

Ala Ala Ser Ala Val Ala Gly Leu Asp Met Thr Met Pro Gly Asp Thr
    290                 295                 300

Ser Phe Asn Thr Gly Leu Ser Tyr Trp Gly Thr Asn Leu Thr Leu Ala
305                 310                 315                 320

Val Leu Asn Gly Thr Val Pro Glu Tyr Arg Ile Asp Asp Met Val Met
                325                 330                 335

Arg Ile Met Ala Ala Phe Phe Lys Thr Gly Gln Thr Leu Asp Leu Pro
            340                 345                 350

Pro Ile Asn Phe Asp Ser Trp Thr Thr Asp Thr Phe Gly Pro Leu His
        355                 360                 365

Phe Ala Val Asn Glu Asp Arg Gln Gln Ile Asn Trp His Val Asn Val
    370                 375                 380

Gln Asp Asn His Gly Ser Leu Ile Arg Glu Ile Ala Ala Lys Gly Thr
385                 390                 395                 400

Val Leu Leu Lys Asn Thr Gly Ser Leu Pro Leu Asn Lys Pro Lys Phe
                405                 410                 415

Leu Val Val Val Gly Asp Asp Ala Gly Pro Asn Pro Ala Gly Pro Asn
            420                 425                 430

Ala Cys Pro Asp Arg Gly Cys Asp Val Gly Thr Leu Gly Met Ala Trp
        435                 440                 445

Gly Ser Gly Ser Ala Asn Phe Pro Tyr Leu Ile Thr Pro Asp Ala Ala
    450                 455                 460

Leu Gln Ala Gln Ala Ile Lys Asp Gly Thr Arg Tyr Glu Ser Val Leu
465                 470                 475                 480

Ser Asn Tyr Gln Leu Asp Gln Thr Lys Ala Leu Val Thr Gln Ala Asn
                485                 490                 495

Ala Thr Ala Ile Val Phe Val Asn Ala Asp Ser Gly Glu Gly Tyr Ile
```

```
            500                 505                 510

Asn Val Asp Gly Asn Glu Gly Asp Arg Lys Asn Leu Thr Leu Trp His
        515                 520                 525

Asp Gly Asp Ala Leu Ile Lys Ser Val Ala Gly Trp Asn Pro Asn Thr
    530                 535                 540

Ile Val Val Ile His Ser Thr Gly Pro Val Leu Val Thr Asp Trp Tyr
545                 550                 555                 560

Asp His Pro Asn Ile Thr Ala Ile Leu Trp Ala Gly Val Pro Gly Gln
                565                 570                 575

Glu Ser Gly Asn Ala Ile Thr Asp Val Leu Tyr Gly Lys Val Asn Pro
            580                 585                 590

Ser Gly Arg Ser Pro Phe Thr Trp Gly Pro Thr Arg Glu Ser Tyr Gly
        595                 600                 605

Thr Asp Val Leu Tyr Thr Pro Asn Asn Gly Lys Gly Ala Pro Gln Gln
    610                 615                 620

Ala Phe Ser Glu Gly Val Phe Ile Asp Tyr Arg His Phe Asp Arg Thr
625                 630                 635                 640

Asn Ala Ser Val Ile Tyr Glu Phe Gly His Gly Leu Ser Tyr Thr Thr
                645                 650                 655

Phe Gln Tyr Ser Asn Ile Gln Val Val Lys Ser Asn Ala Gly Ala Tyr
            660                 665                 670

Lys Pro Thr Thr Gly Thr Thr Ile Pro Ala Pro Thr Phe Gly Ser Phe
        675                 680                 685

Ser Lys Asp Leu Lys Asp Tyr Leu Phe Pro Ser Asp Gln Phe Arg Tyr
    690                 695                 700

Ile Thr Gln Tyr Ile Tyr Pro Tyr Leu Asn Ser Thr Asp Pro Ala Lys
705                 710                 715                 720

Ala Ser Leu Asp Pro His Tyr Gly Lys Thr Ala Ala Glu Phe Leu Pro
                725                 730                 735

Pro His Ala Leu Asp Ser Asn Pro Gln Pro Leu Leu Arg Ser Ser Gly
            740                 745                 750

Lys Asn Glu Pro Gly Gly Asn Arg Gln Leu Tyr Asp Ile Leu Tyr Thr
        755                 760                 765

Val Thr Ala Asp Ile Thr Asn Thr Gly Ser Ile Val Gly Ala Glu Val
    770                 775                 780

Pro Gln Leu Tyr Val Ser Leu Gly Gly Pro Asp Asp Pro Lys Val Val
785                 790                 795                 800

Leu Arg Gly Phe Asp Arg Ile Arg Ile Asp Pro Gly Lys Thr Ala Gln
                805                 810                 815

Phe Arg Val Thr Leu Thr Arg Arg Asp Leu Ser Asn Trp Asp Pro Ala
            820                 825                 830

Ile Gln Asp Trp Val Ile Ser Lys Tyr Pro Lys Lys Val Tyr Ile Gly
        835                 840                 845

Arg Ser Ser Arg Lys Leu Glu Leu Ser Ala Asp Leu Ala
    850                 855                 860


<210> SEQ ID NO 25
<211> LENGTH: 3392
<212> TYPE: DNA
<213> ORGANISM: Chaetomium thermophilum
<220> FEATURE:
<221> NAME/KEY: CDS
<222> LOCATION: (608)..(2405)
<220> FEATURE:
<221> NAME/KEY: Intron
<222> LOCATION: (2406)..(2457)
```

```
<220> FEATURE:
<221> NAME/KEY: CDS
<222> LOCATION: (2458)..(2861)

<400> SEQUENCE: 25

tgcggggttg ctgcgactta attaataact ggcaaaacgg cccggagctc agctctgacc     60

tccgccacat ccgctcggca ccatgccagc gcgttgcaac ggcatgaagc gctcaggttt    120

ttcttccgcc tgctccccac tgccgatggc catctgcacc ccagctcgtc acatttatct    180

cgcgcacagc gtcttcccac cagttgcctt gctcatgacg ctgttaaaga tggccctacc    240

tagccgctga gtcccacaac gccgagatgt ctttggccct ttacaaggca cgccatggcc    300

gtccaaggtc tgttcatgag tgtgtttgtg gggccgaagg acacctcagt ggccacgaaa    360

tgccgccgag cgggccagca catgtcgaga gagacatgga catttatccc cgagatgctg    420

tattagggaa ccggtccttt tctcggagcc gtgatccgag agcgttcggg agtcgttgag    480

taaaagatgt cgagttgccg ttatatatcg cgggcctgta gctatgtgcc ctctattctc    540

acaggttcaa tcatcagtcc tcgccgtgag acgtagcgcg ctgaactagc gctcgatatc    600

ttccgtc atg gct ctt cat gcc ttc ttg ttg ctg gca tca gca ttg ctg      649
        Met Ala Leu His Ala Phe Leu Leu Leu Ala Ser Ala Leu Leu
        1               5                   10

gcc cgg ggt gcc ctg agc caa cct gac aac gtc cgt cgc gct gct ccg      697
Ala Arg Gly Ala Leu Ser Gln Pro Asp Asn Val Arg Arg Ala Ala Pro
15                  20                  25                  30

acc ggg acg gcc gcc tgg gat gcc gcc cac tcg cag gct gcc gct gcc      745
Thr Gly Thr Ala Ala Trp Asp Ala Ala His Ser Gln Ala Ala Ala Ala
                35                  40                  45

gtg tcg aga tta tca cag caa gac aag atc aac att gtc acc ggc gtt      793
Val Ser Arg Leu Ser Gln Gln Asp Lys Ile Asn Ile Val Thr Gly Val
            50                  55                  60

ggc tgg ggt aag ggt cct tgc gtc ggc aat acg aac cct gtc tac agc      841
Gly Trp Gly Lys Gly Pro Cys Val Gly Asn Thr Asn Pro Val Tyr Ser
        65                  70                  75

atc aac tac cca cag ctc tgc ctg cag gat ggc cca ctg ggt atc cgc      889
Ile Asn Tyr Pro Gln Leu Cys Leu Gln Asp Gly Pro Leu Gly Ile Arg
    80                  85                  90

tcc gcc acc agc gtc acg gcc ttc acg ccg ggc att caa gcc gcg tcg      937
Ser Ala Thr Ser Val Thr Ala Phe Thr Pro Gly Ile Gln Ala Ala Ser
95                  100                 105                 110

acc tgg gat gtg gag ttg atc cgg cag cgt ggt gtc tac cta gga cag      985
Thr Trp Asp Val Glu Leu Ile Arg Gln Arg Gly Val Tyr Leu Gly Gln
                115                 120                 125

gag gcc cgg gga act ggc gtg cat gtc ctg ctc ggc ccc gtg gcc ggt     1033
Glu Ala Arg Gly Thr Gly Val His Val Leu Leu Gly Pro Val Ala Gly
            130                 135                 140

gct ctt ggc aag atc ccg cac gga ggc cgt aac tgg gaa gcc ttc ggc     1081
Ala Leu Gly Lys Ile Pro His Gly Gly Arg Asn Trp Glu Ala Phe Gly
        145                 150                 155

tcc gac ccc tac ttg gcc ggt atc gct atg tcc gag acc atc gag ggc     1129
Ser Asp Pro Tyr Leu Ala Gly Ile Ala Met Ser Glu Thr Ile Glu Gly
    160                 165                 170

att cag tcg gag ggt gtg cag gct tgc gcg aag cac tac atc gcc aat     1177
Ile Gln Ser Glu Gly Val Gln Ala Cys Ala Lys His Tyr Ile Ala Asn
175                 180                 185                 190

gag cag gaa ctc aac cgc gag aca atg agc agc aac gtc gac gac cgc     1225
Glu Gln Glu Leu Asn Arg Glu Thr Met Ser Ser Asn Val Asp Asp Arg
                195                 200                 205

act atg cac gag cta tac ctc tgg ccg ttc gcc gac gcc gtg cat tcc     1273
```

-continued

```
Thr Met His Glu Leu Tyr Leu Trp Pro Phe Ala Asp Ala Val His Ser
            210                 215                 220

aac gtg gcc agc gtc atg tgc agc tac aac aag ctc aac ggc acc tgg     1321
Asn Val Ala Ser Val Met Cys Ser Tyr Asn Lys Leu Asn Gly Thr Trp
        225                 230                 235

ctc tgc gag aac gat agg gcc caa aac cag ctg ctt aag agg gag ctc     1369
Leu Cys Glu Asn Asp Arg Ala Gln Asn Gln Leu Leu Lys Arg Glu Leu
    240                 245                 250

ggc ttc cgc ggc tac atc gtg agc gac tgg aac gcg cag cac acc acc     1417
Gly Phe Arg Gly Tyr Ile Val Ser Asp Trp Asn Ala Gln His Thr Thr
255                 260                 265                 270

gtg ggc tcg gcc aac agt ggc atg gac atg acc atg cct ggc agc gac     1465
Val Gly Ser Ala Asn Ser Gly Met Asp Met Thr Met Pro Gly Ser Asp
                275                 280                 285

ttc aac ggc tgg aac gtc ctc tgg ggt ccg cag ctc aac aac gcc gtc     1513
Phe Asn Gly Trp Asn Val Leu Trp Gly Pro Gln Leu Asn Asn Ala Val
            290                 295                 300

aac agc ggc cag gtc tcg cag tcc cgc ctc aac gac atg gtc cag cgc     1561
Asn Ser Gly Gln Val Ser Gln Ser Arg Leu Asn Asp Met Val Gln Arg
        305                 310                 315

att ctt gct gcg tgg tac ctc ctc ggc cag aac tcc gga tac ccg tcc     1609
Ile Leu Ala Ala Trp Tyr Leu Leu Gly Gln Asn Ser Gly Tyr Pro Ser
    320                 325                 330

atc aac ctg cgt gcc aac gtc caa gcc aac cac aag gag aat gtg cgt     1657
Ile Asn Leu Arg Ala Asn Val Gln Ala Asn His Lys Glu Asn Val Arg
335                 340                 345                 350

gcc gta gcc cgc gat ggc atc gtc ctc ctc aag aac gac ggc att ctg     1705
Ala Val Ala Arg Asp Gly Ile Val Leu Leu Lys Asn Asp Gly Ile Leu
                355                 360                 365

cct ctt cag cgt ccc aat aag att gct ctt gtc ggc tcc gcc gca gtc     1753
Pro Leu Gln Arg Pro Asn Lys Ile Ala Leu Val Gly Ser Ala Ala Val
            370                 375                 380

gtc aac ccc cgt ggt atg aac gcc tgc gtg gac cgt ggc tgc aac gag     1801
Val Asn Pro Arg Gly Met Asn Ala Cys Val Asp Arg Gly Cys Asn Glu
        385                 390                 395

ggt gcc ctt ggc atg ggc tgg ggc tca ggc acg gtc gag tat ccc tac     1849
Gly Ala Leu Gly Met Gly Trp Gly Ser Gly Thr Val Glu Tyr Pro Tyr
    400                 405                 410

ttt gtt gcg ccg tat gat gct ctg cgt gag cgg gca cag cgc gat ggc     1897
Phe Val Ala Pro Tyr Asp Ala Leu Arg Glu Arg Ala Gln Arg Asp Gly
415                 420                 425                 430

acg cag atc agt ctg cat gca tcg gac aat aca aac ggg gtt aac aac     1945
Thr Gln Ile Ser Leu His Ala Ser Asp Asn Thr Asn Gly Val Asn Asn
                435                 440                 445

gcc gtg cag ggc gct gac gcg gcg ttt gtg ttc atc act gct gac tcc     1993
Ala Val Gln Gly Ala Asp Ala Ala Phe Val Phe Ile Thr Ala Asp Ser
            450                 455                 460

ggc gaa ggg tac att acc gtt gag ggc cat gct ggc gac cgg aat cat     2041
Gly Glu Gly Tyr Ile Thr Val Glu Gly His Ala Gly Asp Arg Asn His
        465                 470                 475

ctg gat cct tgg cat aat ggt aac cag ctt gtg cag gct gtt gcg cag     2089
Leu Asp Pro Trp His Asn Gly Asn Gln Leu Val Gln Ala Val Ala Gln
    480                 485                 490

gca aat aag aac gtc att gtg gtt gtg cac agc gtt ggg ccg gtt att     2137
Ala Asn Lys Asn Val Ile Val Val Val His Ser Val Gly Pro Val Ile
495                 500                 505                 510

ctg gag acg atc ctc aat acg ccc ggt gtg agg gct gtt gtt tgg gct     2185
Leu Glu Thr Ile Leu Asn Thr Pro Gly Val Arg Ala Val Val Trp Ala
                515                 520                 525
```

```
ggc ttg ccg agc cag gag agc ggt aac gcg ctg gtt gat gtg ctg tac      2233
Gly Leu Pro Ser Gln Glu Ser Gly Asn Ala Leu Val Asp Val Leu Tyr
            530                 535                 540

ggc ctt gtt tcg ccg tcg ggc aag ctt gtc tac acc att gcg aag agc      2281
Gly Leu Val Ser Pro Ser Gly Lys Leu Val Tyr Thr Ile Ala Lys Ser
        545                 550                 555

ccg agc gac tac ccg act agc att gtc cgt ggc gat gat aac ttc cgc      2329
Pro Ser Asp Tyr Pro Thr Ser Ile Val Arg Gly Asp Asp Asn Phe Arg
    560                 565                 570

gag ggt ctg ttc atc gac tac agg cac ttc gat aac gcc cgg atc gag      2377
Glu Gly Leu Phe Ile Asp Tyr Arg His Phe Asp Asn Ala Arg Ile Glu
575                 580                 585                 590

ccc cgt ttc gag ttt ggc ttc ggt ctc t gtaagtctct taccactccg          2425
Pro Arg Phe Glu Phe Gly Phe Gly Leu
                595

ttttgtaaca acccgattct aacatccccc ag ca  tac acc aac ttc agc tat      2477
                                    Ser Tyr Thr Asn Phe Ser Tyr
                                    600                 605

tcc aac ctg ggc atc tcc tcg tcc gca acc gcc ggc cca gcc acg ggc      2525
Ser Asn Leu Gly Ile Ser Ser Ser Ala Thr Ala Gly Pro Ala Thr Gly
            610                 615                 620

ccc acc gtc ccc ggc ggc ccg gcc gac ctc tgg aac tat gtc gcg acc      2573
Pro Thr Val Pro Gly Gly Pro Ala Asp Leu Trp Asn Tyr Val Ala Thr
        625                 630                 635

gtc acg gcg acc gtt acc aac acc ggc ggc gtg gaa ggt gcc gag gtc      2621
Val Thr Ala Thr Val Thr Asn Thr Gly Gly Val Glu Gly Ala Glu Val
    640                 645                 650

gct cag ctg tac atc tct ttg cca tct tcg gct cct gca tcg cca ccg      2669
Ala Gln Leu Tyr Ile Ser Leu Pro Ser Ser Ala Pro Ala Ser Pro Pro
655                 660                 665                 670

aag cag ctt cgt ggc ttt gtc aag ctt aag ttg gcg cct ggt caa agc      2717
Lys Gln Leu Arg Gly Phe Val Lys Leu Lys Leu Ala Pro Gly Gln Ser
                675                 680                 685

ggg acg gca acg ttt aga cta agg aag agg gat ttg gct tat tgg gat      2765
Gly Thr Ala Thr Phe Arg Leu Arg Lys Arg Asp Leu Ala Tyr Trp Asp
            690                 695                 700

gtg ggg agg cag aat tgg gtt gtt cct tcg ggg agg ttt ggc gtg ctt      2813
Val Gly Arg Gln Asn Trp Val Val Pro Ser Gly Arg Phe Gly Val Leu
        705                 710                 715

gtg ggg gct agt tcg agg gat att agg ttg cag ggg gag att gtt gtt      2861
Val Gly Ala Ser Ser Arg Asp Ile Arg Leu Gln Gly Glu Ile Val Val
    720                 725                 730

tagggggtta tgttcagcac ctagttgggg aattgatgtg taagttggag taggggtttt    2921

cgtgtacata cataccattt ggtcaatgtt acgacattta gtttatgaag tttcctggtg    2981

gctaccgctg atgagccctc gtatgatacc cacaatctat atgttttact cttctctttc    3041

ctttttctc ttccttttcc tttattactt cattccttgt gtactttctg tgaacctcca    3101

gtcgaccatc cgacccaatt cgaaagtctt tcctgacctg gttcaggttg gcatattctc    3161

gaaaggatgt cgaccttcct gaccctactg ggctaccggg aaagccctag gatggctgat    3221

ggacagatct ggtgatcaac tatgggaaca ctccggagat ggtgactaat atgcgatggt    3281

catttaaaga gcaccgcttc cagcgatctc cccagttgct cctcaacgat tgacacggcc    3341

aatttatcca gattccggga ttctctgagt gagctgtccc ttttttctag a             3392
```

<210> SEQ ID NO 26
<211> LENGTH: 734
<212> TYPE: PRT
<213> ORGANISM: Chaetomium thermophilum

```
<400> SEQUENCE: 26

Met Ala Leu His Ala Phe Leu Leu Leu Ala Ser Ala Leu Leu Ala Arg
1               5                   10                  15

Gly Ala Leu Ser Gln Pro Asp Asn Val Arg Arg Ala Ala Pro Thr Gly
            20                  25                  30

Thr Ala Ala Trp Asp Ala Ala His Ser Gln Ala Ala Ala Ala Val Ser
        35                  40                  45

Arg Leu Ser Gln Gln Asp Lys Ile Asn Ile Val Thr Gly Val Gly Trp
    50                  55                  60

Gly Lys Gly Pro Cys Val Gly Asn Thr Asn Pro Val Tyr Ser Ile Asn
65                  70                  75                  80

Tyr Pro Gln Leu Cys Leu Gln Asp Gly Pro Leu Gly Ile Arg Ser Ala
                85                  90                  95

Thr Ser Val Thr Ala Phe Thr Pro Gly Ile Gln Ala Ala Ser Thr Trp
            100                 105                 110

Asp Val Glu Leu Ile Arg Gln Arg Gly Val Tyr Leu Gly Gln Glu Ala
        115                 120                 125

Arg Gly Thr Gly Val His Val Leu Leu Gly Pro Val Ala Gly Ala Leu
    130                 135                 140

Gly Lys Ile Pro His Gly Gly Arg Asn Trp Glu Ala Phe Gly Ser Asp
145                 150                 155                 160

Pro Tyr Leu Ala Gly Ile Ala Met Ser Glu Thr Ile Glu Gly Ile Gln
                165                 170                 175

Ser Glu Gly Val Gln Ala Cys Ala Lys His Tyr Ile Ala Asn Glu Gln
            180                 185                 190

Glu Leu Asn Arg Glu Thr Met Ser Ser Asn Val Asp Asp Arg Thr Met
        195                 200                 205

His Glu Leu Tyr Leu Trp Pro Phe Ala Asp Ala Val His Ser Asn Val
    210                 215                 220

Ala Ser Val Met Cys Ser Tyr Asn Lys Leu Asn Gly Thr Trp Leu Cys
225                 230                 235                 240

Glu Asn Asp Arg Ala Gln Asn Gln Leu Leu Lys Arg Glu Leu Gly Phe
                245                 250                 255

Arg Gly Tyr Ile Val Ser Asp Trp Asn Ala Gln His Thr Thr Val Gly
            260                 265                 270

Ser Ala Asn Ser Gly Met Asp Met Thr Met Pro Gly Ser Asp Phe Asn
        275                 280                 285

Gly Trp Asn Val Leu Trp Gly Pro Gln Leu Asn Asn Ala Val Asn Ser
    290                 295                 300

Gly Gln Val Ser Gln Ser Arg Leu Asn Asp Met Val Gln Arg Ile Leu
305                 310                 315                 320

Ala Ala Trp Tyr Leu Leu Gly Gln Asn Ser Gly Tyr Pro Ser Ile Asn
                325                 330                 335

Leu Arg Ala Asn Val Gln Ala Asn His Lys Glu Asn Val Arg Ala Val
            340                 345                 350

Ala Arg Asp Gly Ile Val Leu Leu Lys Asn Asp Gly Ile Leu Pro Leu
        355                 360                 365

Gln Arg Pro Asn Lys Ile Ala Leu Val Gly Ser Ala Ala Val Val Asn
    370                 375                 380

Pro Arg Gly Met Asn Ala Cys Val Asp Arg Gly Cys Asn Glu Gly Ala
385                 390                 395                 400

Leu Gly Met Gly Trp Gly Ser Gly Thr Val Glu Tyr Pro Tyr Phe Val
```

```
                405                 410                 415

Ala Pro Tyr Asp Ala Leu Arg Glu Arg Ala Gln Arg Asp Gly Thr Gln
            420                 425                 430

Ile Ser Leu His Ala Ser Asp Asn Thr Asn Gly Val Asn Asn Ala Val
        435                 440                 445

Gln Gly Ala Asp Ala Ala Phe Val Phe Ile Thr Ala Asp Ser Gly Glu
    450                 455                 460

Gly Tyr Ile Thr Val Glu Gly His Ala Gly Asp Arg Asn His Leu Asp
465                 470                 475                 480

Pro Trp His Asn Gly Asn Gln Leu Val Gln Ala Val Ala Gln Ala Asn
                485                 490                 495

Lys Asn Val Ile Val Val Val His Ser Val Gly Pro Val Ile Leu Glu
            500                 505                 510

Thr Ile Leu Asn Thr Pro Gly Val Arg Ala Val Val Trp Ala Gly Leu
        515                 520                 525

Pro Ser Gln Glu Ser Gly Asn Ala Leu Val Asp Val Leu Tyr Gly Leu
    530                 535                 540

Val Ser Pro Ser Gly Lys Leu Val Tyr Thr Ile Ala Lys Ser Pro Ser
545                 550                 555                 560

Asp Tyr Pro Thr Ser Ile Val Arg Gly Asp Asp Asn Phe Arg Glu Gly
                565                 570                 575

Leu Phe Ile Asp Tyr Arg His Phe Asp Asn Ala Arg Ile Glu Pro Arg
            580                 585                 590

Phe Glu Phe Gly Phe Gly Leu Ser Tyr Thr Asn Phe Ser Tyr Ser Asn
        595                 600                 605

Leu Gly Ile Ser Ser Ser Ala Thr Ala Gly Pro Ala Thr Gly Pro Thr
    610                 615                 620

Val Pro Gly Gly Pro Ala Asp Leu Trp Asn Tyr Val Ala Thr Val Thr
625                 630                 635                 640

Ala Thr Val Thr Asn Thr Gly Gly Val Glu Gly Ala Glu Val Ala Gln
                645                 650                 655

Leu Tyr Ile Ser Leu Pro Ser Ser Ala Pro Ala Ser Pro Pro Lys Gln
            660                 665                 670

Leu Arg Gly Phe Val Lys Leu Lys Leu Ala Pro Gly Gln Ser Gly Thr
        675                 680                 685

Ala Thr Phe Arg Leu Arg Lys Arg Asp Leu Ala Tyr Trp Asp Val Gly
    690                 695                 700

Arg Gln Asn Trp Val Val Pro Ser Gly Arg Phe Gly Val Leu Val Gly
705                 710                 715                 720

Ala Ser Ser Arg Asp Ile Arg Leu Gln Gly Glu Ile Val Val
                725                 730
```

<210> SEQ ID NO 27
<211> LENGTH: 1631
<212> TYPE: DNA
<213> ORGANISM: Thermoascus aurantiacus
<220> FEATURE:
<221> NAME/KEY: CDS
<222> LOCATION: (1)..(609)
<220> FEATURE:
<221> NAME/KEY: Intron
<222> LOCATION: (610)..(674)
<220> FEATURE:
<221> NAME/KEY: CDS
<222> LOCATION: (675)..(1628)

<400> SEQUENCE: 27

```
atg tat cag cgc gct ctt ctc ttc tct ttc ttc ctc gcc gcc gcc cgc       48
Met Tyr Gln Arg Ala Leu Leu Phe Ser Phe Phe Leu Ala Ala Ala Arg
1               5                   10                  15

gcg cag cag gcc ggt acc gta acc gca gag aat cac cct tcc ctg acc       96
Ala Gln Gln Ala Gly Thr Val Thr Ala Glu Asn His Pro Ser Leu Thr
            20                  25                  30

tgg cag caa tgc tcc agc ggc ggt agt tgt acc acg cag aat gga aaa      144
Trp Gln Gln Cys Ser Ser Gly Gly Ser Cys Thr Thr Gln Asn Gly Lys
        35                  40                  45

gtc gtt atc gat gcg aac tgg cgt tgg gtc cat acc acc tct gga tac      192
Val Val Ile Asp Ala Asn Trp Arg Trp Val His Thr Thr Ser Gly Tyr
    50                  55                  60

acc aac tgc tac acg ggc aat acg tgg gac acc agt atc tgt ccc gac      240
Thr Asn Cys Tyr Thr Gly Asn Thr Trp Asp Thr Ser Ile Cys Pro Asp
65                  70                  75                  80

gac gtg acc tgc gct cag aat tgt gcc ttg gat gga gcg gat tac agt      288
Asp Val Thr Cys Ala Gln Asn Cys Ala Leu Asp Gly Ala Asp Tyr Ser
                85                  90                  95

ggc acc tat ggt gtt acg acc agt ggc aac gcc ctg aga ctg aac ttt      336
Gly Thr Tyr Gly Val Thr Thr Ser Gly Asn Ala Leu Arg Leu Asn Phe
            100                 105                 110

gtc acc caa agc tca ggg aag aac att ggc tcg cgc ctg tac ctg ctg      384
Val Thr Gln Ser Ser Gly Lys Asn Ile Gly Ser Arg Leu Tyr Leu Leu
        115                 120                 125

cag gac gac acc act tat cag atc ttc aag ctg ctg ggt cag gag ttt      432
Gln Asp Asp Thr Thr Tyr Gln Ile Phe Lys Leu Leu Gly Gln Glu Phe
    130                 135                 140

acc ttc gat gtc gac gtc tcc aat ctc cct tgc ggg ctg aac ggc gcc      480
Thr Phe Asp Val Asp Val Ser Asn Leu Pro Cys Gly Leu Asn Gly Ala
145                 150                 155                 160

ctc tac ttt gtg gcc atg gac gcc gac ggc gga ttg tcc aaa tac cct      528
Leu Tyr Phe Val Ala Met Asp Ala Asp Gly Gly Leu Ser Lys Tyr Pro
                165                 170                 175

ggc aac aag gca ggc gct aag tat ggc act ggt tac tgc gac tct cag      576
Gly Asn Lys Ala Gly Ala Lys Tyr Gly Thr Gly Tyr Cys Asp Ser Gln
            180                 185                 190

tgc cct cgg gat ctc aag ttc atc aac ggt cag gtacgtcaga agtgataact    629
Cys Pro Arg Asp Leu Lys Phe Ile Asn Gly Gln
        195                 200

agccagcaga gcccatgaat cattaactaa cgctgtcaaa tacag gcc aat gtt gaa    686
                                                  Ala Asn Val Glu
                                                      205

ggc tgg cag ccg tct gcc aac gac cca aat gcc ggc gtt ggt aac cac      734
Gly Trp Gln Pro Ser Ala Asn Asp Pro Asn Ala Gly Val Gly Asn His
        210                 215                 220

ggt tcc tgc tgc gct gag atg gat gtc tgg gaa gcc aac agc atc tct      782
Gly Ser Cys Cys Ala Glu Met Asp Val Trp Glu Ala Asn Ser Ile Ser
    225                 230                 235

act gcg gtg acg cct cac cca tgc gac acc ccc ggc cag acc atg tgc      830
Thr Ala Val Thr Pro His Pro Cys Asp Thr Pro Gly Gln Thr Met Cys
240                 245                 250                 255

cag gga gac gac tgt ggt gga acc tac tcc tcc act cga tat gct ggt      878
Gln Gly Asp Asp Cys Gly Gly Thr Tyr Ser Ser Thr Arg Tyr Ala Gly
                260                 265                 270

acc tgc gac cct gat ggc tgc gac ttc aat cct tac cgc cag ggc aac      926
Thr Cys Asp Pro Asp Gly Cys Asp Phe Asn Pro Tyr Arg Gln Gly Asn
            275                 280                 285

cac tcg ttc tac ggc ccc ggg cag atc gtc gac acc agc tcc aaa ttc      974
His Ser Phe Tyr Gly Pro Gly Gln Ile Val Asp Thr Ser Ser Lys Phe
        290                 295                 300
```

```
acc gtc gtc acc cag ttc atc acc gac gac ggg acc ccc tcc ggc acc      1022
Thr Val Val Thr Gln Phe Ile Thr Asp Asp Gly Thr Pro Ser Gly Thr
    305                 310                 315

ctg acg gag atc aaa cgc ttc tac gtc cag aac ggc aag gta atc ccc      1070
Leu Thr Glu Ile Lys Arg Phe Tyr Val Gln Asn Gly Lys Val Ile Pro
320                 325                 330                 335

cag tcg gag tcg acg atc agc ggc gtc acc ggc aac tca atc acc acc      1118
Gln Ser Glu Ser Thr Ile Ser Gly Val Thr Gly Asn Ser Ile Thr Thr
                340                 345                 350

gag tat tgc acg gcc cag aag gcc gcc ttc ggc gac aac acc ggc ttc      1166
Glu Tyr Cys Thr Ala Gln Lys Ala Ala Phe Gly Asp Asn Thr Gly Phe
            355                 360                 365

ttc acg cac ggc ggg ctt cag aag atc agt cag gct ctg gct cag ggc      1214
Phe Thr His Gly Gly Leu Gln Lys Ile Ser Gln Ala Leu Ala Gln Gly
        370                 375                 380

atg gtc ctc gtc atg agc ctg tgg gac gat cac gcc gcc aac atg ctc      1262
Met Val Leu Val Met Ser Leu Trp Asp Asp His Ala Ala Asn Met Leu
    385                 390                 395

tgg ctg gac agc acc tac ccg act gat gcg gac ccg gac acc cct ggc      1310
Trp Leu Asp Ser Thr Tyr Pro Thr Asp Ala Asp Pro Asp Thr Pro Gly
400                 405                 410                 415

gtc gcg cgc ggt acc tgc ccc acg acc tcc ggc gtc ccg gcc gac gtt      1358
Val Ala Arg Gly Thr Cys Pro Thr Thr Ser Gly Val Pro Ala Asp Val
                420                 425                 430

gag tcg cag tac ccc aat tca tat gtt atc tac tcc aac atc aag gtc      1406
Glu Ser Gln Tyr Pro Asn Ser Tyr Val Ile Tyr Ser Asn Ile Lys Val
            435                 440                 445

gga ccc att ggc agc acc ggc aac cct agc ggc ggc aac cct ccc ggc      1454
Gly Pro Ile Gly Ser Thr Gly Asn Pro Ser Gly Gly Asn Pro Pro Gly
        450                 455                 460

gga aac ccg cct ggc acc acc acc acc cgc cgc cca gcc act acc act      1502
Gly Asn Pro Pro Gly Thr Thr Thr Thr Arg Arg Pro Ala Thr Thr Thr
    465                 470                 475

gga agc tct ccc gga cct acc cag tct cac tac ggc cag tgc ggc ggt      1550
Gly Ser Ser Pro Gly Pro Thr Gln Ser His Tyr Gly Gln Cys Gly Gly
480                 485                 490                 495

att ggc tac agc ggc ccc acg gtc tgc gcc agc ggc aca act tgc cag      1598
Ile Gly Tyr Ser Gly Pro Thr Val Cys Ala Ser Gly Thr Thr Cys Gln
                500                 505                 510

gtc ctg aac cct tac tac tct cag tgc ctg taa                          1631
Val Leu Asn Pro Tyr Tyr Ser Gln Cys Leu
            515                 520


<210> SEQ ID NO 28
<211> LENGTH: 521
<212> TYPE: PRT
<213> ORGANISM: Thermoascus aurantiacus

<400> SEQUENCE: 28

Met Tyr Gln Arg Ala Leu Leu Phe Ser Phe Phe Leu Ala Ala Ala Arg
1               5                   10                  15

Ala Gln Gln Ala Gly Thr Val Thr Ala Glu Asn His Pro Ser Leu Thr
            20                  25                  30

Trp Gln Gln Cys Ser Ser Gly Gly Ser Cys Thr Thr Gln Asn Gly Lys
        35                  40                  45

Val Val Ile Asp Ala Asn Trp Arg Trp Val His Thr Thr Ser Gly Tyr
    50                  55                  60

Thr Asn Cys Tyr Thr Gly Asn Thr Trp Asp Thr Ser Ile Cys Pro Asp
65                  70                  75                  80
```

```
Asp Val Thr Cys Ala Gln Asn Cys Ala Leu Asp Gly Ala Asp Tyr Ser
                85                  90                  95

Gly Thr Tyr Gly Val Thr Thr Ser Gly Asn Ala Leu Arg Leu Asn Phe
            100                 105                 110

Val Thr Gln Ser Ser Gly Lys Asn Ile Gly Ser Arg Leu Tyr Leu Leu
        115                 120                 125

Gln Asp Asp Thr Thr Tyr Gln Ile Phe Lys Leu Leu Gly Gln Glu Phe
    130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Gly Leu Ser Lys Tyr Pro
                165                 170                 175

Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ala Asn Asp Pro Asn Ala Gly Val Gly Asn His Gly
    210                 215                 220

Ser Cys Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
            260                 265                 270

Cys Asp Pro Asp Gly Cys Asp Phe Asn Pro Tyr Arg Gln Gly Asn His
        275                 280                 285

Ser Phe Tyr Gly Pro Gly Gln Ile Val Asp Thr Ser Ser Lys Phe Thr
    290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Gly Asp Asn Thr Gly Phe Phe
        355                 360                 365

Thr His Gly Gly Leu Gln Lys Ile Ser Gln Ala Leu Ala Gln Gly Met
    370                 375                 380

Val Leu Val Met Ser Leu Trp Asp Asp His Ala Ala Asn Met Leu Trp
385                 390                 395                 400

Leu Asp Ser Thr Tyr Pro Thr Asp Ala Asp Pro Asp Thr Pro Gly Val
                405                 410                 415

Ala Arg Gly Thr Cys Pro Thr Thr Ser Gly Val Pro Ala Asp Val Glu
            420                 425                 430

Ser Gln Tyr Pro Asn Ser Tyr Val Ile Tyr Ser Asn Ile Lys Val Gly
        435                 440                 445

Pro Ile Gly Ser Thr Gly Asn Pro Ser Gly Gly Asn Pro Pro Gly Gly
    450                 455                 460

Asn Pro Pro Gly Thr Thr Thr Thr Arg Arg Pro Ala Thr Thr Thr Gly
465                 470                 475                 480

Ser Ser Pro Gly Pro Thr Gln Ser His Tyr Gly Gln Cys Gly Gly Ile
                485                 490                 495
```

```
Gly Tyr Ser Gly Pro Thr Val Cys Ala Ser Gly Thr Thr Cys Gln Val
            500                 505                 510

Leu Asn Pro Tyr Tyr Ser Gln Cys Leu
        515                 520


<210> SEQ ID NO 29
<211> LENGTH: 1734
<212> TYPE: DNA
<213> ORGANISM: Thermoascus aurantiacus
<220> FEATURE:
<221> NAME/KEY: CDS
<222> LOCATION: (1)..(609)
<220> FEATURE:
<221> NAME/KEY: Intron
<222> LOCATION: (610)..(674)
<220> FEATURE:
<221> NAME/KEY: CDS
<222> LOCATION: (675)..(1661)
<220> FEATURE:
<221> NAME/KEY: Intron
<222> LOCATION: (1662)..(1725)
<220> FEATURE:
<221> NAME/KEY: CDS
<222> LOCATION: (1726)..(1731)

<400> SEQUENCE: 29

atg tat cag cgc gct ctt ctc ttc tct ttc ttc ctc gcc gcc gcc cgc       48
Met Tyr Gln Arg Ala Leu Leu Phe Ser Phe Phe Leu Ala Ala Ala Arg
1               5                   10                  15

gcg cag cag gcc ggt acc gta acc gca gag aat cac cct tcc ctg acc       96
Ala Gln Gln Ala Gly Thr Val Thr Ala Glu Asn His Pro Ser Leu Thr
            20                  25                  30

tgg cag caa tgc tcc agc ggc ggt agt tgt acc acg cag aat gga aaa      144
Trp Gln Gln Cys Ser Ser Gly Gly Ser Cys Thr Thr Gln Asn Gly Lys
        35                  40                  45

gtc gtt atc gat gcg aac tgg cgt tgg gtc cat acc acc tct gga tac      192
Val Val Ile Asp Ala Asn Trp Arg Trp Val His Thr Thr Ser Gly Tyr
    50                  55                  60

acc aac tgc tac acg ggc aat acg tgg gac acc agt atc tgt ccc gac      240
Thr Asn Cys Tyr Thr Gly Asn Thr Trp Asp Thr Ser Ile Cys Pro Asp
65                  70                  75                  80

gac gtg acc tgc gct cag aat tgt gcc ttg gat gga gcg gat tac agt      288
Asp Val Thr Cys Ala Gln Asn Cys Ala Leu Asp Gly Ala Asp Tyr Ser
                85                  90                  95

ggc acc tat ggt gtt acg acc agt ggc aac gcc ctg aga ctg aac ttt      336
Gly Thr Tyr Gly Val Thr Thr Ser Gly Asn Ala Leu Arg Leu Asn Phe
            100                 105                 110

gtc acc caa agc tca ggg aag aac att ggc tcg cgc ctg tac ctg ctg      384
Val Thr Gln Ser Ser Gly Lys Asn Ile Gly Ser Arg Leu Tyr Leu Leu
        115                 120                 125

cag gac gac acc act tat cag atc ttc aag ctg ctg ggt cag gag ttt      432
Gln Asp Asp Thr Thr Tyr Gln Ile Phe Lys Leu Leu Gly Gln Glu Phe
    130                 135                 140

acc ttc gat gtc gac gtc tcc aat ctc cct tgc ggg ctg aac ggc gcc      480
Thr Phe Asp Val Asp Val Ser Asn Leu Pro Cys Gly Leu Asn Gly Ala
145                 150                 155                 160

ctc tac ttt gtg gcc atg gac gcc gac ggc gga ttg tcc aaa tac cct      528
Leu Tyr Phe Val Ala Met Asp Ala Asp Gly Gly Leu Ser Lys Tyr Pro
                165                 170                 175

ggc aac aag gca ggc gct aag tat ggc act ggt tac tgc gac tct cag      576
Gly Asn Lys Ala Gly Ala Lys Tyr Gly Thr Gly Tyr Cys Asp Ser Gln
            180                 185                 190

tgc cct cgg gat ctc aag ttc atc aac ggt cag gtacgtcaga agtgataact    629
Cys Pro Arg Asp Leu Lys Phe Ile Asn Gly Gln
```

```
        195                 200

agccagcaga gcccatgaat cattaactaa cgctgtcaaa tacag gcc aat gtt gaa     686
                                                  Ala Asn Val Glu
                                                      205

ggc tgg cag ccg tct gcc aac gac cca aat gcc ggc gtt ggt aac cac       734
Gly Trp Gln Pro Ser Ala Asn Asp Pro Asn Ala Gly Val Gly Asn His
        210                 215                 220

ggt tcc tgc tgc gct gag atg gat gtc tgg gaa gcc aac agc atc tct       782
Gly Ser Cys Cys Ala Glu Met Asp Val Trp Glu Ala Asn Ser Ile Ser
    225                 230                 235

act gcg gtg acg cct cac cca tgc gac acc ccc ggc cag acc atg tgc       830
Thr Ala Val Thr Pro His Pro Cys Asp Thr Pro Gly Gln Thr Met Cys
240                 245                 250                 255

cag gga gac gac tgt ggt gga acc tac tcc tcc act cga tat gct ggt       878
Gln Gly Asp Asp Cys Gly Gly Thr Tyr Ser Ser Thr Arg Tyr Ala Gly
                260                 265                 270

acc tgc gac cct gat ggc tgc gac ttc aat cct tac cgc cag ggc aac       926
Thr Cys Asp Pro Asp Gly Cys Asp Phe Asn Pro Tyr Arg Gln Gly Asn
            275                 280                 285

cac tcg ttc tac ggc ccc ggg cag atc gtc gac acc agc tcc aaa ttc       974
His Ser Phe Tyr Gly Pro Gly Gln Ile Val Asp Thr Ser Ser Lys Phe
        290                 295                 300

acc gtc gtc acc cag ttc atc acc gac gac ggg acc ccc tcc ggc acc      1022
Thr Val Val Thr Gln Phe Ile Thr Asp Asp Gly Thr Pro Ser Gly Thr
    305                 310                 315

ctg acg gag atc aaa cgc ttc tac gtc cag aac ggc aag gta atc ccc      1070
Leu Thr Glu Ile Lys Arg Phe Tyr Val Gln Asn Gly Lys Val Ile Pro
320                 325                 330                 335

cag tcg gag tcg acg atc agc ggc gtc acc ggc aac tca atc acc acc      1118
Gln Ser Glu Ser Thr Ile Ser Gly Val Thr Gly Asn Ser Ile Thr Thr
                340                 345                 350

gag tat tgc acg gcc cag aag gcc gcc ttc ggc gac aac acc ggc ttc      1166
Glu Tyr Cys Thr Ala Gln Lys Ala Ala Phe Gly Asp Asn Thr Gly Phe
            355                 360                 365

ttc acg cac ggc ggg ctt cag aag atc agt cag gct ctg gct cag ggc      1214
Phe Thr His Gly Gly Leu Gln Lys Ile Ser Gln Ala Leu Ala Gln Gly
        370                 375                 380

atg gtc ctc gtc atg agc ctg tgg gac gat cac gcc gcc aac atg ctc      1262
Met Val Leu Val Met Ser Leu Trp Asp Asp His Ala Ala Asn Met Leu
    385                 390                 395

tgg ctg gac agc acc tac ccg act gat gcg gac ccg gac acc cct ggc      1310
Trp Leu Asp Ser Thr Tyr Pro Thr Asp Ala Asp Pro Asp Thr Pro Gly
400                 405                 410                 415

gtc gcg cgc ggt acc tgc ccc acg acc tcc ggc gtc ccg gcc gac gtt      1358
Val Ala Arg Gly Thr Cys Pro Thr Thr Ser Gly Val Pro Ala Asp Val
                420                 425                 430

gag tcg cag tac ccc aat tca tat gtt atc tac tcc aac atc aag gtc      1406
Glu Ser Gln Tyr Pro Asn Ser Tyr Val Ile Tyr Ser Asn Ile Lys Val
            435                 440                 445

gga ccc atc ggc tcg acc gtc cct ggc ctt gac ggc agc aac ccc ggc      1454
Gly Pro Ile Gly Ser Thr Val Pro Gly Leu Asp Gly Ser Asn Pro Gly
        450                 455                 460

aac ccg acc acc acc gtc gtt cct ccc gct tct acc tcc acc tcc cgt      1502
Asn Pro Thr Thr Thr Val Val Pro Pro Ala Ser Thr Ser Thr Ser Arg
    465                 470                 475

ccg acc agc agc act agc tct ccc gtt tcg acc ccg act ggc cag ccc      1550
Pro Thr Ser Ser Thr Ser Ser Pro Val Ser Thr Pro Thr Gly Gln Pro
480                 485                 490                 495

ggc ggc tgc acc acc cag aag tgg ggc cag tgc ggc ggt atc ggc tac      1598
```

```
Gly Gly Cys Thr Thr Gln Lys Trp Gly Gln Cys Gly Gly Ile Gly Tyr
            500                 505                 510

acc ggc tgc act aac tgc gtt gct ggc acc acc tgc act cag ctc aac      1646
Thr Gly Cys Thr Asn Cys Val Ala Gly Thr Thr Cys Thr Gln Leu Asn
        515                 520                 525

ccc tgg tac agc cag gtatgtttct cttccccctt ctagactcgc ttggatttga      1701
Pro Trp Tyr Ser Gln
    530

cagttgctaa catctgctca acag tgc ctg taa                                1734
                           Cys Leu


<210> SEQ ID NO 30
<211> LENGTH: 534
<212> TYPE: PRT
<213> ORGANISM: Thermoascus aurantiacus

<400> SEQUENCE: 30

Met Tyr Gln Arg Ala Leu Leu Phe Ser Phe Phe Leu Ala Ala Ala Arg
1               5                   10                  15

Ala Gln Gln Ala Gly Thr Val Thr Ala Glu Asn His Pro Ser Leu Thr
            20                  25                  30

Trp Gln Gln Cys Ser Ser Gly Gly Ser Cys Thr Thr Gln Asn Gly Lys
        35                  40                  45

Val Val Ile Asp Ala Asn Trp Arg Trp Val His Thr Thr Ser Gly Tyr
    50                  55                  60

Thr Asn Cys Tyr Thr Gly Asn Thr Trp Asp Thr Ser Ile Cys Pro Asp
65                  70                  75                  80

Asp Val Thr Cys Ala Gln Asn Cys Ala Leu Asp Gly Ala Asp Tyr Ser
                85                  90                  95

Gly Thr Tyr Gly Val Thr Thr Ser Gly Asn Ala Leu Arg Leu Asn Phe
            100                 105                 110

Val Thr Gln Ser Ser Gly Lys Asn Ile Gly Ser Arg Leu Tyr Leu Leu
        115                 120                 125

Gln Asp Asp Thr Thr Tyr Gln Ile Phe Lys Leu Leu Gly Gln Glu Phe
    130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Gly Leu Ser Lys Tyr Pro
                165                 170                 175

Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Gln Pro Ser Ala Asn Asp Pro Asn Ala Gly Val Gly Asn His Gly
    210                 215                 220

Ser Cys Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
            260                 265                 270

Cys Asp Pro Asp Gly Cys Asp Phe Asn Pro Tyr Arg Gln Gly Asn His
        275                 280                 285

Ser Phe Tyr Gly Pro Gly Gln Ile Val Asp Thr Ser Ser Lys Phe Thr
    290                 295                 300
```

-continued

```
Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Gly Asp Asn Thr Gly Phe Phe
        355                 360                 365

Thr His Gly Gly Leu Gln Lys Ile Ser Gln Ala Leu Ala Gln Gly Met
    370                 375                 380

Val Leu Val Met Ser Leu Trp Asp Asp His Ala Ala Asn Met Leu Trp
385                 390                 395                 400

Leu Asp Ser Thr Tyr Pro Thr Asp Ala Asp Pro Asp Thr Pro Gly Val
                405                 410                 415

Ala Arg Gly Thr Cys Pro Thr Thr Ser Gly Val Pro Ala Asp Val Glu
            420                 425                 430

Ser Gln Tyr Pro Asn Ser Tyr Val Ile Tyr Ser Asn Ile Lys Val Gly
        435                 440                 445

Pro Ile Gly Ser Thr Val Pro Gly Leu Asp Gly Ser Asn Pro Gly Asn
    450                 455                 460

Pro Thr Thr Thr Val Val Pro Pro Ala Ser Thr Ser Thr Ser Arg Pro
465                 470                 475                 480

Thr Ser Ser Thr Ser Ser Pro Val Ser Thr Pro Thr Gly Gln Pro Gly
                485                 490                 495

Gly Cys Thr Thr Gln Lys Trp Gly Gln Cys Gly Gly Ile Gly Tyr Thr
            500                 505                 510

Gly Cys Thr Asn Cys Val Ala Gly Thr Thr Cys Thr Gln Leu Asn Pro
        515                 520                 525

Trp Tyr Ser Gln Cys Leu
    530
```

TREATMENT OF CELLULOSIC MATERIAL AND ENZYMES USEFUL THEREIN

RELATED APPLICATIONS

This application is a divisional of U.S. application Ser. No. 12/917,603 (pending) which is divisional of U.S. application Ser. No. 12/141,976, filed Jun. 19, 2008 (abandoned), which is a continuation of PCT application no. PCT/FI2006/050558, designating the United States and filed Dec. 15, 2006; which claims the benefit of the filing date of Finnish application no. 20051318, filed Dec. 22, 2005; and U.S. application No. 60/753,258, filed Dec. 22, 2005; each of which is hereby incorporated herein by reference in its entirety for all purposes.

FIELD

The present invention relates to the production of sugar hydrolysates from cellulosic material. More precisely the invention relates to production of fermentable sugars from lignocellulosic material by enzymatic conversion. The fermentable sugars are useful e.g. in the production of bioethanol, or for other purposes. In particular the invention is directed to a method for treating cellulosic material with cellobiohydrolase, endoglucanase, beta-glucosidase, and optionally xylanase, and to enzyme preparations and the uses thereof. The invention is further directed to novel cellulolytic polypeptides, polynucleotides encoding them, and to vectors and host cells containing the polynucleotides. Still further the invention is directed to uses of the polypeptides and to a method of preparing them.

BACKGROUND

Sugar hydrolysates can be used for microbial production of a variety of fine chemicals or biopolymers, such as organic acids e.g. lactic acid, or ethanol or other alcohols e.g. n-butanol, 1,3-propanediol, or polyhydroxyalkanoates (PHAs). The sugar hydrolysates may also serve as raw material for other non-microbial processes, e.g., for enrichment, isolation and purification of high value sugars or various polymerization processes. One of the major uses of the sugar hydrolysates is in the production of biofuels. The production of bioethanol and/or other chemicals may take place in an integrated process in a biorefinery (Wyman 2001).

Limited resources of fossil fuels, and increasing amounts of $CO_2$ released from them and causing the greenhouse phenomenon have raised a need for using biomass as a renewable and clean source of energy. One promising, alternative technology is the production of biofuels i.e. ethanol from cellulosic materials. In the transportation sector biofuels are for the time being the only option, which could reduce the $CO_2$ emissions by an order of magnitude. The ethanol can be used in existing vehicles and distribution systems and thus it does not require expensive infrastructure investments. Sugars derived from lignocellulosic renewable raw materials can also be used as raw materials for a variety of chemical products that can replace oil-based chemicals.

Most of the carbohydrates in plants are in the form of lignocellulose, which essentially consists of cellulose, hemicellulose, pectin and lignin. In a lignocellulose-to-ethanol process the lignocellulosic material is first pretreated either chemically or physically to make the cellulose fraction more accessible to hydrolysis. The cellulose fraction is then hydrolysed to obtain sugars that can be fermented by yeast into ethanol. Lignin is obtained as a main co-product that may be used as a solid fuel.

Bioethanol production costs are high and the energy output is low, and there is continuous research for making the process more economical. Enzymatic hydrolysis is considered the most promising technology for converting cellulosic biomass into fermentable sugars. However, enzymatic hydrolysis is used only to a limited amount at industrial scale, and especially when using strongly lignified material such as wood or agricultural waste the technology is not satisfactory. The cost of the enzymatic step is one of the major economical factors of the process. Efforts have been made to improve the efficiency of the enzymatic hydrolysis of the cellulosic material (Badger 2002).

US 2002/019 2774 A1 describes a continuous process for converting solid lignocellulosic biomass into combustible fuel products. After pretreatment by wet oxidation or steam explosion the biomass is partially separated into cellulose, hemicellulose and lignin, and is then subjected to partial hydrolysis using one or more carbohydrase enzymes (EC 3.2). Celluclast™, a commercial product by Novo Nordisk A/S containing cellulase and xylanase activities is given as an example.

US 2004/000 5674 A1 describes novel enzyme mixtures that can be used directly on lignocellulose substrate, whereby toxic waste products formed during pretreatment processes may be avoided, and energy may be saved. The synergistic enzyme mixture contains a cellulase and an auxiliary enzyme such as cellulase, xylanase, ligninase, amylase, protease, lipidase or glucuronidase, or any combination thereof. Cellulase in considered to include endoglucanase (EG), beta-glucosidase (BG) and cellobiohydrolase (CBH). The examples illustrate the use of a mixture of *Trichoderma* xylanase and cellulase preparations.

Kurabi et al. (2005) have investigated enzymatic hydrolysis of steam-exploded and ethanol organosolv-pretreated Douglas-fir by novel and commercial fungal cellulases. They tested two commercial *Trichoderma reesei* cellulase preparations, and two novel preparations produced by mutant strains of *Trichoderma* sp. and *Penicillium* sp. The *Trichoderma* sp. preparation showed significantly better performance than the other preparations. The better performance was believed to be at least partly due to a significantly higher beta-glucosidase activity, which relieves product inhibition of cellobiohydrolase and endoglucanase.

US 2004/005 3373 A1 pertains a method of converting cellulose to glucose by treating a pretreated lignocellulosic substrate with an enzyme mixture comprising cellulase and a modified cellobiohydrolase I (CBHI). The CBHI has been modified by inactivating its cellulose binding domain (CBD). Advantages of CBHI modification are e.g. better recovery and higher hydrolysis rate with high substrate concentration. The cellulase is selected from the group consisting of EG, CBH and BG. The CBHI is preferably obtained from *Trichoderma*.

US 2005/016 4355 A1 describes a method for degrading lignocellulosic material with one or more cellulolytic enzymes in the presence of at least one surfactant. Additional enzymes such as hemicellulases, esterase, peroxidase, protease, laccase or mixture thereof may also be used. The presence of surfactant increases the degradation of lignocellulosic material compared to the absence of surfactant. The cellulolytic enzymes may be any enzyme involved in the degradation of lignocellulose including CBH, EG, and BG.

There is a huge number of publications disclosing various cellulases and hemicellulases.

Cellobiohydrolases (CBHs) are disclosed e.g. in WO 03/000 941, which relates to CBHI enzymes obtained from various fungi. No physiological properties of the enzymes are provided, nor any examples of their uses. Hong et al. (2003b) characterizes CBHI of *Thermoascus aurantiacus* produced in yeast. Applications of the enzyme are not described. Tuohy et al. (2002) describe three forms of cellobiohydrolases from *Talaromyces emersonii.*

Endoglucanases of the cel5 family (EGs fam 5) are described e.g. in WO 03/062 409, which relates to compositions comprising at least two thermostable enzymes for use in feed applications. Hong et al. (2003a) describe production of thermostable endo-β-1,4-glucanase from *T. aurantiacus* in yeast. No applications are explained. WO 01/70998 relates to β-glucanases from *Talaromyces*. They also describe β-glucanases from *Talaromyces emersonii*. Food, feed, beverage, brewing, and detergent applications are discussed. Lignocellulose hydrolysis is not mentioned. WO 98/06 858 describes beta-1,4-endoglucanase from *Aspergillus niger* and discusses feed and food applications of the enzyme. WO 97/13853 describes methods for screening DNA fragments encoding enzymes in cDNA libraries. The cDNA library is of yeast or fungal origin, preferably from *Aspergillus*. The enzyme is preferably a cellulase. Van Petegem et al. (2002) describe the 3D-structure of an endoglucanase of the cel5 family from *Thermoascus aurantiacus*. Parry et al. (2002) describe the mode of action of an endoglucanase of the cel5 family from *Thermoascus aurantiacus.*

Endoglucanases of the cel7 family (EGs fam 7) are disclosed e.g. in U.S. Pat. No. 5,912,157, which pertains *Myceliphthora* endoglucanase and its homologues and applications thereof in detergent, textile, and pulp. U.S. Pat. No. 6,071,735 describes cellulases exhibiting high endoglucanase activity in alkaline conditions. Uses as detergent, in pulp and paper, and textile applications are discussed. Bioethanol is not mentioned. U.S. Pat. No. 5,763,254 discloses enzymes degrading cellulose/hemicellulose and having conserved amino acid residues in CBD.

Endoglucanases of the cel45 family (EGs fam 45) are described e.g. in U.S. Pat. No. 6,001,639, which relates to enzymes having endoglucanase activity and having two conserved amino acid sequences. Uses in textile, detergent, and pulp and paper applications are generally discussed and treating of lignocellulosic material is mentioned but no examples are given. WO 2004/053039 is directed to detergent applications of endoglucanases. U.S. Pat. No. 5,958,082 discloses the use of endoglucanase, especially from *Thielavia terrestris* in textile application. EP 0495258 relates to detergent compositions containing *Humicola* cellulase. U.S. Pat. No. 5,948,672 describes a cellulase preparation containing endoglucanase, especially from *Humicola* and its use in textile and pulp applications. Lignocellulose hydrolysis is not mentioned.

A small amount of beta-glucosidase (BG) enhances hydrolysis of biomass to glucose by hydrolyzing cellobiose produced by cellobiohydrolases. Cellobiose conversion to glucose is usually the major rate-limiting step. Beta-glucosidases are disclosed e.g. in US 2005/021 4920, which relates to BG from *Aspergillus fumigatus*. The enzyme has been produced in *Aspergillus oryzae* and *Trichoderma reesei*. Use of the enzyme in degradation of biomass or detergent applications is generally discussed but not exemplified. WO02/095 014 describes an *Aspergillus oryzae* enzyme having cellobiase activity. Use in the production of ethanol from biomass is generally discussed but not exemplified. WO2005/074656 discloses polypeptides having cellulolytic enhancing activity derived e.g. from *T. aurantiacus; A. fumigatus; T. terrestris* and *T. aurantiacus*. WO02/26979 discloses enzymatic processing of plant material. U.S. Pat. No. 6,022,725 describes cloning and amplification of the beta-glucosidase gene of *Trichoderma reesei*, and U.S. Pat. No. 6,103,464 describes a method for detecting DNA encoding a beta-glucosidase from a filamentous fungus. No application examples are given.

Xylanases are described e.g. in FR2786784, which relates to a heat-stable xylanase, useful e.g. in treating animal feed and in bread making The enzyme is derived from a thermophilic fungus, particularly of the genus *Thermoascus.*

U.S. Pat. No. 6,197,564 describes enzymes having xylanase activity, and obtained from *Aspergillus aculeatus*. Their application in baking is exemplified. WO 02/24926 relates to *Talaromyces* xylanases. Feed and baking examples are given. WO01/42433 discloses thermostable xylanase from *Talaromyces emersonii* for use in food and feed applications.

The best-investigated and most widely applied cellulolytic enzymes of fungal origin have been derived from *Trichoderma reesei* (the anamorph of *Hypocrea jecorina*). Consequently also most of the commercially available fungal cellulases are derived from *Trichoderma reesei*. However, the majority of cellulases from less known fungi have not been applied in processes of practical importance such as in degrading cellulosic material, including lignocellulose.

There is a continuous need for new methods of degrading cellulosic substrates, in particular lignocellulosic substrates, and for new enzymes and enzyme mixtures, which enhance the efficiency of the degradation. There is also a need for processes and enzymes, which work at high temperatures, thus enabling the use of high biomass consistency and leading to high sugar and ethanol concentrations. This approach may lead to significant saving in energy and investments costs. The high temperature also decreases the risk of contamination during hydrolysis. The present invention aims to meet at least part of these needs.

BRIEF DESCRIPTION

It has now surprisingly been found that cellulolytic enzymes, and especially cellobiohydrolases obtainable from *Thermoascus aurantiacus, Acremonium thermophilum*, or *Chaetomium thermophilum* are particularly useful in hydrolyzing cellulosic material. In addition to cellobiohydrolases these fungi also have endoglucanases, beta-glucosidases and xylanases that are very suitable for degrading cellulosic material. The enzymes are kinetically very effective over a broad range of temperatures, and although they have high activity at high temperatures, they are also very efficient at standard hydrolysis temperatures. This makes them extremely well suited for varying cellulosic substrate hydrolysis processes carried out both at conventional temperatures and at elevated temperatures.

The present invention provides a method for treating cellulosic material with cellobiohydrolase, endoglucanase and beta-glucosidase, whereby said cellobiohydrolase comprises an amino acid sequence having at least 80% identity to SEQ ID NO: 2, 4, 6 or 8, or to an enzymatically active fragment thereof.

The invention further provides an enzyme preparation comprising cellobiohydrolase, endoglucanase and beta-glucosidase, wherein said cellobiohydrolase comprises an amino acid sequence having at least 80% identity to SEQ ID NO: 2, 4, 6 or 8, or to an enzymatically active fragment thereof.

The use of said enzyme preparation for degrading cellulosic material is also provided, as well as the use of said method in a process for preparing ethanol from cellulosic material.

The invention is also directed to a polypeptide comprising a fragment having cellulolytic activity and being selected from the group consisting of:

a) a polypeptide comprising an amino acid sequence having at least 66% identity to SEQ ID NO:4, 79% identity to SEQ ID NO:6, 78% identity to SEQ ID NO:12, 68% identity to SEQ ID NO:14, 72% identity to SEQ ID NO:16, 68% identity to SEQ ID NO:20, 74% identity to SEQ ID NO:22 or 24, or 78% identity to SEQ ID NO:26;

b) a variant of a) comprising a fragment having cellulolytic activity; and c) a fragment of a) or b) having cellulolytic activity.

One further object of the invention is an isolated polynucleotide selected from the group consisting of:

a) a nucleotide sequence of SEQ ID NO: 3, 5, 11, 13, 15, 19, 21, 23 or 25, or a sequence encoding a polypeptide of claim 35;

b) a complementary strand of a)

c) a fragment of a) or b) comprising at least 20 nucleotides; and d) a sequence that is degenerate as a result of the genetic code to any one of the sequences as defined in a), b) or c).

The invention still further provides a vector, which comprises said polynucleotide as a heterologous sequence, and a host cell comprising said vector. *Escherichia coli* strains having accession number DSM 16728, DSM 16729, DSM 17324, DSM 17323, DSM 17729, DSM 16726, DSM 16725, DSM 17325 or DSM 17667 are also included in the invention.

Other objects of the invention are enzyme preparations comprising at least one of the novel polypeptides, and the use of said polypeptide or enzyme preparation in fuel, textile, detergent, pulp and paper, food, feed or beverage industry.

Further provided is a method for preparing a polypeptide comprising a fragment having cellulolytic activity and being selected from the group consisting of:

a) a polypeptide comprising an amino acid sequence having at least 66% identity to SEQ ID NO:4, 79% identity to SEQ ID NO:6, 78% identity to SEQ ID NO:12, 68% identity to SEQ ID NO:14, 72% identity to SEQ ID NO:16, 68% identity to SEQ ID NO:20, 74% identity to SEQ ID NO:22 or 24, or 78% identity to SEQ ID NO:26;

b) a variant of a) comprising a fragment having cellulolytic activity; and c) a fragment of a) or b) having cellulolytic activity, said method comprising transforming a host cell with a vector encoding said polypeptide, and culturing said host cell under conditions enabling expression of said polypeptide, and optionally recovering and purifying the polypeptide produced.

Still further provided is a method of treating cellulosic material with a spent culture medium of at least one microorganism capable of producing a polypeptide as defined above, wherein the method comprises reacting the cellulosic material with the spent culture medium to obtain hydrolysed cellulosic material.

Specific embodiments of the invention are set forth in the dependent claims.

Other objects, details and advantages of the present invention will become apparent from the following drawings, detailed description and examples.

βG_76/Cel3A, and *Thermoascus* βG_81/Cel3A was determined at pH 4.5, 5.5, and 4.5, respectively. The reaction containing 4-nitrophenyl-β-D-glucopyranosid as substrate was performed for 60 min, BSA (100 μg/ml) was added as a stabilizer.

FIG. 8. A) The pH dependency of the heterologously produced *Thermoascus* XYN_30/Xyn10A xylanase activity was determined with birch xylan substrate in a 10 min reaction at 50° C. B) Temperature optimum of XYN_30/Xyn10A was determined at pH 5.3 in a 60 min reaction, BSA (100 μg/ml) was added as a stabilizer.

Figure 9:
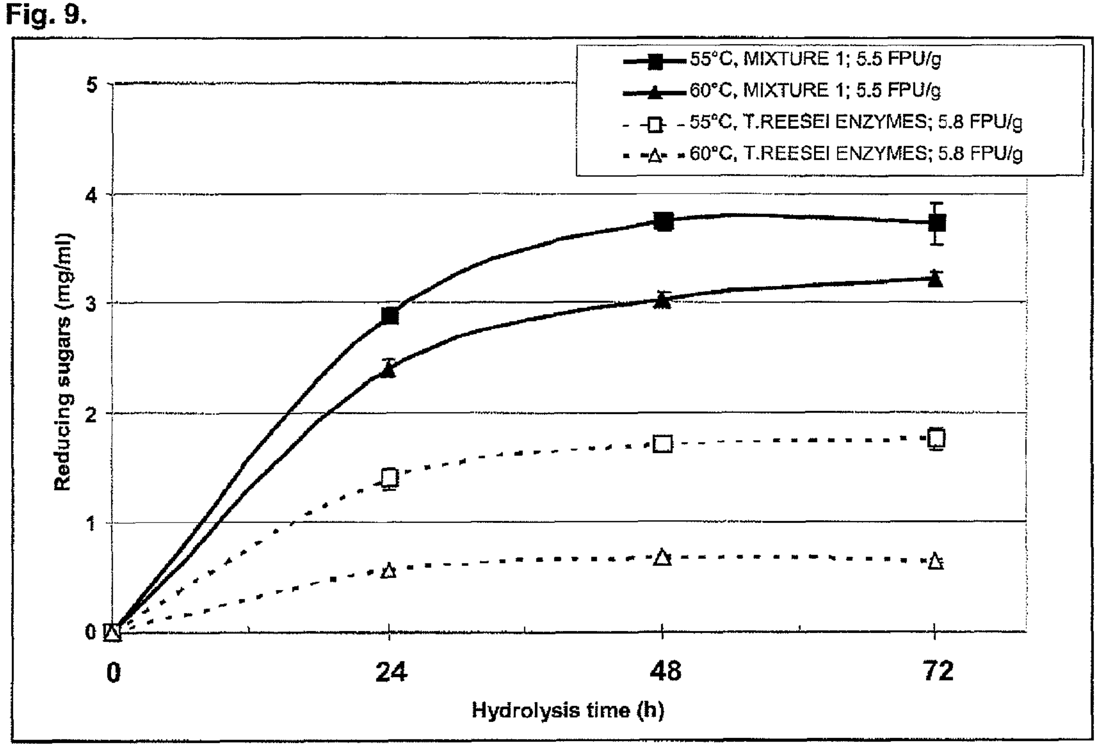

FIG. 9. Hydrolysis of washed steam exploded spruce fibre (10 mg/ml) with a mixture of thermophilic enzymes (MIXTURE 1) and *T. reesei* enzymes at 55 and 60° C. Enzyme dosage is given by FPU/g dry matter of substrate, FPU assayed at 50° C., pH 5. Hydrolysis was carried out for 72 h at pH 5, with mixing. The results are given as mean (±SD) of three separate measurements.

Figure 10:
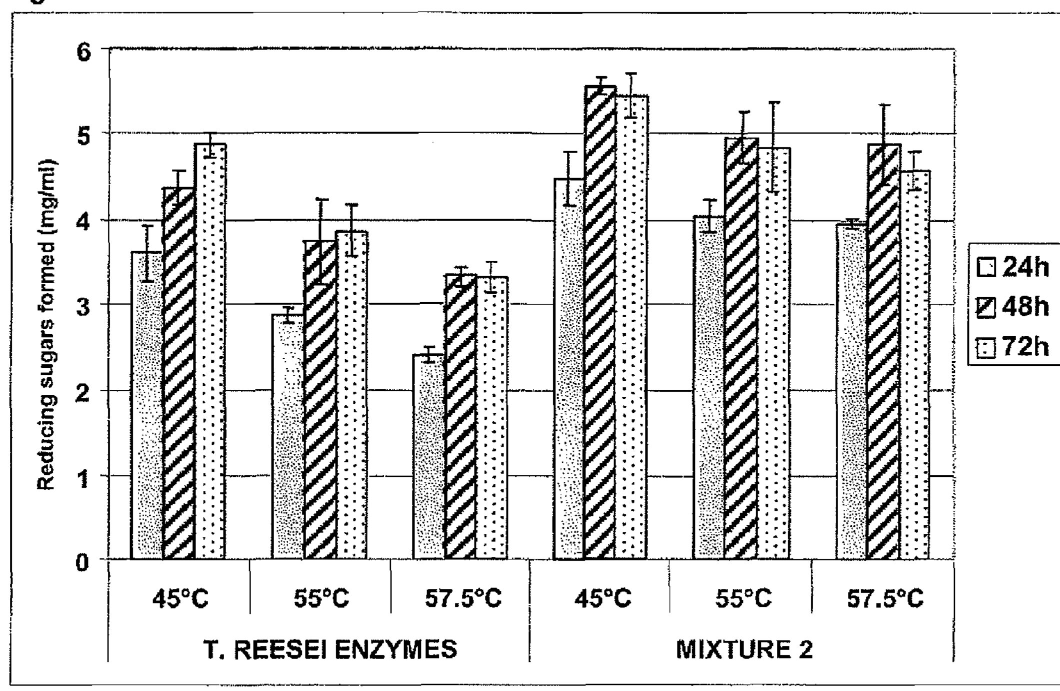

FIG. 10. Hydrolysis of steam exploded corn stover (10 mg/ml) with a mixture of thermophilic enzymes (MIXTURE 2) and *T. reesei* enzymes at 45, 55 and 57.5° C. Enzyme dosage was for "MIXTURE 2" 5 FPU/g dry matter of substrate and for *T. reesei* enzymes 5 FPU/g dry matter Celluclast supplemented with 100 nkat/g dry matter Novozym 188 (filter paper activity was assayed at 50° C., pH 5). Hydrolysis was carried out for 72 h at pH 5, with mixing. The results are given as mean (±SD) of three separate measurements. The substrate contained soluble reducing sugars (ca 0.7 mg/ml). This background sugar content was subtracted from the reducing sugars formed during the hydrolysis.

Figure 11:
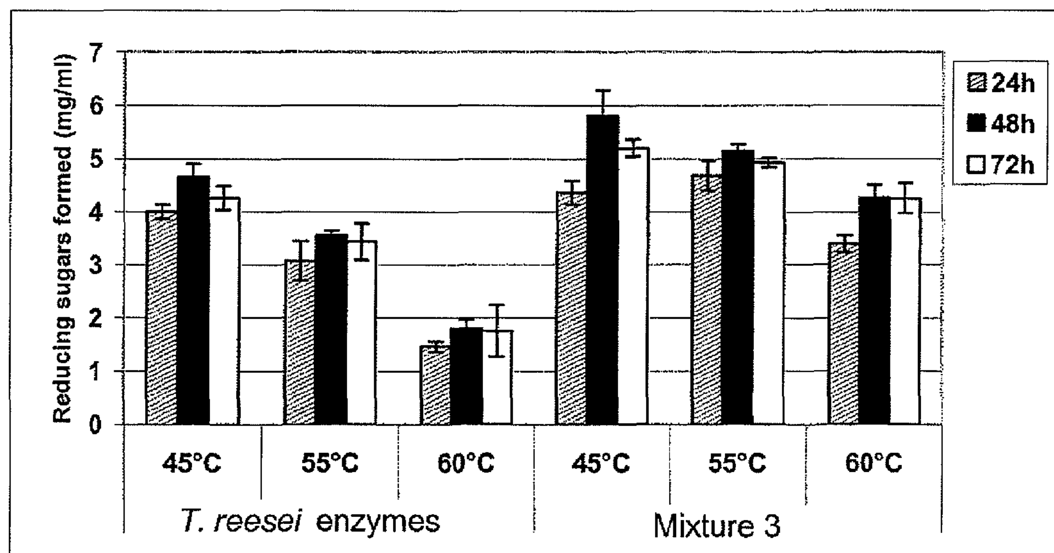

FIG. 11. Hydrolysis of steam exploded corn stover (10 mg/ml) with a mixture of thermophilic enzymes containing a new thermophilic xylanase from *Thermoascus aurantiacus* (MIXTURE 3) and *T. reesei* enzymes at 45, 55 and 60° C. Enzyme dosage was for "MIXTURE 3" 5 FPU/g dry matter of substrate and for *T. reesei* enzymes 5 FPU/g dry matter Celluclast supplemented with 100 nkat/g dry matter Novozym 188 (filter paper activity was assayed at 50° C., pH 5). Hydrolysis was carried out for 72 h at pH 5, with mixing. The results are given as mean (±SD) of three separate measurements. The substrate contained soluble reducing sugars (ca 0.7 mg/ml). This background sugar content was subtracted from the reducing sugars formed during the hydrolysis.

Figure 12:
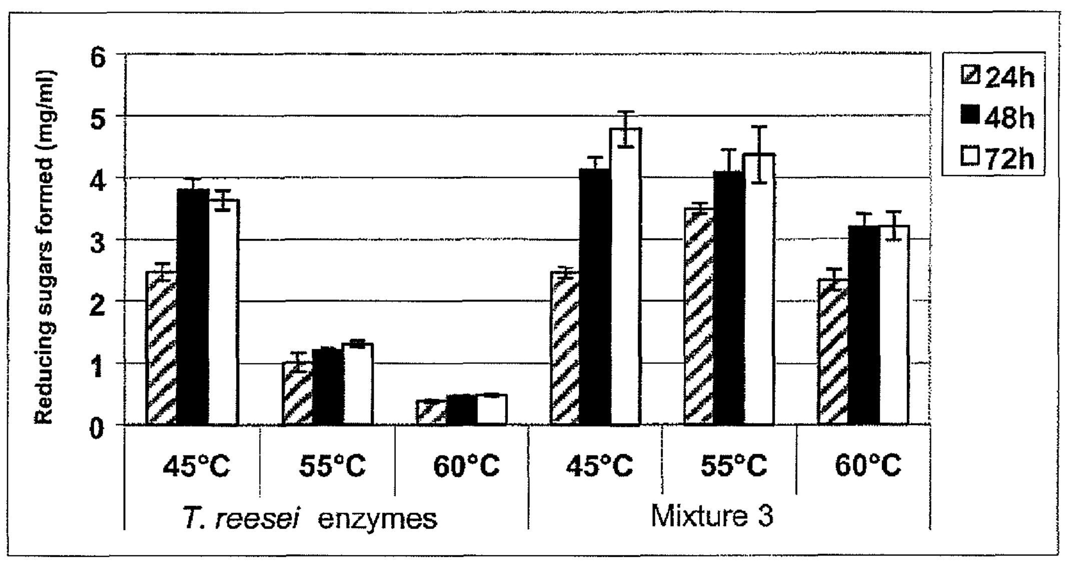

FIG. 12. Hydrolysis of steam exploded spruce fibre (10 mg/ml) with a mixture of thermophilic enzymes containing a new thermophilic xylanase XYN_30/Xyn10A from *Thermoascus aurantiacus* (MIXTURE 3) and *T. reesei* enzymes at 45, 55 and 60° C. Enzyme dosage for "MIXTURE 3" was 5 FPU/g dry matter of substrate and for *T. reesei* enzymes 5 FPU/g dry matter Celluclast supplemented with 100 nkat/g dry matter Novozym 188 (filter paper activity was assayed at 50° C., pH 5). Hydrolysis was carried out for 72 h at pH 5, with mixing. The results are given as mean (±SD) of three separate measurements.

Figure 13:
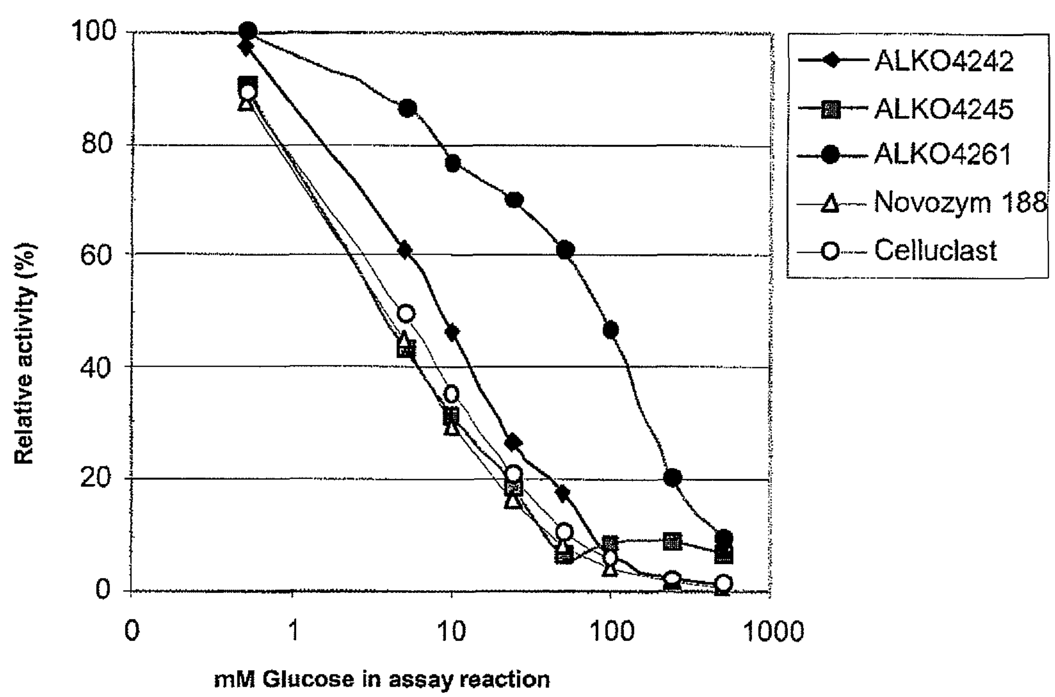

FIG. 13. The effect of glucose on activity of different β-glucosidase preparations. The standard assay using p-nitrophenyl-β-D-glucopyranoside as substrate was carried out in the presence of glucose in the assay mixture. The activity is presented as percentage of the activity obtained without glucose.

Figure 14:
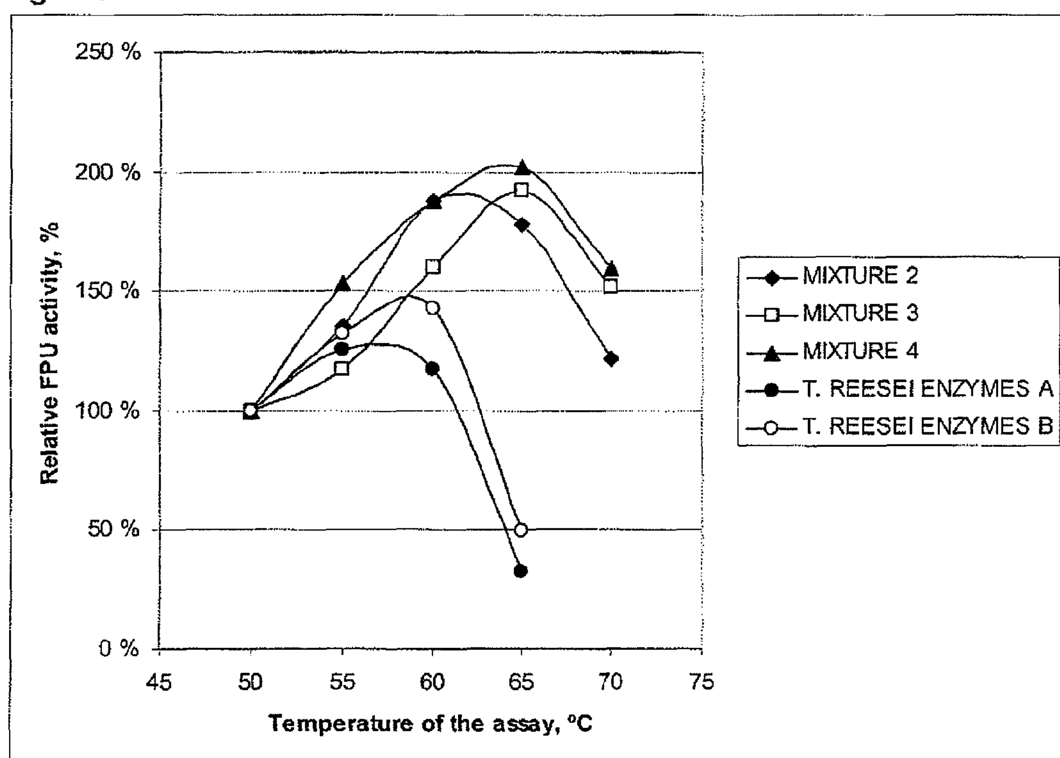

FIG. 14. FPU activities of the enzyme mixtures at temperatures from 50° C. to 70° C., presented as a percentage of the activity under the standard conditions (50° C., 1 h).

Figure 15:
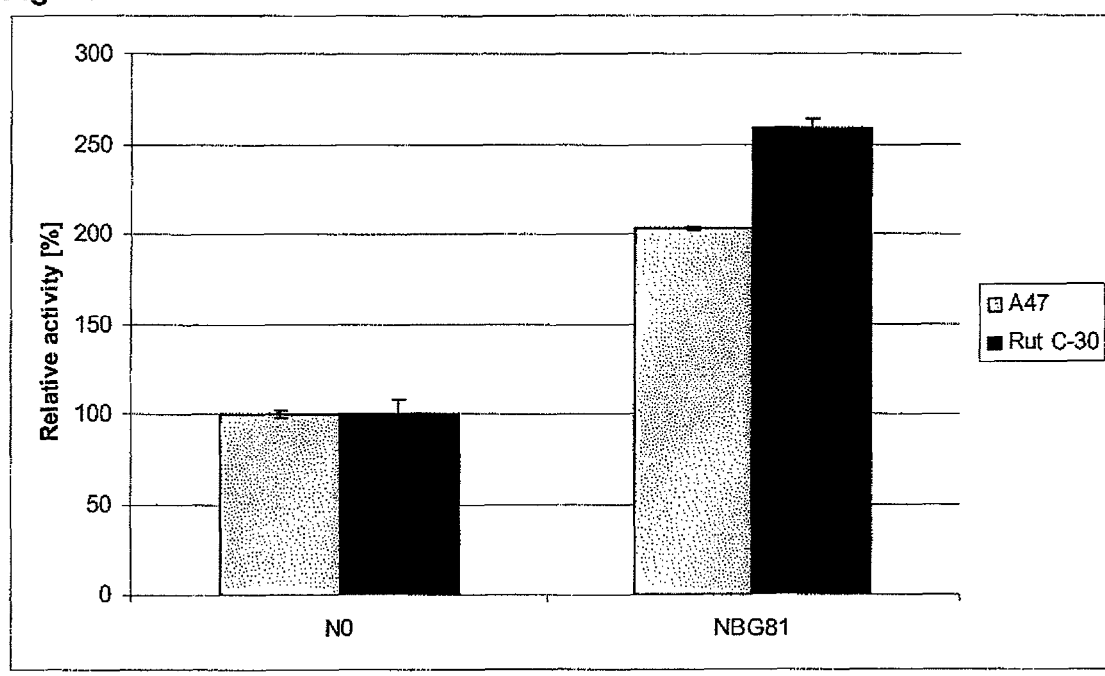

FIG. 15. The relative cellulase activity of two different *T. reesei* strains grown in media containing untreated Nutriose (N0) or BG_81/Cel3A pretreated Nutriose (NBG81) as a carbon source.

DETAILED DESCRIPTION

Cellulose is the major structural component of higher plants. It provides plant cells with high tensile strength helping them to resist mechanical stress and osmotic pressure. Cellulose is a β-1,4-glucan composed of linear chains of glucose residues joined by β-1,4-glycosidic linkages. Cellobiose is the smallest repeating unit of cellulose. In cell walls cellulose is packed in variously oriented sheets, which are embedded in a matrix of hemicellulose and lignin. Hemicellulose is a heterogeneous group of carbohydrate polymers containing mainly different glucans, xylans and mannans. Hemicellulose consists of a linear backbone with β-1,4-linked residues substituted with short side chains usually containing acetyl, glucuronyl, arabinosyl and galactosyl. Hemicellulose can be chemically cross-linked to lignin. Lignin is a complex cross-linked polymer of variously substituted p-hydroxyphenylpropane units that provides strength to the cell wall to withstand mechanical stress, and it also protects cellulose from enzymatic hydrolysis.

Lignocellulose is a combination of cellulose and hemicellulose and polymers of phenol propanol units and lignin. It is physically hard, dense, and inaccessible and the most abundant biochemical material in the biosphere. Lignocellulose containing materials are for example: hardwood and softwood chips, wood pulp, sawdust and forestry and wood industrial waste; agricultural biomass as cereal straws, sugar beet pulp, corn stover and cobs, sugar cane bagasse, stems, leaves, hulls, husks, and the like; waste products as municipal solid waste, newspaper and waste office paper, milling waste of e.g. grains; dedicated energy crops (e.g., willow, poplar, switchgrass or reed canarygrass, and the like). Preferred examples are corn stover, switchgrass, cereal straw, sugarcane bagasse and wood derived materials.

"Cellulosic material" as used herein, relates to any material comprising cellulose, hemicellulose and/or lignocellulose as a significant component. "Lignocellulosic material" means any material comprising lignocellulose. Such materials are e.g. plant materials such as wood including softwood and hardwood, herbaceous crops, agricultural residues, pulp and paper residues, waste paper, wastes of food and feed industry etc. Textile fibres such as cotton, fibres derived from cotton, linen, hemp, jute and man made cellulosic fibres as modal, viscose, lyocel are specific examples of cellulosic materials.

Cellulosic material is degraded in nature by a number of various organisms including bacteria and fungi. Cellulose is typically degraded by different cellulases acting sequentially or simultaneously. The biological conversion of cellulose to glucose generally requires three types of hydrolytic enzymes: (1) Endoglucanases which cut internal beta-1,4-glucosidic bonds; (2) Exocellobiohydrolases that cut the dissaccharide cellobiose from the end of the cellulose polymer chain; (3) Beta-1,4-glucosidases which hydrolyze the cellobiose and other short cello-oligosaccharides to glucose. In other words the three major groups of cellulases are cellobiohydrolases (CBH), endoglucanases (EG) and beta-glucosidases (BG).

Degradation of more complex cellulose containing substrates requires a broad range of various enzymes. For example lignocellulose is degraded by hemicellulases, like xylanases and mannanases. Hemicellulase is an enzyme hydrolysing hemicellulose.

"Cellulolytic enzymes" are enzymes having "cellulolytic activity," which means that they are capable of hydrolysing cellulosic substrates or derivatives thereof into smaller saccharides. Cellulolytic enzymes thus include both cellulases and hemicellulases. Cellulases as used herein include cellobiohydrolase, endoglucanase and beta-glucosidase.

*T. reesei* has a well known and effective cellulase system containing two CBHs, two major and several minor EGs and BGs. *T. reesei* CBHI (Cel7A) cuts sugar from the reducing end of the cellulose chain, has a C-terminal cellulose binding domain (CBD) and may constitute up to 60% of the total secreted protein. *T. reesei* CBHII (Cel6A) cuts sugar from the non-reducing end of the cellulose chain, has an N-terminal cellulose binding domain and may constitute up to 20% of the total secreted protein. Endoglucanases EGI (Cel7B), and EGV (Cel45A) have a CBD in their C-terminus, EGII (Cel5A) has an N-terminal CBD and EGIII (Cel12A) does not have a cellulose binding domain at all. CBHI, CBHII, EGI and EGII are so called "major cellulases" of *Trichoderma* comprising together 80-90% of total secreted proteins. It is known to a man skilled in the art that an enzyme may be active on several substrates and enzymatic activities can be measured using different substrates, methods and conditions. Identifying different cellulolytic activities is discussed for example in van Tilbeurgh et al. 1988.

In addition to a catalytic domain/core expressing cellulolytic activity cellulolytic enzymes may comprise one or more cellulose binding domains (CBDs), also named as carbohydrate binding domains/modules (CBD/CBM), which can be located either at the N- or C-terminus of the catalytic domain. CBDs have carbohydrate-binding activity and they mediate the binding of the cellulase to crystalline cellulose but have little or no effect on cellulase hydrolytic activity of the enzyme on soluble substrates. These two domains are typically connected via a flexible and highly glycosylated linker region.

"Cellobiohydrolase" or "CBH" as used herein refers to enzymes that cleave cellulose from the end of the glucose chain and produce mainly cellobiose. They are also called 1,4-beta-D-glucan cellobiohydrolases or cellulose 1,4-beta-cellobiosidases. They hydrolyze the 1,4-beta-D-glucosidic linkages from the reducing or non-reducing ends of a polymer containing said linkages, such as cellulose, whereby cellobiose is released. Two different CBHs have been isolated from *Trichoderma reesei*, CBHI and CBHII. They have a modular structure consisting of a catalytic domain linked to a cellulose-binding domain (CBD). There are also cellobiohydrolases in nature that lack CBD.

"Endoglucanase" or "EG" refers to enzymes that cut internal glycosidic bonds of the cellulose chain. They are classified as EC 3.2.1.4. They are 1,4-beta-D-glucan 4-glucanohydrolases and catalyze endohydrolysis of 1,4-beta-D-glycosidic linkages in polymers of glucose such as cellulose and derivatives thereof. Some naturally occurring endoglucanases have a cellulose binding domain, while others do not. Some endoglucanases have also xylanase activity (Bailey et al., 1993).

"Beta-glucosidase" or "BG" or "βG" refers to enzymes that degrade small soluble oligosaccharides including cellobiose to glucose. They are classified as EC 3.2.1.21. They are beta-D-glucoside glucohydrolases, which typically catalyze the hydrolysis of terminal non-reducing beta-D-glucose residues. These enzymes recognize oligosaccharides of glucose. Typical substrates are cellobiose and cellotriose. Cellobiose is an inhibitor of cellobiohydrolases, wherefore the degradation of cellobiose is important to overcome end-product inhibition of cellobiohydrolases.

Xylanases are enzymes that are capable of recognizing and hydrolyzing hemicellulose. They include both exohydrolytic and endohydrolytic enzymes. Typically they have endo-1,4-beta-xylanase (EC 3.2.1.8) or beta-D-xylosidase (EC 3.2.1.37) activity that breaks down hemicellulose to xylose. "Xylanase" or "Xyn" in connection with the present invention refers especially to an enzyme classified as EC 3.2.1.8 hydrolyzing xylose polymers of lignocellulosic substrate or purified xylan.

In addition to this cellulases can be classified to various glycosyl hydrolase families according their primary sequence, supported by analysis of the three dimensional structure of some members of the family (Henrissat 1991, Henrissat and Bairoch 1993, 1996). Some glycosyl hydrolases are multifunctional enzymes that contain catalytic domains that belong to different glycosylhydrolase families. Family 3 consists of beta-glucosidases (EC 3.2.1.21) such as Ta BG_81, At BG_101 and Ct BG_76 described herein. Family 5 (formerly known as celA) consists mainly of endoglucanases (EC 3.2.1.4) such as Ta EG_28 described herein. Family 7 (formerly cellulase family celC) contains endoglucanases (EC 3.2.1.4) and cellobiohydrolases (EC 3.2.1.91) such as Ct EG_54, Ta CBH, At CBH_A, At CBH_C and Ct CBH described herein. Family 10 (formerly celF) consists mainly of xylanases (EC 3.2.1.8) such as Ta XYN_30 and At XYN_60 described herein. Family 45 (formerly celK) contains endoglucanases (EC 3.2.1.4) such as At EG_40 and At EG_40_like described herein.

Cellulolytic enzymes useful for hydrolyzing cellulosic material are obtainable from *Thermoascus aurantiacus*, *Acremonium thermophilum*, or *Chaetomium thermophilum*. "Obtainable from" means that they can be obtained from said species, but it does not exclude the possibility of obtaining them from other sources. In other words they may originate from any organism including plants. Preferably they originate from microorganisms e.g. bacteria or fungi. The bacteria may be for example from a genus selected from *Bacillus*, *Azospirillum* and *Streptomyces*. More preferably the enzyme originates from fungi (including filamentous fungi and yeasts), for example from a genus selected from the group consisting of *Thermoascus, Acremonium, Chaetomium, Achaetomium, Thielavia, Aspergillus, Botrytis, Chrysosporium, Collybia, Fomes, Fusarium, Humicola, Hypocrea, Lentinus, Melanocarpus, Myceliophthora, Myriococcum, Neurospora, Penicillium, Phanerochaete, Phlebia, Pleurotus, Podospora, Polyporus, Rhizoctonia, Scytalidium, Pycnoporus, Trametes* and *Trichoderma*.

According to a preferred embodiment of the invention the enzymes are obtainable from *Thermoascus aurantiacus* strain ALKO4242 deposited as CBS 116239, strain ALKO4245 deposited as CBS 116240 presently classified as *Acremonium thermophilium*, or *Chaetomium thermophilum* strain ALKO4265 deposited as CBS 730.95.

The cellobiohydrolase preferably comprises an amino acid sequence having at least 80% identity to SEQ ID NO: 2, 4, 6 or 8, or an enzymatically active fragment thereof.

| Cellobiohydrolase | Gene | Obtainable from | CBD | nucleic acid SEQ ID NO: | amino acid SEQ ID NO: |
|---|---|---|---|---|---|
| Ta CBH | Ta cel7A | *T. aurantiacus* | – | 1 | 2 |
| At CBH_A | At cel7B | *A. thermophilum* | – | 3 | 4 |

-continued

| Cellobio-hydrolase | Gene | Obtainable from | CBD | nucleic acid SEQ ID NO: | amino acid SEQ ID NO: |
|---|---|---|---|---|---|
| At CBH_C | At cel7A | *A. thermophilum* | + | 5 | 6 |
| Ct CBH | Ct cel7A | *C. thermophilum* | + | 7 | 8 |

These CBHs have an advantageous cellulose inhibition constant compared to that of *Trichoderma reesei* CBH, and they show improved hydrolysis results when testing various cellulosic substrates. SEQ ID NO: 2 and 4 do not comprise a CBD. Particularly enhanced hydrolysis results may be obtained when a cellulose binding domain (CBD) is attached to a CBH that has no CBD of its own. The CBD may be obtained e.g. from a *Trichoderma* or *Chaetomium* species, and it is preferably attached to the CBH via a linker. The resulting fusion protein containing a CBH core region attached to a CBD via a linker may comprise an amino acid sequence having at least 80% identity to SEQ ID NO: 28 or 30. Polynucleotides comprising a sequence of SEQ ID NO: 27 or 29 encode such fusion proteins.

The endoglucanase may comprise an amino acid sequence having at least 80% identity to SEQ ID NO: 10, 12, 14 or 16, or an enzymatically active fragment thereof. These endoglucanases have good thermostability.

| Endo-glucanase | Gene | Obtainable from | CBD | nucl. acid SEQ ID NO: | amino acid SEQ ID NO: |
|---|---|---|---|---|---|
| Ta EG_28 | Ta cel5A | *T. aurantiacus* | − | 9 | 10 |
| At EG_40 | At cel45A | *A. thermophilum* | + | 11 | 12 |
| At EG40_like | At cel45B | *A. thermophilum* | − | 13 | 14 |
| Ct EG_54 | Ct cel7B | *C. thermophilum* | + | 15 | 16 |

The beta-glucosidase may comprise an amino acid sequence having at least 80% identity to SEQ ID NO: 22, 24 or 26, or an enzymatically active fragment thereof. These beta-glucosidases have good resistance to glucose inhibition, which is advantageous to avoid end product inhibition during enzymatic hydrolysis of cellulosic material. The beta-glucosidases may also be used in preparing sophorose, a cellulase inducer used in cultivation of *T. reesei*.

| Beta-glucosidase | Gene | Obtainable from | nucleic acid SEQ ID NO: | amino acid SEQ ID NO: |
|---|---|---|---|---|
| Ta BG_81 | Ta cel3A | *T. aurantiacus* | 21 | 22 |
| At BG_101 | At cel3A | *A. thermophilum* | 23 | 24 |
| Ct BG_76 | Ct cel3A | *C. thermophilum* | 25 | 26 |

The xylanase may comprise an amino acid sequence having at least 80% identity to SEQ ID NO: 18 or 20, or an enzymatically active fragment thereof.

| Xylanase | Gene | Obtainable from | CBD | nucleic acid SEQ ID NO: | amino acid SEQ ID NO: |
|---|---|---|---|---|---|
| Xyn_30 | Ta xyn10A | *T. aurantiacus* | + | 17 | 18 |
| Xyn_60 | At xyn10A | *A. thermophilum* | − | 19 | 20 |

By the term "identity" is here meant the global identity between two amino acid sequences compared to each other from the first amino acid encoded by the corresponding gene to the last amino acid. The identity of the full-length sequences is measured by using Needleman-Wunsch global alignment program at EMBOSS (European Molecular Biology Open Software Suite; Rice et al., 2000) program package, version 3.0.0, with the following parameters: EMBLOSUM62, Gap penalty 10.0, Extend penalty 0.5. The algorithm is described in Needleman and Wunsch (1970). The man skilled in the art is aware of the fact that results using Needleman-Wunsch algorithm are comparable only when aligning corresponding domains of the sequence. Consequently comparison of e.g. cellulase sequences including CBD or signal sequences with sequences lacking those elements cannot be done.

According to one embodiment of the invention, a cellulolytic polypeptide is used that has at least 80, 85, 90, 95 or 99% identity to SEQ ID NO: 2, 4, 6, 8, 10, 12, 14, 16, 18, 20, 22, 24 or 26 or at least to its enzymatically active fragment.

By the term "enzymatically active fragment" is meant any fragment of a defined sequence that has cellulolytic activity. In other words an enzymatically active fragment may be the mature protein part of the defined sequence, or it may be only an fragment of the mature protein part, provided that it still has cellobiohydrolase, endoglucanase, beta-glucosidase or xylanase activity.

The cellulolytic enzymes are preferably recombinant enzymes, which may be produced in a generally known manner. A polynucleotide fragment comprising the enzyme gene is isolated, the gene is inserted under a strong promoter in an expression vector, the vector is transferred into suitable host cells and the host cells are cultivated under conditions provoking production of the enzyme. Methods for protein production by recombinant technology in different host systems are well known in the art (Sambrook et al., 1989; Coen, 2001; Gellissen, 2005). Preferably the enzymes are produced as extracellular enzymes that are secreted into the culture medium, from which they can easily be recovered and isolated. The spent culture medium of the production host can be used as such, or the host cells may be removed therefrom, and/or it may be concentrated, filtrated or fractionated. It may also be dried.

Isolated polypeptide in the present context may simply mean that the cells and cell debris have been removed from the culture medium containing the polypeptide. Conveniently the polypeptides are isolated e.g. by adding anionic and/or cationic polymers to the spent culture medium to enhance precipitation of cells, cell debris and some enzymes that have unwanted side activities. The medium is then filtrated using an inorganic filtering agent and a filter to remove the precipitants formed. After this the filtrate is further processed using a semi-permeable membrane to remove excess of salts, sugars and metabolic products.

According to one embodiment of the invention, the heterologous polynucleotide comprises a gene similar to that included in a microorganism having accession number DSM 16723, DSM 16728, DSM 16729, DSM 16727, DSM 17326, DSM 17324, DSM 17323, DSM 17729, DSM 16724, DSM 16726, DSM 16725, DSM 17325 or DSM 17667.

The production host can be any organism capable of expressing the cellulolytic enzyme. Preferably the host is a microbial cell, more preferably a fungus. Most preferably the host is a filamentous fungus. Preferably the recombinant host is modified to express and secrete cellulolytic enzymes as its main activity or one of its main activities. This can be done by deleting major homologous secreted genes e.g. the four major cellulases of *Trichoderma* and by targeting heterologous genes to a locus that has been modified to ensure high expression and production levels. Preferred hosts for producing the cellulolytic enzymes are in particular strains from the genus *Trichoderma* or *Aspergillus*.

The enzymes needed for the hydrolysis of the cellulosic material according to the invention may be added in an enzymatically effective amount either simultaneously e.g. in the form of an enzyme mixture, or sequentially, or as a part of the simultaneous saccharification and fermentation (SSF). Any combination of the cellobiohydrolases comprising an amino acid sequence having at least 80% identity to SEQ ID NO: 2, 4, 6 or 8 or to an enzymatically active fragment thereof may be used together with any combination of endoglucanases and beta-glucosidases. If the cellulosic material comprises hemicellulose, hemicellulases, preferably xylanases are additionally used for the degradation. The endoglucanases, beta-glucosidases and xylanases may be selected from those described herein, but are not limited to them. They can for example also be commercially available enzyme preparations. In addition to cellulases and optional hemicellulases one or more other enzymes may be used, for example proteases, amylases, laccases, lipases, pectinases, esterases and/or peroxidases. Another enzyme treatment may be carried out before, during or after the cellulase treatment.

The term "enzyme preparation" denotes to a composition comprising at least one of the desired enzymes. The preparation may contain the enzymes in at least partially purified and isolated form. It may even essentially consist of the desired enzyme or enzymes. Alternatively the preparation may be a spent culture medium or filtrate containing one or more cellulolytic enzymes. In addition to the cellulolytic activity, the preparation may contain additives, such as mediators, stabilizers, buffers, preservatives, surfactants and/or culture medium components. Preferred additives are such, which are commonly used in enzyme preparations intended for a particular application. The enzyme preparation may be in the form of liquid, powder or granulate. Preferably the enzyme preparation is spent culture medium. "Spent culture medium" refers to the culture medium of the host comprising the produced enzymes. Preferably the host cells are separated from the said medium after the production.

According to one embodiment of the invention the enzyme preparation comprises a mixture of CBH, EG and BG, optionally together with xylanase and/or other enzymes. The CBH comprises an amino acid sequence having at least 80% identity to SEQ ID NO: 2, 4, 6 or 8 or to an enzymatically active fragment thereof, and it may be obtained from *Thermoascus aurantiacus, Acremonium thermophilum*, or *Chaetomium thermophilum*, whereas EG, BG and xylanase may be of any origin including from said organisms. Other enzymes that might be present in the preparation are e.g. proteases, amylases, laccases, lipases, pectinases, esterases and/or peroxidases.

Different enzyme mixtures and combinations may be used to suit different process conditions. For example if the degradation process is to be carried out at a high temperature, thermostable enzymes are chosen. A combination of a CBH of family 7 with an endoglucanase of family 45, optionally in combination with a BG of family 3 and/or a xylanase of family 10 had excellent hydrolysis performance both at 45° C., and at elevated temperatures.

Cellulolytic enzymes of *Trichoderma reesei* are conventionally used at temperatures in the range of about 40-50° C. in the hydrolysis, and at 30-40° C. in SSF. CBH, EG, BG and Xyn obtainable from *Thermoascus aurantiacus, Acremonium thermophilum*, or *Chaetomium thermophilum* are efficient at these temperatures too, but in addition most of them also function extremely well at temperatures between 50° C. and 75° C., or even up to 80° C. and 85° C., such as between 55° C. and 70° C., e.g. between 60° C. and 65° C. For short incubation times enzyme mixtures are functional up to even 85° C., for complete hydrolysis lower temperatures are normally used.

The method for treating cellulosic material with CBH, EG, BG and Xyn is especially suitable for producing fermentable sugars from lignocellulosic material. The fermentable sugars may then be fermented by yeast into ethanol, and used as fuel. They can also be used as intermediates or raw materials for the production of various chemicals or building blocks for the processes of chemical industry, e.g. in so called biorefinery. The lignocellulosic material may be pretreated before the enzymatic hydrolysis to disrupt the fiber structure of cellulosic substrates and make the cellulose fraction more accessible to the cellulolytic enzymes. Current pretreatments include mechanical, chemical or thermal processes and combinations thereof. The material may for example be pretreated by steam explosion or acid hydrolysis.

A number of novel cellulolytic polypeptides were found in *Thermoascus aurantiacus, Acremonium thermophilum*, and *Chaetomium thermophilum*. The novel polypeptides may comprise a fragment having cellulolytic activity and be selected from the group consisting of a polypeptide comprising an amino acid sequence having at least 66%, preferably 70% or 75%, identity to SEQ ID NO: 4, 79% identity to SEQ ID NO: 6, 78% identity to SEQ ID NO: 12, 68%, preferably 70% or 75%, identity to SEQ ID NO: 14, 72%, preferably 75%, identity to SEQ ID NO: 16, 68%, preferably 70% or 75%, identity to SEQ ID NO: 20, 74% identity to SEQ ID NO: 22 or 24, or 78% identity to SEQ ID NO: 26.

The novel polypeptides may also be variants of said polypeptides. A "variant" may be a polypeptide that occurs naturally e.g. as an allelic variant within the same strain, species or genus, or it may have been generated by mutagenesis. It may comprise amino acid substitutions, deletions or insertions, but it still functions in a substantially similar manner to the enzymes defined above i.e. it comprises a fragment having cellulolytic activity.

The cellulolytic polypeptides are usually produced in the cell as immature polypeptides comprising a signal sequence that is cleaved off during secretion of the protein. They may also be further processed during secretion both at the N-terminal and/or C-terminal end to give a mature, enzymatically active protein. A polypeptide "comprising a fragment having cellulolytic activity" thus means that the polypeptide may be either in immature or mature form, preferably it is in mature form, i.e. the processing has taken place.

The novel polypeptides may further be a "fragment of the polypeptides or variants" mentioned above. The fragment may be the mature form of the proteins mentioned above, or it may be only an enzymatically active part of the mature protein. According to one embodiment of the invention, the polypeptide has an amino acid sequence having at least 80, 85, 90, 95, or 99% identity to SEQ ID NO: 4, 6, 12, 14, 16, 20, 22, 24 or 26, or to a cellulolytically active fragment thereof. It may also be a variant thereof, or a fragment thereof having cellobiohydrolase, endoglucanase, xylanase, or beta-glucosidase activity. According to another embodiment of the invention, the polypeptide consists essentially of a cellulolytically active fragment of a sequence of SEQ ID NO: 4, 6, 12, 14, 16, 20, 22, 24 or 26.

The novel polynucleotides may comprise a nucleotide sequence of SEQ ID NO: 3, 5, 11, 13, 15, 19, 21, 23 or 25, or a sequence encoding a novel polypeptide as defined above, including complementary strands thereof. Polynucleotide as used herein refers to both RNA and DNA, and it may be single stranded or double stranded. The polynucleotide may also be a fragment of said polynucleotides comprising at least 20 nucleotides, e.g. at least 25, 30 or 40 nucleotides. According to one embodiment of the invention it is at least 100, 200 or 300 nucleotides in length. Further the polynucleotide may be degenerate as a result of the genetic code to any one of the sequences as defined above. This means that different codons may code for the same amino acid.

According to one embodiment of the invention the polynucleotide is "comprised in" SEQ ID NO: 3, 5, 11, 13, 15, 19, 21, 23 or 25, which means that the sequence has at least part of the sequence mentioned. According to another embodiment of the invention, the polynucleotide comprises a gene similar to that included in a microorganism having accession number DSM 16728, DSM 16729, DSM 17324, DSM 17323, DSM 17729, DSM 16726, DSM 16725, DSM 17325 or DSM 17667.

The novel proteins/polypeptides may be prepared as described above. The novel polynucleotides may be inserted into a vector, which is capable of expressing the polypeptide encoded by the heterologous sequence, and the vector may be inserted into a host cell capable of expressing said polypeptide. The host cell is preferably of the genus *Trichoderma* or *Aspergillus.*

A heterologous gene encoding the novel polypeptides has been introduced on a plasmid into an *Escherichia coli* strain having accession number DSM 16728, DSM 16729, DSM 17324, DSM 17323, DSM 17729, DSM 16726, DSM 16725, DSM 17325 or DSM 17667.

The novel enzymes may be components of an enzyme preparation. The enzyme preparation may comprise one or more of the novel polypeptides, and it may be e.g. in the form of spent culture medium, powder, granules or liquid. According to one embodiment of the invention it comprises cellobiohydrolase, endoglucanase, beta-glucosidase, and optionally xylanase activity and/or other enzyme activities. It may further comprise any conventional additives.

The novel enzymes may be applied in any process involving cellulolytic enzymes, such as in fuel, textile, detergent, pulp and paper, food, feed or beverage industry, and especially in hydrolysing cellulosic material for the production of biofuel comprising ethanol. In the pulp and paper industry they may be used to modify cellulosic fibre for example in treating kraft pulp, mechanical pulp, or recycled paper.

The invention is illustrated by the following non-limiting examples. It should be understood, however, that the embodiments given in the description above and in the examples are for illustrative purposes only, and that various changes and modifications are possible within the scope of the invention.

EXAMPLES

Example 1

Screening for Strains Expressing Cellulolytic Activity and their Cultivation for Purification About 25 fungal strains from the Roal Oy culture collection were tested for cellulolytic activity including beta-glucosidases. After preliminary screening six strains were chosen for further studies. These were *Thermoascus aurantiacus* ALKO4239 and ALKO4242, *Acremonium thermophilum* ALKO4245, *Talaromyces thermophilus* ALKO4246 and *Chaetomium thermophilum* ALKO4261 and ALKO4265.

The strains ALKO4239, ALKO4242 and ALKO4246 were cultivated in shake flasks at 42° C. for 7 d in the medium 3×B, which contains g/litre: Solka Floc cellulose 18, distiller's spent grain 18, oats spelt xylan 9, $CaCO_3$ 2, soybean meal 4.5, $(NH_4)HPO_4$ 4.5, wheat bran 3.0, $KH_2PO_4$ 1.5, $MgSO_4.H_2O$ 1.5, NaCl 0.5, $KNO_3$ 0.9, locust bean gum 9.0, trace element solution #1 0.5, trace element solution #2 0.5 and Struktol (Stow, Ohio, USA) antifoam 0.5 ml; the pH was adjusted to 6.5. Trace element solution #1 has g/litre: $MnSO_4$ 1.6, $ZnSO_4.7H_2O$ 3.45 and $CoCl_2.6H_2O$ 2.0; trace element solution #2 has g/litre: $FeSO_4.7H_2O$ 5.0 with two drops of concentrated $H_2SO_4$.

The strain ALKO4261 was cultivated in shake flasks in the medium lxB, which has one third of each of the constituents of the 3×B medium (above) except it has same concentrations for $CaCO_3$, NaCl and the trace elements. The strain was cultivated at 45° C. for 7 d.

The strain ALKO4265 was cultivated in shake flasks in the following medium, g/l: Solka Floc cellulose 40, Pharmamedia™ (Traders Protein, Memphis, Tenn., USA) 10, corn steep powder 5, $(NH_4)_2 50_4$ 5 and $KH_2PO_4$ 15; the pH was adjusted to 6.5. The strain was cultivated at 45° C. for 7 d.

After the cultivation the cells and other solids were collected by centrifugation down and the supernatant was recovered. For the shake flask cultivations, protease inhibitors PMSF (phenylmethyl-sulphonylfluoride) and pepstatin A were added to 1 mM and 10 µg/ml, respectively. If not used immediately, the preparations were stored in aliquots at −20° C.

For the estimation of the thermoactivity of the enzymes, assays were performed of the shake flask cultivation preparations at 50° C., 60° C., 65° C., 70° C. and 75° C. for 1 h, in the presence of 100 µg bovine serum albumin (BSA)/ml as a stabilizer. Preliminary assays were performed at 50° C. and 65° C. at two different pH values (4.8/5.0 or 6.0) in order to clarify, which pH was more appropriate for the thermoactivity assay.

All shake flask supernatants were assayed for the following activities:

Cellobiohydrolase I—Like Activity ('CBHI') and the Endoglucanase I—Like Activity ('EGI'):

These were measured in 50 mM Na-acetate buffer with 0.5 mM MUL (4-methylumbelliferyl-beta-D-lactoside) as the substrate. Glucose (100 mM) was added to inhibit any interfering beta-glucosidase activity. The liberated 4-methylumbelliferyl was measured at 370 nm. The 'CBHI' and the 'EGI' activities were distinguished by measuring the activity in the presence and absence of cellobiose (5 mM). The activity that is not inhibited by cellobiose represents the 'EGI' activity and the remaining MUL activity represents the 'CBHI' activity (van Tilbeurgh et al, 1988). The assay was performed at pH 5.0 or 6.0 (see below).

The Endoglucanase (CMCase) Activity:

This was assayed with 2% (w/v) carboxymethylcellulose (CMC) as the substrate in 50 mM citrate buffer essentially as described by Bailey and Nevalainen 1981; Haakana et al. 2004. Reducing sugars were measured with the DNS reagent. The assay was performed at pH 4.8 or 6.0 (see below).

Beta-Glucosidase (BGU) Activity:

This was assayed with 4-nitrophenyl-β-D-glucopyranoside (1 mM) in 50 mM citrate buffer as described by Bailey and Nevalainen 1981. The liberated 4-nitrophenol was measured at 400 nm. The assay was performed at pH 4.8 or 6.0 (see below).

The relative activities of the enzymes are presented in FIG. 1. The relative activities were presented by setting the activity at 60° C. as 100% (FIG. 1). All strains produced enzymes, which had high activity at high temperatures (65° C.-75° C.).

For protein purifications. ALKO4242 was also grown in a 2 litre bioreactor (Braun Biostat® B, Braun, Melsungen, Germany) in the following medium, g/litre: Solka Floc cellulose 40, soybean meal 10, $NH_4NO_3$ 5, $KH_2PO_4$ 5, $MgSO_4.7H_2O$ 0.5, $CaCl_2.2H_2O$ 0.05, trace element solution #1 0.5, trace element solution #2 0.5. The aeration was 1 vvm, antifoam control with Struktol, stirring 200-800 rpm and temperature at 47° C. Two batches were run, one at pH 4.7±0.2 ($NH_3/H_2SO_4$) and the other with initial pH of pH 4.5. The cultivation time was 7 d. After the cultivation the cells and other solids were removed by centrifugation.

The strain ALKO4245 was grown in 2 litre bioreactor (Braun Biostat® B, Braun, Melsungen, Germany) in the following medium, g/litre: Solka Floc cellulose 40, corn steep powder 15, distiller's spent grain 5, oats spelt xylan 3, locust bean gum 3, $(NH_4)_2SO_4$ 5 and $KH_2PO_4$ 5. The pH range was 5.2±0.2 ($NH_3/H_2SO_4$), aeration 1 vvm, stirring 300-600 rpm, antifoam control with Struktol and the temperature 42° C. The cultivation time was 4 d. After the cultivation the cells and other solids were removed by centrifugation.

For enzyme purification, ALKO4261 was grown in a 10 litre bioreactor (Braun Biostat® ED, Braun, Melsungen, Germany) in the following medium, g/litre: Solka Floc cellulose 30, distiller's spent grain 10, oats spelt xylan 5, $CaCO_3$ 2, soybean meal 10, wheat bran 3.0, $(NH_4)_2SO_4$ 5, $KH_2PO_4$ 5, $MgSO_4.7H_2O$ 0.5, NaCl 0.5, $KNO_3$ 0.3, trace element solution #1 0.5 and trace element solution #2 0.5. The pH range was 5.2±0.2 ($NH_3/H_2SO_4$), aeration 1 vvm, stirring 200-600 rpm, antifoam control with Struktol and the temperature 42° C. The cultivation time was 5 d. A second batch was grown under similar conditions except that Solka Floc was added to 40 g/l and spent grain to 15 g/l. The supernatants were recovered by centrifugation and filtering through Seitz-K 150 and EK filters (Pall SeitzSchenk Filtersystems GmbH, Bad Kreuznach, Germany). The latter supernatant was concentrated about ten fold using the Pellicon mini ultrafiltration system (filter NMWL 10 kDa; Millipore, Billerica, Mass., USA).

For enzyme purification, ALKO4265 was also grown in a 10 litre bioreactor (Braun Biostat® ED, Braun, Melsungen, Germany) in the same medium as above, except $KH_2PO_4$ was added to 2.5 g/l. The pH range was 5.3±0.3 ($NH_3/H_3PO_4$), aeration 0.6 vvm, stirring 500 rpm, antifoam control with Struktol and the temperature 43° C. The cultivation time was 7 d. The supernatants were recovered by centrifugation and filtering through Seitz-K 150 and EK filters (Pall SeitzSchenk Filtersystems GmbH, Bad Kreuznach, Germany). The latter supernatant was concentrated about 20 fold using the Pellicon mini ultrafiltration system (filter NMWL 10 kDa; Millipore, Billerica, Mass., USA).

Example 2

Purification and Characterization of Cellobiohydrolases from *Acremonium thermophilum* ALKO4245 and *Chaetomium thermophilum* ALKO4265

*Acremonium thermophilum* ALKO4245 and *Chaetomium thermophilum* ALKO4265 were grown as described in Example 1. The main cellobiohydrolases were purified using p-aminobenzyl 1-thio-β-cellobioside-based affinity column, prepared as described by Tomme et al., 1988.

The culture supernatants were first buffered into 50 mM sodium acetate buffer pH 5.0, containing 1 mM δ-gluconolactone and 0.1 M glucose in order to retard ligand hydrolysis in the presence of β-glucosidases. Cellobiohydrolases were eluted with 0.1 M lactose and finally purified by gel filtration chromatography using Superdex 200 HR 10/30 columns in the ÄKTA system (Amersham Pharmacia Biotech). The buffer used in gel filtration was 50 mM sodium phosphate pH 7.0, containing 0.15 M sodium chloride.

Purified cellobiohydrolases were analysed by SDS-polyacrylamide gel electrophoresis and the molecular mass of both proteins was determined to be approximately 70 kDa evaluated on the basis of the molecular mass standards (Low molecular weight calibration kit, Amersham Biosciences). Purified *Acremonium* and *Chaetomium* cellobiohydrolases were designated as At Cel7A and Ct Cel7A, respectively, following the scheme in Henrissat et al. (1998) (Henrissat, 1991; Henrissat and Bairoch, 1993).

The specific activity of the preparations was determined using 4-methylumbelliferyl-β-D-lactoside (MUL), 4-methylumbelliferyl-β-D-cellobioside (MUG2) or 4-methylumbelliferyl-β-D-cellotrioside (MUG3) as substrate (van Tilbeurgh et al., 1988) in 0.05 M sodium citrate buffer pH 5 at 50° C. for 10 min. Endoglucanase and xylanase activities were determined by standard procedures (according to IUPAC, 1987) using carboxymethyl cellulose (CMC) and birch glucuronoxylan (Bailey et al., 1992) as substrates. Specific activity against Avicel was calculated on the basis of reducing sugars formed in a 24 h reaction at 50° C., pH 5.0, with 1% substrate and 0.25 μM enzyme dosage. The protein content of the purified enzyme preparations was measured according to Lowry et al., 1951. To characterize the end products of hydrolysis, soluble sugars liberated in 24 h hydrolysis experiment, as described above, were analysed by HPLC (Dionex). Purified cellobiohydrolase I (CBHI/Cel7A) of *Trichoderma reesei* was used as a reference.

The specific activities of the purified enzymes and that of *T. reesei* CBHI/Cel7A are presented in Table 1. The purified At Cel7A and Ct Cel7A cellobiohydrolases possess higher specific activities against small synthetic substrates as compared to *T. reesei* CBHI/Cel7A. The specific activity against Avicel was clearly higher with the herein disclosed enzymes. Low activities of the purified enzyme preparations against xylan and CMC may either be due to the properties of the proteins themselves, or at least partially to the remaining minor amounts of contaminating enzymes. The major end product of cellulose hydrolysis by all purified enzymes was cellobiose which is typical to cellobiohydrolases.

TABLE 1

Specific activities (nkat/mg) of the purified cellobiohydrolases and the reference enzyme of *T. reesei* (50° C., pH 5.0, 24 h).

| Substrate | *A. thermophilum* ALKO4245 Cel7A | *C. thermophilum* ALKO4265 Cel7A | *T. reesei* Cel7A |
|---|---|---|---|
| Xylan | 11.3 | 6.7 | 1.3 |
| CMC | 26.2 | 5.5 | 1.0 |
| MUG2 | 9.2 | 18.9 | 4.3 |
| MUG3 | 1.3 | 1.5 | 0.9 |
| MUL | 21.5 | 54.0 | 21.9 |
| Avicel | 1.8 | 1.4 | 0.6 |

Thermal stability of the purified cellobiohydrolases was determined at different temperatures. The reaction was performed in the presence of 0.1% BSA at pH 5.0 for 60 min using 4-methylumbelliferyl-β-D-lactoside as substrate. *C. thermophilum* ALKO4265 CBH/Cel7A and *A. thermophilum* ALKO4245 CBH/Cel7A were stable up to 65° and 60° C., respectively. The *T. reesei* reference enzyme (CBHI/Cel7A) retained 100% of activity up to 55° C.

Example 3

Purification and Characterization of an Endoglucanase from *Acremonium thermophilum* ALKO4245

*Acremonium thermophilum* ALKO4245 was grown as described in Example 1. The culture supernatant was incubated at 70° C. for 24 hours after which it was concentrated by ultrafiltration. The pure endoglucanase was obtained by sequential purification with hydrophobic interaction and cation exchange chromatography followed by gel filtration. The endoglucanase activity of the fractions collected during purification was determined using carboxymethyl cellulose (CMC) as substrate (procedure of IUPAC 1987). Protein content was measured by BioRad Assay Kit (Bio-Rad Laboratories) using bovine serum albumine as standard.

The concentrated culture supernatant was applied to a HiPrep 16/10 Butyl FF hydrophobic interaction column equilibrated with 20 mM potassium phosphate buffer pH 6.0, containing 1 M $(NH_4)_2SO_4$. Bound proteins were eluted with the linear gradient from the above buffer to 5 mM potassium phosphate, pH 6.0. Fractions were collected and the endoglucanase activity was determined as described above. The endoglucanase activity was eluted in a broad conductivity area of 120 to 15 mS/cm.

Combined fractions were applied to a HiTrap SP XL cation exchange column equilibrated with 8 mM sodium acetate, pH 4.5. Bound proteins were eluted with a linear gradient from 0 to 0.25 M NaCl in the equilibration buffer. The protein containing endoglucanase activity was eluted at the conductivity area of 3-7 mS/cm. Cation exchange chromatography was repeated and the protein eluate was concentrated by freeze drying.

The dissolved sample was loaded onto a Superdex 75 HR10/30 gel filtration column equilibrated with 20 mM sodium phosphate buffer pH 7.0, containing 0.15 M NaCl. The main protein fraction was eluted from the column with the retention volume of 13.3 ml. The protein eluate was judged to be pure by SDS-polyacryl amide gel electrophoresis and the molecular weight was evaluated to be 40 kDa. The specific activity of the purified protein, designated as At EG_40, at 50° C. was determined to be 450 nkat/mg (procedure of IUPAC 1987, using CMC as substrate).

Thermal stability of the purified endoglucanase was determined at different temperatures. The reaction was performed in the presence of 0.1 mg/ml BSA at pH 5.0 for 60 min using carboxymethyl cellulose as substrate. *A. thermophilum* EG_40/Cel45A was stable up to 80° C. The *T. reesei* reference enzymes EGI (Cel7B) and EGII (Cel5A) retained 100% of activity up to 60° C. and 65° C., respectively.

Example 4

Purification of an Endoglucanase from *Chaetomium thermophilum* ALKO4261

*Chaetomium thermophilum* ALKO4261 was grown as described in Example 1. The pure endoglucanase was obtained by sequential purification with hydrophobic interaction and cation exchange chromatography followed by gel filtration. The endoglucanase activity of the fractions collected during purification was determined using carboxymethyl cellulose (CMC) as substrate (procedure of IUPAC 1987).

Ammonium sulfate was added to the culture supernatant to reach the same conductivity as 20 mM potassium phosphate pH 6.0, containing 1 M $(NH_4)_2SO_4$. The sample was applied to a HiPrep 16/10 Phenyl FF hydrophobic interaction column equilibrated with 20 mM potassium phosphate pH 6.0, containing 1 M $(NH_4)_2SO_4$. Elution was carried out with a linear gradient of 20 to 0 mM potassium phosphate, pH 6.0, followed by 5 mM potassium phosphate, pH 6.0 and water. Bound proteins were eluted with a linear gradient of 0 to 6 M Urea. Fractions were collected and the endoglucanase activity was analysed as described above. The protein containing endoglucanase activity was eluted in the beginning of the urea gradient.

The fractions were combined, equilibriated to 16 mM Tris-HCl pH 7.5 (I=1.4 mS/cm) by 10DG column (Bio-Rad) and applied to a HiTrap DEAE FF anion exchange column equilibrated with 20 mM Tris-HCl, pH 7.5. Bound proteins were eluted with a linear gradient from 0 to 1 M NaCl in the equilibration buffer. Fractions were collected and analyzed for endoglucanase activity as described above. The protein was eluted in the range of 10-20 mS/cm.

The sample was equilibrated to 15 mM sodium acetate, pH 4.5 by 10DG column (Bio-Rad) and applied to a HiTrap SP XL cation exchange column equilibrated with 20 mM sodium acetate pH 4.5. Proteins were eluted with a linear gradient from 0 to 0.4 M sodium acetate, pH 4.5. Endoglucanase activity was eluted in the range of 1-10 mS/cm. The collected sample was lyophilized.

The sample was dissolved in water and applied to a Superdex 75 HR 10/30 gel filtration column equilibrated with 20 mM sodium phosphate pH 6.0, containing 0.15 M NaCl. Fractions were collected and those containing endoglucanase activity were combined. The protein eluate was judged to be pure by SDS-polyacrylamide gel electrophoresis and the molecular mass was evaluated on the basis of molecular mass standards (prestained SDS-PAGE standards, Broad Range, Bio-Rad) to be 54 kDa. The pI of the purified protein, designated as Ct EG_54 was determined with PhastSystem (Pharmacia) to be ca 5.5.

Example 5

Purification of an Endoglucanase from *Thermoascus aurantiacus* ALKO4242

*Thermoascus aurantiacus* ALKO4242 was grown as described in Example 1. The pure endoglucanase was obtained by sequential purification with hydrophobic interaction and anion exchange chromatography followed by gel filtration. The endoglucanase activity of the fractions collected during purification was determined using carboxymethyl cellulose (CMC) as substrate (procedure of IUPAC 1987). Protein content was measured by BioRad Assay Kit (Bio-Rad Laboratories) using bovine serum albumine as standard.

The culture supernatant was applied to a HiPrep 16/10 Butyl hydrophobic interaction column equilibrated with 20 mM potassium phosphate buffer pH 6.0, containing 0.7 M $(NH_4)_2SO_4$. Bound proteins were eluted with 0.2 M $(NH_4)_2SO_4$ (I=39 mS/cm). Fractions containing endoglucanase activity were combined and concentrated by ultrafiltration.

The sample was desalted in 10DG columns (Bio-Rad) and applied to a HiTrap DEAE FF anion exchange column equilibrated with 15 mM Tris-HCL, pH 7.0. Bound proteins were eluted with a linear gradient from 0 to 0.4 M NaCl in the equilibration buffer. The protein containing endoglucanase activity was eluted at the conductivity area of 15-21 mS/cm. Collected fractions were combined and concentrated as above.

The sample was applied to a Sephacryl S-100 HR 26/60 gel filtration column equilibrated with 50 mM sodium acetate buffer pH 5.0, containing 0.05 M NaCl. The protein fraction containing endoglucanase activity was eluted from the column with a retention volume corresponding to a molecular weight of 16 kDa. Collected fractions were combined, concentrated and gel filtration was repeated. The protein eluate was judged to be pure by SDS-polyacryl amide gel electrophoresis and the molecular weight was evaluated to be 28 kDa. The pI of the purified protein, designated as Ta EG_28, was determined in an IEF gel (PhastSystem, Pharmacia) to be about 3.5. The specific activity of Ta EG_28 at 50° C. was determined to be 4290 nkat/mg (procedure of IUPAC 1987, using CMC as substrate).

Example 6

Purification and Characterization of a β-Glucosidase from *Acremonium thermophilum* ALKO4245

*Acremonium thermophilum* ALKO4245 was grown as described in Example 1. The pure β-glucosidase was obtained by sequential purification with hydrophobic interaction and anion exchange chromatography followed by gel filtration. The β-glucosidase activity of the fractions collected during purification was determined using 4-nitrophenyl-β-D-glucopyranoside as substrate (Bailey and Linko, 1990). Protein content was measured by BioRad Assay Kit (Bio-Rad Laboratories) using bovine serum albumine as standard.

The culture supernatant was applied to a HiPrep 16/10 Phenyl Sepharose FF hydrophobic interaction column equilibrated with 20 mM potassium phosphate pH 6.0, containing 1 M $(NH_4)_2SO_4$. Bound proteins were eluted with a linear gradient from the equilibration buffer to 5 mM potassium phosphate in the conductivity area 137-16 mS/cm. Collected fractions were combined and concentrated by ultrafiltration.

The sample was desalted in 10DG columns (Bio-Rad) and applied to a HiTrap DEAE FF anion exchange column equilibrated with 10 mM potassium phosphate pH 7.0. Bound proteins were eluted with a linear gradient from the equilibration buffer to the same buffer containing 0.25 M NaCl in the conductivity area 1.5-12 mS/cm. Anion exchange chromatography was repeated as above, except that 4 mM potassium phosphate buffer pH 7.2 was used. Proteins were eluted at the conductivity area of 6-9 mS/cm. Fractions containing β-glucosidase activity were collected, combined, and concentrated.

The active material from the anion exchange chromatography was applied to a Sephacryl S-300 HR 26/60 column equilibrated with 20 mM sodium phosphate pH 6.5, containing 0.15 M NaCl. The protein with β-glucosidase activity was eluted with a retention volume corresponding to a molecular weight of 243 kDa. The protein was judged to be pure by SDS-polyacrylamide gel electrophoresis and the molecular weight was evaluated to be 101 kDa. The pI of the purified protein, designated as At βG_101, was determined in an IEF gel (PhastSystem, Pharmacia) to be in the area of 5.6-4.9. The specific activity of At βG_101 at 50° C. was determined to be 1100 nkat/mg (using 4-nitrophenyl-β-D-glucopyranoside as substrate, Bailey and Linko, 1990).

Thermal stability of the purified β-glucosidase was determined at different temperatures. The reaction was performed in the presence of 0.1 mg/ml BSA at pH 5.0 for 60 min using 4-nitrophenyl-β-D-glucopyranoside as substrate. *A. thermophilum* βG_101 was stable up to 70° C. The *Aspergillus* reference enzyme (Novozym 188) retained 100% of activity up to 60°.

Example 7

Purification of a β-Glucosidase from *Chaetomium thermophilum* ALKO4261

*Chaetomium thermophilum* ALKO4261 was grown as described in Example 1. The pure β-glucosidase was obtained by sequential purification with hydrophobic interaction, anion and cation exchange chromatography followed by gel filtration. The β-glucosidase activity of the fractions collected during purification was determined using 4-nitrophenyl-β-D-glucopyranoside as substrate (Bailey and Linko, 1990).

The culture supernatant was applied to a HiPrep 16/10 Phenyl Sepharose FF hydrophobic interaction column equilibrated with 20 mM potassium phosphate pH 6.0, containing 0.8 M $(NH_4)_2SO_4$. The elution was carried out with a linear gradient from the equilibration buffer to 3 mM potassium phosphate, pH 6.0, followed by elution with water and 6 M urea. The first fractions with β-glucosidase activity were eluted in the conductivity area of 80-30 mS/cm. The second β-glucosidase activity was eluted with 6 M urea. The active fractions eluted by urea were pooled and desalted in 10DG columns (Bio-Rad) equilibrated with 10 mM Tris-HCl pH 7.0.

After desalting, the sample was applied to a HiTrap DEAE FF anion exchange column equilibrated with 15 mM Tris-HCl pH 7.0. The protein did not bind to the column but was eluted during the sample feed. This flow-through fraction was desalted in 10DG columns (Bio-Rad) equilibrated with 7 mM Na acetate, pH 4.5.

The sample from the anion exchange chromatography was applied to a HiTrap SP FF cation exchange column equilibrated with 10 mM sodium acetate pH 4.5. Bound proteins were eluted with a linear gradient from 10 mM to 400 mM sodium acetate, pH 4.5. The fractions with β-glucosidase activity eluting in conductivity area of 6.5-12 mS/cm were collected, desalted in 10DG columns (Bio-Rad) equilibrated with 7 mM sodium acetate, pH 4.5 and lyophilized.

The lyophilized sample was diluted to 100 μl of water and applied to a Superdex 75 HF10/30 gel filtration column equilibrated with 20 mM sodium phosphate pH 4.5, containing 0.15 M NaCl. The β-glucosidase activity was eluted at a retention volume of 13.64 ml. Collected fractions were combined, lyophilized and dissolved in water. The protein was judged to be pure by SDS-polyacryl amide gel electrophoresis and the molecular weight was evaluated to be 76 kDa. The protein was designated as Ct βG_76.

Example 8

Purification and Characterization of a β-Glucosidase from *Thermoascus aurantiacus* ALKO4242

*Thermoascus aurantiacus* ALKO4242 was grown as described in Example 1. The pure β-glucosidase was obtained by sequential purification with hydrophobic interaction, anion and cation exchange chromatography followed by gel filtration. The β-glucosidase activity of the fractions collected during purification was determined using 4-nitrophenyl-β-D-glucopyranoside as substrate (Bailey and Linko, 1990). Protein content was measured by BioRad Assay Kit (Bio-Rad Laboratories) using bovine serum albumine as standard.

The culture supernatant was applied to a HiPrep 16/10 Phenyl Sepharose FF hydrophobic interaction column equilibrated with 20 mM potassium phosphate pH 6.0, containing 0.7 M $(NH_4)_2SO_4$. Bound proteins were eluted with a linear gradient from 0.2 M $(NH_4)_2SO_4$ to 5 mM potassium phosphate, pH 6.0. The β-glucosidase activity was eluted during the gradient in the conductivity area of 28.0-1.1 mS/cm. Fractions were combined and concentrated by ultrafiltration.

The sample was desalted in 10DG columns (Bio-Rad) and applied to a HiTrap DEAE FF anion exchange column equilibrated with 20 mM Tris-HCl pH 7.0. The enzyme was eluted with a linear gradient from 0 to 0.2 M NaCl in the equilibration buffer and with delayed elution by 20 mM Tris-HCl, containing 0.4 M NaCl. The sample eluting in the conductivity area of ca. 10-30 mS/cm was concentrated by ultrafiltration and desalted by 10DG column (Bio-Rad).

The sample was applied to a HiTrap SP XL cation exchange column equilibrated with 9 mM sodium acetate pH 4.5. The enzyme was eluted with a linear gradient from 10 mM to 400 mM NaAc and by delayed elution using 400 mM NaAc pH 4.5 Proteins with β-glucosidase activity were eluted broadly during the linear gradient in the conductivity area of 5.0-11.3 mS/cm.

The active material from the cation exchange chromatography was applied to a Sephacryl S-300 HR 26/60 column equilibrated with 20 mM sodium phosphate pH 7.0, containing 0.15 M NaCl. The protein with β-glucosidase activity was eluted with a retention volume corresponding to a molecular weight of 294 kDa. Collected fractions were combined, lyophilized and dissolved in water. The protein was judged to be pure by SDS-polyacrylamide gel electrophoresis and the molecular weight was evaluated to be 81 kDa, representing most likely the monomeric form of the protein. Isoelectric focusing (IEF) was carried out using a 3-9 pI gel. After silver staining, a broad area above pI 5.85 was stained in addition to a narrow band corresponding to pI 4.55. The specific activity of the purified protein, designated as Ta βG_81, at 50° C. was determined to be 600 nkat/mg using 4-nitrophenyl-β-D-glucopyranoside as substrate (Bailey and Linko, 1990).

Thermal stability of the purified β-glucosidase was determined at different temperatures. The reaction was performed in the presence of 0.1 mg/ml BSA at pH 5.0 for 60 min using 4-nitrophenyl-β-D-glucopyranoside as substrate. *T. aurantiacus* βG_81 was stable up to 75° C. The *Aspergillus* reference enzyme (Novozym 188) retained 100% of activity up to 60° C.

Example 9

Purification of a Xylanase from *Acremonium thermophilum* ALKO4245

*Acremonium thermophilum* ALKO4245 was grown as described in Example 1. The culture supernatant was incubated at 70° C. for 24 hours after which, it was concentrated by ultrafiltration. The pure xylanase was obtained by sequential purification with hydrophobic interaction and cation exchange chromatography followed by gel filtration. The xylanase activity was determined using birch xylan as substrate (procedure of IUPAC 1987). Protein was assayed by BioRad Protein Assay Kit (Bio-Rad Laboratories) using bovine serum albumin as standard.

The concentrated culture supernatant was applied to a HiPrep 16/10 Butyl FF hydrophobic interaction column equilibrated with 20 mM potassium phosphate buffer pH 6.0, containing 1 M $(NH_4)_2SO_4$. Bound proteins were eluted with the linear gradient from the above buffer to 5 mM potassium phosphate, pH 6.0. The protein fraction was eluted in a broad conductivity area of 120 to 15 mS/cm.

The sample from the hydrophobic interaction column was applied to a HiTrap SP XL cation exchange column equilibrated with 8 mM sodium acetate, pH 4.5. The protein did not bind to this column but was eluted in the flow-through during sample feed. This eluate was concentrated by ultrafiltration. The hydrophobic chromatography was repeated as described above. The unbound proteins were collected and freeze dried.

The dissolved sample was loaded onto the Superdex 75 HR10/30 gel filtration column equilibrated with 20 mM sodium phosphate buffer pH 7.0, containing 0.15 M NaCl. The protein eluted from the column with the retention volume of 11.2 ml was judged to be pure by SDS-polyacryl amide gel electrophoresis. The molecular mass of the purified protein was evaluated on the basis of molecular mass standards (prestained SDS-PAGE standards, Broad Range, Bio-Rad) to be 60 kDa. The specific activity of the protein, designated as At XYN_60, at 50° C. was determined to be 1800 nkat/mg (procedure of IUPAC 1987, using birch xylan as substrate). The relative activity was increased about 1.2 fold at 60° C. and 1.65 fold at 70° C. (10 min, pH 5.0) as compared to 50° C. The specific activity against MUG2 (4-methylumbelliferyl-β-D-cellobioside), MUL (4-methylumbelliferyl-beta-D-lactoside) and MUG3 (4-methylumbelliferyl-β-D-cellotrioside) were 54, 33 and 78 nkat/mg (50° C. pH 5.0 10 min), respectively. This is in agreement with the fact that the family 10 xylanases also show activity against the aryl glucopyranosides (Biely et al. 1997).

Example 10

Purification of a Xylanase from *Thermoascus aurantiacus* ALKO4242

*Thermoascus aurantiacus* ALKO4242 was grown as described in Example 1. The pure xylanase was obtained by sequential purification with hydrophobic interaction, anion, and cation exchange chromatography followed by gel filtration. The xylanase activity was determined using birch xylan as substrate (procedure of IUPAC 1987). Protein was assayed by BioRad Protein Assay Kit (Bio-Rad Laboratories) using bovine serum albumin as standard.

The culture supernatant was applied to a HiPrep 16/10 Phenyl Sepharose FF hydrophobic interaction column equilibrated with 20 mM potassium phosphate buffer pH 6.0, containing 0.7 M $(NH_4)_2SO_4$. Bound proteins were eluted with a two-step elution protocol. The elution was carried out by dropping the salt concentration first to 0.2 M $(NH_4)_2SO_4$ and after that a linear gradient from 20 mM potassium phosphate pH 6.0, containing 0.2 M $(NH_4)_2SO_4$ to 5 mM potassium phosphate pH 6.0 was applied. The protein was eluted with 0.2 M $(NH_4)_2SO_4$ (I=39 mS/cm).

The sample was desalted in 10DG columns (Bio-Rad) and applied to a HiTrap DEAE FF anion exchange column equilibrated with 15 mM Tris-HCL, pH 7.0. The protein did not bind to the anion exchange column but was eluted in the flow-through. The conductivity of the sample was adjusted to correspond that of 20 mM sodium acetate, pH 4.5 by adding water and pH was adjusted to 4.5 during concentration by ultrafiltration.

The sample was applied to a HiTrap SP XL cation exchange column equilibrated with 20 mM sodium acetate, pH 4.5. Bound proteins were eluted with a linear gradient from the equilibration buffer to the same buffer containing 1 M NaCl. The enzyme was eluted at the conductivity area of 1-7 mS/cm. The sample was lyophilized and thereafter dissolved in water.

The lyophilised sample was dissolved in water and applied to a Superdex 75 HR 10/30 gel filtration column equilibrated with 20 mM sodium phosphate pH 7.0, containing 0.15 M NaCl. The protein was eluted from the column with a retention volume corresponding to a molecular weight of 26 kDa. The protein was judged to be pure by SDS-polyacrylamide gel electrophoresis. The molecular mass of the pure protein was 30 kDa as evaluated on the basis of molecular mass standards (prestained SDS-PAGE standards, Broad Range, Bio-Rad). The pI of the purified protein, designated as Ta XYN_30 was determined with PhastSystem (Pharmacia) to be ca. 6.8. The specific activity of Ta XYN_30 at 50° C. was determined to be 4800 nkat/mg (procedure of IUPAC 1987, using birch xylan as substrate).

Example 11

Internal Amino Acid Sequencing

The internal peptides were sequenced by electrospray ionization combined to tandem mass spectrometry (ESI-MS/MS) using the Q-TOF1 (Micromass) instrument. The protein was first alkylated and digested into tryptic peptides. Generated peptides were desalted and partially separated by nano liquid chromatography (reverse-phase) before applying to the Q-TOF1 instrument. The internal peptide sequences for *Chaetomium thermophilum* and *Acremonium thermophilum* cellobiohydrolases are shown in Table 2. The peptides from *Chaetomium* CBH were obtained after the corresponding cbh gene had been cloned. The peptides determined from *Acremonium* CBH were not utilized in the cloning of the corresponding gene.

TABLE 2

Internal peptide sequences determined from *Chaetomium thermophilum* ALKO4265 CBH (1_C-4_C) and *Acremonium thermophilum* ALKO4245 CBH (1_A-4_A).

| Peptide | Sequence |
|---|---|
| Peptide 1_C | T P S T N D A N A G F G R |
| Peptide 2_C | V A F S N T D D F N R |
| Peptide 3_C | F S N T D D F N R K |
| Peptide 4_C | P G N S L/I T Q E Y C D A Q/K K |
| Peptide 1_A | V T Q F I/L T G |
| Peptide 2_A | M G DT S F Y G P G |
| Peptide 3_A | C D P D G C D F N |
| Peptide 4_A | S G N S L/I T T D F |

I/L = leucine and isoleucine have the same molecular mass and cannot be distinguished in ESI-MS/MS analysis Q/K = the molecular mass of glutamine and lysine differs only 0.036 Da and cannot be distinguished in ESI-MS/MS analysis The internal peptide sequences of purified endoglucanases, β-glucosidases, and xylanases of *Acremonium thermophilum* ALKO4245, *Chaetomium thermophilum* ALKO4261 and *Thermoascus aurantiacus* ALKO4242 are listed in Table 3, Table 4 and Table 5.

TABLE 3

Internal peptide sequences determined from *Acremonium thermophilum* ALKO4245 EG_40, *Chaetomium thermophilum* ALKO4261 EG_54 and *Thermoascus aurantiacus* ALKO4242 EG_28 endoglucanases.

| Protein | Peptide | Sequence[a] |
|---|---|---|
| At EG_40 | Peptide 1 | Q S C S S F P A P L K P G C Q W R |
| | Peptide 2 | Y A L T F N S G P V A G K |
| | Peptide 3 | V Q C P S E L T S R |
| | Peptide 4 | N Q P V F S C S A D W Q R |
| | Peptide 5 | Y W D C C K P S C G W P G K |
| | Peptide 6 | P T F T |
| Ct EG_54 | Peptide 1 | E P E P E V T Y Y V |
| | Peptide 2 | Y Y L L D Q T E Q Y |
| | Peptide 3 | R Y C A C M D L W E A N S R |
| | Peptide 4 | P G N T P E V H P Q/K |
| | Peptide 5 | S I/L A P H P C N Q/K |
| | Peptide 6 | Q Q Y E M F R |
| | Peptide 7 | A L N D D F C R |
| | Peptide 8 | W G N P P P R |
| Ta EG_28 | Peptide 1 | I/L T S A T Q W L R |
| | Peptide 2 | G C A I/L S A T C V S S T I/L G Q E R |
| | Peptide 3 | P F M M E R |
| | Peptide 4 | Q Y A V V D P H N Y G R |

[a] I/L = leucine and isoleucine have the same molecular mass and cannot be distinguished in ESI-MS/MS analysis, Q/K = the molecular mass of glutamine and lysine differs only 0.036 Da and cannot be distinguished is ESI-MS/MS analysis.

TABLE 4

Internal peptide sequences determined from *Acremonium thermophilum* ALKO4245 βG_101, *Chaetomium thermophilum* ALKO4261 βG_76 and *Thermoascus aurantiacus* ALKO4242 βG_81 beta-glucosidases.

| Protein | Peptide | Sequence[a] |
|---|---|---|
| At βG_101 | Peptide 1 | S P F T W G P T R |
| | Peptide 2 | V V V G D D A G N P C |
| | Peptide 3 | A F V S Q L T L L E K |
| | Peptide 4 | G T D V L/I Y T P N N K |
| | Peptide 5 | Q P N P A G P N A C V L/I R |
| Ct βG_76 | Peptide 1 | E G L F I D Y R |
| | Peptide 2 | P G Q S G T A T F R |
| | Peptide 3 | E T M S S N V D D R |
| | Peptide 4 | I A L V G S A A V V |
| | Peptide 5 | M W L C E N D R |
| | Peptide 6 | YP Q L C L Q D G P L G I R |
| | Peptide 7 | E L N G Q N S G Y P S I |
| Ta βG_81 | Peptide 1 | T P F T W G K |
| | Peptide 2 | L C L Q D S L P G V R |
| | Peptide 3 | G V D V Q L G P V A G V A P R |
| | Peptide 4 | V N L T L E |
| | Peptide 5 | F T G V F G E D V V G |
| | Peptide 6 | N D L P L T G Y E K |

[a] I/L = leucine and isoleucine have the same molecular mass and cannot be distinguished in ESI-MS/MS analysis

TABLE 5

Internal peptide sequences determined from *Acremonium thermophilum* ALKO4245 XYN_60 and *Thermoascus aurantiacus* ALKO4242 XYN_30 xylanases.

| Protein | Peptide | Sequence |
|---|---|---|
| At XYN_60 | Peptide 1 | Y N D Y N L E Y N Q K |
| | Peptide 2 | F G Q V T P E N |
| | Peptide 3 | V D G D A T Y M S Y V N N K |
| | Peptide 4 | K P A W T S V S S V L A A K |
| | Peptide 5 | S Q G D I V P R A K |
| Ta XYN_30 | Peptide 1 | V Y F G V A T D Q N R |
| | Peptide 2 | N A A I I Q A D F G Q V T P E N S M K |
| | Peptide 3 | G H T L V W H S Q L P S W V S S I T D K |
| | Peptide 4 | N H I T T L M T R |
| | Peptide 5 | A W D V V N E A F N E D G S L R |
| | Peptide 6 | L Y I N D Y N L D S A S Y P K |
| | Peptide 7 | A S T T P L L F D G N F N P |
| | | K P A Y N A I V Q D L Q Q |
| | Peptide 8 | Q T V F L N V I G E D Y I P I A F Q T A R |

Example 12

Construction of Genomic Libraries for *Thermoascus aurantiacus, Chaetomium thermophilum* and *Acremonium thermophilum*

The genomic library of *Chaetomium thermophilum* ALKO4265 and *Acremonium thermophilum* ALKO4245 were made to Lambda DASH®II vector (Stratagene, USA) according to the instructions from the supplier. The chromosomal DNAs, isolated by the method of Raeder and Broda (1985), were partially digested with Sau3A. The digested DNAs were size-fractionated and the fragments of the chosen size (≈5-23 kb) were dephosphorylated and ligated to the BamHI digested lambda vector arms. The ligation mixtures were packaged using Gigapack III Gold packaging extracts according to the manufacturer's instructions (Stratagene, USA). The titers of the *Chaetomium thermophilum* and *Acremonium thermophilum* genomic libraries were $3.6\times10^6$ pfu/ml and $3.7\times10^5$ pfu/ml and those of the amplified libraries were $6.5\times10^{10}$ pfu/ml and $4.2\times10^8$ pfu/ml, respectively.

Lambda FIX® II/Xho I Partial Fill-In Vector Kit (Stratagene, USA) was used in the construction of the genomic libraries for *Thermoascus aurantiacus* ALKO4242 and *Chaetomium thermophilum* ALKO4261 according to the instructions from the supplier. The chromosomal DNAs, isolated by the method of Raeder and Broda (1985), were partially digested with Sau3A. The digested DNAs were size-fractionated and the fragments of the chosen size (≈6-23 kb) were filled-in and ligated to the XhoI digested Lambda FIX II vector arms. The ligation mixtures were packaged using Gigapack III Gold packaging extracts according to the manufacturer's instructions (Stratagene, USA). The titers of the *Thermoascus aurantiacus ALKO*4242 and *Chaetomium thermophilum* ALKO4261 genomic libraries were $0.2\times10^6$ and $0.3\times10^6$ pfu/ml and those of the amplified libraries were $1.8\times10^9$ and $3.8\times10^9$ pfu/ml, respectively.

Example 13

Cloning of the Cellobiohydrolase (cbh/cel7) Genes from *Thermoascus aurantiacus, Chaetomium thermophilum* and *Acremonium thermophilum*

Standard molecular biology methods were used in the isolation and enzyme treatments of DNA (plasmids, DNA fragments), in *E. coli* transformations, etc. The basic methods used are described in the standard molecular biology handbooks, e.g., Sambrook et al. (1989) and Sambrook and Russell (2001).

The probes for screening the genomic libraries which were constructed as described in Example 12 were amplified by PCR using the *Thermoascus aurantiacus* ALKO4242, *Chaetomium thermophilum* ALKO4265 and *Acremonium thermophilum* ALKO4245 genomic DNAs as templates in the reactions. Several primers tested in PCR reactions were designed according to the published nucleotide sequence (WO 03/000941, Hong et al., 2003b). The PCR reaction mixtures contained 50 mM Tris-HCl, pH 9.0, 15 mM $(NH_4)_2SO_4$, 0.1% Triton X-100, 1.5 mM $MgCl_2$, 0.2 mM dNTPs, 5 μM each primer and 1 units of Dynazyme EXT DNA polymerase (Finnzymes, Finland) and ≈0.5-1 μg of the genomic DNA. The conditions for the PCR reactions were the following: 5 min initial denaturation at 95° C., followed by 30 cycles of 1 min at 95° C., either 1 min annealing at 62° C. (±8° C. gradient) for *Thermoascus* ALKO4242 and *Chaetomium* ALKO4265 templates or 1 min annealing at 58° C. (±6° C. gradient) for *Acremonium* ALKO4245 template, 2 min extension at 72° C. and a final extension at 72° C. for 10 min.

DNA products of the expected sizes (calculated from published cbh sequences) were obtained from all genomic templates used. The DNA fragments of the expected sizes were isolated from the most specific PCR reactions and they were cloned to pCR® Blunt-TOPO® vector (Invitrogen, USA). The inserts were characterized by sequencing and by performing Southern blot hybridizations to the genomic DNAs digested with several restriction enzymes. The PCR fragments, which were chosen to be used as probes for screening of the *Thermoascus aurantiacus, Chaetomium thermophilum* and *Acremonium thermophilum* genomic libraries are presented in Table 6.

TABLE 6

The primers used in the PCR reactions and probes chosen for screening of the cbh/cel7 genes from *Thermoascus aurantiacus, Chaetomium thermophilum* and *Acremonium thermophilum* genomic libraries. The genomic template DNA and the name of the plasmid containing the probe fragment are shown.

| Gene | Forward primer | Reverse primer | Template DNA | Fragment (kb) | Plasmid |
|---|---|---|---|---|---|
| Ta cbh | TCEL11 atgcgaactggcgttgggtcc | TECL12 gaatttggagctagtgtcgacg | *Thermoascus* ALKO4242 | 0.8 kb | pALK1633 |
| Ct cbh | TCEL7 cgatgccaactggcgctggac | TCEL8 ttcttggtggtgtcgacggtc | *Chaetomium* ALKO4265 | 0.8 kb | pALK1632 |
| At cbh | TCEL13 agctcgaccaactgctacacg | TCEL4 accgtgaacttcttgctggtg | *Acremonium* ALKO4245 | 0.7 kb | pALK1634 |

The deduced amino acid sequences from all these probes had homology to several published CBH sequences (BLAST program, version 2.2.9 at NCBI, National Center for Biotechnology Information; Altschul et al., 1990) of glycoside hydrolase family 7 (Henrissat, 1991; Henrissat and Bairoch, 1993).

The inserts from the plasmids listed in Table 6 were labeled with digoxigenin according to the supplier's instructions (Roche, Germany), and the amplified genomic libraries ($2\times10^5$-$3\times10^5$ plaques) were screened with the labeled probe fragments. The hybridization temperature for the filters was 68° C. and the filters were washed 2×5 min at RT using 2×SSC-0.1% SDS followed by 2×15 min at 68° C. using 0.1×SSC-0.1% SDS with the homologous probes used. Several positive plaques were obtained from each of the hybridizations. In screening of the *Acremonium* ALKO4245 genomic libraries, some of the positive plaques were strongly hybridizing to the probe in question but, in addition, there was an amount of plaques hybridizing more weakly to the probes. This suggested that other cellobiohydrolase gene(s) might be present in the genome, causing cross-reaction. From four to five strongly hybridizing plaques were purified from *Thermoascus* ALKO4242 and *Chaetomium* ALKO4265 genomic library screenings. In the case of the *Acremonium thermophilum* ALKO4245, four out of six purified plaques hybridized weakly by the probe used. The phage DNAs were isolated and characterized by Southern blot hybridizations. The chosen restriction fragments hybridizing to the probe were subcloned to pBluescript II KS+ vector and the relevant regions of the clones were sequenced.

In total four cbh/cel7 genes were cloned; one from *Thermoascus aurantiacus* ALKO4242, one from *Chaetomium thermophilum* ALKO4265 and two from *Acremonium thermophilum* ALKO4245 (at the early phase of the work, these had the codes At_cbh_C and At_cbh_A, and were then designated as At cel7A and At cel7B, respectively). Table 7 summarizes the information on the probes used for screening the genes, the phage clones from which the genes were isolated, the chosen restriction fragments containing the full-length genes with their promoter and terminator regions, the plasmid names, and the DSM deposit numbers for the *E. coli* strains carrying these plasmids.

TABLE 7

The probes used for cloning of cbh/cel7 genes, the phage clone and the subclones chosen, the plasmid number and the number of the deposit of the corresponding *E. coli* strain.

| Gene | Probe used in screening | Phage clone | The fragment subcloned to pBluescript II | Plasmid no | *E. coli* deposit no |
|---|---|---|---|---|---|
| Ta cel7A | pALK1633 | F12 | 3.2 kb XbaI | pALK1635 | DSM 16723 |
| Ct cel7A | pALK1632 | F36 | 2.3 kb PvuI-HindIII | pALK1642 | DSM 16727 |
| At cel7B | pALK1634 | F6 | 3.1 kb EcoRI | pALK1646 | DSM 16728 |
| At cel7A | pALK1634 | F2 | 3.4 kb XhoI | pALK1861 | DSM 16729 |

The relevant information on the genes and the deduced protein sequences (SEQ ID NO: 1-8) are summarized in Table 8 and Table 9, respectively.

The peptide sequences of the purified CBH proteins from *Chaetomium thermophilum* ALKO4265 and *Acremonium thermophilum* ALKO4245 (Table 2) were found from the deduced amino acid sequences of the clones containing the Ct cel7A and At cel7A genes. Thus, it could be concluded that the genes encoding the purified CBH/Cel7 proteins from *Chaetomium thermophilum* and *Acremonium thermophilum* were cloned.

TABLE 8

Summary on the cbh/cel7 genes isolated from *Thermoascus aurantiacus* ALKO4242, *Chaetomium thermophilum* ALKO4265 and *Acremonium thermophilum* ALKO4245.

| Cbh gene | Length with introns (bp)[a] | Coding region (bp)[b] | No of introns | Lengths of introns (bp) | SEQ ID NO: |
|---|---|---|---|---|---|
| Ta cel7A | 1439 | 1371 | 1 | 65 | 1 |
| Ct cel7A | 1663 | 1596 | 1 | 64 | 7 |
| At cel7B | 1722 | 1377 | 3 | 134, 122, 87 | 3 |
| At cel7A | 1853 | 1569 | 4 | 88, 53, 54, 86 | 5 |

[a] The STOP codon is included.

[b] The STOP codon is not included.

TABLE 9

Summary of amino acid sequences deduced from the cbh/cel7 gene sequences from *Thermoascus aurantiacus* ALKO4242, *Chaetomium thermophilum* ALK4265 and Acremonium thermophilum ALKO4245. ss, signal sequence.

| CBH protein | No of aas | Length of ss NN/HMM[a | C-terminal CBD[b | Predicted MW (Da, ss not incl)[c | Predicted pI (ss not incl) | Putative N-glycosylation sites[d | SEQ ID NO: |
|---|---|---|---|---|---|---|---|
| Ta Cel7A | 457 | 17/17 | NO | 46 873 | 4.44 | 2 | 2 |
| Ct Cel7A | 532 | 18/18 | YES, T497 to L532 | 54 564 | 5.05 | 3 | 8 |
| At Cel7B | 459 | 21/21 | NO | 47 073 | 4.83 | 2 | 4 |
| At Cel7A | 523 | 17/17 | YES, Q488 to L523 | 53 696 | 4.67 | 4 | 6 |

[a The prediction on the signal sequence was made using the program SignalP V3.0 (Nielsen et al., 1997; Bendtsen et al., 2004); the NN value was obtained using neural networks and HMM value using hidden Markov models.
[b The cellulose-binding domain (CBD), the amino acids of the C-terminal CBD region are indicated (M1 (Met #1) included in numbering)
[c The predicted signal sequence was not included. The prediction was made using the Compute pI/MW tool at ExPASy server (Gasteiger et al., 2003).
[d The number of sequences N-X-S/T.

The deduced amino acid sequences of *Thermoascus aurantiacus* Cel7A and *Acremonium thermophilum* Cel7A (core, without the CBD) were most homologous to each other (analyzed by Needleman-Wunsch global alignment, EMBOSS 3.0.0 Needle, with Matrix EBLOSUM62, Gap Penalty 10.0 and Extend Penalty 0.5; Needleman and Wunsch, 1970). In addition, the deduced *Acremonium thermophilum* Cel7A had a lower identity to the deduced *Chaetomium thermophilum* Cel7A. The *Acremonium thermophilum* Cel7B was most distinct from the CBH/Cel7 sequences of the invention.

The deduced *Chaetomium* Cel7A sequence possessed the highest identities (analyzed by Needleman-Wunsch global alignment, EMBOSS Needle, see above) to polypeptides of *Chaetomium thermophilum, Scytalidium thermophilum* and *Thielavia australiensis* CBHI described in WO 03/000941. Similarly, the deduced *Thermoascus aurantiacus* Cel7A sequence was highly identical to the published CBHI of the *Thermoascus aurantiacus* (WO 03/000941, Hong et al., 2003b). *Acremonium thermophilum* Cel7B had significantly lower identities to the previously published sequences, being more closely related to the CBHI polypeptide from *Oryza sativa*. The highest homologies of the deduced *Acremonium thermophilum* Cel7A sequence were to *Exidia gladulosa* and *Acremonium thermophilum* CBHI polynucleotides (WO 03/000941). The alignment indicates that the cloned *Thermoascus aurantiacus* ALKO4242*, Chaetomium thermophilum* ALKO4265 and *Acremonium thermophilum* ALKO4245 sequences encode the CBH proteins having high homology to the polypeptides of the glycoside hydrolase family 7, therefore these were designated as Cel7A or Cel7B (Henrissat et al. 1998).

The comparison of the deduced amino acid sequences of the cbh/cel7 genes from *Thermoascus aurantiacus* ALKO4242*, Chaetomium thermophilum* ALKO4265 and *Acremonium thermophilum* ALKO4245 *Thielavia* to each other, and further to the sequences found from the databases, are shown in Table 10.

TABLE 10

The highest homology sequences to the deduced amino acid sequences of the cbh/cel7 genes from *Thermoascus aurantiacus* ALKO4242, *Chaetomium thermophilum* ALKO4265 and *Acremonium thermophilum* ALKO4245. The alignment was made using Needleman-Wunsch global alignment (EMBLOSUM62, Gap penalty 10.0, Extend penalty 0.5).

| Organism, enzyme and accession number | Identity, (%) |
|---|---|
| **Thermoascus aurantiacus* Cel7A | 100.0 |
| *Thermoascus aurantiacus*, AY840982 | 99.6 |
| *Thermoascus aurantiacus*, AX657575 | 99.1 |
| *Thermoascus aurantiacus*, AF421954 | 97.8 |
| *Talaromyces emersonii*, AY081766 | 79.5 |
| *Chaetomidium pingtungium*, AX657623 | 76.4 |
| *Trichophaea saccata*, AX657607 | 73.4 |
| **Acremonium thermophilum* Cel7A (core) | 70.6 |
| *Emericella nidulans*, AF420020 (core) | 70.4 |
| **Chaetomium thermophilum* Cel7A (core) | 66.4 |
| **Chaetomium thermophilum* Cel7A | 100.0 |
| *Chaetomium thermophilum*, AY861347 | 91.9 |
| *Chaetomium thermophilum*, AX657571 | 91.7 |
| *Scytalidium thermophilum*, AX657627 | 74.7 |
| *Thielavia australiensis*, AX657577 | 74.6 |
| *Acremonium thermophilum*, AX657569 | 72.3 |
| *Exidia glandulosa*, AX657613 | 68.0 |
| **Acremonium thermophilum* Cel7A | 66.9 |
| **Thermoascus aurantiacus* Cel7A (core) | 66.4 |
| *Exidia glandulosa*, AX657615 | 60.8 |
| *Chaetomium pingtungium*, AX657623 | 60.7 |
| **Acremonium thermophilum* Cel7B (core) | 60.2 |
| **Acremonium thermophilum* Cel7B | 100.0 |
| *Oryza sativa*, AK108948 | 66.1 |
| *Exidia glandulosa*, AX657615 | 65.0 |
| *Acremonium thermophilum*, AX657569 (core) | 64.8 |
| *Thermoascus aurantiacus*, AX657575 | 64.8 |
| **Acremonium thermophilum* Cel7A | 64.6 |
| **Thermoascus aurantiacus* Cel7A | 64.4 |
| *Trichophaea saccata*, AX657607 | 63.6 |
| **Chaetomium thermophilum* Cel7A (core) | 60.2 |
| **Acremonium thermophilum* Cel7A | 100.0 |
| *Exidia glandulosa*, AX657613 | 77.9 |
| *Exidia glandulosa*, AX657615 | 77.9 |
| *Acremonium thermophilum*, AX657569 | 77.5 |
| *Thielavia australiensis*, AX657577 | 71.0 |
| **Thermoascus aurantiacus* Cel7A (core) | 70.6 |
| *Scytalidium thermophilum*, AX657627 | 67.5 |

TABLE 10-continued

The highest homology sequences to the deduced amino acid sequences of the cbh/cel7 genes from *Thermoascus aurantiacus* ALKO4242, *Chaetomium thermophilum* ALKO4265 and *Acremonium thermophilum* ALKO4245. The alignment was made using Needleman-Wunsch global alignment (EMBLOSUM62, Gap penalty 10.0, Extend penalty 0.5).

| Organism, enzyme and accession number | Identity, (%) |
|---|---|
| *Chaetomium thermophilum*, AX657571 | 67.5 |
| *Chaetomium pingtungium*, AX657623 | 67.3 |
| **Chaetomium thermophilum* Cel7A | 66.9 |
| **Acremonium thermophilum* Cel7B (core) | 64.6 |

*indicates an amino acid sequence derived from one of the cellobiohydrolase genes cloned in this work.
'Core' indicates alignment without the CBD.

Example 14

Production of Recombinant CBH/Cel7 Proteins in *Trichoderma reesei*

Figure 1A:
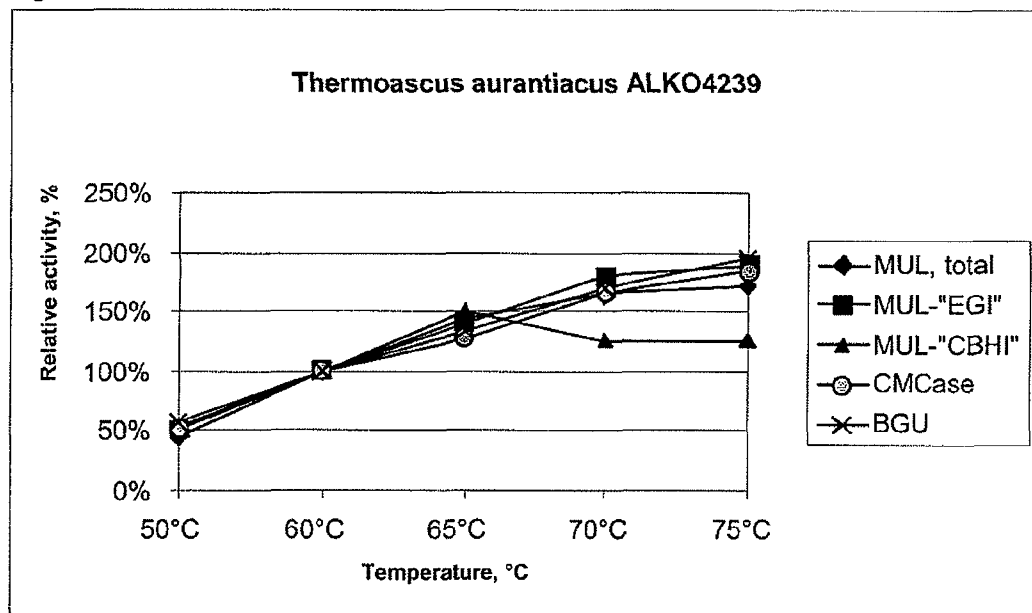
FIG. 1. Temperature dependencies of the cellulase and beta-glucosidase activities in the supernatants of the tested six fungal strains. The incubation time in the assay was 60 min at the given temperature, the assay pH was 5.0 (MUL-activity) or 4.8 (CMCase or BGU). Activity obtained at 60° C. is set as the relative activity of 100%. A) *Thermoascus aurantiacus* ALKO4239, B) *Thermoascus aurantiacus* ALKO4242, C) *Acremonium thermophilum* ALKO4245, D) *Talaromyces thermophilus* ALKO4246, E) *Chaetomium thermophilum* ALKO4261, F) *Chaetomium thermophilum* ALKO4265.
Figure 1B:
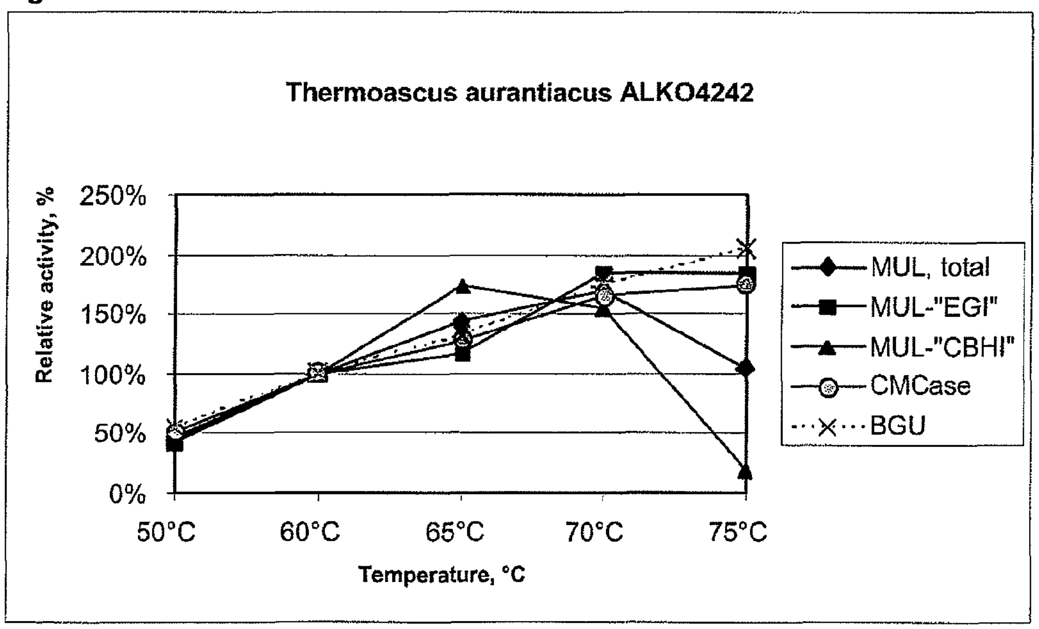
Figure 1C:
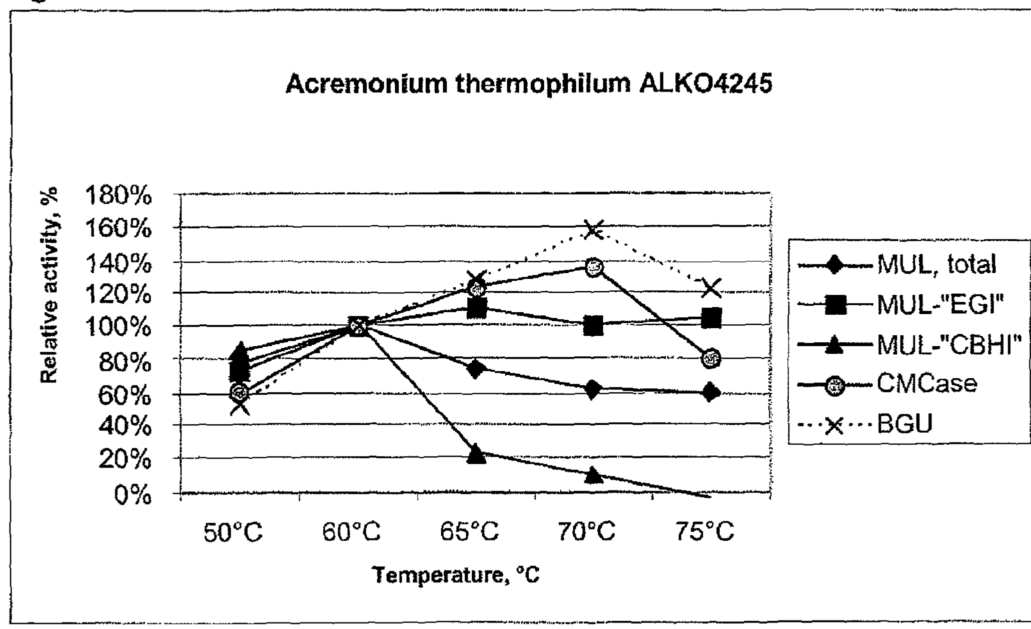
Figure 1D:
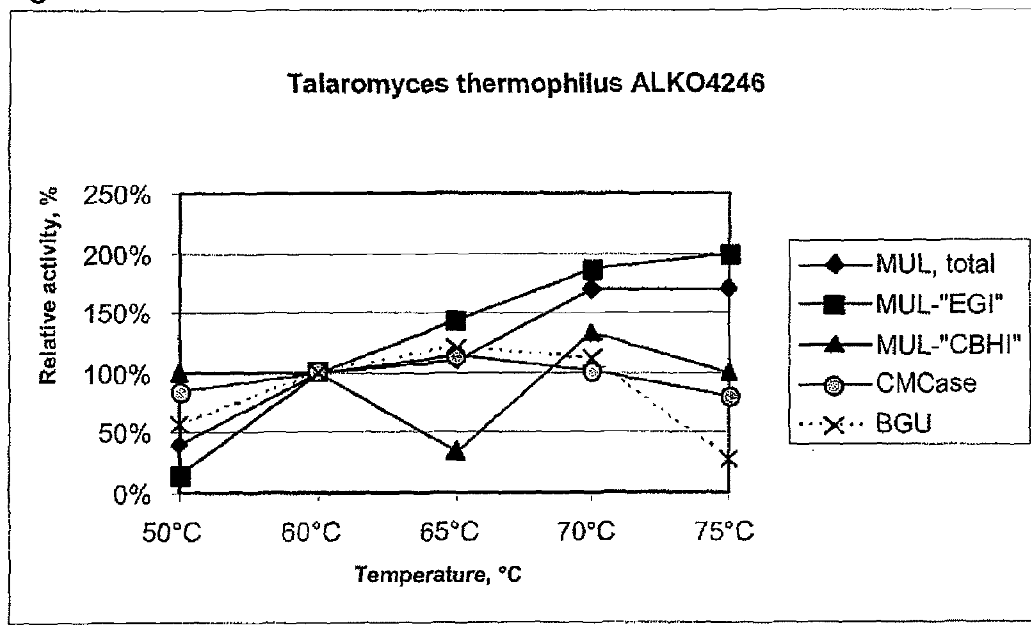
Figure 1E:
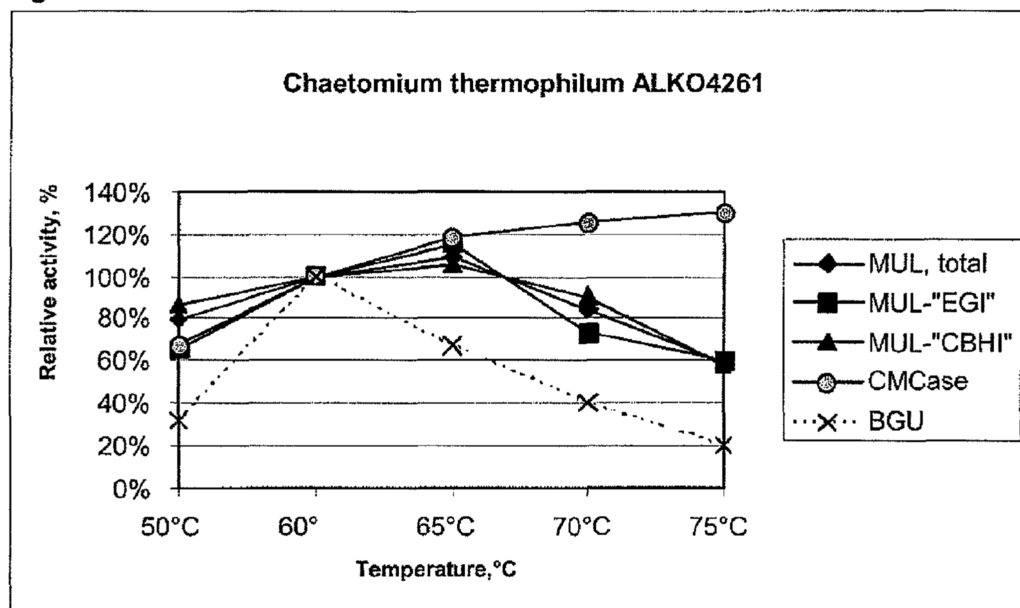
Figure 1F:
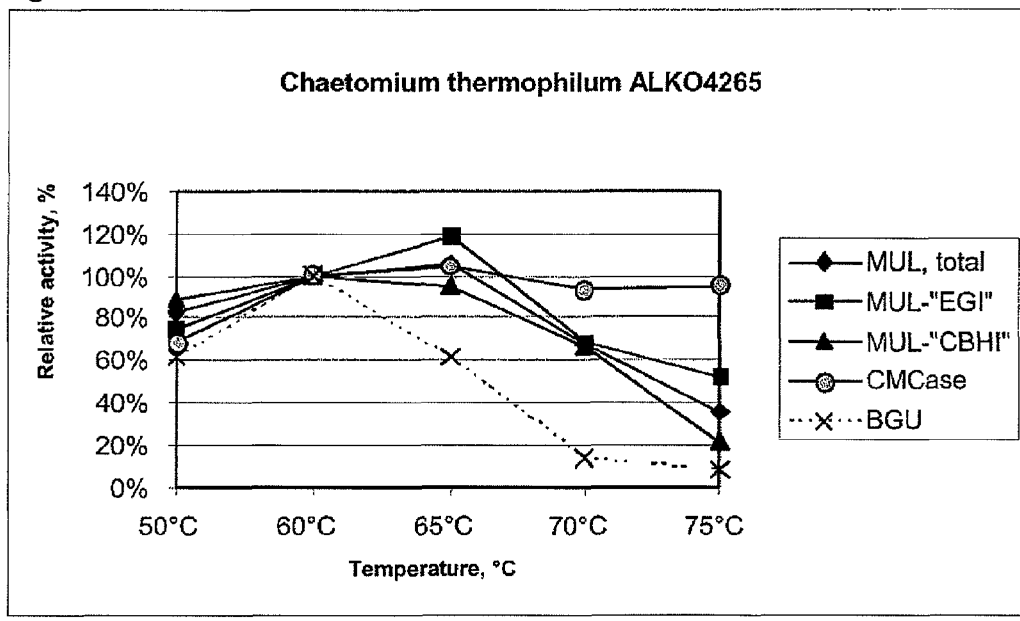
Figure 2:
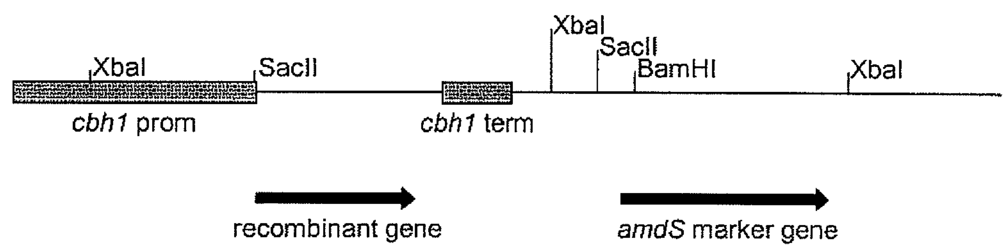
FIG. 2. Schematic picture of the expression cassettes used in the transformation of *Trichoderma reesei* protoplasts for producing the recombinant fungal proteins. The recombinant genes were under the control of *T. reesei* cbh1 (cel7A) promoter (cbh1 prom) and the termination of the transcription was ensured by using *T. reesei* cbh1 terminator sequence (cbh1 term). The amdS gene was included as a transformation marker.

Expression plasmids were constructed for production of the recombinant CBH/Cel7 proteins from *Thermoascus aurantiacus* (Ta Cel7A), *Chaetomium thermophilum* (Ct Cel7A) and *Acremonium thermophilum* (At Cel7A, At Cel7B; at early phase of the work these proteins had the temporary codes At CBH_C and At CBH_A, respectively). The expression plasmids constructed are listed in Table 11. The recombinant cbh/cel7 genes, including their own signal sequences, were exactly fused to the *T. reesei* cbh1 (cel7A) promoter by PCR. The transcription termination was ensured by the *T. reesei* cel7A terminator and the *A. nidulans* amdS marker gene was used for selection of the transformants as described in Paloheimo et al. (2003). The linear expression cassettes (FIG. 2), were isolated from the vector backbones after EcoRI digestion and were transformed into *T. reesei* A96 and A98 protoplasts (both strains have the genes encoding the four major cellulases CBHI/Cel7A, CBHII/Cel6A, EGI/Cel7B and EGII/Cel5A deleted). The transformations were performed as in Penttilä et al. (1987) with the modifications described in Karhunen et al. (1993), selecting with acetamide as a sole nitrogen source. The transformants were purified on selection plates through single conidia prior to sporulating them on PD.

TABLE 11

The expression cassettes constructed to produce CBH/Cel7 proteins of *Thermoascus aurantiacus* ALKO4242 (Ta Cel7A), *Chaetomium thermophilum* ALKO4265 (Ct Cel7A), and *Acremonium thermophilum* ALKO4245 (At Cel7A, At Cel7B) in *Trichoderma reesei*. The overall structure of the expression cassettes was as described in FIG. 2. The cloned cbh/cel7 genes were exactly fused to the *T. reesei* cbh1/cel7A promoter.

| CBH/Cel7 | Expression plasmid | Size of the expr. cassette[a] | cel7A terminator[b] |
|---|---|---|---|
| Ta Cel7A | pALK1851 | 9.0 kb | 245 bp (XbaI) |
| Ct Cel7A | pALK1857 | 9.2 kb | 240 bp (HindIII) |
| At Cel7B | pALK1860 | 9.4 kb | 361 bp (EcoRI) |
| At Cel7A | pALK1865 | 9.5 kb | 427 bp (EcoRV) |

[a]The expression cassette for T. reesei transformation was isolated from the vector backbone by using EcoRI digestion.
[b]The number of the nucleotides from the genomic cbh1/cel7A terminator region after the STOP codon. The restriction site at the 3'-end, used in excising the genomic gene fragment, is included in the parenthesis.

The CBH/Cel7 production of the transformants was analysed from the culture supernatants of the shake flask cultivations (50 ml). The transformants were grown for 7 days at 28° C. in a complex lactose-based cellulase-inducing medium (Joutsjoki et al. 1993) buffered with 5% $KH_2PO_4$. The cellobiohydrolase activity was assayed using 4-methylumbelliferyl-β-D-lactoside (MUL) substrate according to van Tilbeurgh et al., 1988. The genotypes of the chosen transformants were confirmed by using Southern blots in which several genomic digests were included and the respective expression cassette was used as a probe. Heterologous expression of the Ta Cel7A, Ct Cel7A, At Cel7A and At Cel7B proteins was analyzed by SDS-PAGE with subsequent Coomassive staining. The findings that no cellobiohydrolase activity or heterologous protein production in SDS-PAGE could be detected for the At Cel7B transformants containing integrated expression cassette, suggest that At Cel7B is produced below detection levels in *Trichoderma* using the described experimental design.

Figure 3A:
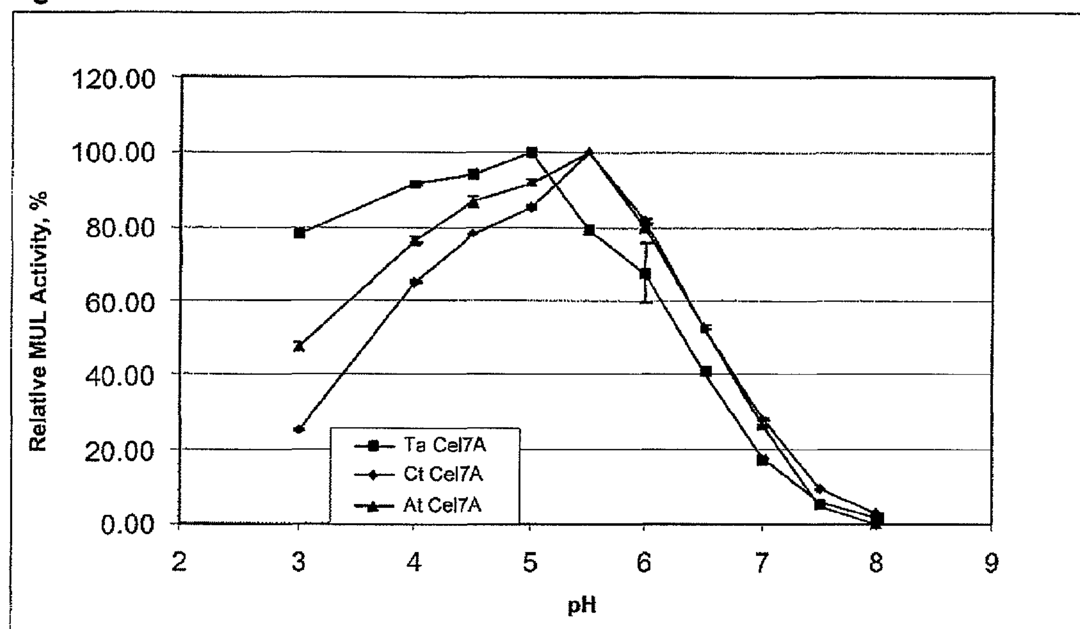
FIG. 3. A) pH optima of the recombinant CBH/Cel7 protein preparations from *Thermoascus aurantiacus* ALKO4242, *Chaetomium thermophilum* ALKO4265 and *Acremonium thermophilum* ALKO4245 determined on 4-methylumbelliferyl-β-D-lactoside (MUL) at 50° C., 10 min. The results are given as mean (±SD) of three separate measurements. B) Thermal stability of recombinant CBH/Cel7 protein preparations from *Thermoascus aurantiacus* ALKO4242, *Chaetomium thermophilum* ALKO4265 and *Acremonium thermophilum* ALKO4245 determined on 4-methylumbelliferyl-β-D-lactoside (MUL) at the optimum pH for 60 min. The results are given as mean (±SD) of three separate measurements. Both reactions contained BSA (100 μg/ml) as a stabilizer.
Figure 3B:
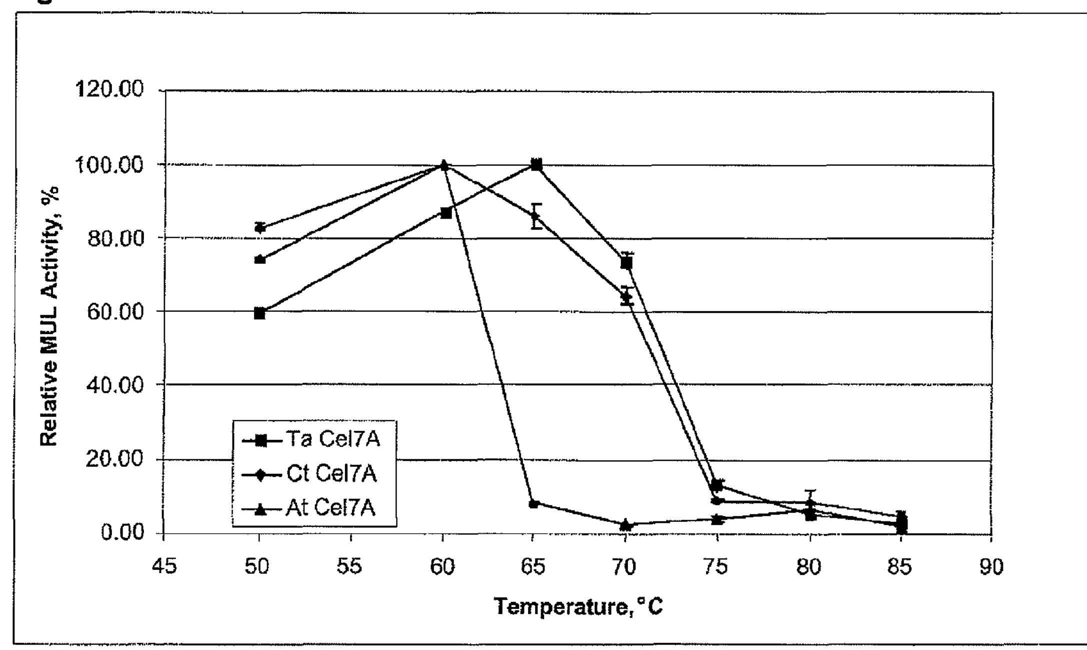

The recombinant CBH/Cel7 enzyme preparations were characterized in terms of pH optimum and thermal stability. The pH optimum of the recombinant CBH/Cel7 proteins from *Thermoascus aurantiacus, Chaetomium thermophilum*, and *Acremonium thermophilum* were determined in the universal McIlvaine buffer within a pH range of 3.0-8.0 using 4-methylumbelliferyl-β-D-lactoside (MUL) as a substrate (FIG. 3A). The pH optimum for Ct Cel7A and At Cel7A enzymes is at 5.5, above which the activity starts to gradually drop. The pH optimum of the recombinant crude Ta Cel7A is at 5.0 (FIG. 3A). Thermal stability of the recombinant Cel7 enzymes was determined by measuring the MUL activity in universal McIlvaine buffer at the optimum pH with reaction time of 1 h. As shown from the results Ta Cel7A and Ct Cel7A retained more than 60% of their activities at 70° C., whereas At Cel7A showed to be clearly less stable at the higher temperatures (≤65° C.) (FIG. 3B).

The chosen CBH/Cel7 transformants were cultivated in lab bioreactors at 28° C. in the medium indicated above for 3-4 days with pH control 4.4±0.2 ($NH_3/H_3PO_4$) to obtain material for the application tests. The supernatants were recovered by centrifugation and filtering through Seitz-K 150 and EK filters (Pall SeitzSchenk Filtersystems GmbH, Bad Kreuznach, Germany).

Example 15

Production of the Recombinant *Thermoascus aurantiacus Cel*7A+CBD Fusion Proteins in *T. reesei*

*Thermoascus aurantiacus* Cel7A (AF478686, Hong et al., 2003b; SEQ ID. NO: 1) was fused to linker and CBD of *Trichoderma reesei* CBHI/Cel7A (AR088330, Srisodsuk et al. 1993) (=Tr CBD) followed by the production of the fusion protein (SEQ ID NO: 28 corresponding nucleic acid SEQ ID. NO: 27) in the *T. reesei* as was described in FI20055205/U.S. Ser. No. 11/119,526; filed Apr. 29, 2005. In addition, *Thermoascus aurantiacus* Cel7A was fused to linker and CBD of *Chaetomium thermophilum* Cel7A (SEQ ID. NO: 7) (Ct CBD). For that purpose, the coding sequence of the linker and the CBD of *Chaetomium thermophilum* Cel7A were synthesized by PCR using following primers:

```
5'-TTAAACATATGTTATCTACTCCAACATCAAGGTCGGACCCATCGG
CTCGACCGTCCCTGGCCTTGAC-3' (forward sequence)
And

5'-TATATGCGGCCGCAAGCTTTACCATCAAGTTACTCCAGCAAATCA
GGGAACTG-3' (reverse sequence).
```

The PCR reaction mixture contained 1× DyNAzyme™ EXT reaction buffer (Finnzymes, Finland), 15 mM $Mg^{2+}$, 0.2 mM dNTPs, 2 μM of each primer, 0.6 units of DyNAzyme™ EXT DNA polymerase (Finnzymes, Finland), and approximately 75 ng/30 μl of template DNA, containing full-length cel7A gene from the *Chaetomium thermophilum*. The conditions for the PCR reaction were the following: 2 min initial denaturation at 98° C., followed by 30 cycles of 30 sec at 98° C., 30 sec annealing at 68° C. (±4° C. gradient), 30 sec extension at 72° C. and a final extension at 72° C. for 10 min. The specific DNA fragment in PCR reaction was obtained at annealing temperature range from 64° C. to 68.5° C. The synthesized CBD fragment of the *Chaetomium thermophilum* was ligated after *Thermoascus aurantiacus* cel7A gene resulting in a junction point of GPIGST between the domains. The PCR amplified fragment in the plasmid was confirmed by sequencing (SEQ ID. NO: 29). The constructed fusion cel7A gene was exactly fused to the *T. reesei* cbh1 (cel7A) promoter. The transcription termination was ensured by the *T. reesei* cel7A terminator and the *A. nidulans* amdS marker gene was used for selection of the transformants as described in Paloheimo et al. (2003).

The linear expression cassette was isolated from the vector backbone after NotI digestion and was transformed to *T. reesei* A96 protoplasts. The transformations were performed as in Penttilä et al. (1987) with the modifications described in Karhunen et al. (1993), selecting with acetamide as a sole nitrogen source. The transformants were purified on selection plates through single conidia prior to sporulating them on PD.

*Thermoascus aurantiacus* Cel7A+CBD (SEQ ID. NO: 28 and 30) production of the transformants was analyzed from the culture supernatants of the shake flask cultivations (50 ml). The transformants were grown for 7 days in a complex cellulase-inducing medium (Joutsjoki et al. 1993) buffered with 5% $KH_2PO_4$ at pH 5.5. The cellobiohydrolase activity was assayed using 4-methylumbelliferyl-β-D-lactoside (MUL) substrate according to van Tilbeurgh et al., 1988. The genotypes of the chosen transformants were confirmed by using Southern blots in which several genomic digests were included and the expression cassette was used as a probe. The SDS-PAGE analyses showed that the recombinant *Thermoascus aurantiacus* Cel7A+CBD enzymes were produced as stable fusion proteins in *T. reesei*.

The chosen transformant producing the Ta Cel7A+Tr CBD fusion protein (SEQ ID. NO: 28) was also cultivated in 2 litre bioreactor at 28° C. in the medium indicated above for 3-4 days with pH control 4.4±0.2 ($NH_3/H_3PO_4$) to obtain material for the application tests. The supernatants were recovered by centrifugation and filtering through Seitz-K 150 and EK filters (Pall SeitzSchenk Filtersystems GmbH, Bad Kreuznach, Germany).

Example 16

Comparison of the Michaelis-Menten and Cellobiose Inhibition Constants of Purified Recombinant Cellobiohydrolases The Michaelis-Menten and cellobiose inhibition constants were determined from the cellobiohydrolases produced heterologously in *T. reesei* (Examples 14 and 15). The enzymes were purified as described in Example 2. Protein concentrations of purified enzymes were measured by their absorption at 280 nm using a theoretical molar extinction coefficient, which were calculated from the amino acid sequences (Gill and von Hippel, 1989).

Kinetic constants (Km and kcat values) and cellobiose inhibition constant (Ki) for Tr CBHI/Cel7A, Ta CBH/Cel7A, At CBH/Cel7A and Ct CBH/Cel7A, were measured using CNPLac (2-Chloro-4-nitrophenyl-β-D-lactoside) as substrate at ambient temperature (22° C.) in 50 mM sodium phosphate buffer, pH 5.7. For the determination of the inhibition constant (Ki), eight different substrate concentrations (31-4000 μM) in the presence of a range of five inhibitor concentrations (0-100 μM or 0-400 μM), which bracket the Ki value, were used. All experiments were performed in microtiter plates and the total reaction volume was 200 μl. The initial rates were in each case measured by continuous monitoring the release of the chloro-nitrophenolate anion (CNP, 2-Chloro-4-nitrophenolate) through measurements at 405 nm using Varioscan (Thermolabsystems) microtiter plate reader. The results were calculated from CNP standard curve (from 0 to 100 μM). Enzyme concentrations used were: Tr CBHI/Cel7A 2.46 μM, Ta CBH/Cel7A 1.58 μM, Ct CBH/Cel7A 0.79 μM and At CBH/Cel7A 3 μM. The Km and kcat constants were calculated from the fitting of the Michaelis-Menten equation using the programme of Origin. Lineweaver-Burk plots, replots (LWB slope versus [Glc2; cellobiose]) and Hanes plots were used to distinguish between competitive and mixed type inhibition and to determine the inhibition constants (Ki).

The results from the kinetic measurements are shown in Table 12 and Table 13. As can be seen, Ct CBH/Cel7A has clearly the higher turnover number (kcat) on CNPLac and also the specificity constant (kcat/Km) is higher as compared to CBHI/Cel7A of *T. reesei*. Cellobiose (Glc2) is a competitive inhibitor for all the measured cellulases, and the Tr CBHI/Cel7A (used as a control) has the strongest inhibition (i.e. the lowest Ki value) by cellobiose. The At CBH/Cel7A had over 7-fold higher inhibition constant as compared to that of Tr CBHI/Cel7A. These results indicate that all three novel cellobiohydrolases could work better on cellulose hydrolysis due to decreased cellobiose inhibition as compared to *Trichoderma reesei* Cel7A cellobiohydrolase I.

TABLE 12

Comparison of the cellobiose inhibition constants of four GH family 7 cellobiohydrolases, measured on CNPLac in 50 mM sodium phosphate buffer pH 5.7, at 22° C.

| Enzyme | Ki (μM) | Type of inhibition |
|---|---|---|
| Ct Cel7A | 39 | competitive |
| Ta Cel7A | 107 | competitive |
| At Cel7A | 141 | competitive |
| Tr Cel7A | 19 | competitive |

TABLE 13

Comparison of the Michaelis-Menten kinetic constants of *Chaetomium thermophilum* cellobiohydrolase Cel7A to CBHI/Cel7A of *T. reesei*, measured on CNPLac in 50 mM sodium phosphate buffer pH 5.7, at 22° C.

| Enzyme | kcat ($min^{-1}$) | Km (μM) | kcat/Km ($min^{-1}$ $M^{-1}$) |
|---|---|---|---|
| Ct Cel7A | 18.8 | 1960 | 9.5 103 |
| Tr Cel7A | 2.6 | 520 | 5.0 103 |

Example 17

Hydrolysis of Crystalline Cellulose (Avicel) by the Recombinant Cellobiohydrolases The purified recombinant cellobiohydrolases Ct Cel7A, Ta Cel7A, Ta Cel7A+Tr CBD, Ta Cel7A+Ct CBD, At Cel7A as well as the core version of Ct Cel7A (see below) were tested in equimolar amounts in crystalline cellulose hydrolysis at two temperatures, 45° C. and 70° C.; the purified *T. reesei* Tr Cel7A and its core version (see below) were used as comparison. The crystalline cellulose (Ph 101, Avicel; Fluka, Bucsh, Switzerland) hydrolysis assays were performed in 1.5 ml tube scale 50 mM sodium acetate, pH 5.0. Avicel was shaken at 45° C. or at 70° C., with the enzyme solution (1.4 μM), and the final volume of the reaction mixture was 325 μl. The hydrolysis was followed up to 24 hours taking samples at six different time points and stopping the reaction by adding 163 μl of stop reagent containing 9 vol of 94% ethanol and 1 vol of 1 M glycine (pH 11). The solution was filtered through a Millex GV13 0.22 μm filtration unit (Millipore, Billerica, Mass., USA). The formation of soluble reducing sugars in the supernatant was determined by para-hydroxybenzoic-acidhydrazide (PAHBAH) method (Lever, 1972) using a cellobiose standard curve (50 to 1600 μM cellobiose). A freshly made 0.1 M PAHBAH (Sigma-Aldrich, St. Louis, Mo., USA) in 0.5 M NaOH (100 μl) solution was added to 150 μl of the filtered sample and boiled for 10 minutes after which the solution was cooled on ice. The absorbance of the samples at 405 nm was measured.

The core versions of the cellobiohydrolases harboring a CBD in their native form were obtained as follows: Ct Cel7A and Tr Cel7A were exposed to proteolytic digestion to remove the cellulose-binding domain. Papain (Papaya Latex, 14 U/mg, Sigma) digestion of the native cellobiohydrolases was performed at 37° C. for 24 h in a reaction mixture composed of 10 mM L-cystein and 2 mM EDTA in 50 mM sodium acetate buffer (pH 5.0) with addition of papain (two papain concentrations were tested: of one fifth or one tenth amount of papain of the total amount of the Cel7A in the reaction mixture). The resultant core protein was purified with DEAE Sepharose FF (Pharmacia, Uppsala, Sweden) anion exchange column as described above. The product was analysed in SDS-PAGE.

Figure 4A:
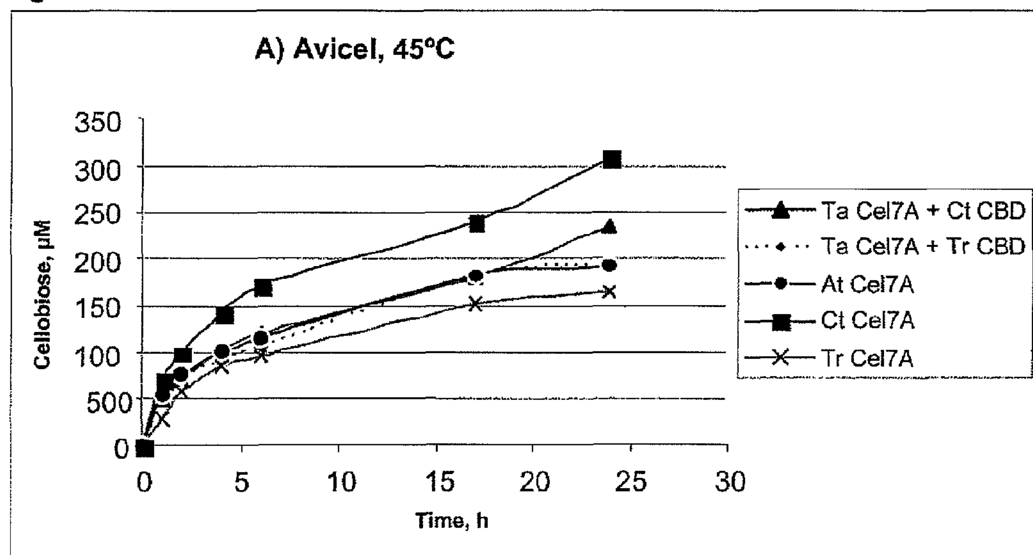
FIG. 4. Crystalline cellulose (Avicel) hydrolysis by the purified recombinant cellobiohydrolases at 45° C. Substrate concentration 1% (w/v), pH 5.0, enzyme concentration 1.4 μM. A) Cellobiohydrolases harboring a CBD, B) cellobiohydrolases (core) without a CBD.
Figure 4B:
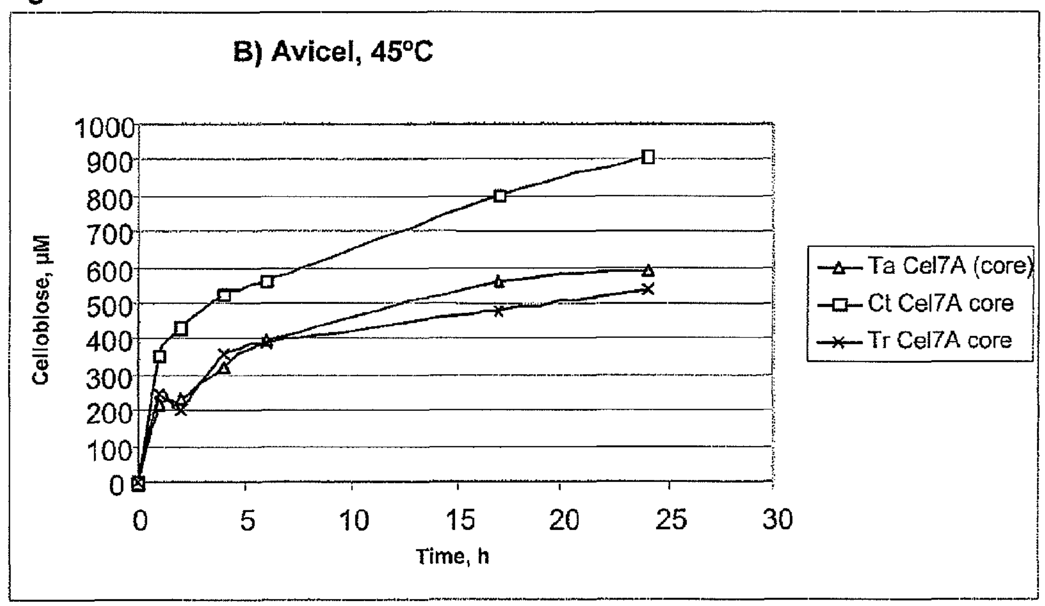
Figure 5A:
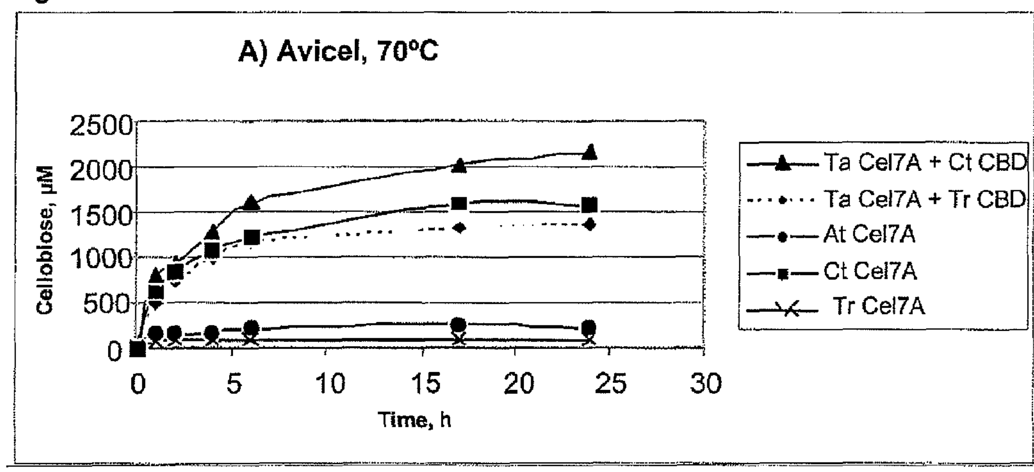
FIG. 5. Crystalline cellulose (Avicel) hydrolysis by the purified recombinant cellobiohydrolases at 70° C. Substrate concentration 1% (w/v), pH 5.0, enzyme concentration 1.4 μM. A) Cellobiohydrolases harboring a CBD, B) cellobiohydrolases (core) without a CBD.
Figure 5B:
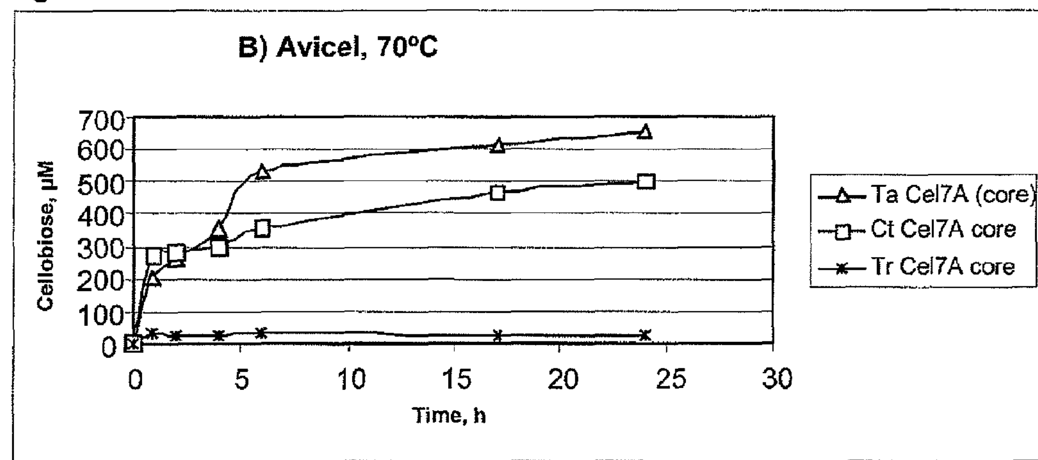

The hydrolysis results at 45° C. and 70° C. are shown in FIG. 4 and FIG. 5, respectively. The results show clearly that all the cellobiohydrolases show faster and more complete hydrolysis at both temperatures as compared to the state-of-art cellobiohydrolase *T. reesei* Cel7A. At 70° C. the thermostable cellobiohydrolases from *Thermoascus aurantiacus* ALKO4242 and *Chaetomium thermophilum* ALKO4265 are superior as compared to the *T. reesei* Cel7A, also in the case where the *Thermoascus* Cel7A core is linked to the CBD of *T. reesei* Cel7A (Ta Cel7A+Tr CBD). It was surprising that the cellobiohydrolases isolated and cloned in this work are superior, when harboring a CBD, in the rate and product formation in crystalline cellulose hydrolysis also at the conventional hydrolysis temperature of 45° C. when compared to the state-of-art cellobiohydrolase *T. reesei* Cel7A (CBHI) at the same enzyme concentration. The results are also in agreement with those enzyme preparations (At Cel7A and Ct Cel7A), which were purified from the original hosts and tested in Avicel hydrolysis (50° C., 24 h) (Example 2, Table 1).

Example 18

Cloning of *Acremonium thermophilum* ALKO4245, *Chaetomium thermophilum* ALKO4261, and *Thermoascus aurantiacus* ALKO4242 Endoglucanase Genes Standard molecular biology methods were used as described in Example 13. The construction of the *Acremonium, Chaetomium*, and *Thermoascus* genomic libraries has been described in Example 12.

The peptides derived from the purified *Acremonium* and *Chaetomium* endoglucanases shared homology with several endoglucanases of glycosyl hydrolase family 45 such as *Melanocarpus albomyces* Cel45A endoglucanase (AJ515703) and *Humicola insolens* endoglucanase (A35275), respectively. Peptides derived from the *Thermoascus* endoglucanase shared almost 100% identity with the published *Thermoascus aurantiacus* EG1 endoglucanase sequence (AF487830). To amplify a probe for screening of the *Acremonium* and *Chaetomium* genomic libraries, degenerate primers were designed on the basis of the peptide sequences. The order of the peptides in the protein sequence and the corresponding sense or anti-sense nature of the primers was deduced from the comparison with the homologous published endoglucanases. Primer sequences and the corresponding peptides are listed in Table 14. Due to almost 100% identity of the *Thermoascus* peptides with the published sequence, the endoglucanase gene was amplified by PCR directly from the genomic DNA.

TABLE 14

Oligonucleotides synthesized and used as PCR primers to amplify a probe for screening of *Acremonium thermophilum* cel45A (EG_40) and *Chaetomium thermophilum* cel7B (EG_54) gene from the corresponding genomic libraries.

| Protein | Peptide | Primer location[a] | Primer sequence[b] |
|---|---|---|---|
| At EG_40 | Peptide 5<br>WFQNADN[c] | 1-6 | TAYTGGGAYTGYTGYAARCC<br>RTTRTCNGCRTTYTGRAACCA |
| Ct EG_54 | Peptide 7 | 3-7 | GCAAGCTTCGRCARAARTCRTCRTT[d] |
| | Peptide 2 | 5-9 | GGAATTCGAYCARACNGARCARTA[e] |

[a]Amino acids of the peptide used for designing the primer sequence
[b]N = A, C, G, or T; R = A or G; Y = C or T
[c]Peptide not derived from the purified *Acremonium* EG_40 protein, but originates from the *M. albomyces* Cel45A sequence (AJ515703) homologous to EG_40.
[d]A HindIII restriction site was added to the 5' end of the oligonucleotide
[e]An EcoRI restriction site was added to the 5' end of the oligonucleotide The *Acremonium thermophilum* cel45A gene specific probe to screen the genomic library was amplified with the forward (TAYTGGGAYTGYTGYAARCC) and reverse (RTTRTCNGCRTTYTGRAACCA) primers using genomic DNA as a template. The PCR reaction mixtures contained 50 mM Tris-HCl, pH 9.0, 15 mM $(NH_4)_2SO_4$, 0.1% Triton X-100, 1.5 mM $MgCl_2$, 0.1 mM dNTPs, 0.5 μg each primer, 1 unit of Dynazyme EXT DNA polymerase (Finnzymes, Finland) and approximately 0.5 μg of *Acremonium* genomic DNA. The conditions for PCR reactions were the following: 5 min initial denaturation at 95° C., followed by 30 cycles of 1 min at 95° C., 1 min annealing at 50-60° C., 2 min extension at 72° C. and a final extension at 72° C. for 10 min. For amplification of the *Chaetomium thermophilum* cel7B gene (coding for Ct EG_54) specific probe, a forward primer (GGAATTCGAYCARACNGARCARTA) and a reverse primer (GCAAGCTTCGRCARAARTCRTCRTT) were used. The PCR reaction mixtures contained 10 mM Tris-HCl, pH 8.8, 50 mM KCl, 0.1% Triton X-100, 1.5 mM $MgCl_2$, 0.2 mM dNTPs, 250 pmol each primer, 2 unit of Dynazyme II DNA polymerase (Finnzymes, Finland) and approximately 2 μg of *Chaetomium* genomic DNA. The conditions for PCR reaction were as described above, except that annealing was performed at 45-50° C.

Two PCR products were obtained from the *Acremonium* PCR reaction. DNA fragments of about 0.6 kb and 0.8 kb were isolated from agarose gel and were cloned into the pCR4-TOPO® TA vector (Invitrogen, USA) resulting in plasmids pALK1710 and pALK1711, respectively. The DNA products were characterized by sequencing and by performing Southern blot hybridizations to the genomic *Acremonium* DNA digested with several restriction enzymes. The hybridization patterns obtained with the two fragments in stringent washing conditions suggest that two putative endoglucanase genes could be screened from the *Acremonium* genomic library. The deduced amino acid sequences of both PCR products have homology to several published endoglucanase sequences of glycosyl hydrolase family 45 (BLAST program, National Center for Biotechnology Information; Altschul et al., 1990).

One PCR product of expected size (estimated from the homologous *Humicola insolens* endoglucanase sequence, A35275) was obtained from the *Chaetomium* PCR reaction. This DNA fragment of about 0.7 kb was cloned into the pCR4-TOPO® TA vector (Invitrogen, USA) resulting in plasmid pALK2005 and analyzed as described above. The deduced amino acid sequence of the PCR product has homology to several published cellulase sequences of glycosyl hydrolase family 7 (BLAST program, version 2.2.9 at NCBI, National Center for Biotechnology Information; Altschul et al., 1990).

The insert from plasmids pALK1710, pALK1711, and pALK2005 was isolated by restriction enzyme digestion and labeled with digoxigenin according to the supplier's instructions (Roche, Germany). About 1-2×$10^5$ plaques from the amplified *Acremonium* or *Chaetomium* genomic library were screened. The temperature for hybridisation was 68° C. and the filters were washed 2×5 min at RT using 2×SSC-0.1% SDS followed by 2×15 min at 68° C. using 0.1×SSC-0.1% SDS. Several positive plaques were obtained, of which five to six strongly hybridizing plaques were purified from each screening. Phage DNAs were isolated and analysed by Southern blot hybridization. Restriction fragments hybridizing to the probe were subcloned into the pBluescript II KS+ vector (Stratagene, USA) and the relevant parts were sequenced. In all cases the subcloned phage fragment contains the full-length gene of interest. Table 15 summarises the information of the probes used for screening of the endoglucanase genes, phage clones from which the genes were isolated, chosen restriction fragments containing the full-length genes with their promoter and terminator regions, names of plasmids containing the subcloned phage fragment, and the deposit numbers in the Deutsche Sammlung von Mikroorganismen and Zellkulturen GmbH culture collection (DSM) for *E. coli* strains carrying these plasmids.

TABLE 15

Probes used for cloning of endoglucanase gene, phage clone and the subclone chosen, plasmid name and the corresponding deposit number of the *E. coli* strain.

| Gene | Genomic library | Probe used in screening | Phage clone | Subcloned fragment | Plasmid | *E. coli* deposit no. |
|---|---|---|---|---|---|---|
| At cel45A | *A. thermophilum* ALKO4245 | pALK1710 | P24 | 5.5 kb SmaI | pALK1908 | DSM 17324 |
| At cel45B | *A. thermophilum* ALKO4245 | pALK1711 | P41 | 6.0 kb XhoI | pALK1904 | DSM 17323 |
| Ct cel7B | *C. thermophilum* ALKO4261 | pALK2005 | P55 | 5.1 kb BamHI | pALK2010 | DSM 17729 |

*Thermoascus aurantiacus* cel5A gene (coding for EG_28) (SEQ ID NO: 9) was amplified directly from the isolated genomic DNA by PCR reaction. The forward (ATTAACCGCGGACTGCGCATCATGAAGCTCGGCTCTCTCGTGCTC) and reverse (AACTGAGGCATAGAAACTGACGTCATATT) primers that were used for amplification were designed on the basis of the published *T. aurantiacus* eg1 gene (AF487830). The PCR reaction mixtures contained 1× Phusion HF buffer, 0.3 mM dNTPs, 0.5 μM of each primer, 2 units of Phusion™ DNA polymerase (Finnzymes, Finland) and approximately 0.25 μg of *Thermoascus* genomic DNA. The conditions for PCR reactions were the following: 5 min initial denaturation at 95° C., followed by 25 cycles of 30 s at 95° C., 30 s annealing at 57-67° C., 2.5 min extension at 72° C. and a final extension at 72° C. for 5 min. The amplified 1.3 kb product containing the exact gene (from START to STOP codon) was cloned as a SacII-PstI fragment into the pBluescript II KS+ vector. Two independent clones were sequenced and one clone was selected and designated as pALK1926. The deposit number of the *E. coli* strain containing pALK1926 in the Deutsche Sammlung von Mikroorganismen and Zellkulturen GmbH culture collection is DSM 17326.

Relevant information of the genes and the deduced protein sequences (SEQ ID NO: 9-16) are summarized in Table 16 and Table 17, respectively. Peptide sequences of the purified *Acremonium* EG_40 (gene At cel45A), *Chaetomium* EG_54 (gene Ct cel7B), and *Thermoascus* EG_28 (gene Ta cel5A) endoglucanases were found in the corresponding deduced amino acid sequences of the cloned genes confirming that appropriate genes were cloned.

TABLE 16

Summary of the endoglucanase genes isolated from *Acremonium thermophilum*, *Chaetomium thermophilum*, and *Thermoascus aurantiacus*.

| Endoglucanase gene | Length with introns (bp)[a] | Coding region (bp)[b] | No of introns | Lengths of introns (bp) | SEQ ID NO: |
|---|---|---|---|---|---|
| At cel45A | 1076 | 891 | 2 | 59, 123 | 11 |
| At cel45B | 1013 | 753 | 2 | 155, 102 | 13 |
| Ct cel7B | 1278 | 1275 | — | — | 15 |
| Ta cel5A | 1317 | 1005 | 5 | 55, 60, 59, 74, 61 | 9 |

[a]The STOP codon is included.
[b]The STOP codon is not included.

TABLE 17

Summary of the deduced endoglucanase sequences of *Acremonium thermophilum*, *Chaetomium thermophilum*, and *Thermoascus aurantiacus*. ss, signal sequence.

| Endoglucanase protein | No of aas | Length of ss NN/HMM[a] | CBD[b] | Predicted MW (Da, ss not incl)[c] | Predicted pI (ss not incl) | Putative N-glycosylation sites[d] | SEQ ID NO: |
|---|---|---|---|---|---|---|---|
| At EG_40 | 297 | 21/21 | Yes, K265 to L297 | 28625 | 4.79 | 2 | 12 |
| At EG_40_like | 251 | 20/20 | No | 23972 | 6.11 | 2 | 14 |
| Ct EG_54 | 425 | 17/17 | No | 45358 | 5.44 | 1 | 16 |
| Ta EG_28 | 335 | 30(e | No | 33712 | 4.30 | 1 | 10 |

[a]The prediction of the signal sequence was made using the program SignalP V3.0 (Nielsen et al., 1997; Bendtsen et al., 2004); the NN value was obtained using neural networks and HMM value using hidden Markov models.
[b]Presence of a cellulose binding domain in the protein, the amino acids of the C-terminal CBD are indicated (numbering according to the full length polypeptide)
[c]The predicted signal sequence is not included. Prediction was made using the Compute pI/MW tool at ExPASy server (Gasteiger et al., 2003).
[d]The putative N-glycosylation sites N-X-S/T were predicted using the program NetNGlyc 1.0 (Gupta et al., 2004).
(eAccording to Hong et al. 2003a The deduced protein sequences of *Acremonium* EG_40 (At Cel45A) and EG_40_like (At Cel45B), *Chaetomium* EG_54 (Ct Cel7B), and *Thermoascus* EG_28 (Ta Cel5A) endoglucanases share homology with cellulases of glycosyl hydrolase family 45 (*Acremonium*), family 7 (*Chaetomium*), and family 5 (*Thermoascus*), thus identifying the isolated genes as members of these gene families. The closest homologies of the *Acremonium* endoglucanases EG_40/Cel45A and EG_40_like/Cel45B are endoglucanases of *Thielavia terrestris* (CQ827970, 77.3% identity) and *Myceliophthora thermophile* (AR094305, 66.9% identity), respectively (Table 18). The two isolated *Acremonium* family 45 endoglucanases share only an identity of 53.7% with each other. Of these enzymes only EG_40/Cel45A contains a cellulose binding domain (CBD).

The closest homology for the predicted protein sequence of *Chaetomium* EG_54/Cel7B endoglucanase is found in the *Melanocarpus albomyces* Cel7A cellulase sequence (AJ515704). The identity between these two protein sequences is 70.6%.

The protein sequence of the isolated *Thermoascus aurantiacus* endoglucanase is completely identical with that of the published *T. aurantiacus* EGI (AF487830, Table 18). The closest homology was found in a β-glucanase sequence of *Talaromyces emersonii* (AX254752, 71.1% identity).

TABLE 18

Comparison of the deduced *Acremonium thermophilum* EG_40, EG_40_like/Cel45B, *Chaetomium thermophilum* EG_54/Cel7B, and *Thermoascus aurantiacus* EG_28/Cel5A endoglucanases with their homologous counterparts. The alignment was performed using the Needle programme of the EMBOSS programme package.

| Organism, enzyme, and accession number | Identity (%) |
|---|---|
| *Acremonium thermophilum* EG_40 | 100.0 |
| *Thielavia terrestris* EG45, CQ827970 | 77.3 |
| *Melanocarpus albomyces* Cel45A, AJ515703 | 75.3 |
| *Neurospora crassa*, hypothetical XM_324477 | 68.9 |
| *Humicola grisea* var thermoidea, EGL3, AB003107 | 67.5 |
| *Humicola insolens* EG5, A23635 | 67.3 |
| *Myceliophthora thermophila* fam 45, AR094305 | 57.9 |
| **Acremonium thermophilum* EG_40_like | 53.7 |
| *Acremonium thermophilum* EG_40_like | 100.0 |
| *Myceliophthora thermophila* fam 45, AR094305 | 66.9 |
| *Magnaporthe grisea* 70-15 hypothetical, XM_363402 | 61.9 |
| *Thielavia terrestris* EG45, CQ827970 | |
| **Acremonium thermophilum* EG_40 | 56.8 |
| *Melanocarpus albomyces* Cel45A, AJ515703 | 53.7 |
| | 52.8 |
| *Chaetomium thermophilum* EG_54 | 100.0 |
| *Melanocarpus albomyces* Cel7A, AJ515704 | 70.6 |
| *Humicola grisea* var thermoidea EGI, D63516 | 68.8 |
| *Humicola insolens* EGI, AR012244 | 67.7 |
| *Myceliophthora thermophila* EGI, AR071934 | 61.7 |
| *Fusarium oxysporum* var lycopercisi EGI, AF29210 | 53.5 |
| *Fusarium oxysporum* EGI, AR012243 | 52.6 |
| *Thermoascus aurantiacus* EG_28 | 100.0 |
| *Thermoascus aurantiacus* EG, AX812161 | 100.0 |
| *Thermoascus aurantiacus* EGI, AY055121 | 99.4 |
| *Talaromyces emersonii* β-glucanase, AX254752 | 71.1 |
| *Talaromyces emersonii* EG, AF440003 | 70.4 |
| *Aspergillus niger* EG, A69663 | 70.1 |

TABLE 18-continued

Comparison of the deduced *Acremonium thermophilum* EG_40, EG_40_like/Cel45B, *Chaetomium thermophilum* EG_54/Cel7B, and *Thermoascus aurantiacus* EG_28/Cel5A endoglucanases with their homologous counterparts. The alignment was performed using the Needle programme of the EMBOSS programme package.

| Organism, enzyme, and accession number | Identity (%) |
|---|---|
| *Aspergillus niger* EG, A62441 | 69.9 |
| *Aspergillus niger* EG, AF331518 | 69.6 |
| *Aspergillus aculeatus* EGV, AF054512 | 68.5 |

*indicates an endoglucanase encoded by a gene cloned in this work.

Example 19

Production of Recombinant Endoglucanases in *Trichoderma reesei*

Expression plasmids were constructed for production of the recombinant *Acremonium EG*_40/Cel45A, EG_40_like/Cel45B, and *Thermoascus* EG_28/Cel5A proteins as described in Example 14. Linear expression cassettes (Table 19) were isolated from the vector backbone by restriction enzyme digestion, transformed into *T. reesei* A96 and transformants purified as described in Example 14.

TABLE 19

The expression cassettes constructed for production of *Acremonium thermophilum* EG_40/Cel45A, EG_40_like/Cel45B, and *Thermoascus aurantiacus* EG_28/Cel5A endoglucanases in *Trichoderma reesei*. The schematic structure of the expression cassettes is described in FIG. 2.

| Endoglucanase | Expression plasmid | Size of the expression cassette[a] | Heterologous terminator[b] |
|---|---|---|---|
| At EG_40 | pALK1920 | 10.9 kb NotI | 156 bp (HindIII) |
| At EG_40_like | pALK1921 | 8.6 kb EcoRI | 282 bp (SspI) |
| Ta EG_28 | pALK1930 | 8.6 kb NotI | none |

[a]The expression cassette for *T. reesei* transformation was isolated from the vector backbone by EcoRI or NotI digestion.
[b]The number of nucleotides after the STOP codon of the cloned gene that are included in the expression cassette are indicated. The restriction site at the 3'-region of the gene that was used in construction of the expression cassette is indicated in parenthesis.

The endoglucanase production of the transformants was analyzed from the culture supernatants of shake flask cultivations (50 ml). Transformants were grown as in Example 14 and the enzyme activity of the recombinant protein was measured from the culture supernatant as the release of reducing sugars from carboxymethylcellulose (2% (w/v) CMC) at 50° C. in 50 mM citrate buffer pH 4.8 essentially as described by Bailey and Nevalainen 1981; Haakana et al. 2004. Production of the recombinant proteins was also detected from culture supernatants by SDS-polyacrylamide gel electrophoresis. *Acremonium* EG_40-specific polyclonal antibodies were produced in rabbits (University of Helsinki, Finland). The expression of EG_40 was verified by Western blot analysis with anti-EG_40 antibodies using the ProtoBlot Western blot AP system (Promega). The genotypes of the chosen transformants were analysed by Southern blotting using the expression cassette as a probe.

Figure 6A:
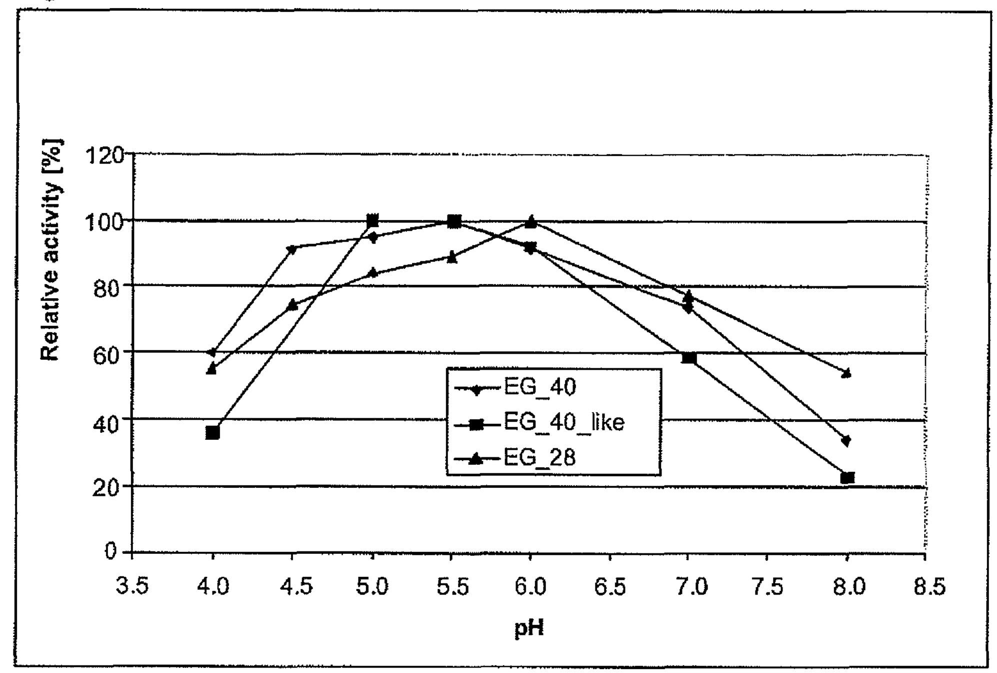
FIG. 6. A) The pH dependency of the heterologously produced *Acremonium* EG_40/Cel45A, EG_40_like/Cel45B and *Thermoascus* EG_28/Cel5A activity was determined with CMC substrate in a 10 min reaction at 50° C. B) Temperature optimum of the *Acremonium* EG_40/Cel45A, EG_40_like/Cel45B and *Thermoascus* EG_28/Cel5A was determined at pH 5.5, 4.8, and 6.0, respectively. The reaction containing CMC as substrate was performed for 60 min, except for EG_28/Cel5A for 10 min. BSA (100 μg/ml) was added as a stabilizer.
Figure 6B:
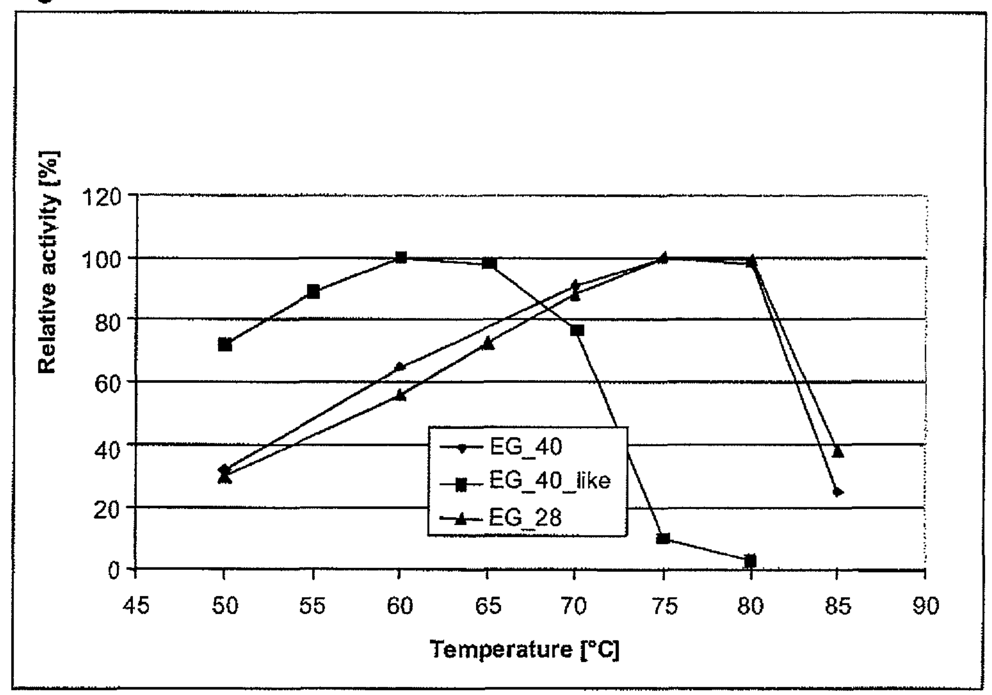

The pH optimum of the heterologously produced endoglucanases was determined in the universal McIlvaine's buffer within a pH range of 4.0-8.0 using carboxymethylcellulose as substrate. As shown in FIG. 6 A the broadest pH range (4.5-6.0) is that of the *Acremonium* EG_40/Cel45A protein, the optimum being at pH 5.5. The pH optima for the other heterologously produced endoglucanases are pH 5.0-5.5 and 6.0 for *Acremonium* EG_40_like/Cel45B and *Thermoascus* EG_28/Cel5A, respectively. The optimal temperature for enzymatic activity of these endoglucanases was determined at the temperature range of 50-85° C. as described above. The highest activity of the enzymes was determined to be at 75° C., 60° C., and 75° C. for the *Acremonium* EG_40/Cel45A, EG_40_like/Cel45B, and *Thermoascus* EG_28/Cel5A, respectively (FIG. 6B).

The chosen transformants were cultivated, as described in Example 14, in a 2 litre bioreactor for four days (28° C., pH 4.2) to obtain material for the application tests.

Example 20

Cloning of *Acremonium thermophilum* ALKO4245, *Chaetomium thermophilum* ALKO4261, and *Thermoascus aurantiacus* ALKO4242 Beta-Glucosidase Genes Standard molecular biology methods were used as described in Example 13. The construction of the *Acremonium, Chaetomium*, and *Thermoascus* genomic libraries has been described in Example 12.

The peptides derived from the purified *Acremonium, Chaetomium*, and *Thermoascus* β-glucosidases shared homology with several β-glucosidases of glycosyl hydrolase family 3 such as *Acremonium cellulolyticus* (BD168028), *Trichoderma viride* (AY368687), and *Talaromyces emersonii* (AY072918) β-glucosidases, respectively. To amplify a probe for screening of the *Acremonium, Chaetomium*, or *Thermoascus* genomic libraries, degenerate primers were designed on the basis of the peptide sequences. The order of the peptides in the protein sequence and the corresponding sense or anti-sense nature of the primers was deduced from the comparison with the homologous published β-glucosidases. Primer sequences and the corresponding peptides are listed in Table 20.

TABLE 20

Oligonucleotides synthesized and used as PCR primers to amplify a probe for screening of *Acremonium* thermophilum cel3A (βG_101), *Chaetomium thermophilum* cel3A (βG_76), and *Thermoascus aurantiacus* cel3A (βG_81) gene from the corresponding genomic libraries.

| Protein | Peptide | Primer location[a] | Primer Sequence[b] |
|---|---|---|---|
| At βG_101 | EKVNLT[c] | | GARAARGTNAAYCTNAC |
| | Peptide 4 | 6-11 | YTTRCCRTTRTTSGGRGTRTA |
| Ct βG_76 | Peptide 6 | 4-9 | TNTGYCTNCARGAYGG |
| | Peptide 1 | 3-8 | TCRAARTGSCGRTARTCRATRAASAG |
| Ta βG_81 | Peptide 3 | 1-5 | AARGGYGTSGAYGTSCAR |
| | Peptide 1 | 2-7 | YTTRCCCCASGTRAASGG |

[a]Amino acids of the peptide used for designing the primer sequence
[b]To reduce degeneracy, some codons were chosen according to fungal preference. N = A, C, G, or T; R = A or G; S = C or G; Y = C or T
[c]Peptide not derived from the purified *Acremonium* βG_101 protein, but originates from the *A. cellulolyticus* β-glucosidase sequence (BD168028) homologous to βG_101.

The probes for screening genomic libraries constructed were amplified with the listed primer combinations (Table 20) using *Acremonium, Chaetomium*, or *Thermoascus* genomic DNA as template. The PCR reaction mixtures contained 50 mM Tris-HCl, pH 9.0, 15 mM $(NH_4)_2SO_4$, 0.1% Triton X-100, 1.5 mM $MgCl_2$, 0.1-0.2 mM dNTPs, 0.25 μg each primer, 1 unit of Dynazyme EXT DNA polymerase (Finnzymes, Finland) and approximately 0.5 μg of genomic DNA. The conditions for PCR reactions were the following: 5 min initial denaturation at 95° C., followed by 30 cycles of 1 min at 95° C., 1 min annealing at 40° C. (*Acremonium* DNA as a template), at 50° C. (*Chaetomium* DNA as a template), or at 63° C. (*Thermoascus* DNA as a template), 2-3 min extension at 72° C. and a final extension at 72° C. for 5-10 min.

Specific PCR products of expected size (estimated from the homologous β-glucosidase sequences BD168028, AY072918, and AY368687) were isolated from the agarose gel. DNA fragments of about 1.8 kb (*Acremonium*), 1.5 kb (*Chaetomium*), and 1.52 kb (*Thermoascus*) were cloned into the pCR4-TOPO® TA vector (Invitrogen, USA) resulting in plasmids pALK1924, pALK1935, and pALK1713, respectively. The DNA products were characterized by sequencing and by performing Southern blot hybridizations to the genomic DNA digested with several restriction enzymes. The hybridization patterns in stringent washing conditions suggest that one putative β-glucosidase gene could be isolated from the *Acremonium, Chaetomium*, and *Thermoascus* genomic library. The deduced amino acid sequences of all three PCR products have homology to several published β-glucosidase sequences of glycosyl hydrolase family 3 (BLAST program, National Center for Biotechnology Information; Altschul et al., 1990).

The insert from plasmids pALK1713, pALK1924, and pALK1935 was isolated by restriction enzyme digestion and labeled with digoxigenin according to the supplier's instructions (Roche, Germany). About 1-2×$10^5$ plaques from the amplified *Acremonium, Chaetomium*, or *Thermoascus* genomic library were screened as described in Example 18. Several positive plaques were obtained, of which five to six strongly hybridizing plaques were purified from each screening. Phage DNAs were isolated and analysed by Southern blot hybridization. Restriction fragments hybridizing to the probe were subcloned into the pBluescript II KS+ vector (Stratagene, USA) and the relevant parts were sequenced. In all cases the subcloned phage fragment contains the full-length gene of interest. Table 21 summarises the information of the probes used for screening of the β-glucosidase genes, phage clones from which the genes were isolated, chosen restriction fragments containing the full-length genes with their promoter and terminator regions, names of plasmids containing the subcloned phage fragment, and the deposit numbers in the Deutsche Sammlung von Mikroorganismen and Zellkulturen GmbH culture collection (DSM) for *E. coli* strains carrying these plasmids.

TABLE 21

Probes used for cloning of β-glucosidase gene, phage clone and the subclone chosen, plasmid name and the corresponding deposit number of the *E. coli* strain.

| Gene | Genomic library | Probe used in screening | Phage clone | Subcloned fragment | Plasmid | *E. coli* deposit no. |
|---|---|---|---|---|---|---|
| At cel3A | *A. thermophilum* ALKO4245 | pALK1924 | P44 | 6.0 kb HindIII | pALK1925 | DSM 17325 |
| Ct cel3A | *C. thermophilum* ALKO4261 | pALK1935 | P51 | 7.0 kb XbaI | pALK2001 | DSM 17667 |
| Ta cel3A | *T. aurantiacus* ALKO4242 | pALK1713 | P21 | 5.3 kb BamHI | pALK1723 | DSM 16725 |

Relevant information of the genes and deduced protein sequences (SEQ ID NO: 21-26) are summarized in Table 22 and Table 23, respectively. Peptide sequences of the purified *Acremonium* βG_101 (At Cel3A), *Chaetomium* βG_76 (Ct Cel3A), and *Thermoascus* βG_81 (Ta Cel3A) proteins were found in the corresponding deduced amino acid sequences of the cloned genes confirming that appropriate genes were cloned.

TABLE 22

Summary of the β-glucosidase genes isolated from *Acremonium thermophilum*, *Chaetomium thermophilum*, and *Thermoascus aurantiacus*.

| β-glucosidase gene | Length with introns (bp)[a] | Coding region bp)[b] | No of introns | Lengths of introns (bp) | SEQ ID NO: |
|---|---|---|---|---|---|
| At cel3A | 2821 | 2583 | 3 | 92, 74, 69 | 23 |
| Ct cel3A | 2257 | 2202 | 1 | 52 | 25 |
| Ta cel3A | 3084 | 2529 | 7 | 134, 67, 56, 64, 59, 110, 62 | 21 |

[a]The STOP codon is included.
[b]The STOP codon is not included.

TABLE 23

Summary of the deduced β-glucosidase sequences of *Acremonium thermophilum*, *Chaetomium thermophilum*, and *Thermoascus aurantiacus*. ss, signal sequence.

| β-glucosidase protein | No of aas | Length of ss NN/HMM[a] | CBD[b] | Predicted MW (Da, ss not incl)[c] | Predicted pI ss not incl) | Putative N-glycosylation sites[d] | SEQ ID NO: |
|---|---|---|---|---|---|---|---|
| At βG_101 | 861 | 19/18 | No | 91434 | 5.46 | 8 | 24 |
| Ct βG_76 | 734 | 20/20 | No | 76457 | 6.3 | 2 | 26 |
| Ta βG_81 | 843 | 19/19 | No | 89924 | 4.95 | 8 | 22 |

[a]The prediction of the signal sequence was made using the program SignalP V3.0 (Nielsen et al., 1997; Bendtsen et al, 2004); the NN value was obtained using neural networks and HMM value using hidden Markov models.
[b]Presence of a cellulose binding domain in the protein.
[c]The predicted signal sequence is not included. Prediction was made using the Compute pI/MW tool at ExPASy server (Gasteiger et al., 2003).
[d]The putative N-glycosylation sites N-X-S/T were predicted using the program NetNGlyc 1.0 (Gupta et al., 2004).

The deduced protein sequences of *Acremonium* βG_101/Cel3A, *Chaetomium* βG_76/Cel3A, and *Thermoascus* βG_81/Cel3A β-glucosidases share homology with enzymes of glycosyl hydrolase family 3, thus identifying that the isolated genes belong to this gene family. The closest counterparts of the *Acremonium, Chaetomium*, and *Thermoascus* β-glucosidases are those of *Magnaporthe grisea* (β-glucosidase, AY849670), *Neurospora crassa* (hypothetical, XM_324308), and *Talaromyces emersonii* (β-glucosidase, AY072918), respectively (Table 24). The highest sequence identity (73.2%) found was that of *C. thermophilum* βG_76/Cel3A to *N. crassa* hypothetical protein indicating that novel enzymes genes were cloned.

TABLE 24

Comparison of the deduced *Acremonium thermophilum* βG_101/Cel3A, *Chaetomium thermophilum* βG_76/Cel3A, and *Thermoascus aurantiacus* βG_81/Cel3A β-glucosidases with their homologous counterparts. The alignment was performed using the Needle programme of the EMBOSS programme package.

| Organism, enzyme, and accession number | Identity (%) |
|---|---|
| **Acremonium thermophilum* βG_101 | 100.0 |
| *Magnaporthe grisea* β-glucosidase, AY849670 | 73.1 |
| *Neurospora crassa* hypothetical, XM_330871 | 71.1 |
| *Trichoderma reesei* Cel3B, AY281374 | 65.2 |
| **Thermoascus aurantiacus* βG_81 | 62.2 |
| *Aspergillus aculeatus* β-glucosidase, D64088 | 59.5 |
| *Talaromyces emersonii* β-glucosidase, AY072918 | 58.9 |
| *Aspergillus oryzae*, AX616738 | 58.2 |
| *Acremonium cellulolyticus* β-glucosidase, BD168028 | 57.2 |
| **Chaetomium thermophilum* βG_76 | 40.9 |
| *Chaetomium thermophilum* βG_76 | 100.0 |
| *Neurospora crassa*, hypothetical XM_324308 | 76.9 |
| *Magnaporthe grisea*, hypothetical XM_364573 | 70.2 |
| *Trichoderma viridae* BGI, AY368687 | 65.8 |
| *Acremonium cellulolyticus* β-glucosidase, BD168028 | 41.2 |
| **Acremonium thermophilum* βG_101 | 40.9 |
| *Trichoderma reesei* Cel3B, AY281374 | 40.0 |
| **Thermoascus aurantiacus* βG_81 | 39.9 |
| **Thermoascus aurantiacus* βG_81 | 100.0 |
| *Talaromyces emersonii* β-glucosidase, AY072918 | 73.2 |
| *Aspergillus oryzae*, AX616738 | 69.5 |
| *Aspergillus aculeatus* β-glucosidase, D64088 | 68.0 |
| *Acremonium cellulolyticus* β-glucosidase, BD168028 | 65.7 |
| **Acremonium thermophilum* βG_101 | 62.2 |
| *Trichoderma reesei* Cel3B, AY281374 | 57.9 |
| **Chaetomium thermophilum* βG_76 | 39.9 |

*indicates a β-glucosidase encoded by a gene cloned in this work.

Example 21

Production of Recombinant Beta-Glucosidases in *Trichoderma reesei*

Expression plasmids were constructed for production of the recombinant *Acremonium* βG_101/Cel3A, *Chaetomium* βG_76/Cel3A, and *Thermoascus* βG_81/Cel3A proteins as described in Example 14. Linear expression cassettes (Table 25) were isolated from the vector backbone by restriction enzyme digestion, transformed into *T. reesei* A96 or A33 (both strains have the genes encoding the four major cellulases CBHI/Cel7A, CBHII/Cel6A, EGI/Cel7B and EGII/Cel5A deleted) and transformants purified as described in Example 14.

TABLE 25

The expression cassettes constructed for production of *Acremonium thermophilum* βG_101/Cel3A, *Chaetomium thermophilum* βG_76/Cel3A, and *Thermoascus aurantiacus* βG_81/Cel3A β-glucosidases in *Trichoderma reesei*. The schematic structure of the expression cassettes is described in FIG. 2.

| β-glucosidase | Expression plasmid | Size of the expression cassette[a] | Heterologous terminator[b] |
|---|---|---|---|
| At βG_101 | pALK1933 | 10.5 kb NotI | 300 bp (HindIII) |
| Ct βG_76 | pALK2004 | 10.1 kb EcoRI | 528 bp (XbaI) |
| Ta βG_81 | pALK1914 | 10.9 kB EcoRI | 452 bp (ApoI) |

[a]The expression cassette for T. reesei transformation was isolated from the vector backbone by EcoRI or NotI digestion.
[b]The number of nucleotides after the STOP codon of the cloned gene that are included in the expression cassette are indicated. The restriction site at the 3'-region of the gene that was used in construction of the expression cassette is indicated in parenthesis.

The beta-glucosidase production of the transformants was analyzed from the culture supernatants of shake flask cultivations (50 ml). Transformants were grown as in Example 14 and the enzyme activity of the recombinant protein was measured from the culture supernatant using 4-nitrophenyl-β-D-glucopyranoside substrate as described by Bailey and Nevalainen 1981. Production of the recombinant proteins was also detected from culture supernatants by SDS-polyacrylamide gel electrophoresis. In addition, the expression of *Thermoascus* βG_81 was verified by Western blot analysis with anti-βG_81 antibodies as described in Example 19. The genotypes of the chosen transformants were analysed by Southern blotting using the expression cassette as a probe.

Figure 7A:
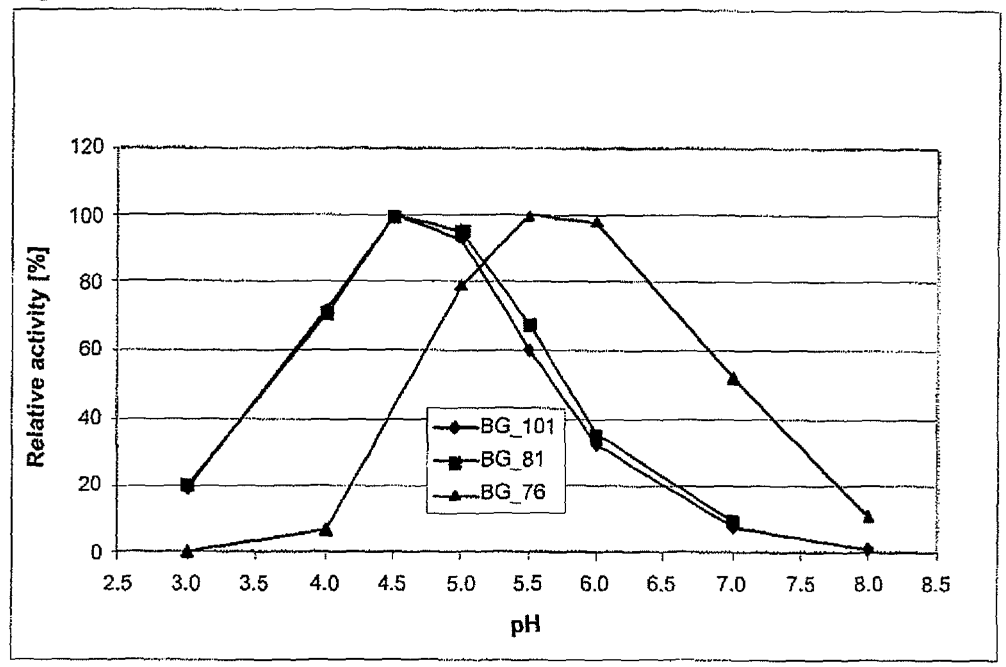
FIG. 7. A) The pH dependency of the heterologously produced *Acremonium* BG_101/Cel3A, *Chaetomium* BG_76/Cel3A, and *Thermoascus* BG_81/Cel3A activity was determined with 4-nitrophenyl-β-D-glucopyranoside substrate in a 10 min reaction at 50° C. B) Temperature optimum of the *Acremonium* βG_101/Cel3A, *Chaetomium*
Figure 7B:
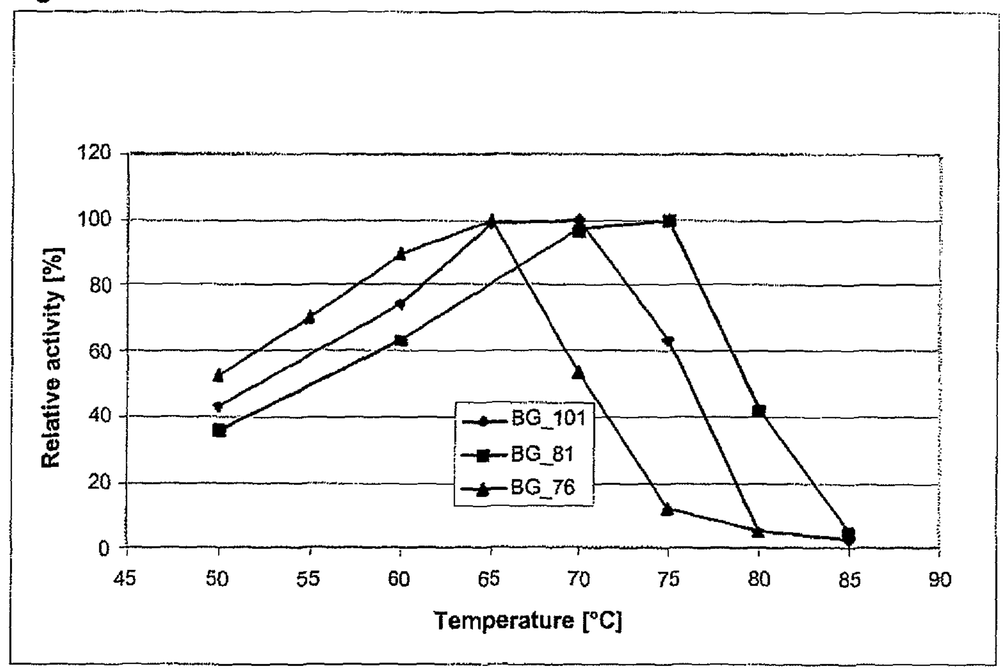

The pH optimum of the heterologously produced β-glucosidases was determined in the universal McIlvaine's buffer within a pH range of 3.0-8.0 using 4-nitrophenyl-β-D-glucopyranoside as substrate. The pH optima for the *Acremonium* βG_101, *Chaetomium* βG_76, and *Thermoascus* βG_81 are pH 4.5, 5.5, and 4.5, respectively (FIG. 7A). The optimal temperature for enzymatic activity of these β-glucosidases was determined at the temperature range of 50-85° C. as described above. The highest activity of the enzymes was determined to be at 70° C., 65° C., and 75° C. for the *Acremonium* βG_101/Cel3A, *Chaetomium* βG_76/Cel3A, and *Thermoascus* βG_81/Cel3A, respectively (FIG. 7B).

The chosen transformants were cultivated, as described in Example 14, in a 2 litre bioreactor for four days (28° C., pH 4.2) to obtain material for the application tests.

Example 22

Cloning of *Acremonium thermophilum* ALKO4245 and *Thermoascus aurantiacus* ALKO4242 Xylanase Genes Standard molecular biology methods were used as described in Example 13. The construction of the *Acremonium* genomic library has been described in Example 12.

The peptides derived from the purified *Acremonium* xylanase shared homology with xylanases of the glycosyl hydrolase family 10 such as *Humicola grisea* XYNI (AB001030). All peptides derived from the *Thermoascus* xylanase were completely identical with the published *Thermoascus aurantiacus* XYNA sequence (AJ132635) thus identifying the purified protein as the same enzyme. Due to this the *Thermoascus* xylanase gene was amplified by PCR from the genomic DNA.

To amplify a probe for screening of the *Acremonium* xylanase gene from the genomic library, degenerate primers were designed on the basis of the peptide sequences (Example 11, Table 5). The order of the peptides in the protein sequence and the corresponding sense or antisense nature of the primers was deduced from the comparison with the homologous *Humicola insolens* XYNI sequence (AB001030). The sense primer sequence (GAYGGYGAYGCSACYTAYATG) is based on Peptide 3 (amino acids 2-8) and anti-sense primer (YTTYTGRTCRTAYTCSAGRTTRTA) on Peptide 1 (amino acids 4-11).

A PCR product of expected size (estimated from the homologous *Humicola insolens* XYNI sequence AB001030) was obtained from the reaction. This DNA fragment of about 0.7 kb was cloned into the pCR4-TOPO® TA vector (Invitrogen, USA) resulting in plasmid pALK1714, and was characterized by sequencing. The deduced amino acid sequence of the PCR product has homology to several published xylanase sequences of glycosyl hydrolase family 10 (BLAST program, National Center for Biotechnology Information; Altschul et al., 1990).

The insert from plasmid pALK1714 was isolated by restriction enzyme digestion and labeled with digoxigenin according to the supplier's instructions (Roche, Germany). About $1\text{-}2\times10^5$ plaques from the amplified *Acremonium* genomic library were screened as described in Example 18. Several positive plaques were obtained, of which five strongly hybridizing plaques were purified. Phage DNAs were isolated and analysed by Southern blot hybridization. A 3.0 kb XbaI restriction fragment hybridizing to the probe was subcloned into the pBluescript II KS+ vector (Stratagene, USA) resulting in plasmid pALK1725. Relevant parts of pALK1725 were sequenced and found to contain the full-length *Acremonium thermophilum* xyn10A gene (SEQ ID NO: 19). The deposit number of the *E. coli* strain containing pALK1725 in the Deutsche Sammlung von Mikroorganismen and Zellkulturen GmbH culture collection is DSM 16726.

*Thermoascus aurantiacus* xyn10A gene (SEQ ID NO: 17) was amplified directly from the isolated genomic DNA by PCR reaction. The forward (TTATACCGCGGGAAGCCATGGTTCGACCAACGATCCTAC) and reverse (TTATAGGATCCACCGGTCTATACTCACTGCTGCAGGTCCTG) primers that were used in the amplification of the gene were designed on the basis of the published *T. aurantiacus* xynA gene (AJ132635). The PCR reaction mixtures contained 50 mM Tris-HCl, pH 9.0, 15 mM $(NH_4)_2SO_4$, 0.1% Triton X-100, 1.5 mM $MgCl_2$, 0.3 mM dNTPs, 1 μM each primer, 1 unit of Dynazyme EXT DNA polymerase (Finnzymes, Finland) and approximately 0.5 μg of *Thermoascus* genomic DNA. The conditions for PCR reactions were the following: 5 min initial denaturation at 95° C., followed by 30 cycles of 1 min at 95° C., 1 min annealing at 60-66° C., 3 min extension at 72° C. and a final extension at 72° C. for 10 min. The amplified 1.9 kb product containing the exact gene (from START to STOP codon) was cloned as a SacII-BamHI fragment into the pBluescript II KS+ vector. Three independent clones were sequenced and one clone was selected and designated as pALK1715. The deposit number of the *E. coli* strain containing pALK1715 in the Deutsche Sammlung von Mikroorganismen and Zellkulturen GmbH culture collection is DSM 16724.

Relevant information of the genes and deduced protein sequences (SEQ ID NO: 17-20) are summarized in Table 26 and Table 27, respectively. Peptide sequences of the purified *Acremonium* XYN_60 and *Thermoascus* XYN_30 proteins were found in the corresponding deduced amino acid sequences of the cloned genes (At xyn10A and Ta xyn10A, respectively) confirming that appropriate genes were cloned.

TABLE 26

Summary of the xylanase genes isolated from *Acremonium thermophilum* and *Thermoascus aurantiacus*.

| Xylanase gene | Length with introns (bp)[a] | Coding region (bp)[b] | No of introns | Lengths of introns (bp) | SEQ ID NO: |
|---|---|---|---|---|---|
| At xyn10A | 1471 | 1248 | 2 | 135, 85 | 19 |
| Ta xyn10A | 1913 | 987 | 10 | 73, 74, 68, 103, 69, 65, 93, 66, 100, 212 | 17 |

[a]The STOP codon is included.

[b]The STOP codon is not included.

TABLE 27

Summary of the deduced xylanase sequences of *Acremonium thermophilum* and *Thermoascus aurantiacus*. ss, signal sequence.

| Xylanase protein | No of aas | Length of ss NN/HMM[a] | CBD[b] | Predicted MW (Da, ss not incl)[c] | Predicted pI (ss not incl) | Putative N-glycosylation sites[d] | SEQ ID NO: |
|---|---|---|---|---|---|---|---|
| At XYN_60 | 416 | 19/19 | Yes, W385 to L416 | 42533 | 6.32 | 1-2 | 20 |
| Ta XYN_30 | 329 | 26(e | No | 32901 | 5.81 | 0 | 18 |

[a]The prediction of the signal sequence was made using the program SignalP V3.0 (Nielsen et al., 1997; Bendtsen et al, 2004); the NN value was obtained using neural networks and HMM value using hidden Markov models.
[b]Presence of a carbohydrate binding domain CBD, the amino acids of the C-terminal CBD are indicated (numbering according to the full length polypeptide)
[c]The predicted signal sequence is not included. Prediction was made using the Compute pI/MW tool at ExPASy server (Gasteiger et al., 2003).
[d]The putative N-glycosylation sites N-X-S/T were predicted using the program NetNGlyc 1.0 (Gupta et al., 2004).
[e]According to Lo Leggio et al., 1999

The deduced protein sequences of *Acremonium* and *Thermoascus* xylanases share homology with several enzymes of glycosyl hydrolase family 10, identifying the corresponding genes as members of family 10 xylanases. The closest counterpart for the *Acremonium* XYN_60/Xyn10A found is the *Humicola grisea* XYLI (AB001030) showing 67.1% identity with XYN_60 (Table 28). The predicted protein sequence of the isolated *Thermoascus aurantiacus* XYN_30/Xyn10A xylanase is completely identical with that of the published *T. aurantiacus* XYNA (P23360, Table 28). The closest homology was found in a xylanase sequence of *Aspergillus niger* (A62445, 69.7% identity).

TABLE 28

Comparison of the deduced *Acremonium thermophilum* XYN_60/Xyn10A and *Thermoascus aurantiacus* XYN_30/Xyn10A xylanases with their homologous counterparts. The alignment was performed using the Needle programme of the EMBOSS programme package.

| Organism, enzyme, and accession number | Identity (%) |
|---|---|
| **Thermoascus aurantiacus* XYN_30 | 100.0 |
| *Thermoascus aurantiacus* XynA, P23360 | 100.0 |
| *Thermoascus aurantiacus* XynA, AF127529 | 99.4 |
| *Aspergillus niger* xylanase, A62445 | 69.7 |
| *Aspergillus aculeatus* xylanase, AR137844 | 69.9 |
| *Aspergillus terreus* fam 10 xyn, DQ087436 | 65.0 |
| *Aspergillus sojae*, XynXI AB040414 | 63.8 |
| *Penicillium chrysogenum* xylanase, AY583585 | 62.5 |
| **Acremonium thermophilum* XYN_60 | 100.0 |
| *Humicola grisea* XYL I, AB001030 | 67.1 |
| *Magnaporthe grisea* 70-15, hypothetical XM_364947 | 63.8 |
| *Aspergillus aculeatus* xylanase, AR149839 | 53.7 |
| *Talaromyces emersonii* xylanase, AX403831 | 51.8 |
| *Gibberella zeae* xylanase, AY575962 | 51.4 |
| *Magnaporthe grisea* XYL5, AY144348 | 48.5 |
| *Talaromyces emersonii*, AX172287 | 46.9 |

*indicates a xylanase encoded by a gene cloned in this work.

Example 23

Production of Recombinant Xylanases in *Trichoderma reesei*

Expression plasmids were constructed for production of the recombinant *Acremonium* XYN_60/Xyn10A and *Thermoascus* XYN_30/Xyn10A proteins as described in Example 14. Linear expression cassettes (Table 29) were isolated from the vector backbone by restriction enzyme digestion, transformed into *T. reesei* A96, and transformants purified as described in Example 14.

TABLE 29

The expression cassettes constructed for production of *Acremonium thermophilum* XYN_60/Xyn10A and *Thermoascus aurantiacus* XYN_30/Xyn10A xylanases in *Trichoderma reesei*. The schematic structure of the expression cassettes is described in FIG. 2.

| Xylanase | Expression plasmid | Size of the expression cassette[a] | Heterologous terminator[b] |
|---|---|---|---|
| At XYN_60 | pALK1912 | 9.0 kb | 150 by (BamHI) |
| Ta XYN_30 | pALK1913 | 9.3 kb | none |

[a]The expression cassette for *T. reesei* transformation was isolated from the vector backbone by EcoRI digestion.
[b]The number of nucleotides after the STOP codon of the cloned gene that are included in the expression cassette are indicated. The restriction site at the 3'-region of the gene that was used in construction of the expression cassette is indicated in parenthesis.

The xylanase production of the transformants was analyzed from the culture supernatants of shake flask cultivations (50 ml). Transformants were grown as in Example 14 and the enzyme activity of the recombinant protein was measured from the culture supernatant as the release of reducing sugars from birch xylan (1% w/v) at 50° C. in 50 mM citrate buffer pH 5.3 as described by Bailey and Poutanen 1989. Production of the recombinant protein was also analyzed from culture supernatant by SDS-polyacrylamide gel electrophoresis. In addition, the expression of both xylanases was determined by Western blot analysis with anti-XYN_30 or anti-XYN_60 antibodies as described in Example 19. The genotypes of the chosen transformants were analysed by Southern blotting using the expression cassette as a probe.

Figure 8A:
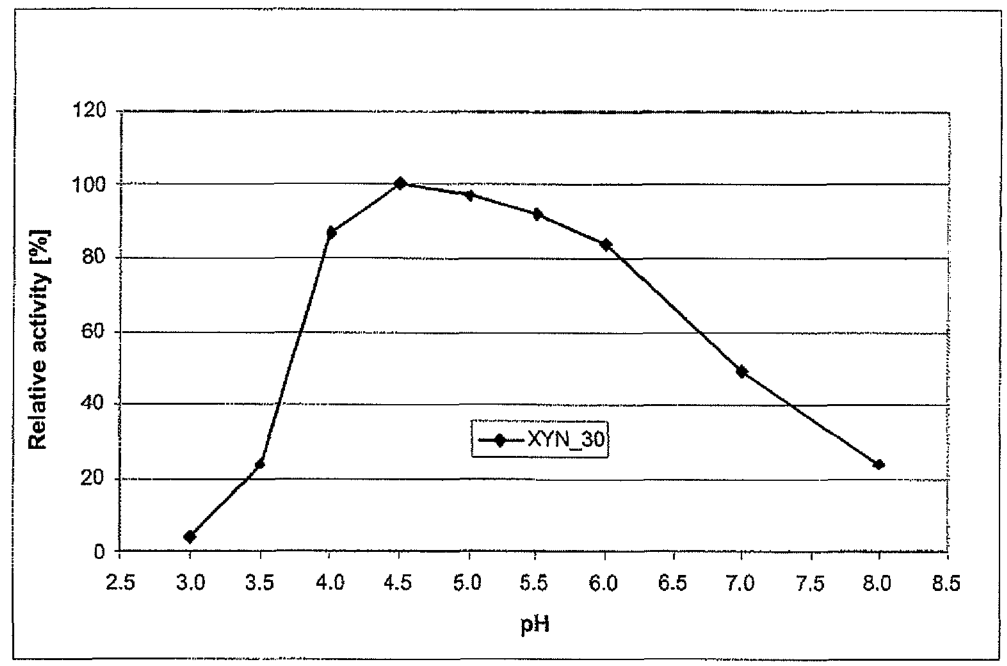
Figure 8B:
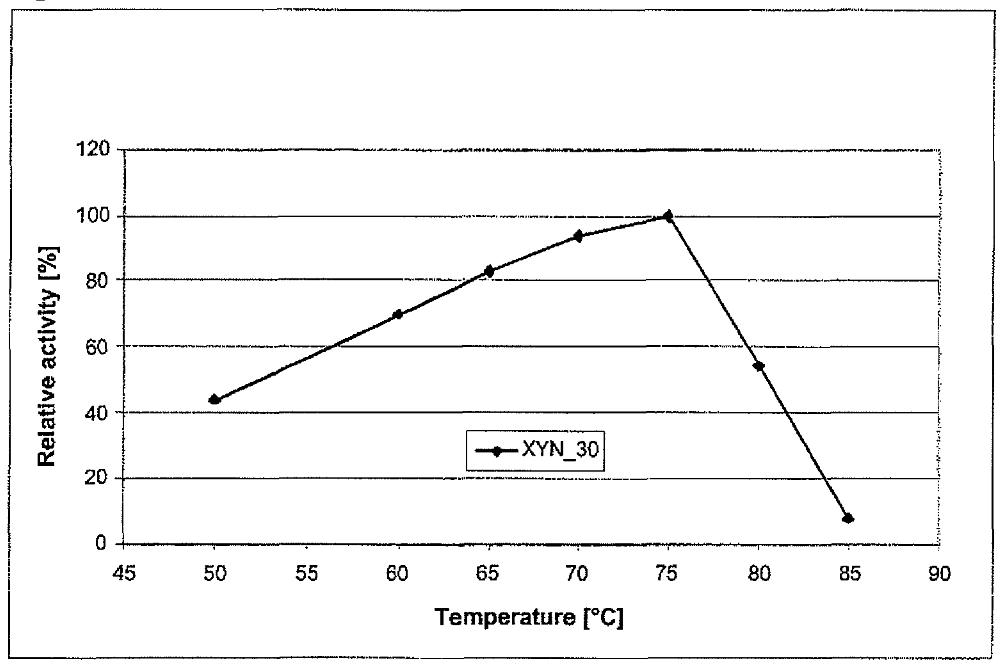

*Thermoascus* XYN_30/Xyn10A was produced in *T. reesei* and the pH optimum of the heterologously produced protein was determined in the universal McIlvaine's buffer within a pH range of 3.0-8.0 using birch xylan as substrate (FIG. 8A). The optimal pH was determined to be 4.5. The temperature optimum for the enzymatic activity of XYN_30 was determined to be 75° C. (FIG. 8B).

The chosen transformants were cultivated, as described in Example 14, in a 2 litre bioreactor for four days (28° C., pH 4.2) to obtain material for the application tests.

Example 24

Performance of the Recombinant Cellobiohydrolases in the Hydrolysis

The performance of the purified recombinant cellobiohydrolases was evaluated in the hydrolysis studies with purified *T. reesei* enzymes. Hydrolysis was carried out with controlled mixtures of purified enzymes on several pre-treated substrates. Culture filtrates of *T. reesei*, containing different cloned CBH/Cel7 enzymes were obtained as described in Examples 14 and 15, and the CBH enzymes were purified by affinity chromatography as described in Example 2. In addition, pure *T. reesei* cellulases (purified as described by Suurnäkki et al., 2000) were used in the enzyme mixtures. The cellobiohydrolases used in the experiment were:

*Thermoascus aurantiacus* ALKO4242 CBH (Ta Cel7A)

*Thermoascus aurantiacus* ALKO4242 CBH (Ta Cel7A) with genetically attached CBD of *Trichoderma reesei* (Ta Cel7A+Tr CBD)

*Thermoascus aurantiacus* ALKO4242 CBH (Ta Cel7A) with genetically attached CBD of *Chaetomium thermophilum* (Ta Cel7A+Ct CBD)

*Acremonium thermophilum* ALKO4245 CBH (At Cel7A)

*Chaetomium thermophilum* ALKO4265 CBH (Ct Cel7A).

Each CBH/Cel7 to be tested (dosage 14.5 mg/g dry matter of substrate) was used either together with EGII/Cel5A of *T. reesei* (3.6 mg/g) or with a mixture containing *T. reesei* EGI/Cel7B (1.8 mg/g), EGII/Cel5A (1.8 mg/g), xylanase pI 9 (Tenkanen et al. 1992) (5000 nkat/g) and acetyl xylan esterase (AXE) (Sundberg and Poutanen, 1991) (250 nkat/g). All mixtures were supplemented with additional β-glucosidase from a commercial enzyme preparation Novozym 188 (176 nkat/g d.w.). Triplicate tubes containing the enzyme mixture and 10 mg (dry matter)/ml of the substrate suspended in 0.05 M sodium acetate were incubated in mixing by magnetic stirring at 45° C. for 48 h. Reference samples with inactivated enzymes and corresponding substrates were also prepared. The release of hydrolysis products was measured as reducing sugars with DNS method using glucose as standard (Table 30).

The following substrates were used in the experiment:

Crystalline cellulose (Avicel)

Washed steam pre-treated spruce fibre (impregnation with 3% w/w $SO_2$ for 20 min, followed by steam pre-treatment at 215° C. for 5 min), dry matter 25.9% (SPRUCE).

Washed wet oxidized corn stover fibre (WOCS).

Washed steam pre-treated willow fibre (pre-treatment for 14 min at 210° C.), dry matter 23.0% (WILLOW).

TABLE 30

Hydrolysis products with CBH enzymes (45° C., pH 5.0). Reaction products after 48 h hydrolysis as reducing sugars (mg/ml), measured glucose as standard.

| Enzymes | | Substrates | | | |
|---|---|---|---|---|---|
| CBH | Additional enzymes | Avicel | SPRUCE | WOCS | WILLOW |
| Ta Cel7A | EGII, bG | 2.0 | 2.0 | 2.8 | 2.0 |
| Ta Cel7A + Tr CBD | EGII, bG | 5.8 | 4.0 | 4.4 | 4.0 |
| Ta Cel7A + Ct CBD | EGII, bG | 4.9 | 3.7 | 4.6 | 3.7 |
| At Cel7A | EGII, bG | 5.3 | 3.3 | 4.5 | 3.3 |
| Ct Cel7A | EGII, bG | 6.0 | 2.6 | 3.4 | 2.6 |
| Cel7A of *T. reesei* | EGII, bG | 4.7 | 2.9 | 2.9 | 2.9 |
| Ta Cel7A | EGII, EGI, XYL, AXE, bG | nd | nd | 4.3 | 2.8 |
| Ta Cel7A + Tr CBD | EGII, EGI, XYL, AXE, bG | nd | nd | 7.2 | 5.9 |
| Ta Cel7A + Ct CBD | EGII, EGI, XYL, AXE, bG | nd | nd | 7.2 | 5.6 |
| At Cel7A | EGII, EGI, XYL, AXE, bG | nd | nd | 6.4 | 5.4 |
| Ct Cel7A | EGII, EGI, XYL, AXE, bG | nd | nd | 5.6 | 4.0 |
| Cel7A of T. reesei | EGII, EGI, XYL, AXE, bG | nd | nd | 6.0 | 4.1 |

Abbreviations:
CBH = cellobiohydrolase;
EGI = endoglucanase I (Cel7B) of *T. reesei*, EGII = endoglucanase II (Cel5A) of *T. reesei*;
bG = β-glucosidase (from Novozym 188);
XYL = xylanase pI 9 (XYN II) of *T. reesei*,
AXE = acetyl xylan esterase of *T. reesei*;
nd = not done.

In Table 30 the different cellobiohydrolases have been compared based on the same protein dosage in the hydrolysis. The results show that on cellulosic substrates (Avicel and spruce fibre) Cel7A of *Thermoascus aurantiacus* with genetically attached CBD showed clearly higher hydrolysis than *T. reesei* CBHI/Cel7A. Without CBD, *T. aurantiacus* Cel7A was less efficient on these substrates. The performance of *Acremonium thermophilum* and *Chaetomium thermophilum* cellobiohydrolases was also better than that of *T. reesei* CBHI/Cel7A on several substrates; in particular, *C. thermophilum* Cel7A showed high efficiency on pure cellulose (Avicel).

In the case of substrates containing notable amounts of hemicellulose (willow and corn stover) the CBH/Cel7 enzymes clearly needed additionally both hemicellulases and endoglucanases to perform efficiently. If no additional hemicellulases were present, Cel7A of *T. aurantiacus* with genetically attached CBD showed again clearly highest hydrolysis. With the most important hemicellulose-degrading enzymes (xylanase, acetyl xylan esterase and EGI) Cel7A of *T. aurantiacus* with genetically attached CBD performed again with highest efficiency. *A. thermophilum* Cel7A was more efficient than *T. reesei* enzyme and *C. thermophilum* Cel7A produced hydrolysis products on the same level than *T. reesei* CBHI/Cel7A. The cellulose binding domain of *T. reesei* seemed to give slightly better efficiency than CBD of *C. thermophilum* in the hydrolytic performance of *T. aurantiacus* Cel7A, even though the difference was rather small.

It can be concluded that when CBHI/Cel7A was replaced in the mixture of *Trichoderma* enzymes by the herein produced cellobiohydrolases, the hydrolysis efficiency as judged by this experimental arrangements was clearly improved in the case of *T. aurantiacus* Cel7A with genetically attached CBD, and also improved in the case of *A. thermophilum* Cel7A and *C. thermophilum* Cel7A. Considering also the better temperature stability of the herein produced cellobiohydrolases, the results indicate that the performance of cellulase enzyme mixtures in higher temperatures than 45° C. can be clearly improved by using the herein produced cellobiohydrolases.

Example 25

Performance of the Recombinant Endoglucanases in the Hydrolysis

The preparations containing the endoglucanases were compared in hydrolysis studies mixed with the purified CBH/Cel7 and CBH/Cel6 enzymes on several pre-treated substrates. Culture filtrates of *T. reesei*, containing different cloned endoglucanase enzymes were obtained as described in Example 19. The enzymes were enriched by removing thermolabile proteins from the mixtures by a heat treatment (60° C., 2 h, pH 5) and the supernatant was used for the hydrolysis studies. In addition, pure *T. reesei* cellulases (purified as described by Suurnäkki et al., 2000) were used in the enzyme mixtures. The endoglucanases used in the experiment were:

*Acremonium thermophilum* ALKO4245 endoglucanase At EG_40/Cel45A (ALKO4245 EG_40)

*Acremonium thermophilum* ALKO4245 endoglucanase At EG_40_like/Cel45B (ALKO4245 EG_40_like)

*Thermoascus aurantiacus* ALKO4242 endoglucanase Ta EG_28/Cel5A (ALKO4242 EG_28).

The following substrates were used in the experiment:

Washed steam pre-treated spruce fibre (impregnation with 3% $SO_2$ for 20 min, followed by steam pre-treatment at 215° C. for 5 min), dry matter 25.9% (SPRUCE).

Steam exploded corn stover fibre (steam pre-treatment at 210° C. for 5 min), dry matter 31.0% (SECS).

The endoglucanases to be studied (dosage 840 nkat/g dry matter, based on endoglucanase activity against HEC according to IUPAC, 1987) were used either with cellobiohydrolases of *T. reesei* (CBHI/Cel7A, 8.1 mg/g d.m. and CBHII/Cel6A, 2.0 mg/g d.m.) or with *Thermoascus aurantiacus* Cel7A with genetically attached CBD of *T. reesei* (10.1 mg/g d.m.). Purified (Suurnäkki et al., 2000) EGI (Cel7B) and EGII (Cel5A) of *T. reesei* were also included in the experiments for comparison. All mixtures were supplemented with additional β-glucosidase from Novozym 188 (to make the total β-glucosidase dosage 560 nkat/g d.w., the relatively high dosage was used to compensate the differences in the background activities of the different EG preparations). Triplicate tubes were incubated in mixing at 45° C. for 48 h and reference samples with inactivated enzymes and corresponding substrates were prepared. The release of hydrolysis products was measured as reducing sugars with DNS method using glucose as standard (Table 31).

TABLE 31

Hydrolysis products with different endoglucanase preparations when used together with cellobiohydrolases from *T. reesei* or with *T. aurantiacus Cel7A harbouring CBD of T. reesei*. Reaction products after 48 h hydrolysis (45° C., pH 5.0) as reducing sugars (mg/ml), measured glucose as standard.

| Enzymes | | Substrate | |
|---|---|---|---|
| Endoglucanase | CBH/Cel7 | SPRUCE | SECS |
| no added EG | CBHI and CBHII of *T. reesei* | 2.4 | 3.2 |
| EGI | CBHI and CBHII of *T. reesei* | 3.5 | 4.6 |
| EGII | CBHI and CBHII of *T. reesei* | 3.8 | 3.5 |
| At EG_40 | CBHI and CBHII of *T. reesei* | 4.9 | 4.3 |
| At EG_40like | CBHI and CBHII of *T. reesei* | 4.5 | 4.8 |
| Ta EG_28 | CBHI and CBHII of *T. reesei* | 3.0 | 3.9 |
| no added EG | *T. aurantiacus* Cel7A + Tr CBD | 1.8 | 2.1 |
| EG I | *T. aurantiacus* Cel7A + Tr CBD | nd. | 4.2 |
| EG II | *T. aurantiacus* Cel7A + Tr CBD | 3.2 | nd. |
| At EG_40 | *T. aurantiacus* Cel7A + Tr CBD | 4.8 | 4.0 |
| Ta EG_28 | *T. aurantiacus* Cel7A + Tr CBD | 1.5 | nd. |

Abbreviations:
CBHI = cellobiohydrolase I (Cel7A) of *T. reesei*;
CBHII = cellobiohydrolase II (Cel6A) of *T. reesei*;
EGI = endoglucanase I (Cel7B) of *T. reesei*,
EGII = endoglucanase II (Cel5A) of *T. reesei*;
bG = β-glucosidase (from Novozym 188);
nd. = not done.

In Table 31 the different endoglucanases have been compared based on the same activity dosage in the hydrolysis. This may favour enzymes with low specific activity against the substrate (hydroxyethyl cellulose) used in the assay and underestimate the efficiency of enzymes with high specific activity against hydroxyethyl cellulose. In any case, the results show that *Acremonium thermophilum* endoglucanases perform very well in the hydrolysis when affecting together with both cellobiohydrolases used in the mixture. *A. thermophilum* endoglucanases have similar performance to *T. reesei* EGI/Cel7B which is a very efficient enzyme on hemicellulose-containing corn stover substrate due to its strong xylanase side activity. *T. aurantiacus* endoglucanase Cel5A (ALKO4242 EG_28) showed lower hydrolysis than *T. reesei* enzymes.

It can be concluded that the endoglucanases from *A. thermophilum* perform with comparable or enhanced efficiency when compared to the corresponding *Trichoderma* enzymes in the hydrolysis as judged by this experimental arrangement. Considering also the temperature stability of the herein described endoglucanases, the results indicate that the performance of cellulase enzyme mixtures in higher temperatures than 45° C. can be improved by using the herein described endoglucanases.

Example 26

Hydrolysis of Steam Pre-Treated Spruce at High Temperatures

Washed steam exploded spruce fibre (impregnation with 3% w/w $SO_2$ for 20 min, followed by steam pre-treatment at 215° C. for 5 min), with dry matter of 25.9% was suspended in 5 ml of 0.05 M sodium acetate buffer in the consistency of 10 mg/ml. This substrate was hydrolysed using different enzyme mixtures in test tubes with magnetic stirring in the water bath adjusted in different temperatures for 72 h. For each sample point, a triplicate of test tubes was withdrawn from hydrolysis, boiled for 10 min in order to terminate the enzyme hydrolysis, centrifuged, and the supernatant was analysed for reaction products from hydrolysis. The blanks containing the substrate alone (only buffer added instead of enzymes) were also incubated in the corresponding conditions.

A mixture of thermophilic cellulases was prepared using the following components:

Thermophilic CBH/Cel7 preparation containing *Thermoascus aurantiacus* ALKO4242 Cel7A with genetically attached CBD of *T. reesei* CBHI/Cel7A. The protein preparation was produced as described in Example 15 and purified according to Example 2 resulting in the purified Ta Cel7A+Tr CBD preparation with protein content of 5.6 mg/ml.

Thermophilic endoglucanase preparation containing *Acremonium thermophilum* ALKO4245 endoglucanase At EG_40/Cel45A. The protein was produced in *T. reesei* as described in Example 19. In order to enrich the thermophilic components, the spent culture medium was heat treated (60° C. for 2 hours). The preparation obtained contained protein 4.9 mg/ml and endoglucanase activity (according to IUPAC, 1987) 422 nkat/ml.

Thermophilic β-glucosidase preparation prepared as described in Example 21 containing *Thermoascus aurantiacus* ALKO4242 β-glucosidase Ta βG_81/Cel3A. In order to enrich the thermophilic components, the fermentor broth was heat treated (65° C. for 2 hours). The preparation obtained contained 4.3 mg/ml protein and β-glucosidase activity of 6270 nkat/ml (according to Bailey and Linko, 1990).

These enzyme preparations were combined as follows (per 10 ml of mixture): CBH/Cel7-preparation 4.51 ml, endoglucanase preparation 5.19 ml and β-glucosidase preparation 0.29 ml. This mixture was used as "MIXTURE 1" of the thermophilic enzymes.

As a comparison and reference, a state-of art mixture of commercial *Trichoderma reesei* enzymes was constructed combining (per 10 ml): 8.05 ml Celluclast 1.5 L FG (from Novozymes A/S) and 1.95 ml Novozym 188 (from Novozymes A/S). This was designated as "*T. reesei* ENZYMES."

Enzymes were dosed on the basis of the FPU activity of the mixtures: "MIXTURE 1" using the dosage of 5.5 FPU per 1 gram of dry matter in the spruce substrate, and "*T. Reesei* ENZYMES" using 5.8 FPU per 1 gram of dry matter in the spruce substrate.

Samples were taken from the hydrolysis after 24, 48 and 72 h and treated as described above. The hydrolysis products were quantified using the assay for reducing sugars (Bernfeld, 1955), using glucose as standard. The amount of hydrolysis products as reducing sugars is presented in FIG. 9.

The results clearly show better performance of the herein described enzymes as compared to the state-of-art *Trichoderma* enzymes in 55° C. and 60° C. on the spruce substrate. On the basis of HPLC analysis the maximum yield of sugars from the substrate would be 5.67 mg per 10 mg of dry spruce substrate. Because of the relatively low dosage of enzyme the final sugar yields were clearly lower. For thermostable enzymes the sugar yield based on reducing sugar assay was 66% and 57% of theoretical in 55° C. and 60° C., respectively. For state-of art *Trichoderma* enzymes it was only 31% and 11% in 55° C. and 60° C., respectively.

Example 27

Hydrolysis of Steam Pre-Treated Corn Stover at High Temperatures

Steam exploded corn stover fibre (treatment at 195° C. for 5 min), with dry matter of 45.3% was suspended in 5 ml of 0.05 M sodium acetate buffer in the consistency of 10 mg/ml. The treatments and measurements were performed as described in Example 26.

A mixture of herein described thermophilic cellulases was constructed using the following components:

Thermophilic CBH preparation containing *Thermoascus aurantiacus* ALKO4242 Cel7A with genetically attached CBD of *T. reesei* CBHI/Cel7A (Ta Cel7A+Tr CBD, Example 15). The protein content of the preparation was 31 mg/ml.

Thermophilic endoglucanase preparation containing *Acremonium thermophilum* ALKO4245 endoglucanase At EG_40/Cel45A was obtained as described in Example 19. The concentrated enzyme preparation contained endoglucanase activity (according to IUPAC, 1987) of 2057 nkat/ml.

Thermophilic β-glucosidase preparation containing *Thermoascus aurantiacus* ALKO 4242 β-glucosidase Ta βG_81/Cel3A was obtained as described in Example 21 containing β-glucosidase activity (according to Bailey and Linko, 1990) of 11500 nkat/ml.

Thermophilic xylanase product containing an AM24 xylanase originating from *Nonomuraea flexuosa* DSM43186. The product was prepared by using a recombinant *Trichoderma reesei* strain that had been transformed with the expression cassette pALK1502, as described in WO2005/100557. The solid product was dissolved in water to make a 10% solution and an enzyme preparation with xylanase activity (assayed according to Bailey et al., 1992) of 208000 nkat/ml was obtained.

These enzyme preparations were combined as follows (per 10 ml of mixture): CBH/Cel7 preparation 7.79 ml, endoglucanase preparation 0.96 ml, β-glucosidase preparation 1.14 ml and xylanase preparation 0.31 ml. This mixture was used as "MIXTURE 2" of the thermophilic enzymes.

As a comparison and reference, a state-of art mixture of commercial *Trichoderma reesei* enzymes was constructed by combining (per 10 ml) 8.05 ml Celluclast 1.5 L FG (from Novozymes A/S) and 1.95 ml Novozym 188 (from Novozymes A/S). This was designated as "*T. reesei* ENZYMES."

Samples were taken from the hydrolysis after 24, 48 and 72 h and treated as described above. The hydrolysis products were quantified using the assay for reducing sugars (Bernfeld, 1955), using glucose as standard. The results from the substrate blanks were subtracted from the samples with enzymes, and the concentration of hydrolysis products as reducing sugars is presented in FIG. 10.

The results clearly show better performance of the herein described enzymes as compared to the state-of-art *Trichoderma* enzymes. In 45° C. the mixture of thermophilic enzymes showed more efficient hydrolysis as compared to *T. reesei* enzymes: The hydrolysis was faster and higher sugar yields were also obtained. On the basis of HPLC analysis the maximum yield of sugars (including free soluble sugars in the unwashed substrate that was used) from the substrate would be 5.73 mg per 10 mg of dry substrate. Thus, the hydrolysis by the MIXTURE 2 enzymes was nearly complete within 48 hours. In 55° C. and 57.5° C. the herein described thermophilic enzymes showed also clearly better performance in the hydrolysis as compared to the state-of art *Trichoderma* enzymes.

Example 28

Hydrolysis of Pre-Treated Corn Stover at High Temperatures Using Mixture with a Thermostable Xylanase The procedure explained in Example 27 was repeated except that the xylanase product XT 02026A3 was replaced by thermophilic xylanase preparation containing *Thermoascus aurantiacus* ALKO4242 xylanase Ta XYN_30/Xyn10A produced in *T. reesei*. The fermentor broth, produced as described in Example 23 contained xylanase activity of 132 000 nkat/ml (assayed according to Bailey et al., 1992).

These enzyme preparations were combined as follows (per 10 ml of mixture): CBH/Cel7-preparation 7.64 ml, endoglucanase preparation 0.96 ml, β-glucosidase preparation 1.15 ml and xylanase preparation 0.25 ml. This mixture was used as "MIXTURE 3" of the thermophilic enzymes.

As a comparison and reference, a state-of-art mixture of commercial *Trichoderma reesei* enzymes was constructed by combining (per 10 ml) 8.05 ml Celluclast 1.5 L FG (from Novozymes A/S) and 1.95 ml Novozym 188 (from Novozymes A/S). This was designated as "*T. reesei* ENZYMES."

Samples were taken from the hydrolysis after 24, 48 and 72 h and treated as described above. The hydrolysis products were quantified using the assay for reducing sugars (Bernfeld, 1955), using glucose as standard. The results from the substrate blanks were subtracted from the samples with enzymes, and the concentration of hydrolysis products as reducing sugars is presented in FIG. 11.

The results clearly show better performance of the mixture of the herein described enzymes as compared to the state-of-art *Trichoderma* enzymes. In 45° C. the mixture of thermophilic enzymes showed more efficient hydrolysis as compared to *T. reesei* enzymes. In 55° C. and 60° C. the herein described thermophilic enzymes showed clearly better performance in the hydrolysis as compared to the state-of art *Trichoderma* enzymes. The performance of the new enzyme mixture at 60° C. was at the same level than the performance of state-of-art enzymes at 45° C.

Example 29

Hydrolysis of Pre-Treated Spruce at High Temperatures Using Mixture with a Thermostable Xylanase Procedure as described in Example 28 was repeated with washed steam exploded spruce fibre (impregnation with 3% w/w $SO_2$ for 20 min, followed by steam pre-treatment at 215° C. for 5 min, with dry matter of 25.9%) as substrate using hydrolysis temperatures 45° C., 55° C. and 60° C. Samples were taken from the hydrolysis after 24, 48 and 72 h and treated as described above. The hydrolysis products were quantified using the assay for reducing sugars (Bernfeld, 1955), using glucose as standard. The results from the substrate blanks were subtracted from the samples with enzymes, and the concentration of hydrolysis products as reducing sugars is presented in FIG. 12.

The results clearly show better performance of the mixture of herein described enzymes as compared to the state-of-art *Trichoderma* enzymes in all the temperatures studied. At 45° C. the mixture of thermophilic enzymes showed more efficient hydrolysis as compared to *T. reesei* enzymes, evidently due to the better stability in long term hydrolysis. At 55° C. the efficiency of the mixture of herein described enzymes was still on the same level than at 45° C., whereas the state-of-art mixture was inefficient with the substrate used in this temperature. At 60° C. the herein described thermophilic enzymes showed decreased hydrolysis although the hydrolysis was nearly at the same level as the performance of the state-of-art enzymes at 45° C.

Example 30

Evaluation of Glucose Inhibition of β-Glucosidases from *Acremonium thermophilium* ALKO4245, *Chaetomium thermophilum* ALKO4261 and *Thermoascus aurantiacus* ALKO4242

The culture filtrates produced by *Acremonium thermophilium* ALKO4245, *Chaetomium thermophilum* ALKO4261 and *Thermoascus aurantiacus* ALKO4242 strains are described in Example 1. The β-glucosidase activities (measured according to Bailey and Linko, 1990) of these preparations were 21.4 nkat/ml, 5.6 nkat/ml and 18.6 nkat/ml, respectively. For comparison, commercial enzymes Celluclast 1.5 L (β-glucosidase 534 nkat/ml) and Novozym 188 (β-glucosidase 5840 nkat/ml) were also included in the experiment.

In order to evaluate the sensitivity of the different β-glucosidases towards glucose inhibition, the standard activity assay procedure was performed in the presence of different concentrations of glucose. The substrate (p-nitrophenyl-β-D-glucopyranoside) solutions for β-glucosidase activity assay were supplemented by glucose so that the glucose concentration in the assay mixture was adjusted to the values from 0 to 0.5 M. Except this glucose addition the assay was performed using the standard procedure (Bailey and Linko, 1990). The activities in the presence of varying glucose concentrations as a percentage of the activity without glucose are presented in FIG. 13.

The results show that β-glucosidases from *C. thermophilum* and *T. aurantiacus* were affected less by glucose inhibition than the β-glucosidases present in the commercial enzymes: *Aspergillus*-derived β-glucosidase in Novozym 188 or *Trichoderma*-derived β-glucosidase in Celluclast 1.5 L. *A. thermophilum* enzyme showed behaviour comparable to *T. reesei* enzyme of Celluclast. Especially *C. thermophilum* enzyme was clearly less affected by high glucose concentration. Thus, these results indicate that considering glucose inhibition the use of the new β-glucosidases, especially from strains *Acremonium thermophilium* ALKO4242 and *Chaetomium thermophilum* ALKO4261, would give clear advantages in hydrolysis in industrial conditions with high glucose concentration.

Example 31

Filter Paper Activity of Enzyme Mixtures in High Temperatures

Filter paper activity of enzyme preparations was measured according to the method of IUPAC (1987) as described in the procedure except enzyme reaction was performed at temperatures from 50° C. to 70° C. The calculated FPU activity is based on the amount of enzyme required to hydrolyse 4% of filter paper substrate in 1 h under the experimental conditions. The FPU activity is considered to represent the total overall cellulase activity of an enzyme preparation.

The enzyme mixtures were MIXTURE 2 prepared as described in Example 27, MIXTURE 3 prepared as described in Example 28, and MIXTURE 4. MIXTURE 4 was prepared by combining enzyme preparations described in Example 27 as follows (per 10 ml of mixture): CBH/Cel7-preparation 7.84 ml, endoglucanase preparation 0.99 ml and β-glucosidase preparation 1.17 ml.

The enzyme mixtures used as reference, representing the state-of art-mixtures, were:

"*T. reesei* ENZYMES A" prepared as preparation "*T. reesei* ENZYMES" described in Example 26.

"*T. reesei* ENZYMES B" was constructed combining (per 10 ml) 8.05 ml Econase CE (a commercial *T. reesei* cellulase preparation from AB Enzymes Oy, Rajamäki, Finland) and 1.95 ml Novozym 188 (from Novozymes A/S).

The FPU activities measured for the enzyme preparations at different temperatures are presented in FIG. 14 as percentages of the activity under standard (IUPAC, 1987) conditions (at 50° C.).

Results clearly show that the mixtures of the invention show higher overall cellulase activity in elevated (60-70°) temperatures as compared to the state-of art mixtures based on enzymes from *Trichoderma* and *Aspergillus*.

Example 32

Use of the Novel Beta-Glucosidases in Preparation of Sophorose

A high concentration starch hydrolysate mixture (Nutriose 74/968, Roquette) was treated with *Thermoascus aurantiacus* βG_81/Cel3A enriched enzyme preparation produced as described in Example 21 to produce a sugar mixture containing appreciable amounts of cellulase inducer (sophorose) to overcome the glucose repression.

The Ta βG_81/Cel3A enriched enzyme preparation was added to a 70% (w/w) Nutriose solution to a final concentration of 1 g total protein/litre. The container of the mixture was incubated in a water bath at 65° C. for 3 days with constant stirring and used as a carbon source in a shake flask medium for two different *Trichoderma*-strains (A47 and Rut-C30). The effect of the enzyme treatment was measured as an endoglucanase activity formed during a 7 days shake flask cultivation. As a reference cultivations were performed under the same conditions with untreated Nutriose as a carbon source. More than two-fold increase in the activities was obtained in the shake flask cultivations performed on Ta βG_81/Cel3A pretreated Nutriose media with the strains tested. Results are shown in FIG. 15.

List of deposited organisms

| Strain | Plasmid contained | Deposition authority | Deposition date | Deposition number |
|---|---|---|---|---|
| *Acremonium thermophilum* ALKO4245 | — | CBS[(1)] | 20 Sep 2004 | CBS 116240 |
| *Thermoascus aurantiacus* ALKO4242 | — | CBS[(1)] | 20 Sep 2004 | CBS 116239 |
| *Chaetomium thermophilum* ALKO4265 | — | CBS[(2)] | Nov. 8, 1995 | CBS 730.95[(4)] |
| *Escherichia coli* | pALK1635 | DSMZ[(3)] | 16 Sep 2004 | DSM 16723 |
| *Escherichia coli* | pALK1642 | DSMZ | 16 Sep 2004 | DSM 16727 |
| *Escherichia coli* | pALK1646 | DSMZ | 16 Sep 2004 | DSM 16728 |
| *Escherichia coli* | pALK1861 | DSMZ | 16 Sep 2004 | DSM 16729 |
| *Escherichia coli* | pALK1715 | DSMZ | 16 Sep 2004 | DSM 16724 |
| *Escherichia coli* | pALK1723 | DSMZ | 16 Sep 2004 | DSM 16725 |
| *Escherichia coli* | pALK1725 | DSMZ | 16 Sep2004 | DSM 16726 |
| *Escherichia coli* | pALK1904 | DSMZ | 13 May 2005 | DSM 17323 |
| *Escherichia coli* | pALK1908 | DSMZ | 13 May 2005 | DSM 17324 |
| *Escherichia coli* | pALK1925 | DSMZ | 13 May 2005 | DSM 17325 |
| *Escherichia coli* | pALK1926 | DSMZ | 13 May 2005 | DSM 17326 |
| *Escherichia coli* | pALK2001 | DSMZ | 18 Oct 2005 | DSM 17667 |
| *Escherichia coli* | pALK2010 | DSMZ | 18 Nov 2005 | DSM 17729 |

(1)the Centralbureau Voor Schimmelcultures at Uppsalalaan 8, 3584 CT, Utrecht, the Netherlands (2)the Centralbureau Voor Schimmelcultures at Oosterstraat 1, 3742 SK BAARN, The Netherlands (3)Deutsche Sammlung von Mikroorganismen and Zellkulturen GmbH (DSMZ), Mascheroder Weg 1 b, D-38124 Braunschweig, Germany (4)[After termination of the current deposit period, samples will be stored under agreements as to make the strain available beyond the enforceable time of the patent.]

REFERENCES

Altschul S., Gish W., Miller W., Myers E. W. and Lipman D. J., (1990) "Basic local alignment search tool," *J. Mol. Biol.* 215: 403-410.

Badger, P. C. (2002) "Ethanol from cellulose: a general review," In: *Trends in New Crops and New Uses*, J. Janick and A. Whipkey (eds.). ASHS Press, Alexandria, Va., USA, pp. 17-21.

Bailey M. J. and K. M. H. Nevalainen (1981) "Induction, isolation and testing of stable *Trichoderma reesei* mutants with improved production of solubilizing cellulose," *Enz. Microbiol. Technol.,* 3:153-157.

Bailey, M. J., Biely, P. and Poutanen, K. (1992) "Interlaboratory testing for assay of xylanase activity," *J. Biotechnol.,* 23:257-270.

Bailey, M. J. and Linko, M. (1990) "Production of β-galactosidase by *Aspergillus oryzae* in submerged bioreactor cultivation," *J. Biotechnol.,* 16:57-66.

Bailey M. J. and Poutanen K. (1989) "Production of xylanases by strains of *Aspergillus," Appl. Microbiol. Biotechnol.,* 30:5-10.

Bailey M., Siika-aho M., Valkeajärvi A. and Penttilä M. (1993) "Hydrolytic properties of two cellulases of *Trichoderma reesei* expressed in yeast," *Biotehnol. Appl. Biochem.,* 17:65-76.

Bendtsen J. D., Nielsen H., von Heijne G. and Brunak S. (2004) "Improved prediction of signal peptides: SignalP 3.0," *J. Mol. Biol.,* 340:783-795.

Bernfeld, B. (1955) "Amylases, α and β," In: *Methods in Enzymology*, vol. 1, Eds. Colowick, S. P. and Kaplan, N. O. Academic Press, New York, pp. 149-158.

Biely P., Vrsanska M., Tenkanen M., Kluepfel D. (1997) "Endo-beta-1,4-xylanase families: differences in catalytic properties," *Journal of Biotechnology,* 57:151-166.

Coen, D. M. (2001) "The polymerase chain reaction," In: *Current Protocols in Molecular Biology*, Ausubel, F. M., Brent, R., Kingston, R. E., More, D. D., Seidman, J. G., Smith, K. and Struhl, K. (eds.), John Wiley & Sons. Inc., Hoboken, USA.

Gasteiger, E., Gattiker A., Hoogland C., Ivanyi I., Appel R. D. and Bairoch A. (2003) "ExPASy: the proteiomics server for in-depth protein knowledge and analysis," *Nucleic Acids Res.,* 31:3784-3788.

Gellissen, G. (ed.) (2005) "Production of recombinant proteins," *Novel Microbial and Eukaryotic Expression Systems*, Wiley-VCH Verlag Gmbh & Co. Weinheim, Germany.

Gill, S. C, and von Hippel, P. H. (1989) "Calculation of protein extinction coefficients from amino acid sequence data," *Anal. Biochem.,* 182:319-326.

Gupta, R., E. Jung and S. Brunak. (2004) "Prediction of N-glycosylation sites in human proteins," in preparation: www.cbs.dtu.dk/services/NetNGlyc/.

Haakana H., Miettinen-Oinonen A., Joutsjoki V., Mäntylä A., Suominen P, and Vehmaanperä J. (2004) "Cloning of cellulase genes from *Melanocarpus albomyces* and their efficient expression in *Trichoderma reesei," Enz. Microbiol. Technol.,* 34:159-167.

Henrissat B. (1991) "A classification of glycosyl hydrolases based on amino acid sequence similarities," *Biochem. J.,* 280:309-316.

Henrissat B. and Bairoch A. (1993) "New families in the classification of glycosyl hydrolases based on amino acid sequence similarities," *Biochem. J.,* 293:781-788.

Henrissat B. and Bairoch A. (1996) "Updating the sequence-based classification of glycosyl hydrolases," *Biochem. J.,* 316:695-696.

Henrissat B., Teeri T. T. and Warren R. A. J. (1998) "A scheme for designating enzymes that hydrolyse the polysaccharides in the cell wall of plants," *FEBS Letters,* 425: 352-354.

Hong J., H. Tamaki, K. Yamamoto, and Kumagai H. (2003a) "Cloning of a gene encoding a thermo-stabile endo-β-1,4-glucanase from *Thermoascus aurantiacus* and its expression in yeast," *Biotech. Letters,* 25:657-661.

Hong J., Tamaki H., Yamamoto K. and Kumagai H. (2003b) "Cloning of a gene encoding thermostable cellobiohydrolase from *Thermoascus aurantiacus* and its expression in yeast," *Appl. Microbiol. Biotechnol.,* 63:42-50.

IUPAC (International Union of Pure and Applied Chemistry) (1987) "Measurement of cellulase activities," *Pure and Appl. Chem.,* 59:257-268.

Joutsjoki, V. V., Torkkeli T. K. and Nevalainen K. M. H. (1993) "Transformation of *Trichoderma reesei* with the Hormoconis resinae glucoamylase P (gamP) gene: production of a heterologous glucoamylase by *Trichoderma reesei," Curr. Genet.,* 24:223-228.

Karhunen T., Mäntylä A., Nevalainen K. M. H. and Suominen P. L. (1993) "High frequency one-step gene replacement in *Trichoderma reesei*. I. Endoglucanase I overproduction," *Mol. Gen. Genet.,* 241:515-522.

Kurabi A., Berlin A, Gilkes N., Kilburn D., Markov A., Skomarovsky A., Gusakov A., Okunev O., Sinitsyn A., Gregg D. Xie D. and Saddler J. (2005) "Enzymatic hydrolysis of steam-exploded and ethanol organosolv-pretreated Douglas-Fir by novel and commercial fungal cellulases," *Appl. Biochem and Biotechn*. Vol. 121-124:219-229.

Lever, M. (1972) "A new reaction for colorimetric determination of carbohydrates," *Anal. Biochem.,* 47:276-279.

Lo Leggio, L., Kalogiannis S., Bhat M. K., and Pickersgill R. W. (1999) "High resolution structure and sequence of the *T. aurantiacus* xylanase I: implications for evolution of thermostability in family 10 xylanases and enzymes with (beta) alpha-barrel architecture," *Proteins* 36(3):295-306.

Lowry, O., Rosenbrough, N., Farr, A. and Randall, R. (1951) "Protein measuremen with the Folin phenol reagent," *J. Biol. Chem.* 193:265-275.

Needleman S, and Wunsch C. (1970) "A general method applicable to the search for similarities in the amino acid sequence of two proteins," *Journal of Molecular Biology,* 48:443-453.

Nielsen H., Engelbrecht J., Brunak S, and von Heijne G. (1997) "Identification of prokaryotic and eykaryotic signal peptides and prediction of their cleavage sites," *Protein Engineering,* 10:1-6.

Paloheimo M., Mäntylä A., Kallio J., and Suominen P. (2003) "High-yield production of a bacterial xylanase in the filamentous fungus *Trichoderma reesei* requires a carrier polypeptide with an intact domain structure," *Appl. Env. Microbiol.,* 69:7073-7082.

Parry N., Beever D., Owen E., Nerinckx W. Claeyssens M, Van Beeumen J. and Bhat M. (2002) "Biochemical characterization and mode of action of a thermostable endoglucanase purified from *Thermoascus aurantiacus," Arch. of Biochem. and Biophys.,* 404:243-253.

Penttilä M., Nevalainen H., Rättö M., Salminen E. and Knowles J. (1987) "A versatile transformation system for the cellulolytic filamentous fungus *Trichoderma reesei," Gene,* 61:155-164.

Raeder U. and Broda P. (1985) "Rapid preparation of DNA from filamentous fungi," *Lett. Appl. Microbiol.,* 1:17-20.

Rice P, Longden I and Bleasby A. (2000). "EMBOSS: The European Molecular Biology Open Software Suite," *Trends in Genetics,* 16:276-277.

Sambrook J., Fritsch E. F. and Maniatis T. (1989) *Molecular Cloning, A Laboratory Manual*, Cold Spring Harbor Laboratory, New York, US.

Sambrook J. and Russell D. W. (2001) *Molecular Cloning, A Laboratory Manual*, Cold Spring Harbor Laboratory, New York, US.

Srisodsuk M, Reinikainen T, Penttilä M and Teeri T. (1993) "Role of the interdomain linker peptide of *Trichoderma reesei* cellobiohydrolase I in its interaction with crystalline cellulose," *J. Biol. Chem*., Oct. 5, 268(28): 20756-20761.

Sundberg, M., and Poutanen, K. (1991) "Purification and properties of two acetylxylan esterases of *Trichoderma reesei," Biotechnol. Appl. Biochem.,* 13:1-11.

Suurnäkki, A., Tenkanen M., Siika-aho, M., Niku-Paavola, M.-L., Viikari, L. and Buchert, J. (2000) "*Trichoderma reesei* cellulases and their core domains in the hydrolysis and modification of chemical pulp," *Cellulose* 7:189-209.

Tenkanen, M., Puls, J. and Poutanen, K (1992) Two major xylanases of *Trichoderma reesei*. Enzyme Microbiol. Technol. 14: 566-574.

Tomme, P. McRae, S., Wood, T. and Claeyssens, M. (1988) "Chromatographic separation of cellulolytic enzymes," *Methods in Enzymol.,* 160:187-192.

Tuohy M., Walsh J., Murray P., Claeyssens M., Cuffe M., Savage A. and Coughan M. (2002) "Kinetic parameters and mode of action of cellobiohydrolases produced by *Talaromyces emersonii," Biochem. Biophys. Acta,* 1596:366-380 (abstract).

Van Petegem et at (2002) "Atomic resolution structure of major endoglucanase from *Thermoascus aurantiacus," Biochem. and Biophys. Res. Comm.,* 296:161-166.

Van Tilbeurgh, H., Loonties, F., de Bruyne, C. and Claeyssens, M. (1988) "Fluorogenic and chromogenic glycosides as substrates and ligands of carbohydrases," *Methods Enzymol.,* 160:45-59.

Wyman, C. E. (2001) "Twenty years of trials, tribulations, and research progress in bioethanol technology," *Applied Biochemistry and Biotechnology,* 91-93: 5-21.

The invention claimed is:

1. A cellobiohydrolase fusion protein comprising a cellobiohydrolase core region having at least 95% sequence identity to SEQ ID NO:2, to which a cellulose binding domain obtained from *Trichoderma reesei* or *Chaetomium thermophilum* has been genetically attached, wherein the cellobiohydrolase fusion protein displays enhanced crystalline cellulose hydrolysis at temperatures of 45° C. and 70° C. as compared to the cellobiohydrolase *T. reesei* Cel7A.

2. The cellobiohydrolase fusion protein of claim 1, wherein the cellulose binding domain is obtained from *T. reesei* CBHI/Cel7A.

3. The cellobiohydrolase fusion protein of claim 1, comprising an amino acid sequence having at least 80% identity to SEQ ID NO:28 or SEQ ID NO:30.

4. The cellobiohydrolase fusion protein of claim 1, comprising the amino acid sequence of SEQ ID NO:28 or SEQ ID NO:30.

5. An enzyme preparation comprising cellobiohydrolase, endoglucanase and beta-glucosidase, wherein said cellobiohydrolase comprises the fusion protein of any one of claims 1-2 and 3-4.

6. The enzyme preparation of claim 5, wherein the endoglucanase comprises an amino acid sequence having at least 80% identity to SEQ ID NO: 10, 12, 14 or 16, or to an enzymatically active fragment thereof.

7. The enzyme preparation of claim 5, wherein the beta-glucosidase comprises an amino acid sequence having at least 80% identity to SEQ ID NO: 22, 24 or 26, or to an enzymatically active fragment thereof.

8. The enzyme preparation of claim 5, further comprising a xylanase.

9. The enzyme preparation of claim 8, wherein the xylanase comprises an amino acid sequence having at least 80% identity to SEQ ID NO: 18 or 20, or to an enzymatically active fragment thereof.

10. The enzyme preparation of claim 5, which is in the form of spent culture medium, powder, granules, or liquid.

11. A method for treating cellulosic material with cellobiohydrolase, endoglucanase and beta-glucosidase, whereby said cellobiohydrolase comprises the fusion protein of any one of claims 1-2 and 4-5.

12. The method of claim 11, wherein the cellulosic material is lignocellulosic material.

13. The method of claim 11, comprising further treating lignocellulosic material with a xylanase.

14. The method of claim 11, wherein the cellulosic material is selected from the group consisting of corn stover, switchgrass, cereal straw, sugarcane bagasse and wood derived materials.

15. The method of claim 11, wherein the cellulosic material is reacted with said enzymes to obtain hydrolysed cellulosic material, which is used in a process for preparing ethanol from cellulosic material.

* * * * *